United States Patent
Cha et al.

(10) Patent No.: US 10,797,259 B2
(45) Date of Patent: *Oct. 6, 2020

(54) ORGANIC LIGHT-EMITTING DIODE WITH HIGH EFFICIENCY

(71) Applicant: SFC CO., LTD., Cheongju-si (KR)

(72) Inventors: Soon-Wook Cha, Goyang-si (KR); Sang-woo Park, Seoul (KR); Jung-ho Yoo, Seosan-si (KR); Ji-Hwan Kim, Anyang-si (KR); Sung woo Kim, Seoul (KR); Hyeon Jun Jo, Busan (KR)

(73) Assignee: SFC CO., LTD., Cheongju-si (KR)

( * ) Notice: Subject to any disclaimer, the term of this patent is extended or adjusted under 35 U.S.C. 154(b) by 39 days.

This patent is subject to a terminal disclaimer.

(21) Appl. No.: 15/632,605

(22) Filed: Jun. 26, 2017

(65) Prior Publication Data

US 2018/0019430 A1    Jan. 18, 2018

(30) Foreign Application Priority Data

Jul. 14, 2016  (KR) .................. 10-2016-0089454

(51) Int. Cl.
| | | |
|---|---|---|
| *H01L 51/50* | (2006.01) | |
| *C09K 11/06* | (2006.01) | |
| *H01L 51/00* | (2006.01) | |
| *C07D 307/91* | (2006.01) | |
| *H01L 51/52* | (2006.01) | |

(52) U.S. Cl.
CPC .......... *H01L 51/506* (2013.01); *C07D 307/91* (2013.01); *C09K 11/06* (2013.01); *H01L 51/006* (2013.01); *H01L 51/0061* (2013.01); *H01L 51/5088* (2013.01); *H01L 51/5203* (2013.01); *C09K 2211/1018* (2013.01); *H01L 51/0054* (2013.01); *H01L 51/5012* (2013.01)

(58) Field of Classification Search
CPC .................................................. H01L 51/506
See application file for complete search history.

(56) References Cited

U.S. PATENT DOCUMENTS

| | | | | |
|---|---|---|---|---|
| 10,014,479 B2 * | 7/2018 | Kim | ............ | H01L 51/0061 |
| 10,468,603 B2 * | 11/2019 | Cha | ............ | H01L 51/50 |
| 2012/0056165 A1 * | 3/2012 | Kawamura | ............ | C09K 11/06 |
| | | | | 257/40 |
| 2012/0138907 A1 | 6/2012 | Murase et al. | | |
| 2016/0204355 A1 * | 7/2016 | Kim | ............ | H01L 51/0061 |
| | | | | 257/40 |
| 2018/0013071 A1 * | 1/2018 | Cha | ............ | C09K 11/06 |
| 2019/0067588 A1 * | 2/2019 | Cha | ............ | H01L 51/0061 |

FOREIGN PATENT DOCUMENTS

| | | | | |
|---|---|---|---|---|
| CN | 104987309 A | 10/2015 | | |
| CN | 105037173 A | 11/2015 | | |
| KR | 1020080015865 A | 2/2008 | | |
| KR | 1020120047706 A | 5/2012 | | |
| KR | 1020120049135 A | 5/2012 | | |
| KR | 20140076170 A * | 6/2014 | | |
| KR | 1020140083107 A | 7/2014 | | |
| KR | 1020150043020 A | 4/2015 | | |
| KR | 2015124677 A * | 11/2015 | | |
| KR | 1020160081531 A | 7/2016 | | |
| WO | WO-2010010924 A1 * | 1/2010 | ......... | C07C 13/567 |
| WO | WO2016108419 A1 | 7/2016 | | |
| WO | WO-2016126022 A1 * | 8/2016 | ......... | C09K 11/06 |
| WO | WO2016042781 A1 | 4/2017 | | |
| WO | WO-2017146397 A1 * | 8/2017 | ......... | C07C 211/54 |

OTHER PUBLICATIONS

Office Action of KR1020160089454 from Korean Patent Office, dated Dec. 6, 2017.
Extended European Search Report of EP17179994 from European Patent Office, dated Oct. 19, 2017.
Office Action from China National Intellectual Property Administration of 201710550762.2, dated Feb. 6, 2020.

* cited by examiner

*Primary Examiner* — Matthew P Coughlin
(74) *Attorney, Agent, or Firm* — STIP Law Group, LLC

(57) ABSTRACT

Disclosed is an organic light-emitting diode, comprising: a first electrode; a second electrode facing the first electrode; and a light-emitting layer interposed therebetween, wherein the light-emitting layer contains at least one selected from among the amine compounds represented by the following Chemical Formula A or Chemical Formula B and the pyrene compound represented by the following Chemical Formula C, plus the anthracene compound represented by the following Chemical Formula D. The structures of Chemical Formulas A to D are as defined in the specification.

16 Claims, 1 Drawing Sheet

| 80 |
|----|
| 70 |
| 60 |
| 50 |
| 40 |
| 30 |
| 20 |
| 10 |

ORGANIC LIGHT-EMITTING DIODE WITH HIGH EFFICIENCY

CROSS-REFERENCE TO RELATED APPLICATIONS

This application claims the priority of the Korean Patent Application NO 10-2016-0089454 filed on Jul. 14, 2016, in the Korean Intellectual Property Office, the disclosure of which is incorporated herein by reference.

BACKGROUND OF THE INVENTION

1. Field of the Invention

The present disclosure relates to an organic light-emitting diode characterized by high efficiency and, more particularly, to an organic light-emitting diode containing in a light-emitting layer thereof host and dopant materials of certain structures that impart the feature of high efficiency to the organic light-emitting diode.

2. Description of the Prior Art

Organic light-emitting diodes (OLEDs), based on self-luminescence, enjoy the advantage of having a wide viewing angle and being able to be made thinner and lighter than liquid crystal displays (LCDs). In addition, an OLED display exhibits a very fast response time. Accordingly, OLEDs find applications in the illumination field as well as the full-color display field.

Materials used as organic layers in OLEDs may be divided into luminescent materials and charge transport materials, for example, a hole injection material, a hole transport material, an electron injection material, and an electron transport material.

The light-emitting mechanism forms the basis for classification of the luminescent materials as fluorescent or phosphorescent materials, which use excitons in singlet and triplet states, respectively.

Meanwhile, when a single material is employed as the luminescent material, intermolecular actions cause the wavelength of maximum luminescence to shift toward a longer wavelength, resulting in reduced color purity and light emission efficiency. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of dopant because the wavelength of the host moves to the wavelength range of the dopant.

With regard to related arts pertaining to dopant compounds in the light-emitting layer, reference may be made to Korean Patent Publication No. 10-2008-0015865 (Feb. 20, 2008), which describes an OLED using an arylamine-coupled indenofluorene derivative, and Korean Patent Publication No. 10-2012-0047706 (May 14, 2012), which describes an organic photoelectric device using a compound in which dibenzofuran or dibenzothiophene coexists with fluorene or carbazole.

Further, Korean Patent Application No. 10-2015-0043020, pertaining to a related art of host compound in the light-emitting layer, discloses an OLED employing an anthracene derivative as a fluorescent host.

In spite of enormous efforts including the documents describing the related art, there is still the continued need to develop OLEDs that exhibit higher light emission efficiency.

RELATED ART DOCUMENT

Korean Patent Publication No. 10-2008-0015865 A (Feb. 20, 2008)

Korean Patent Publication No. 10-2012-0047706 A (May 14, 2012)

Korean Patent Publication No. 10-2015-0043020 A (Apr. 22, 2015)

SUMMARY OF THE INVENTION

Accordingly, the purpose to be achieved by the present disclosure is to provide a novel OLED, characterized by high light emission efficiency, comprising a dopant and a host of specific structures.

To accomplish the technical purpose, the present disclosure provides an OLED, comprising a first electrode, a second electrode facing the first electrode, and a light-emitting layer interposed therebetween, wherein the light-emitting layer contains at least one selected from among the amine compounds represented by the following Chemical Formula A or Chemical Formula B and the pyrene compound represented by the following Chemical Formula C, plus the anthracene compound represented by the following Chemical Formula D:

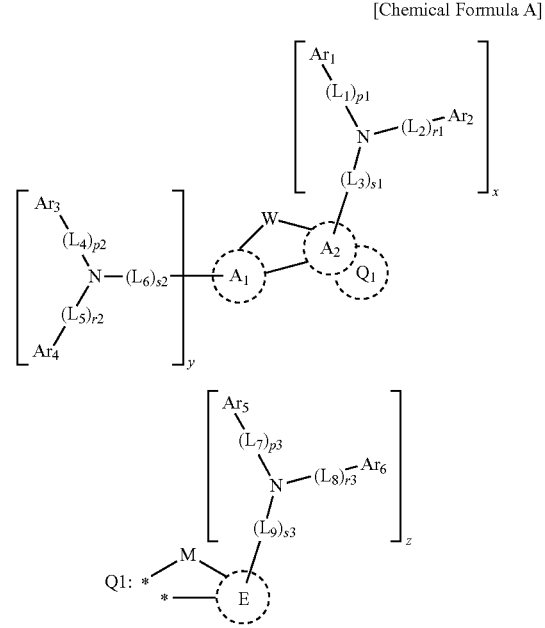

[Chemical Formula A]

-continued

[Chemical Formula B]

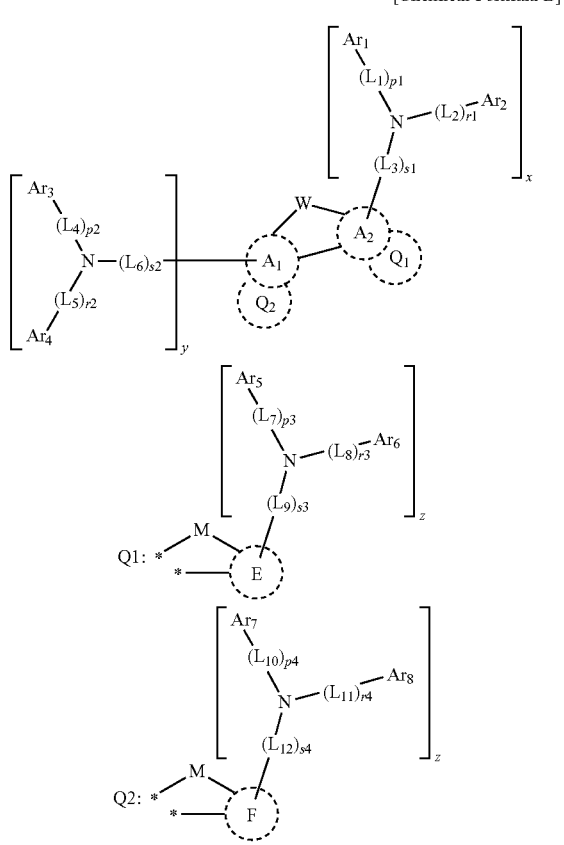

wherein, $A_1$, $A_2$, E, and F may be the same or different and are each independently a substituted or unsubstituted aromatic hydrocarbon ring of 6 to 50 carbon atoms, or a substituted or unsubstituted aromatic heterocyclic ring of 2 to 40 carbon atoms, wherein two adjacent carbon atoms of the aromatic ring $A_1$ and two adjacent carbon atoms of the aromatic ring $A_2$ form a 5-membered fused ring together with W;

linkers $L_1$ to $L_{12}$ may be the same or different and are each independently selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

W is selected from among $CR_1R_2$, $SiR_1R_2$, $GeR_1R_2$, O, S, and $NR_1$,

M is any one selected from among $N-R_3$, $CR_4R_5$, $SiR_6R_7$, $GeR_8R_9$, O, S, and Se;

$R_1$ to $R_9$, and $Ar_1$ to $Ar_8$ may be the same or different and are each independently any one selected from among a hydrogen, a deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ may be bonded to each other to form a mono- or polycyclic aliphatic or aromatic ring, which may be a heterocyclic ring bearing a heteroatom selected from among N, O, P, Si, S, Ge, Se, and Te as a ring member;

p1 to p4, r1 to r4, and s1 to s4 are each independently an integer of 1 to 3, with the proviso that when any of them is 2 or greater, the corresponding linkers may be the same or different;

x is an integer of 1 or 2, and y and z may be the same or different and are each independently an integer of 0 to 3;

$Ar_1$ may form a ring with $Ar_2$, $Ar_3$ may form a ring with $Ar_4$, $Ar_5$ may form a ring with $Ar_6$, and $Ar_7$ may form a ring with $Ar_8$;

two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring,

[Chemical Formula C]

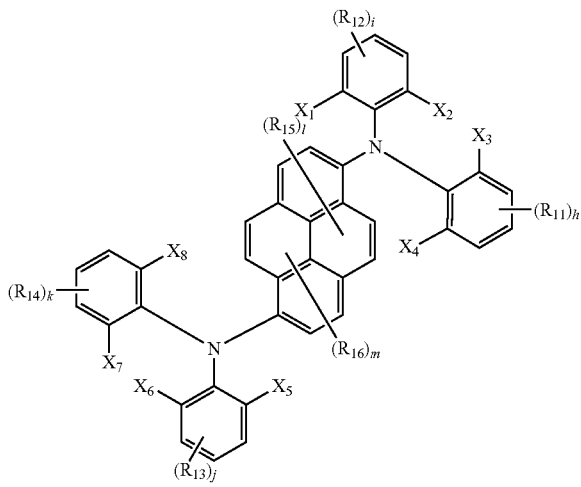

wherein, $R_{11}$ to $R_{16}$ may be the same or different and are each independently any one selected from among a hydrogen, a deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that each of the unsubstituted carbon atoms of the aromatic ring moieties of $R_{11}$ to $R_{16}$ is bound with a hydrogen atom or a deuterium atom;

h, i, j, and k are each an integer of 0 to 3, with the proviso that when each of them is 2 or greater, the corresponding $R_{11}$'s to $R_{14}$'s are each the same or different;

l and m are each an integer of 0 to 4, with the proviso that when each of them are 2 or greater, the corresponding $R_{15}$'s and $R_{16}$'s are each the same or different;

wherein a bond may be formed between $R_{11}$ and adjacent $X_1$ or $X_2$, between $R_{12}$ and adjacent $X_3$ or $X_4$, between $R_{13}$ and adjacent $X_5$ or $X_6$, and between $R_{14}$ and adjacent $X_7$ or $X_8$, or when each of $R_{11}$ to $R_{14}$ exists in duplicate or more, individual $R_{11}$'s to $R_{14}$'s may be bonded to each other to form a mono- or polycyclic aliphatic or aromatic ring, which may be heterocyclic ring bearing a heteroatom selected from among, N, O, P, Si, S, Ge, Se, and Te as a ring member, wherein $X_1$ to $X_8$ may be the same or different and are each independently selected from among a hydrogen, a deuterium, and a substituted or unsubstituted alkyl of 1 to 20 carbon atoms, with the proviso that at least $X_1$, $X_2$, $X_5$ and $X_6$ among $X_1$ to $X_8$ are each a substituted or unsubstituted alkyl of 1 to 20 carbon atoms.

[Chemical Formula D]

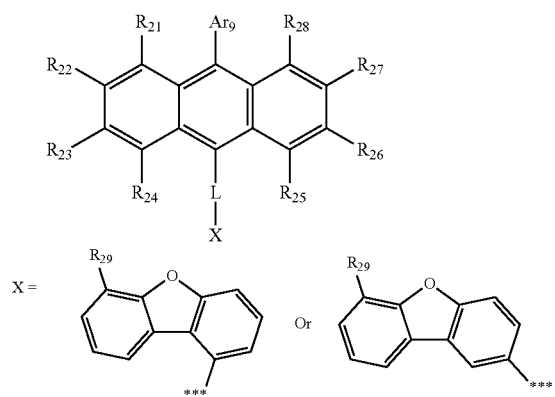

wherein, $Ar_9$ is a substituted or unsubstituted aryl of 6 to 50 carbon atoms, or a substituted or unsubstituted heteroaryl of 2 to 50 carbon atoms, $R_{21}$ to $R_{28}$ may be the same or different and are each independently selected from among a hydrogen, a deuterium, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 2 to 50 carbon atoms bearing O, N or S as a heteroatom, a substituted or unsubstituted silyl of 1 to 30 carbon atoms, a cyano, a nitro, and a halogen, $R_{29}$ is any one selected from among a deuterium, a substituted or unsubstituted alkyl of 1 to 30 carbon atoms, and a substituted or unsubstituted aryl of 6 to 50 carbon atoms, linker L is selected from among a single bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms, "***" of X denotes a bonding site to be linked to linker L, wherein the term 'substituted' in the expression 'substituted or unsubstituted' used in Chemical Formulas A, B, C, and D means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

BRIEF DESCRIPTION OF THE DRAWINGS

The above and other aspects, features and advantages of the present invention will be more apparent from the following detailed description taken in conjunction with the accompanying drawings, in which:

FIG. 1 is a schematic cross-sectional view of an OLED according to some embodiments of the present disclosure.

DETAILED DESCRIPTION OF THE EXEMPLARY EMBODIMENTS

The present invention may be variously modified and include various exemplary embodiments in which specific exemplary embodiments will be described in detail hereinbelow. However, it shall be understood that the specific exemplary embodiments are not intended to limit the present invention thereto and cover all the modifications, equivalents and substitutions which belong to the idea and technical scope of the present invention.

Below, a detailed description will be given of the present disclosure.

To accomplish the technical purpose, the present disclosure addresses an OLED, comprising a first electrode, a second electrode facing the first electrode, and a light-emitting layer interposed therebetween, wherein the light-emitting layer contains at least one selected from among the amine compounds represented by Chemical Formula A or Chemical Formula B and the pyrene compound represented by Chemical Formula C, plus the anthracene compound represented by Chemical Formula D.

Count is taken of the range of the alkyl or aryl moiety in phrases "a substituted or unsubstituted alkyl of 1 to 30 carbon atoms", "a substituted or unsubstituted aryl of 6 to 50 carbon atoms", etc., as used herein. The expression for a number of carbon atoms in "a substituted or unsubstituted alkyl of 1 to 30 carbon atoms", "a substituted or unsubstituted aryl of 6 to 50 carbon atoms" means the total number of carbon atoms in the alkyl or aryl radical or moiety alone, exclusive of the number of carbon atoms of the substituent. For instance, a phenyl group with a butyl at the para position falls within the scope of an aryl of 6 carbon atoms, even if it is substituted with a butyl radical of four carbon atoms.

As used herein, the term "aryl" as a substituent used in the compounds of the present disclosure means an organic radical derived from an aromatic hydrocarbon by removing a hydrogen atom and may include a 5- to 7-membered single or fused ring system and further a fused ring that is formed by adjacent substituents on the organic radical.

Concrete examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—$NH_2$, —NH(R), or —N(R')(R'') wherein R' and R'' are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms bearing one to three heteroatoms selected from among N, O, P, Si, S, Ge, Se, and Te. In the aromatic system, two or more rings may be fused. One or more hydrogen atoms on the heteroaryl may be substituted with the same substituents as in the aryl.

As used herein, the term "heteroaromatic ring" refers to an aromatic hydrocarbon ring bearing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted with the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted with the same substituent as in the aryl.

Representative among examples of the substituent silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atoms of the silyl may be substituted with the same substituent as in the aryl.

The amine compound, useful in the organic light-emitting diode of the present invention, represented by Chemical Formula A or B has the structural feature that if Structural Formula $Q_1$ is connected to the $A_2$ ring in Chemical Formula A, the amine moiety containing $Ar_1$ and $Ar_2$ must be bonded to the $A_2$ ring and that if Structural Formula $Q_2$ and $Q_1$ are connected respectively to $A_1$ and $A_2$ rings in Chemical Formula B, the amine moiety containing $Ar_1$ and $Ar_2$ must be bonded to the $A_2$ ring.

According to some embodiments of the present disclosure, $A_1$, $A_2$, E and F in Chemical Formula A or B may be the same or different and are each independently substituted or unsubstituted aromatic hydrocarbon rings of 6 to 50 carbon atoms.

As stated above, when $A_1$, $A_2$, E and F in Chemical Formula A or B are each independently substituted or unsubstituted aromatic hydrocarbon rings of 6 to 50 carbon atoms, the substituted or unsubstituted aromatic hydrocarbon rings of 6 to 50 carbon atoms may be the same or different and are each independently selected from among compounds represented by Structural Formulas 10 to 21.

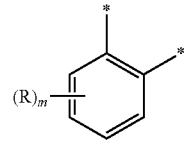

[Str. Formula 10]

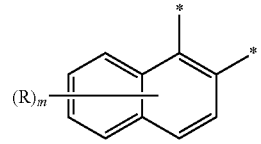

[Str. Formula 11]

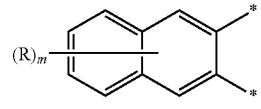

[Str. Formula 12]

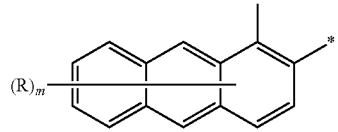

[Str. Formula 13]

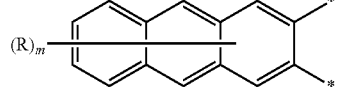

[Str. Formula 14]

[Str. Formula 15]

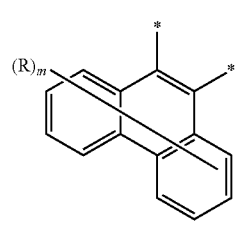

[Str. Formula 16]

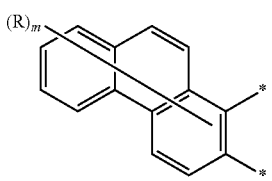

[Str. Formula 17]

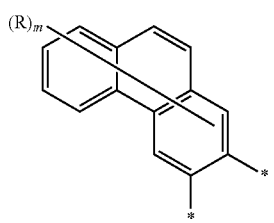

[Str. Formula 18]

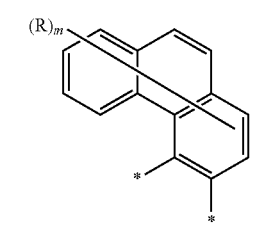

[Str. Formula 19]

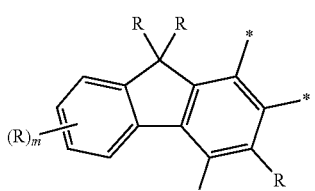

[Str. Formula 20]

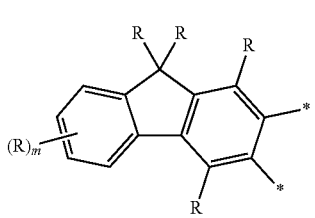

[Str. Formula 21]

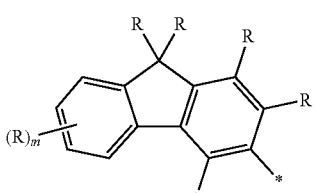

wherein

"-*" denotes a bonding site for forming a 5-membered ring containing W or a bonding site for forming a 5-membered ring containing M of the structural Formula $Q_1$ and $Q_2$;

when one of the aromatic hydrocarbon rings of [Str. Formula 10] to [Str. Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are the same as defined above for $R_1$ and $R_2$, and m is an integer of 1 to 8, with the proviso that when m is 2 or greater or when two or more R's exist, the corresponding R's may be the same or different.

In addition, the linkers $L_1$ to $L_{12}$ in Chemical Formulas A and B and the linker L in Chemical Formula D may be the same or different and may each be a single bond or any one selected from among the following Structural Formulas 22 to 30:

[Str. Formula 22]

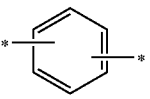

[Str. Formula 23]

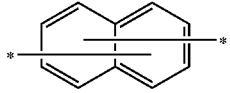

[Str. Formula 24]

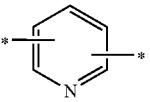

[Str. Formula 25]

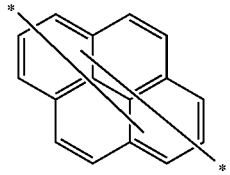

[Str. Formula 26]

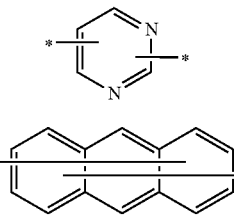

[Str. Formula 27]

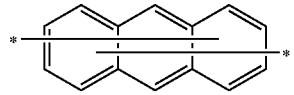

[Str. Formula 28]

[Str. Formula 29]

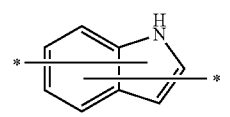

[Str. Formula 30]

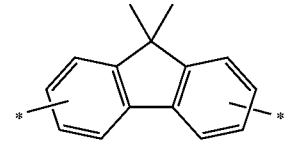

In the linkers, each of the unsubstituted carbon atoms of the aromatic ring moiety is bound with a hydrogen atom or a deuterium atom.

In one embodiment according to the present disclosure, p1 to p4, r1 to r4, and s1 to s4 in Chemical Formula A or B may each be 1 or 2, and x may be 1. In a particular embodiment, x and y may each be 1 and z may be 0 or 1.

According to a specific embodiment of the present disclosure, the substituents $R_1$ to $R_9$ and $Ar_1$ to $Ar_8$ in the amine compound represented by Chemical Formula A or B may be the same or different and may each be independently any one selected from among a hydrogen, a deuterium, a substituted or unsubstituted aryl of 6 to 20 carbon atoms, a substituted or unsubstituted cycloalkyl of 3 to 30 carbon atoms, a substituted or unsubstituted heteroaryl of 2 to 20 carbon atoms bearing at least one heteroatom selected from among O, N, S, and Si, a cyano, and a halogen.

In the amine compound of Chemical Formula A or B according to some embodiments of the present disclosure, $A_1$, $A_2$, E, F, $Ar_1$ to $Ar_8$, $L_1$ to $L_{12}$, and $R_1$ to $R_9$ may have as a substituent any one selected from the group consisting of a cyano, a halogen, an alkyl of 1 to 6 carbon atoms, an aryl of 6 to 18 carbon atoms, an arylalkyl of 6 to 18 carbon atoms, a heteroaryl of 3 to 18 carbon atoms, an alkylsilyl of 1 to 12 carbon atoms, and an arylsilyl of 6 to 18 carbon atoms.

The pyrene compound, represented by Chemical Formula C, useful in the OLED according to the present disclosure, has the pyrene skeleton represented by the following Diagram 1 with two respective aryl amines bonded at positions 3 and 8 thereto.

[Diagram 1]

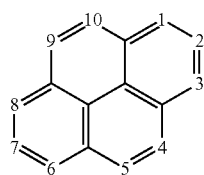

Here, each of the two aryl amines bonded to the pyrene skeleton bears a nitrogen atom to which aryl radicals are bonded at least one of which has a substituted or unsubstituted alkyl of 1 to 20 carbon atoms at the ortho positions relative to the nitrogen atom.

In this regard, adjacent ones of the substituents on the aryl radicals may be coupled to each other to form aliphatic or aromatic mono- or polycyclic rings which may bear at least one heteroatom selected from among N, O, P, Si, S, Ge, Se, and Te as a ring member.

In Chemical Formula C, h, i, j, and k are each an integer of 0 to 2, with the proviso that when each of them is 2, corresponding $R_{11}$'s to $R_{14}$'s may be individually the same or different.

In Chemical Formula C, $R_{11}$ to $R_{16}$ may be the same or different and may each be independently any one selected among a hydrogen, a deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted alkoxy of 1 to 30 carbon atoms, a substituted or unsubstituted alkylsilyl of 1 to 30 carbon atoms, and a substituted or unsubstituted arylsilyl of 6 to 30 carbon atoms.

In the pyrene compound represented by Chemical Formula C, the substituents $R_{15}$ and $R_{16}$ may each be a hydrogen or a deuterium.

Further, the two amine moieties of the pyrene compound represented by Chemical Formula C may be the same. When the two amine moieties are the same, the pyrene compound may be prepared by reacting halogenated pyrene such as dibromopyrene with an amine compound.

In addition, the pyrene compound represented by Chemical Formula C may be asymmetric as the two amine moieties are different. When the two amine moieties are different, they may be allowed to sequentially participate in reaction with a pyrene to afford the pyrene compound.

For the sequential reaction of different amines, a pyrene derivative having one amine bonded thereto is purified and then reacted with the other amine. In the case of two different amines, an asymmetric pyrene derivative results.

In Chemical Formula D, linking occurs between the carbon atom at position 9 of the anthracene moiety and the carbon atom at position 1 or 2 of the substituted or unsubstituted dibenzofuran moiety, as shown in the following Diagram 2, through the linker L or directly when the linker L is single bond. The dibenzofuran moiety has a substituent $R_{29}$ bonded to the carbon atom at position 6 on the ring opposite to the ring involved in the linkage to the anthracene moiety.

Here, the substituent $R_{29}$ may be any one selected from among a deuterium atom, a substituted or unsubstituted alkyl of 1 to 30 carbon atoms, and a substituted or unsubstituted aryl of 6 to 50 carbon atoms, and particularly from among a substituted or unsubstituted alkyl of 1 to 30 carbon atoms and a substituted or unsubstituted aryl of 6 to 50 carbon atoms.

[Diagram 2]

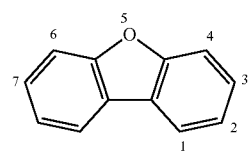

The light-emitting layer of the OLED according to the present disclosure comprises a host and a dopant, wherein the amine compound represented by Chemical Formula A or B and the pyrene compound represented by Chemical Formula C are each used as the dopant, and the anthracene compound represented by Chemical Formula D is used as the host, whereby the OLED of the present disclosure can exhibit the effect of high efficiency, compared to conventional OLEDs.

In addition, the substituent $Ar_9$ on the anthracene compound of Chemical Formula D may be represented by the following Structural Formula 31:

[Str. Formula 31]

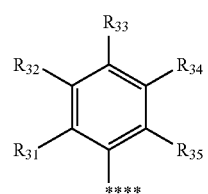

wherein,

"-****" denotes a bonding site to be linked to the anthracene moiety of Chemical Formula D, and the substituents $R_{31}$ to $R_{35}$ may be the same or different and are each independently selected from among a hydrogen, a deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, and a substituted or unsubstituted alkoxy of 1 to 30 carbon atoms.

In Chemical Formula D, the substituents $R_{21}$ to $R_{28}$ and $R_{31}$ to $R_{35}$ may each be a hydrogen or a deuterium, and L may be a single bond or a substituted or unsubstituted arylene of 6 to 20 carbon atoms.

The amine compound represented by Chemical Formula A or B may be any one selected from among, but not limited to, the following Chemical Formulas 1 to 239:

<Chemical Formula 1>

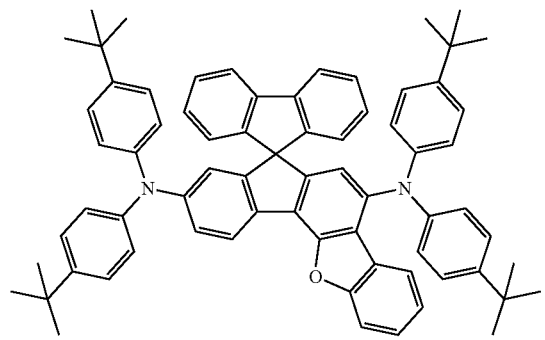

<Chemical Formula 2>

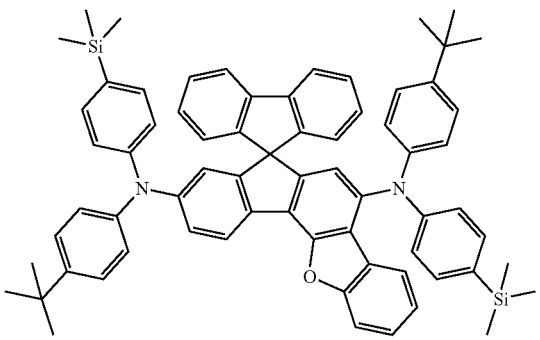

<Chemical Formula 3>

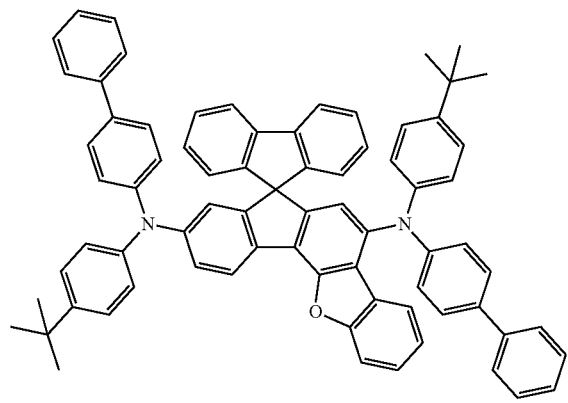

<Chemical Formula 4>

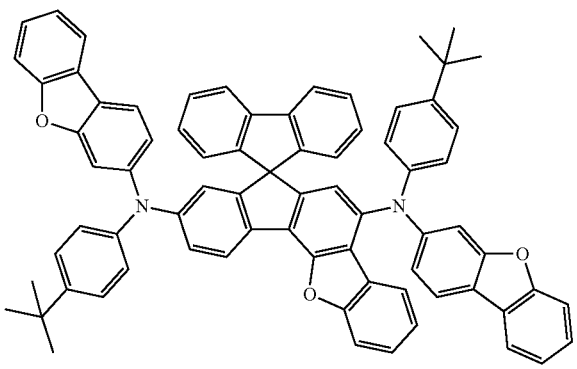

<Chemical Formula 5>

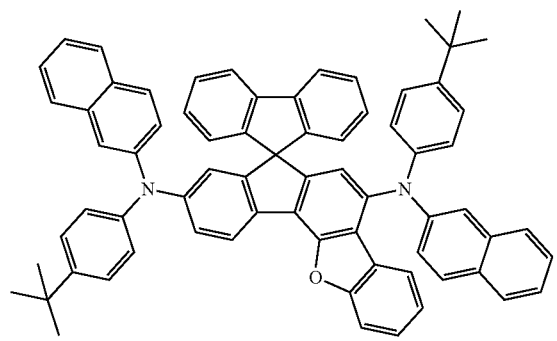

<Chemical Formula 6>

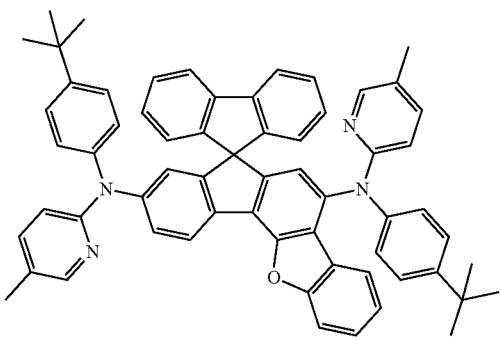

-continued
<Chemical Formula 7>
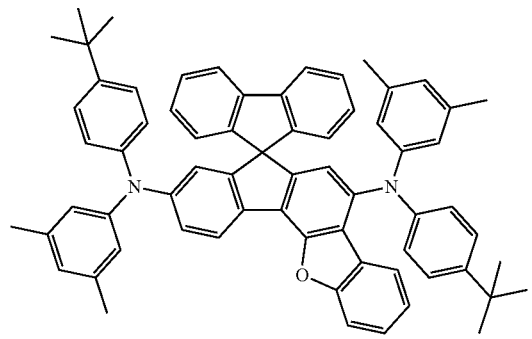
<Chemical Formula 8>
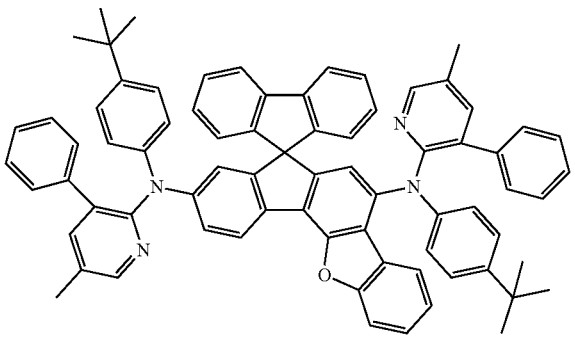
<Chemical Formula 9>
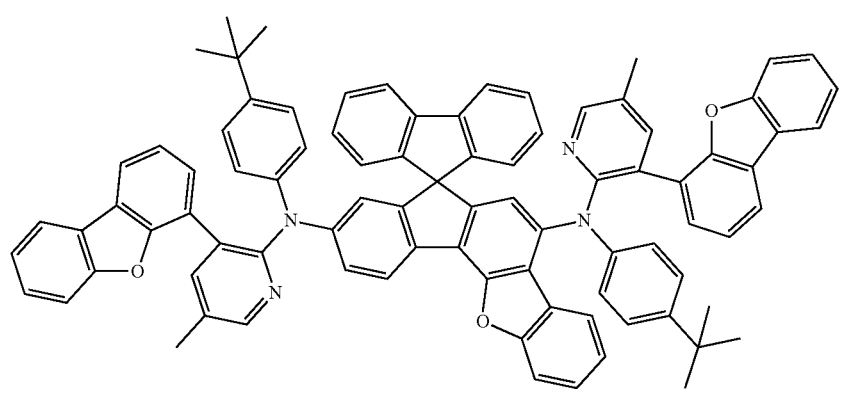
<Chemical Formula 10>
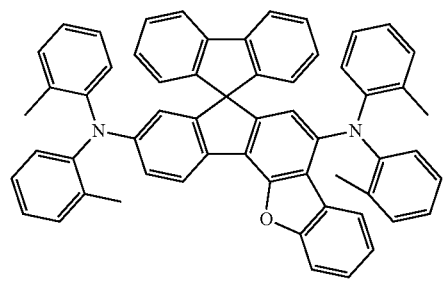
<Chemical Formula 11>
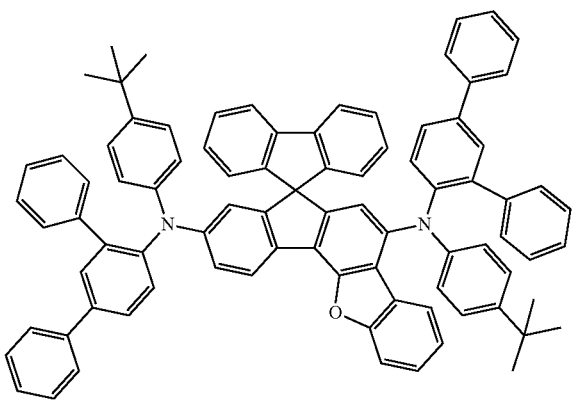
<Chemical Formula 12>
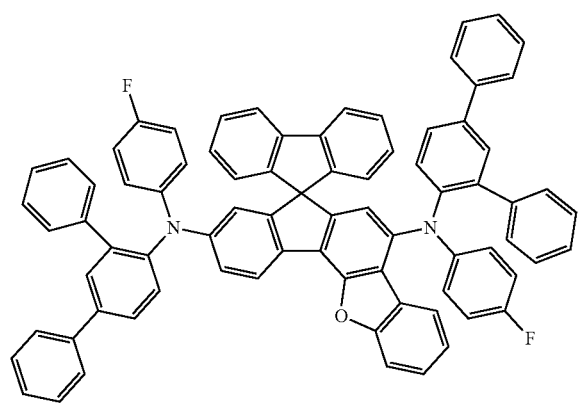
<Chemical Formula 13>
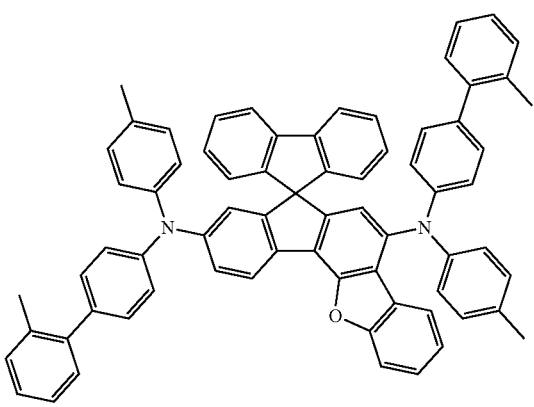

-continued
<Chemical Formula 14>
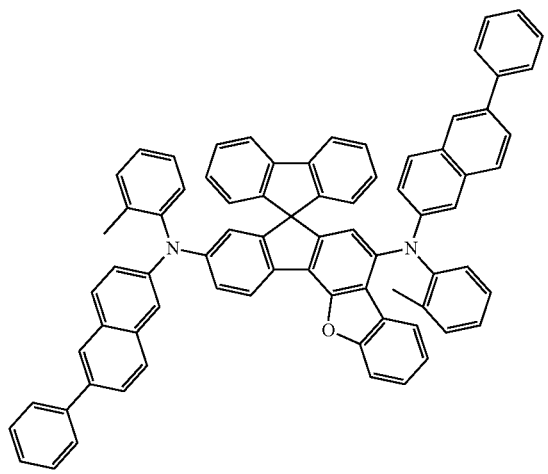
<Chemical Formula 15>
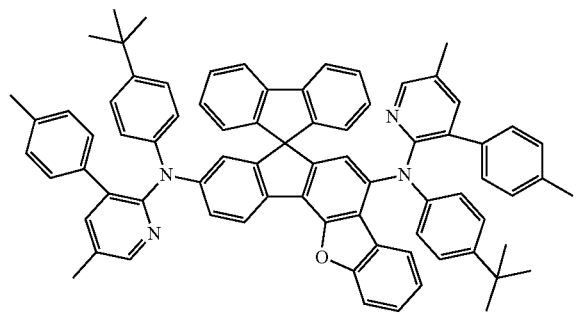
<Chemical Formula 16>
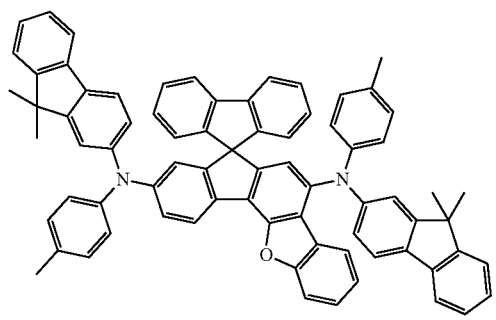
<Chemical Formula 17>
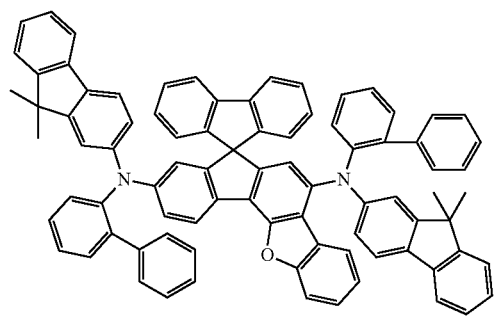
<Chemical Formula 18>
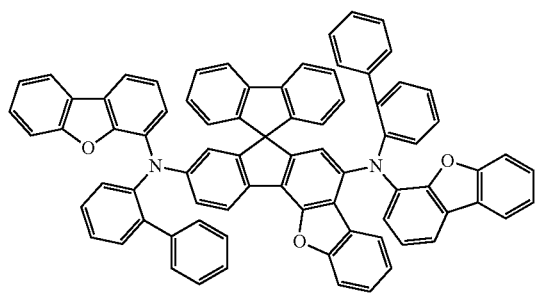
<Chemical Formula 19>
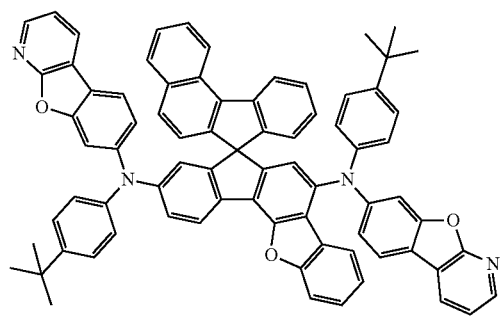
<Chemical Formula 20>
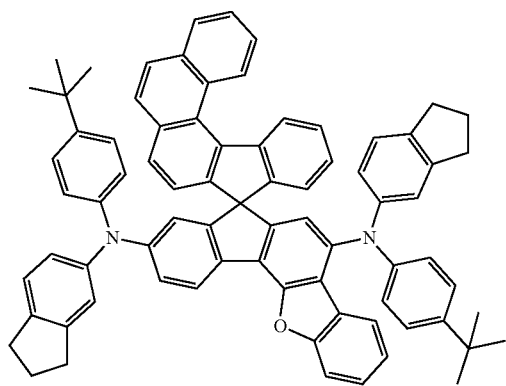
<Chemical Formula 21>
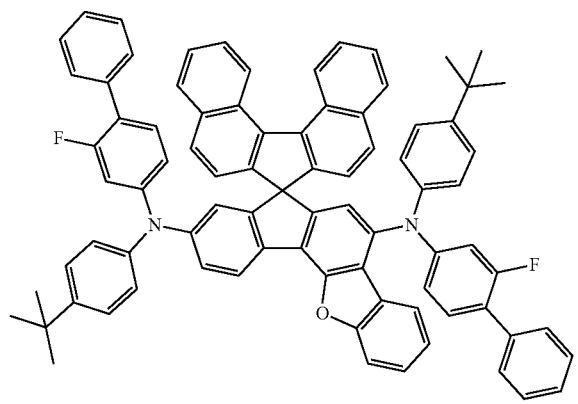

<Chemical Formula 22>
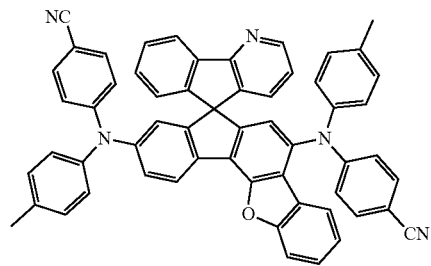
<Chemical Formula 23>
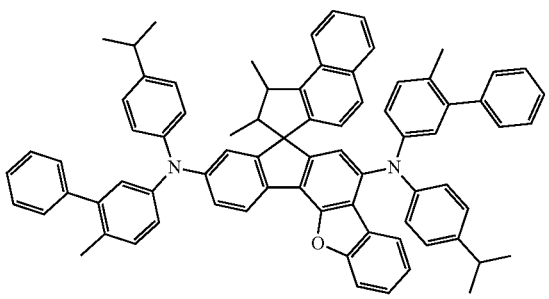
<Chemical Formula 24>
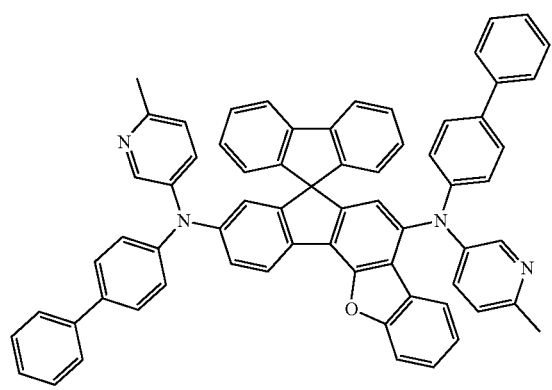
<Chemical Formula 25>
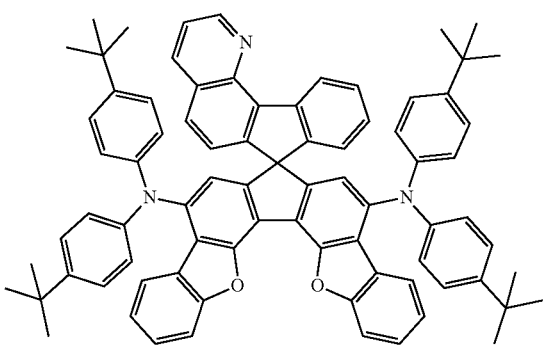
<Chemical Formula 26>
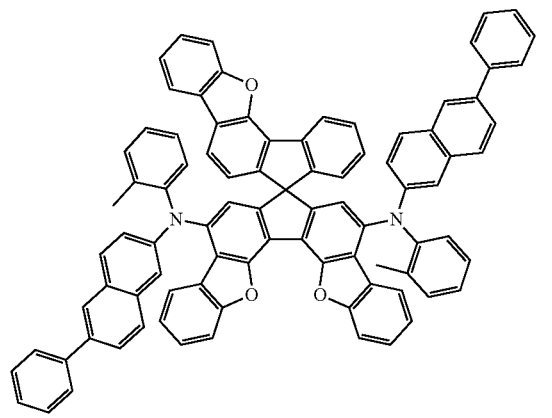
<Chemical Formula 27>
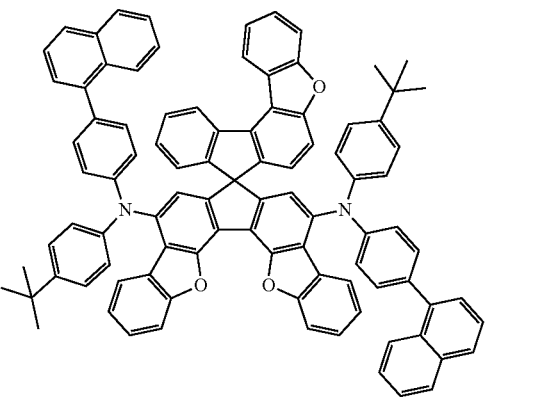
<Chemical Formula 28>
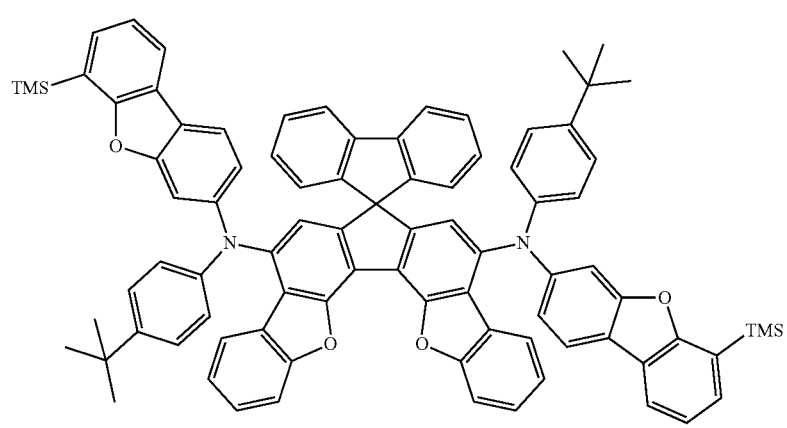

-continued
<Chemical Formula 29>
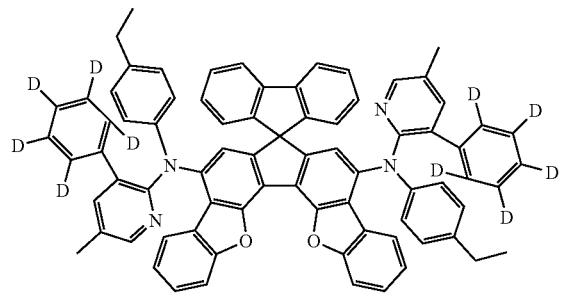
<Chemical Formula 30>
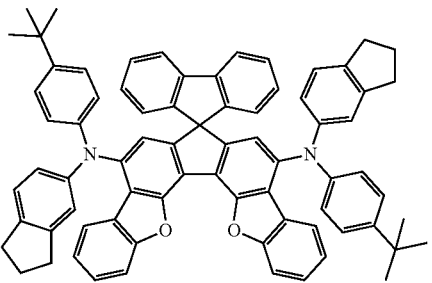
<Chemical Formula 31>
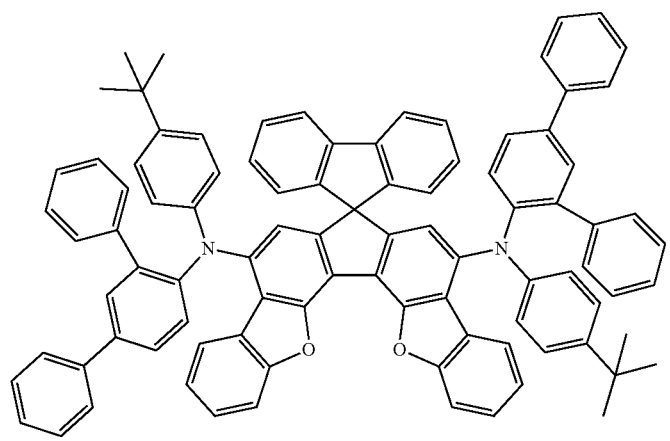
<Chemical Formula 32>
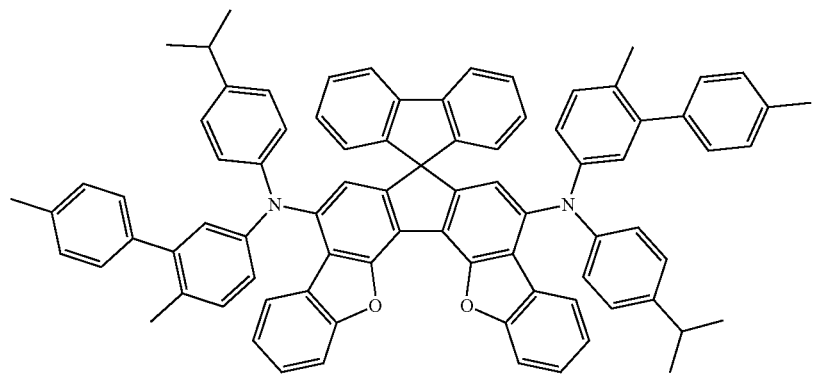
<Chemical Formula 33>
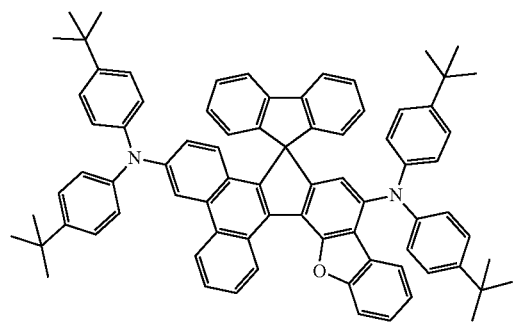
<Chemical Formula 34>
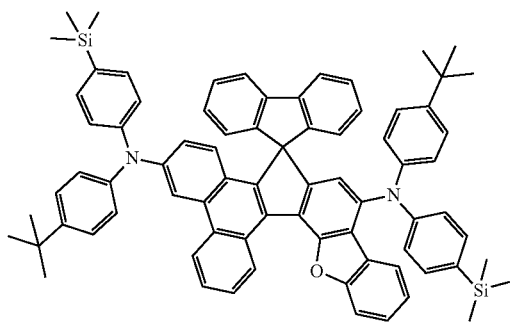

-continued
<Chemical Formula 35>
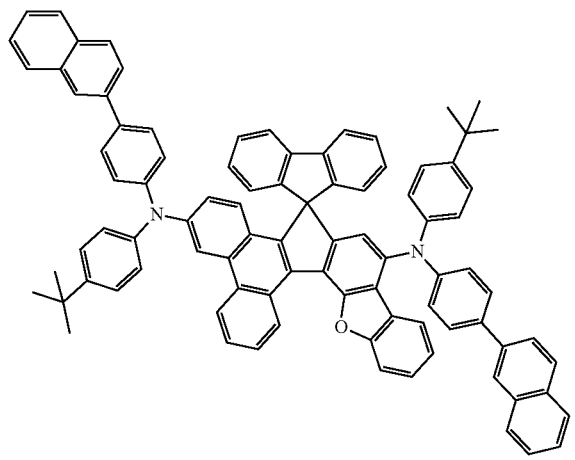
<Chemical Formula 36>
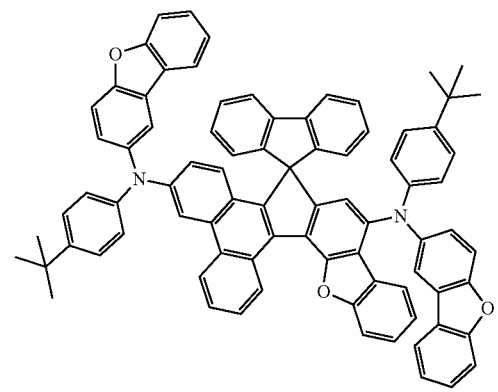
<Chemical Formula 37>
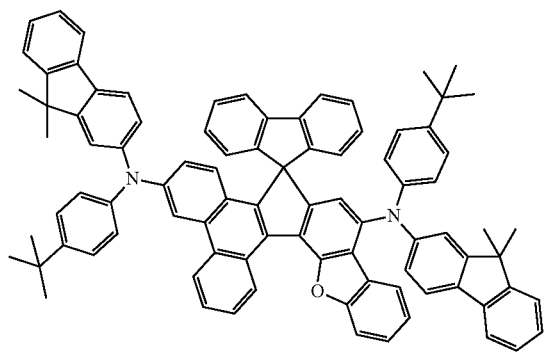
<Chemical Formula 38>
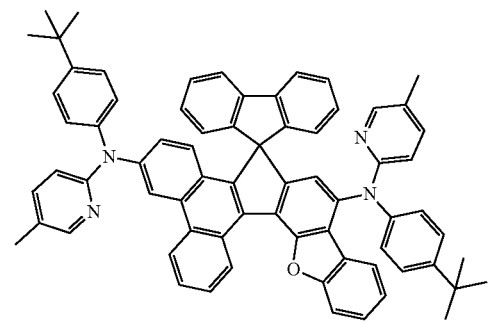
<Chemical Formula 39>
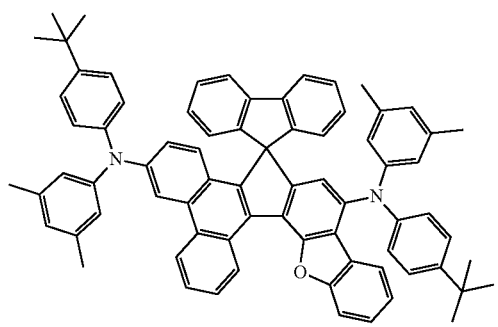
<Chemical Formula 40>
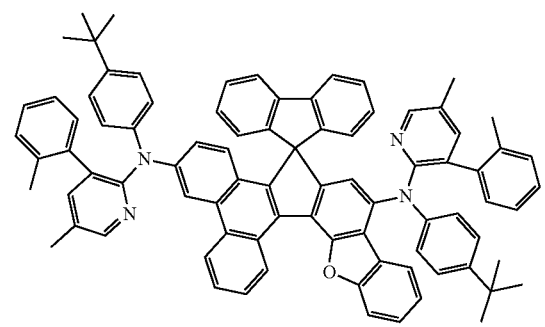
<Chemical Formula 41>
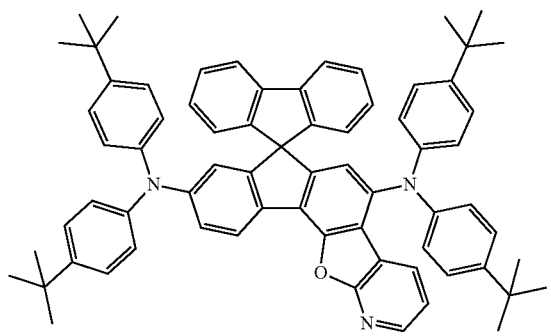
<Chemical Formula 42>
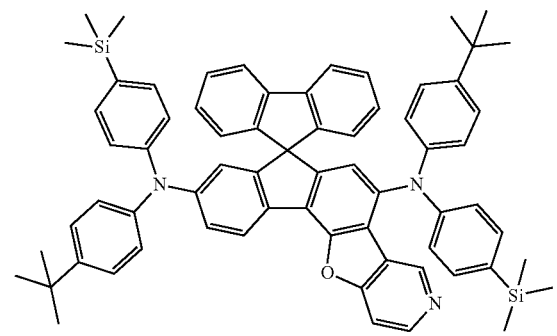

-continued
<Chemical Formula 43>
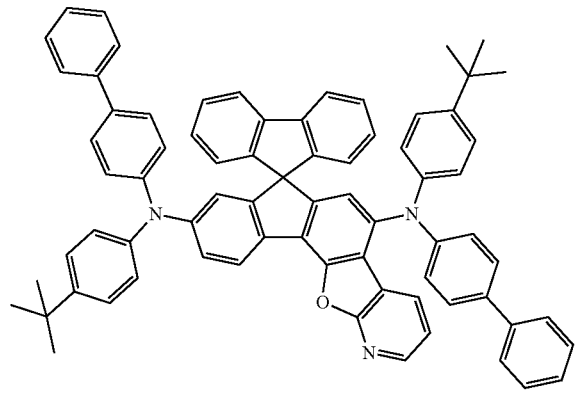
<Chemical Formula 44>
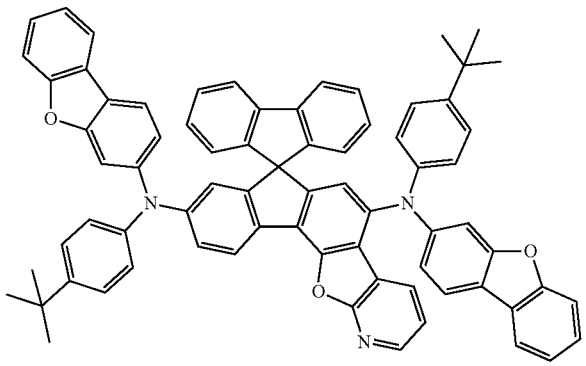
<Chemical Formula 45>
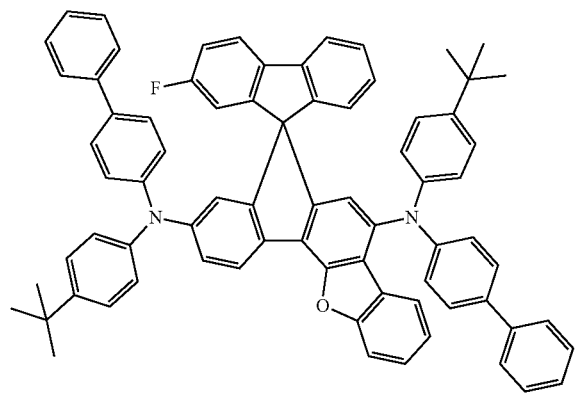
<Chemical Formula 46>
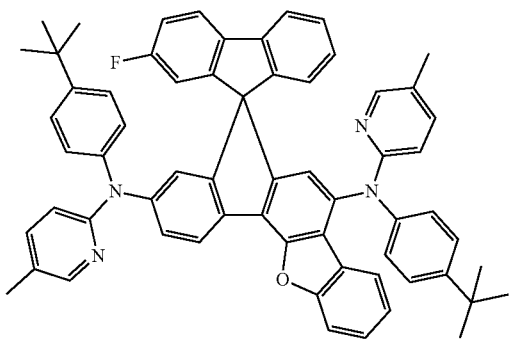
<Chemical Formula 47>
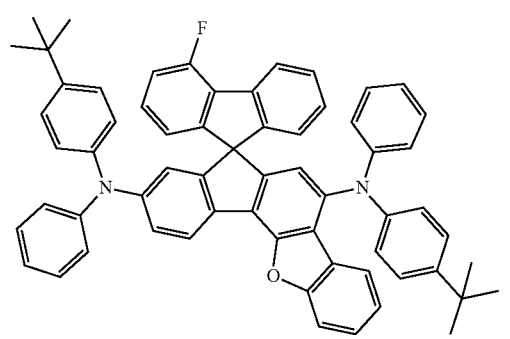
<Chemical Formula 48>
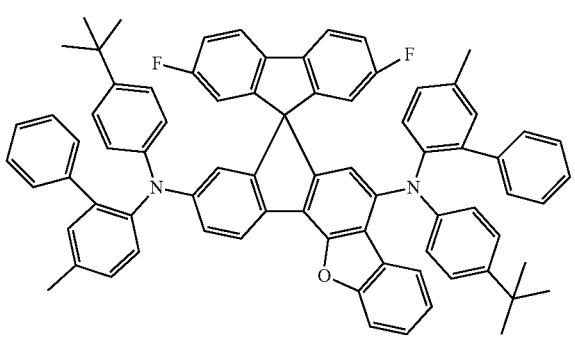
<Chemical Formula 49>
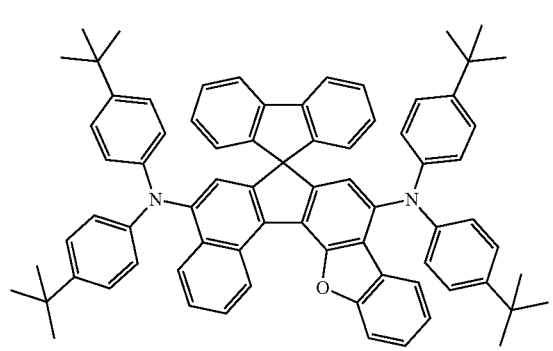
<Chemical Formula 50>
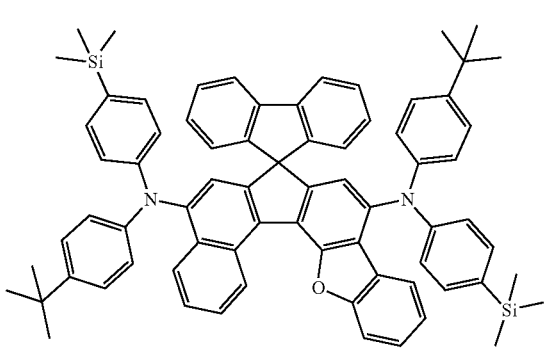

-continued
<Chemical Formula 51>
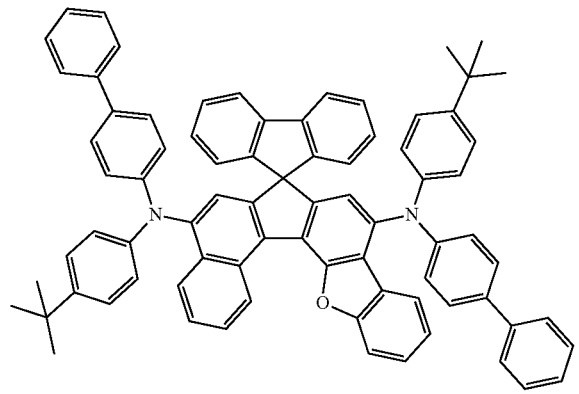
<Chemical Formula 52>
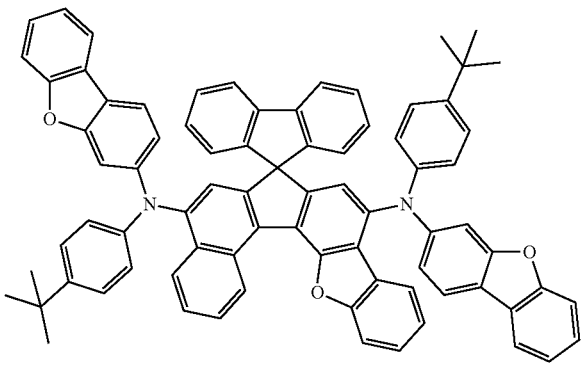
<Chemical Formula 53>
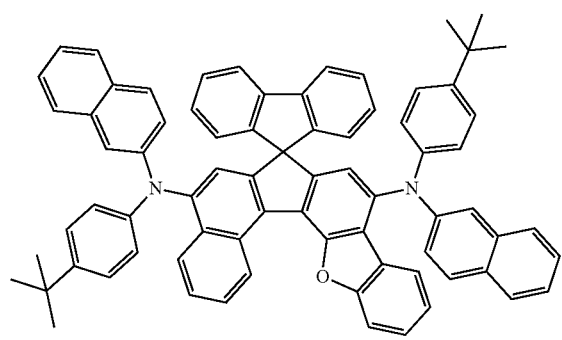
<Chemical Formula 54>
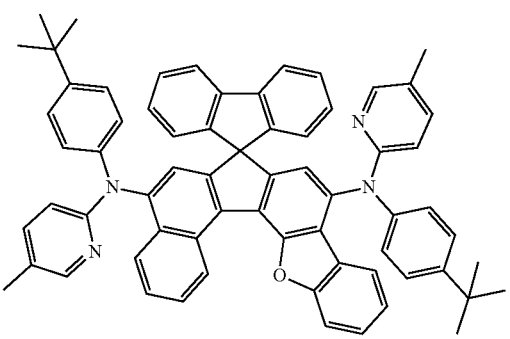
<Chemical Formula 55>
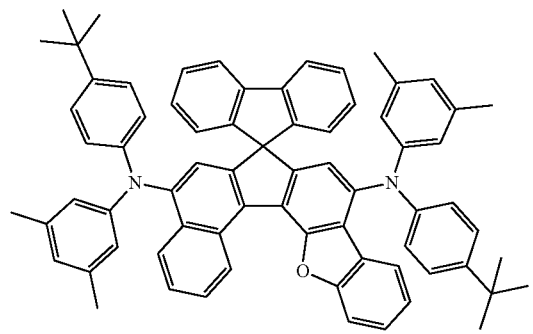
<Chemical Formula 56>
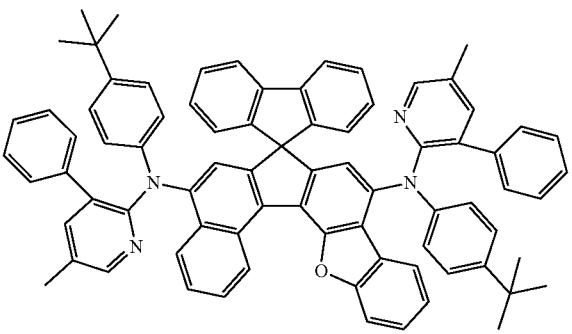
<Chemical Formula 57>
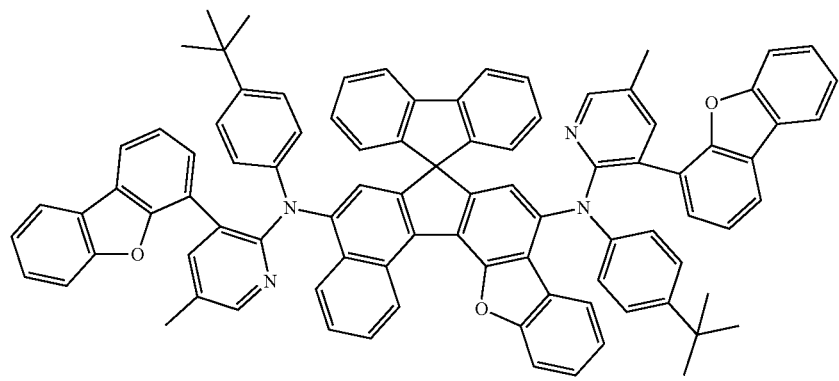

-continued
<Chemical Formula 58>
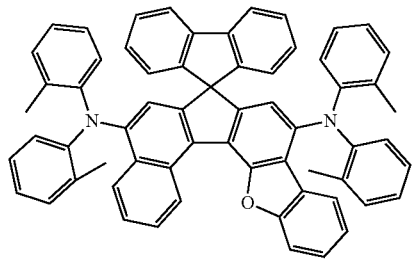
<Chemical Formula 59>
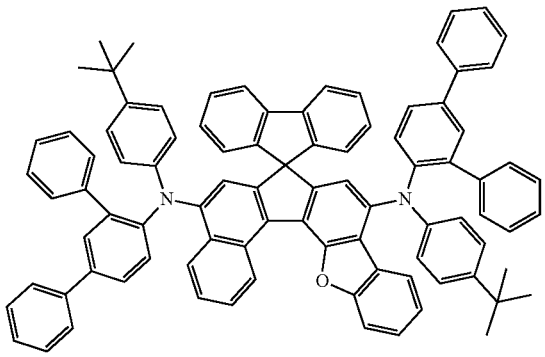
<Chemical Formula 60>
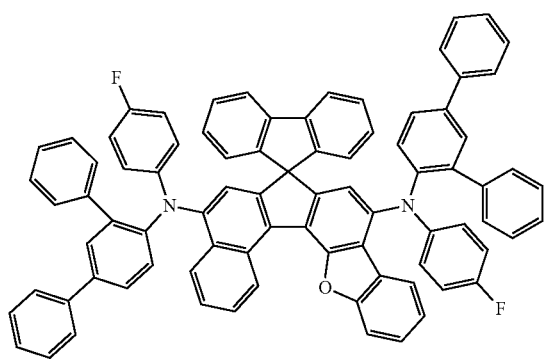
<Chemical Formula 61>
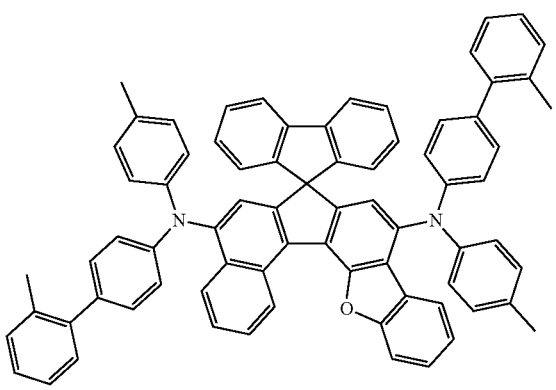
<Chemical Formula 62>
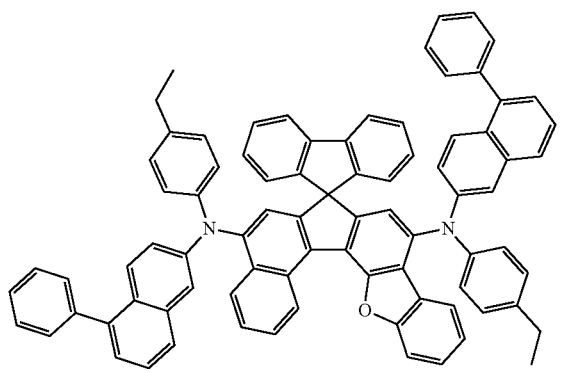
<Chemical Formula 63>
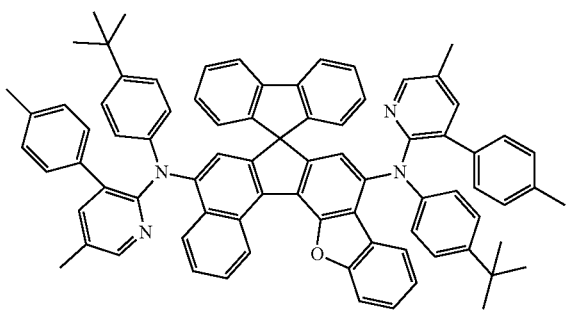
<Chemical Formula 64>
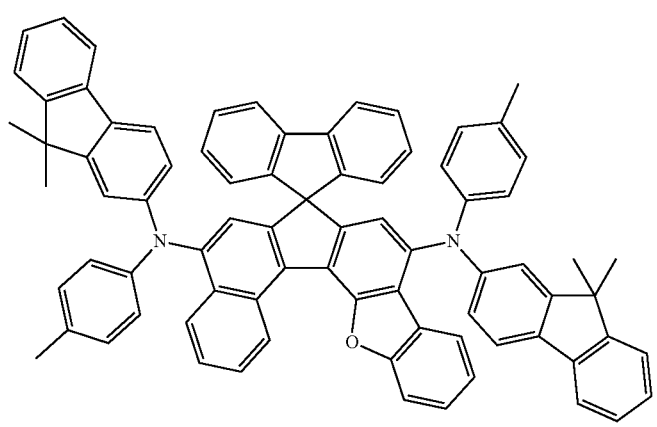

<Chemical Formula 65>
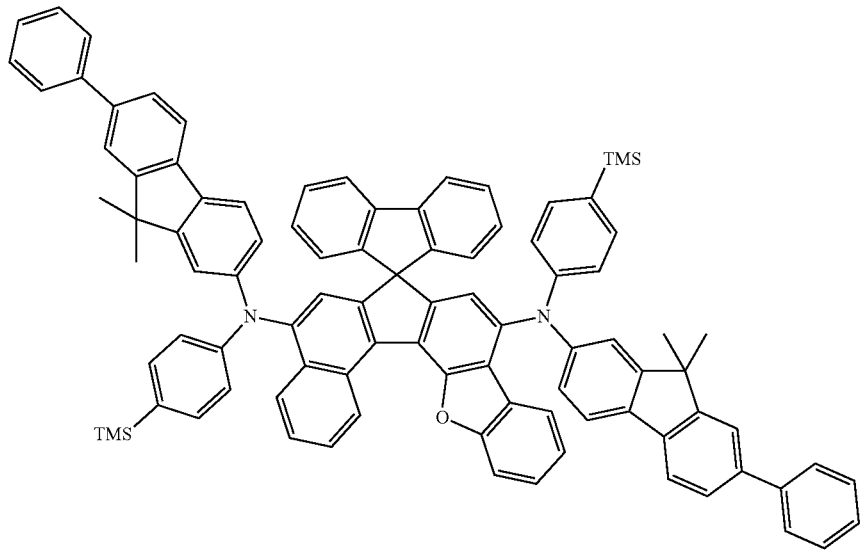
<Chemical Formula 66>
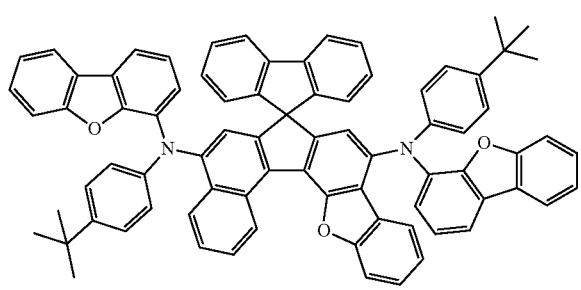
<Chemical Formula 67>
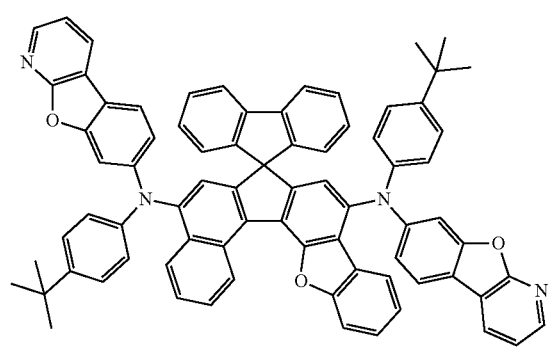
<Chemical Formula 68>
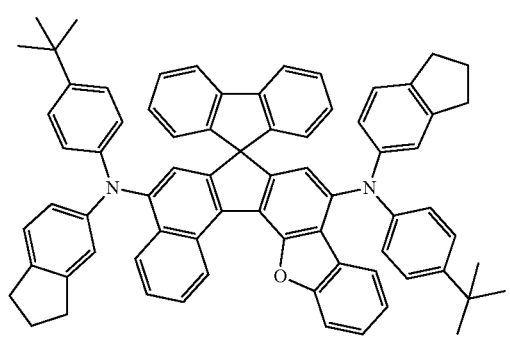
<Chemical Formula 69>
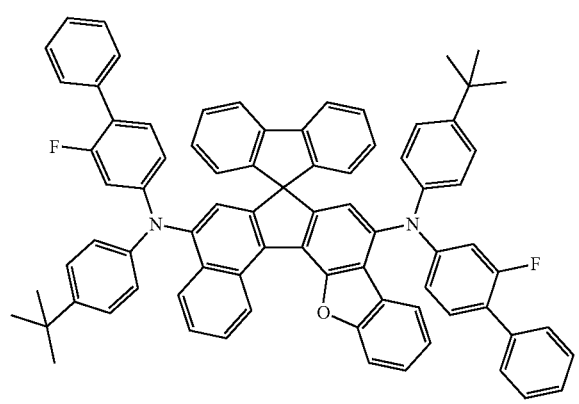
<Chemical Formula 70>
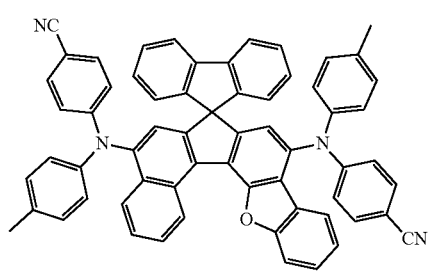
<Chemical Formula 71>
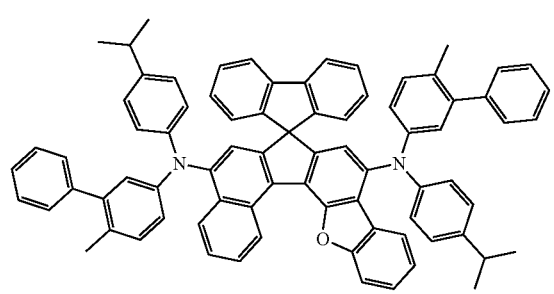

-continued
<Chemical Formula 72>
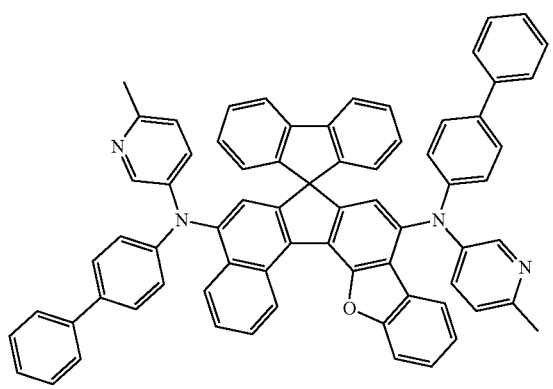
<Chemical Formula 73>
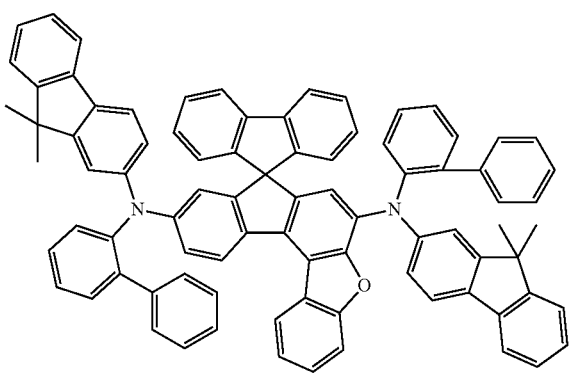
<Chemical Formula 74>
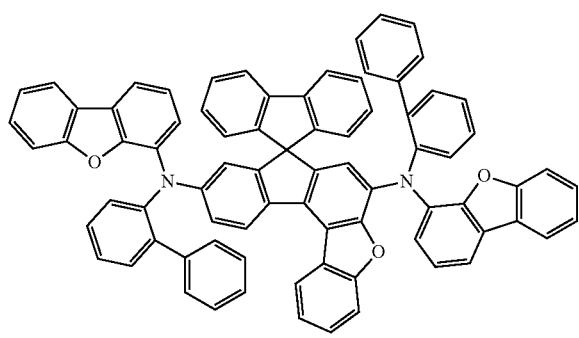
<Chemical Formula 75>
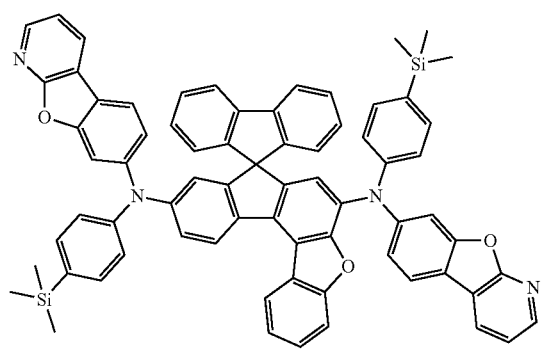
<Chemical Formula 76>
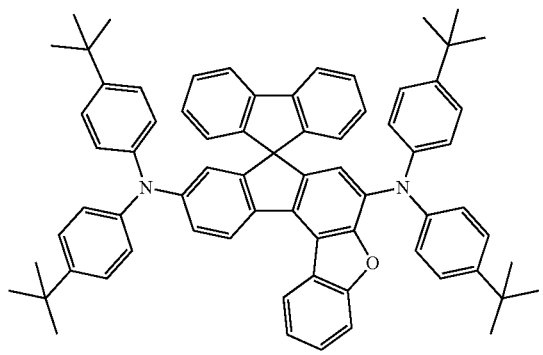
<Chemical Formula 77>
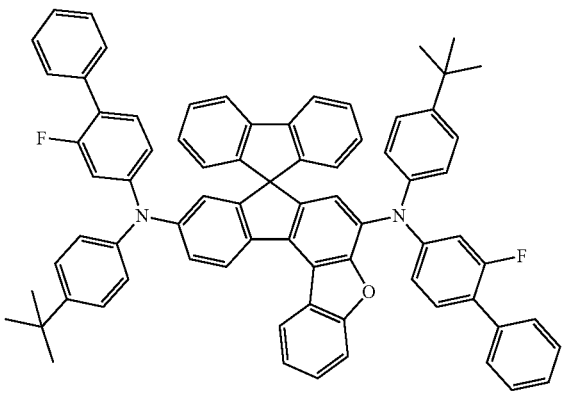
<Chemical Formula 78>
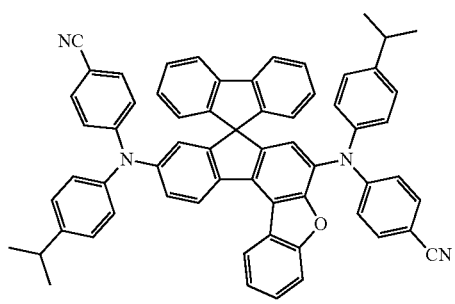
<Chemical Formula 79>
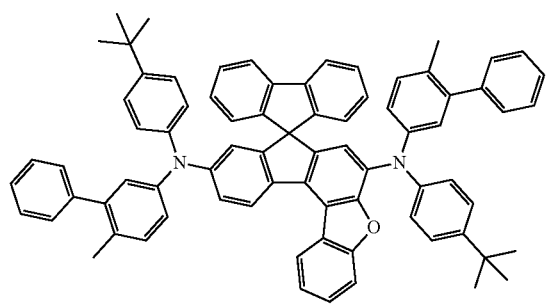

-continued
<Chemical Formula 80>
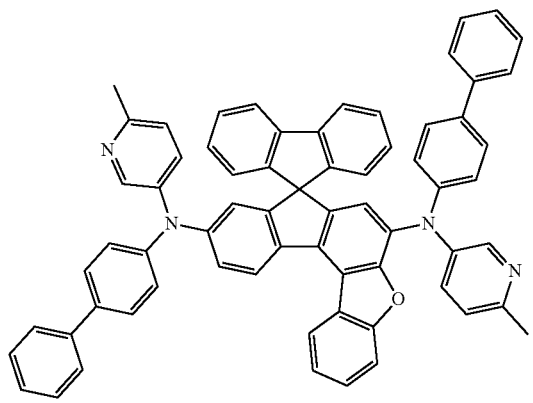
<Chemical Formula 81>
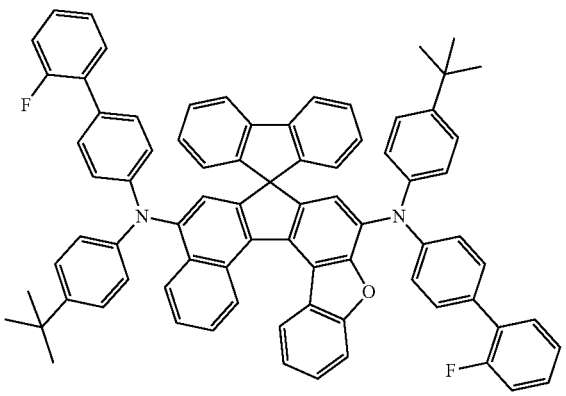
<Chemical Formula 82>
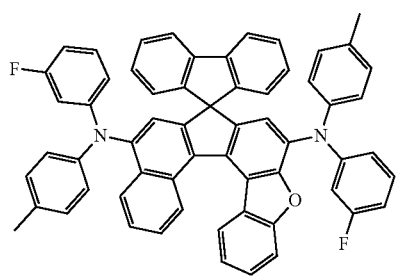
<Chemical Formula 83>
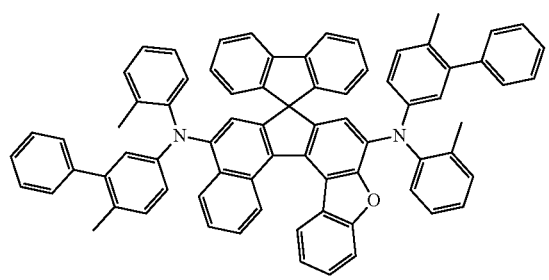
<Chemical Formula 84>
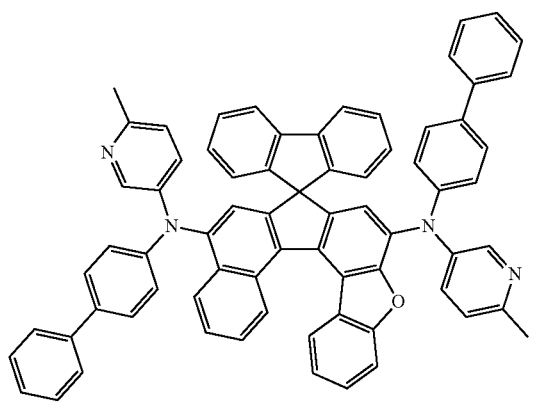
<Chemical Formula 85>
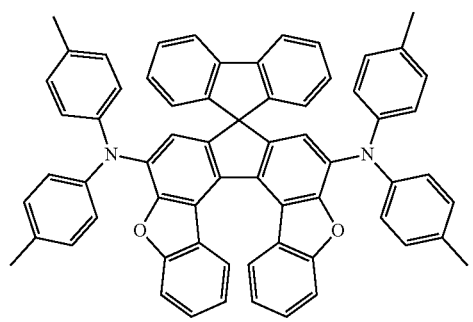
<Chemical Formula 86>
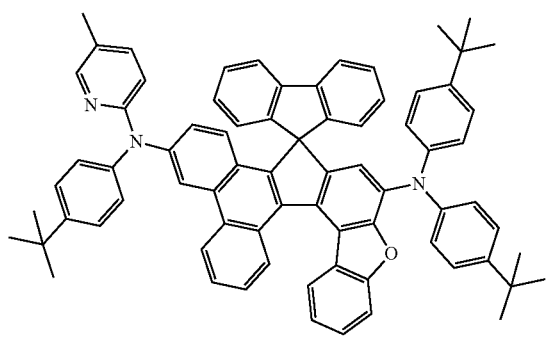
<Chemical Formula 87>
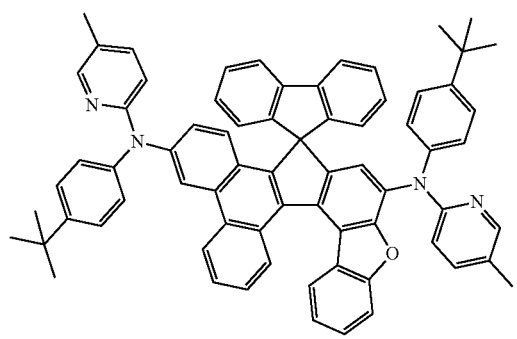

-continued
<Chemical Formula 88>
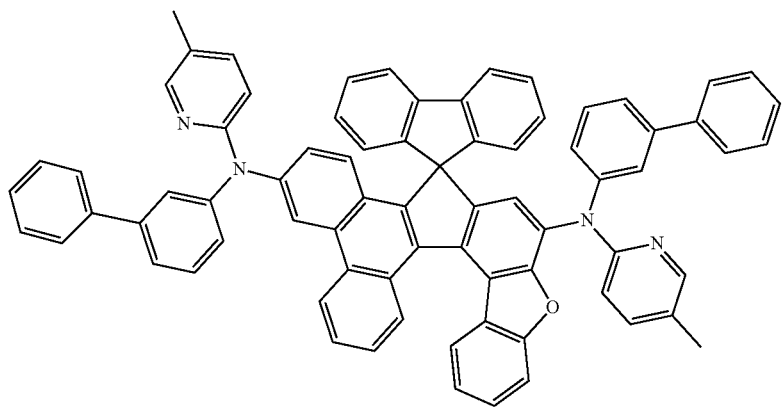
<Chemical Formula 89>
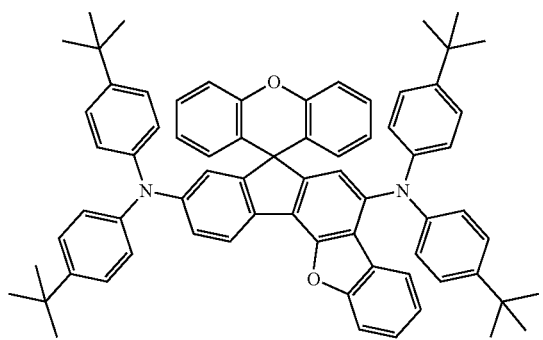
<Chemical Formula 90>
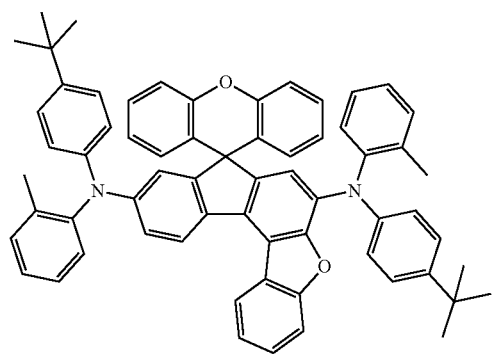
<Chemical Formula 91>
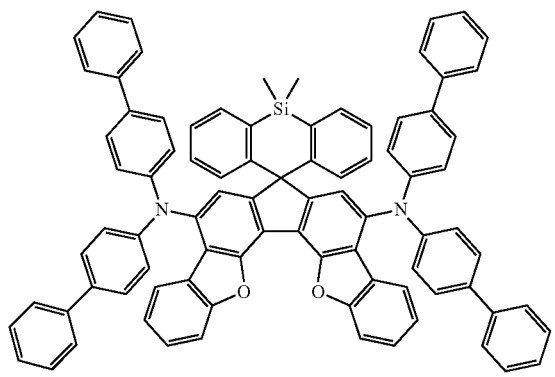
<Chemical Formula 92>
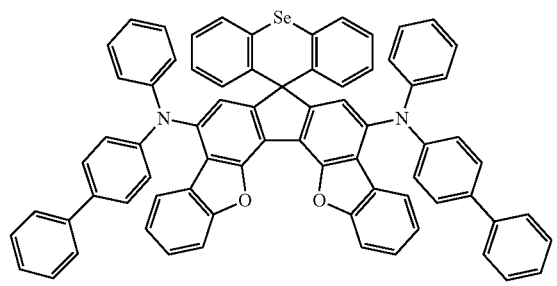
<Chemical Formula 93>
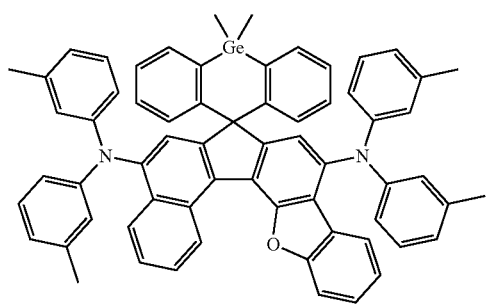
<Chemical Formula 94>
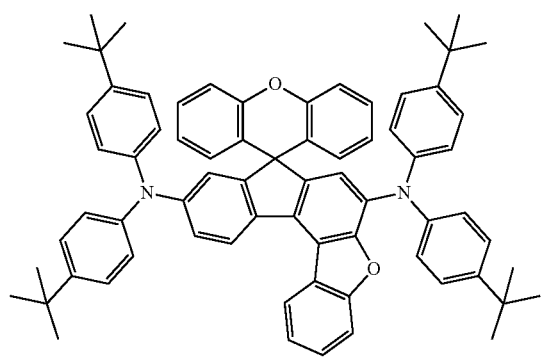

-continued
<Chemical Formula 95>
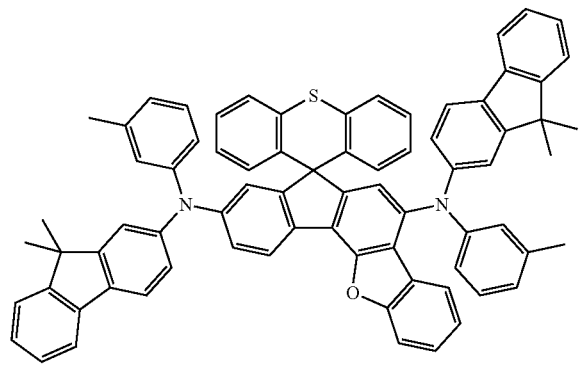
<Chemical Formula 96>
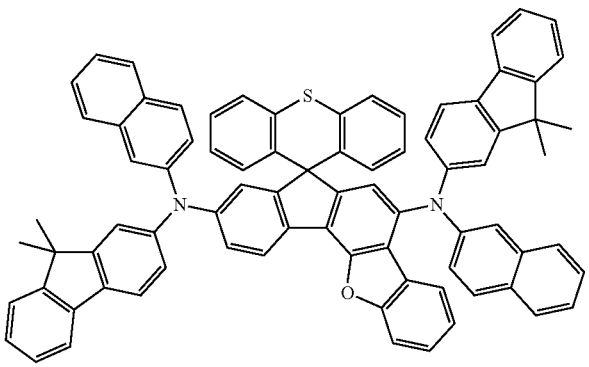
<Chemical Formula 97>
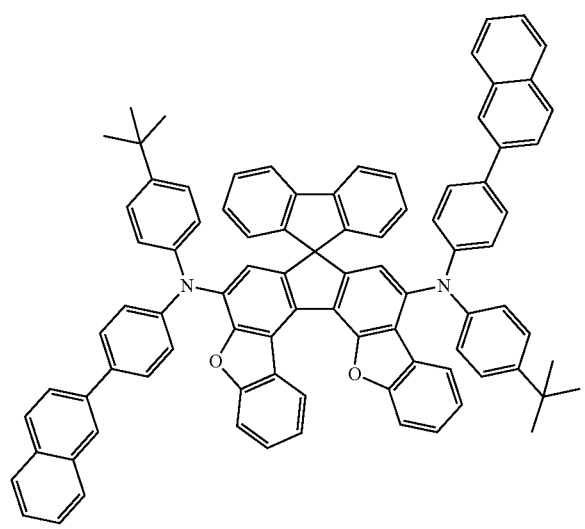
<Chemical Formula 98>
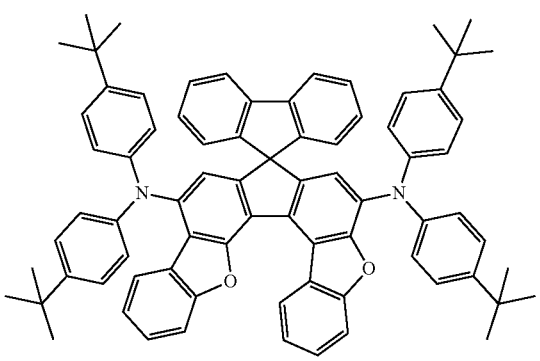
<Chemical Formula 99>
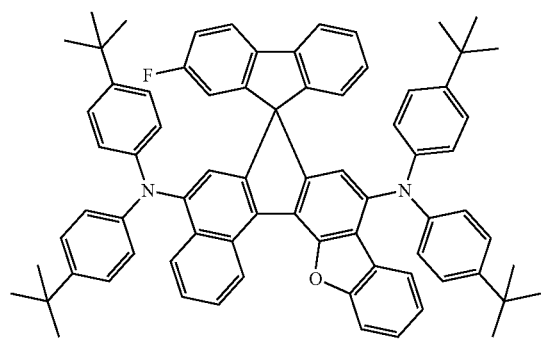
<Chemical Formula 100>
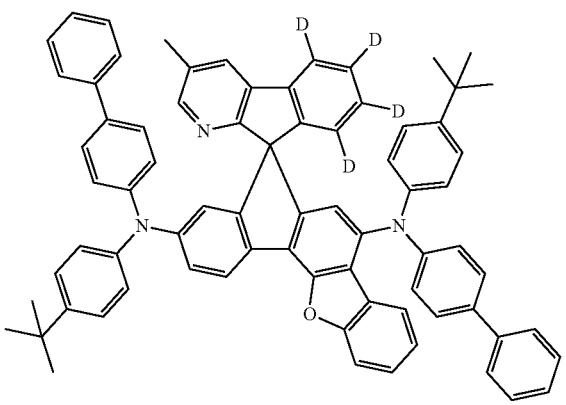

-continued
<Chemical Formula 101>
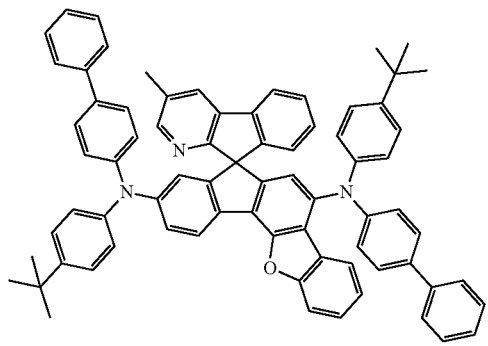
<Chemical Formula 102>
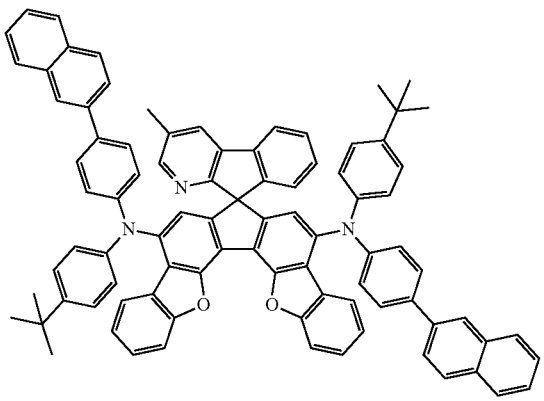
<Chemical Formula 103>
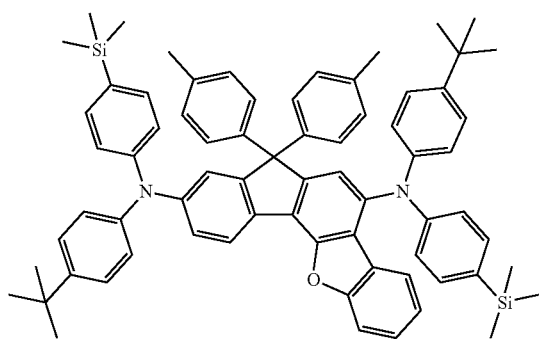
<Chemical Formula 104>
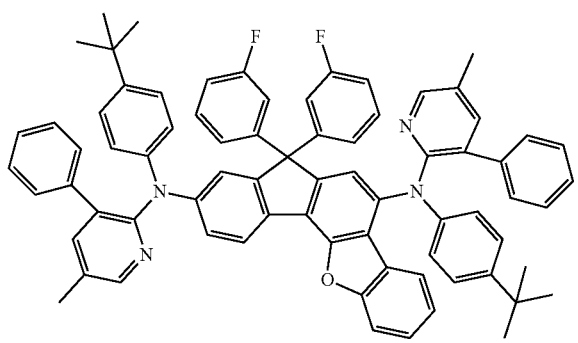
<Chemical Formula 105>
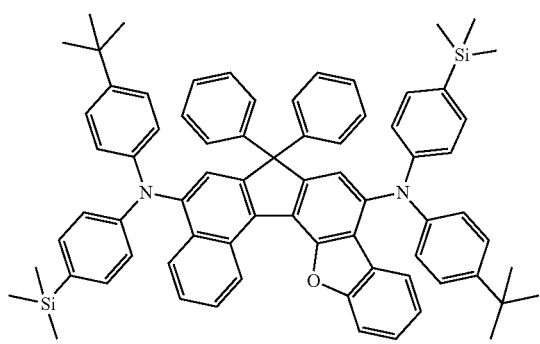
<Chemical Formula 106>
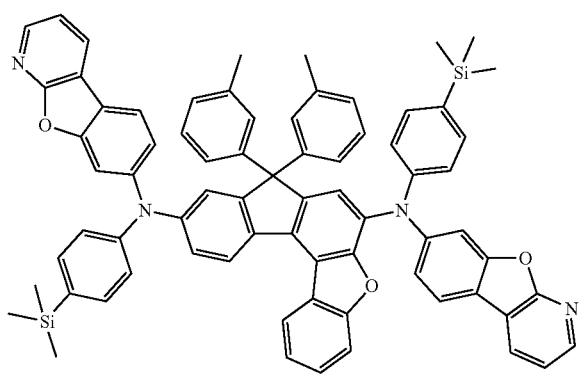
<Chemical Formula 107>
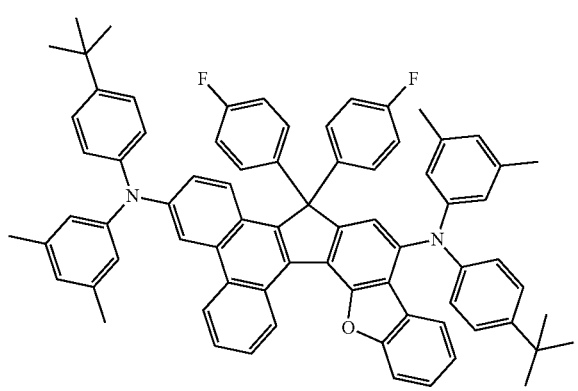
<Chemical Formula 108>
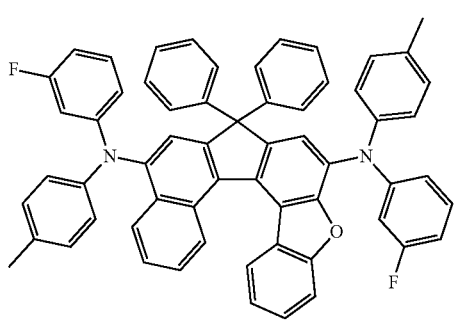

<Chemical Formula 109>
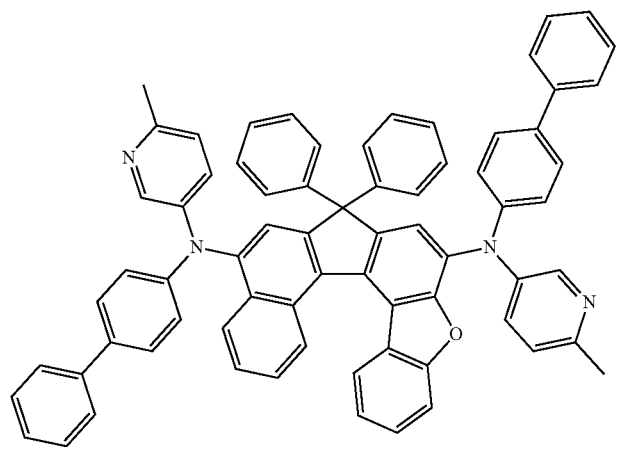
<Chemical Formula 110>
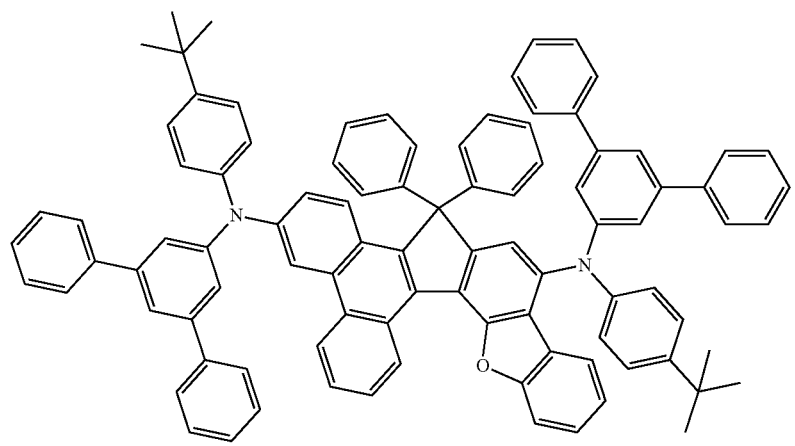
<Chemical Formula 111>
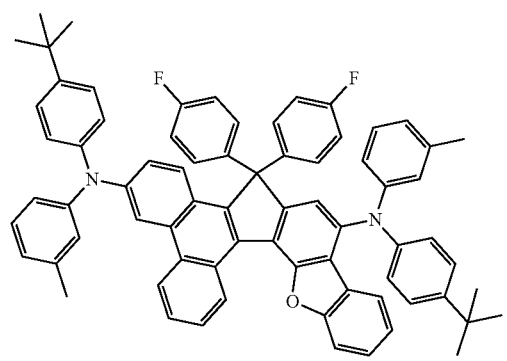
<Chemical Formula 112>
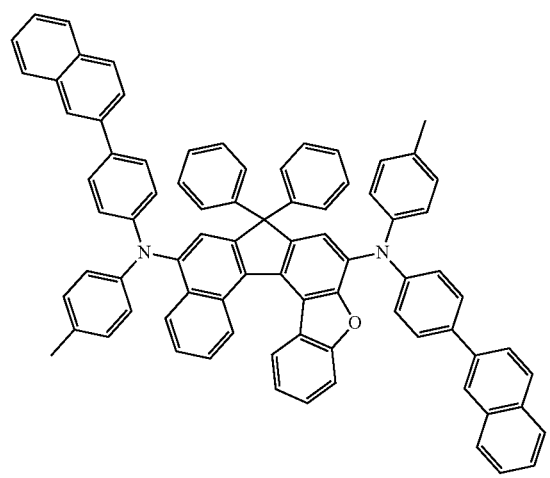

<Chemical Formula 113>
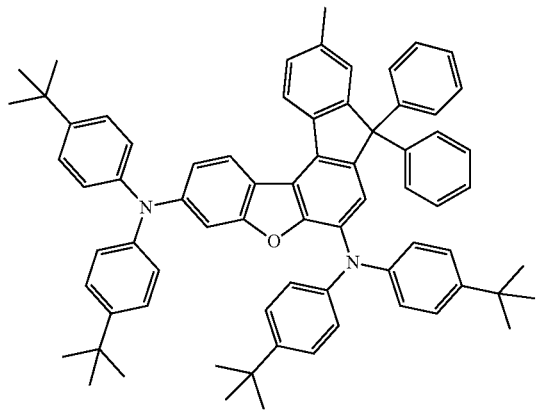
<Chemical Formula 114>
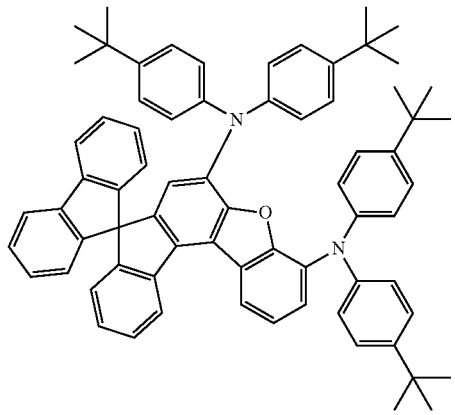
<Chemical Formula 115>
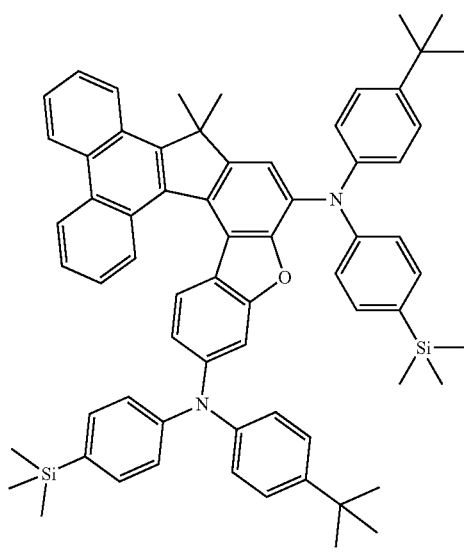
<Chemical Formula 116>
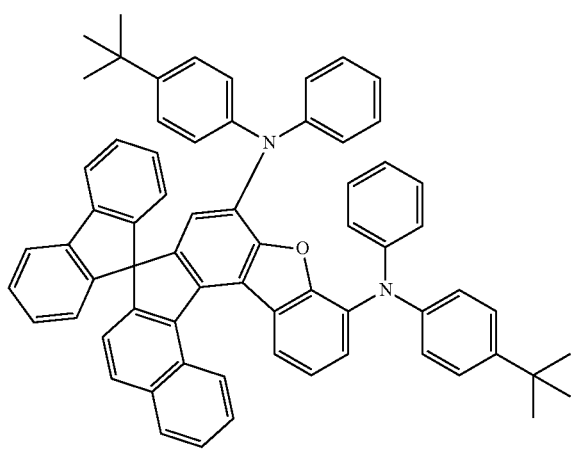
<Chemical Formula 117>
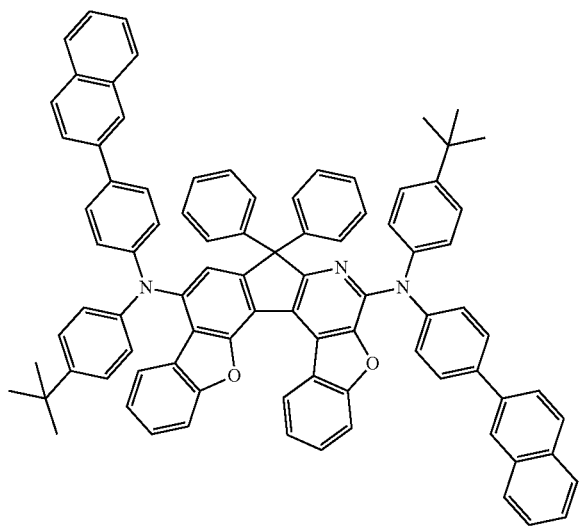
<Chemical Formula 118>
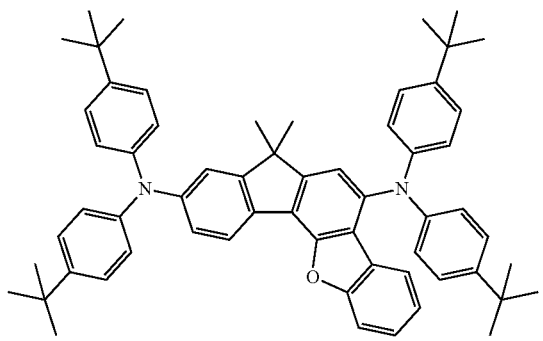

<Chemical Formula 119>
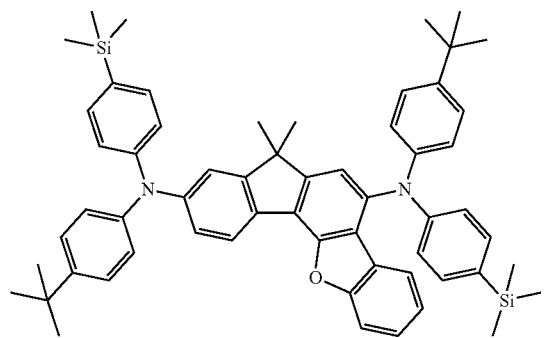
<Chemical Formula 120>
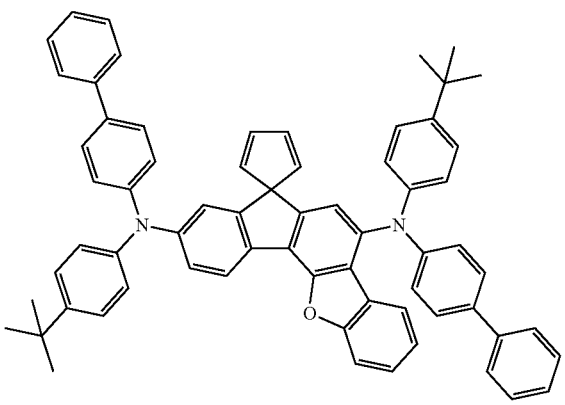
<Chemical Formula 121>
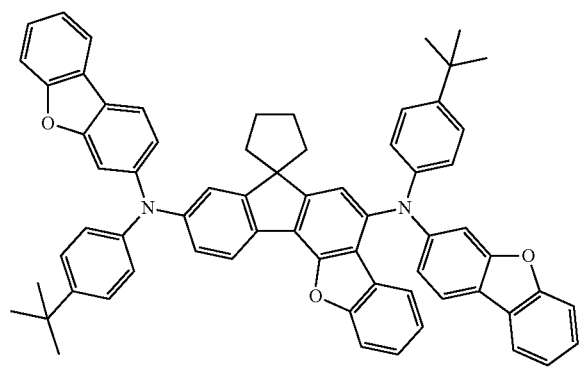
<Chemical Formula 122>
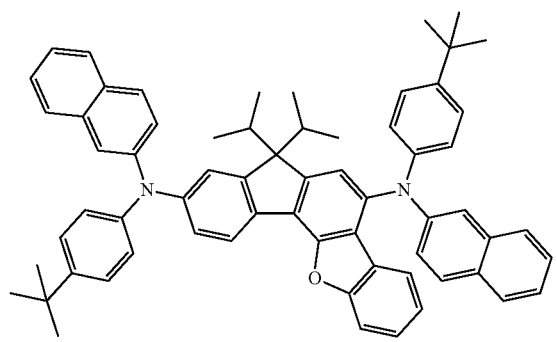
<Chemical Formula 123>
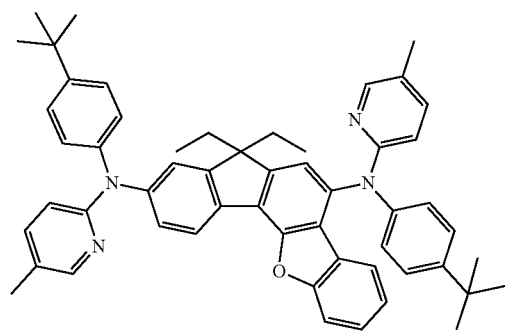
<Chemical Formula 124>
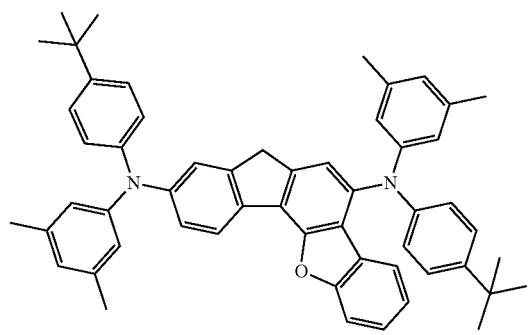
<Chemical Formula 125>
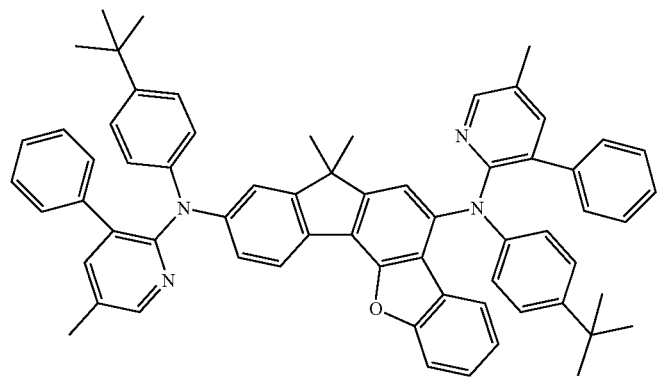

<Chemical Formula 126>
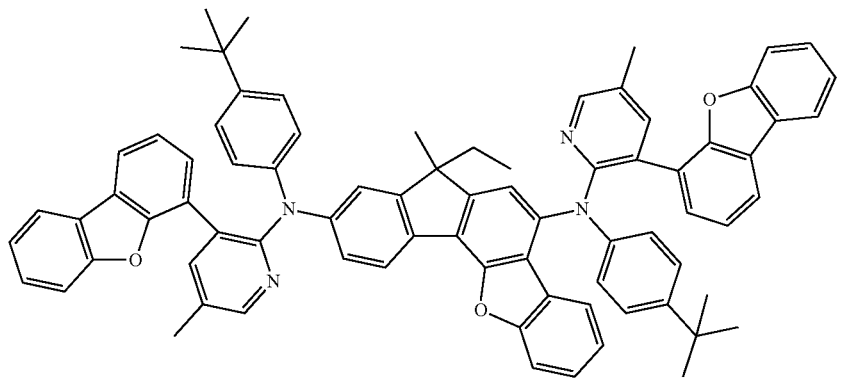
<Chemical Formula 127>
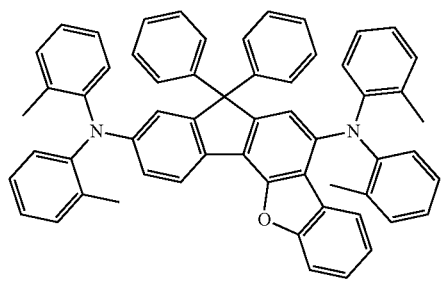
<Chemical Formula 128>
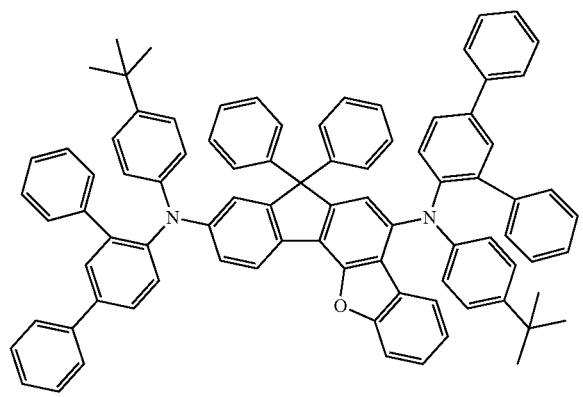
<Chemical Formula 129>
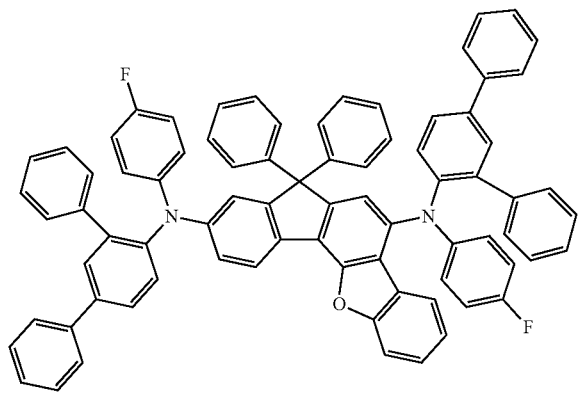
<Chemical Formula 130>
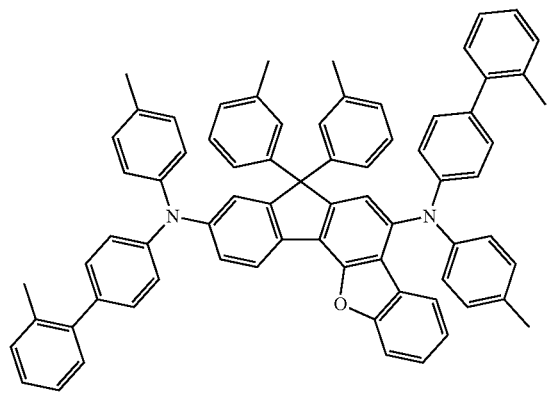

-continued
<Chemical Formula 131>
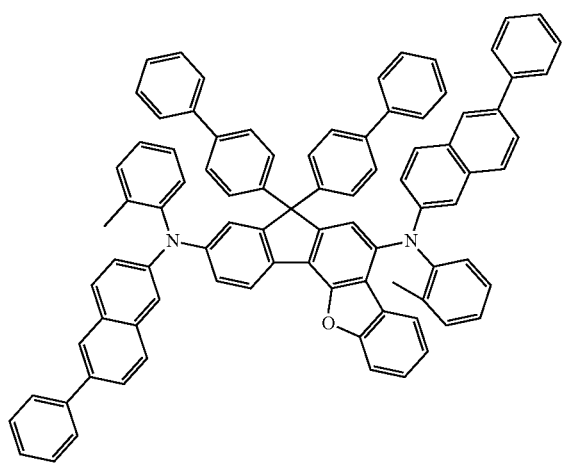
<Chemical Formula 132>
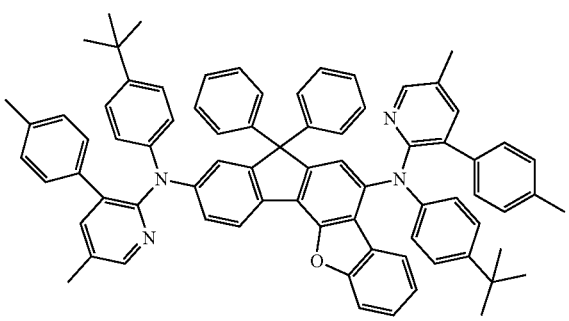
<Chemical Formula 133>
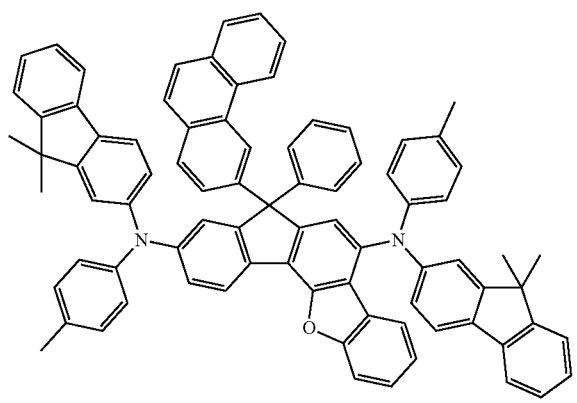
<Chemical Formula 134>
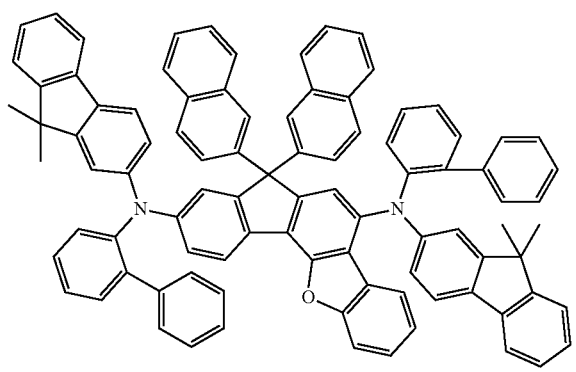
<Chemical Formula 135>
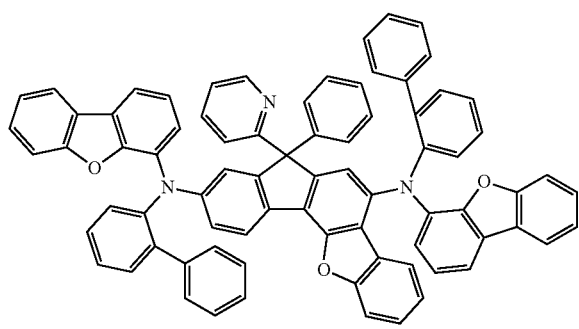
<Chemical Formula 136>
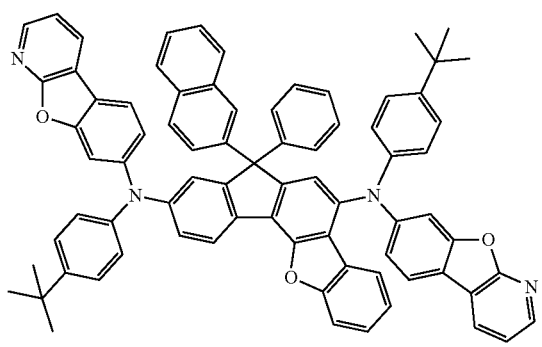

<Chemical Formula 137>
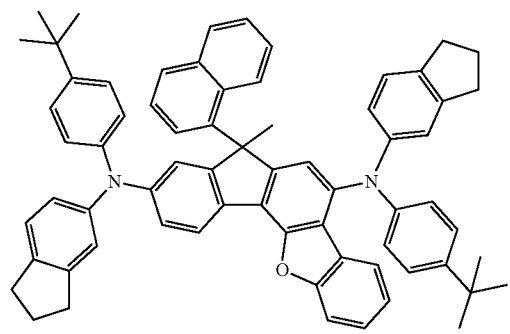
<Chemical Formula 138>
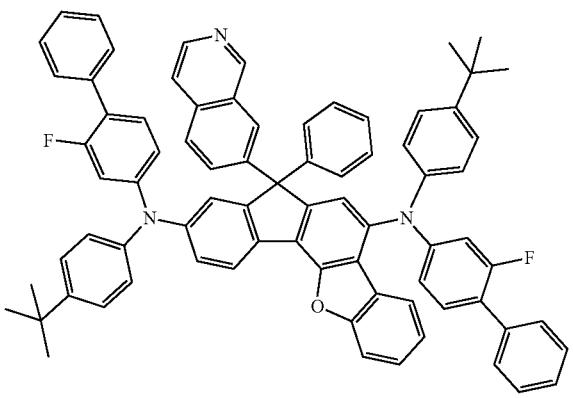
<Chemical Formula 139>
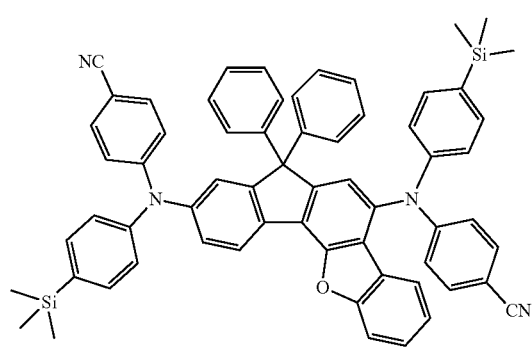
<Chemical Formula 140>
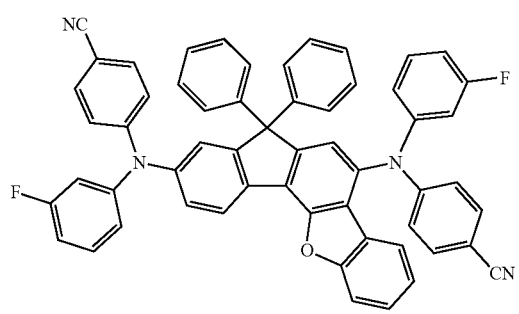
<Chemical Formula 141>
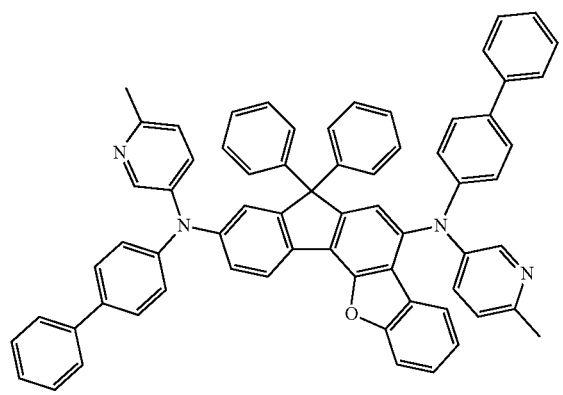
<Chemical Formula 142>
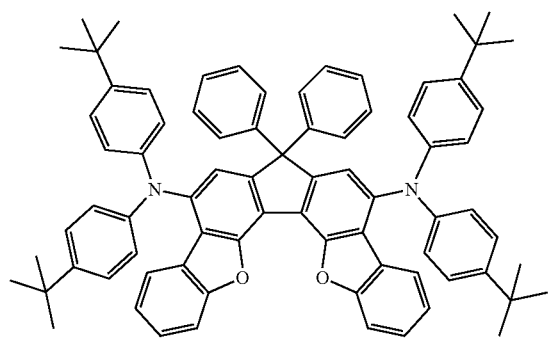
<Chemical Formula 143>
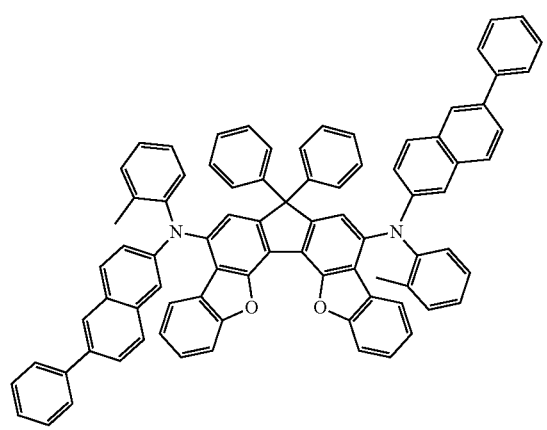
<Chemical Formula 144>
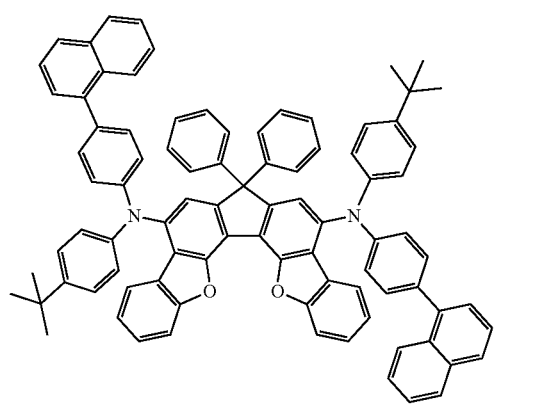

<Chemical Formula 145>
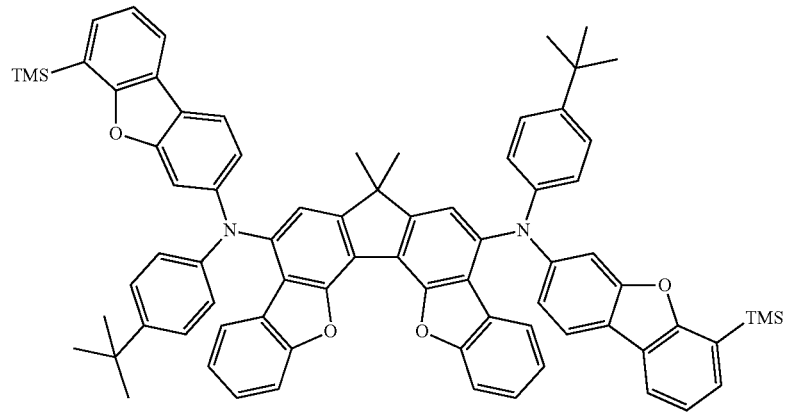
<Chemical Formula 146>
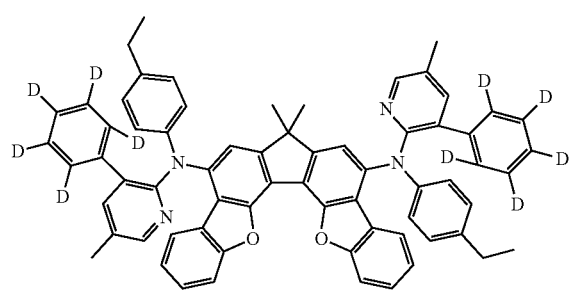
<Chemical Formula 147>
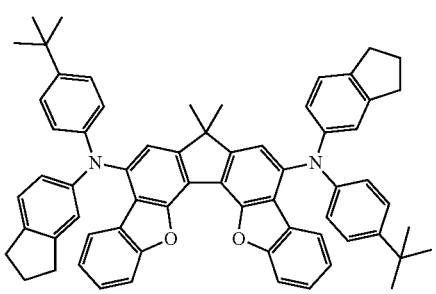
<Chemical Formula 148>
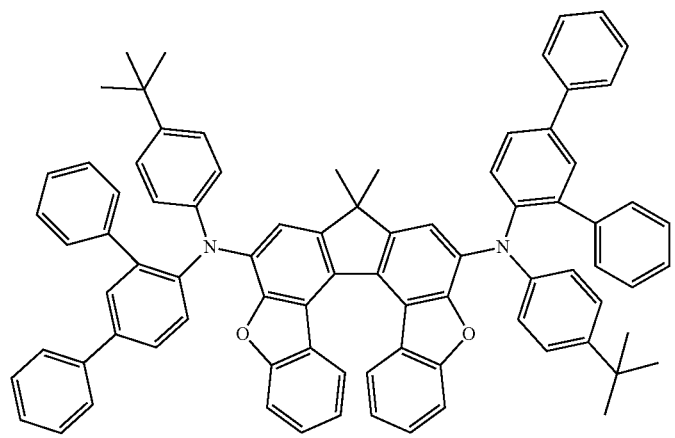
<Chemical Formula 149>
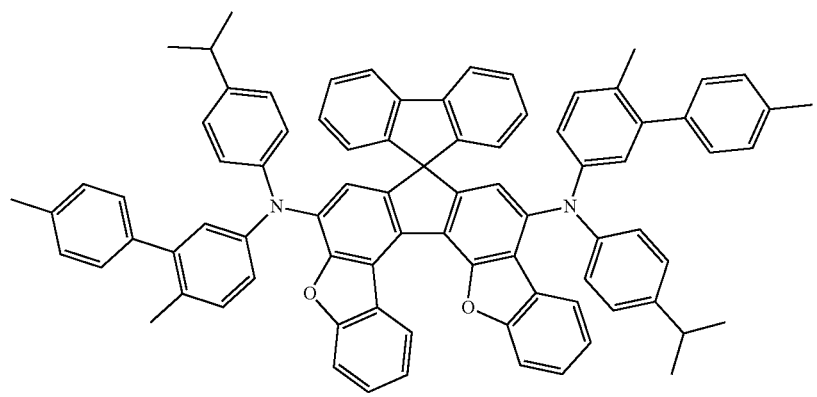

-continued
<Chemical Formula 150>
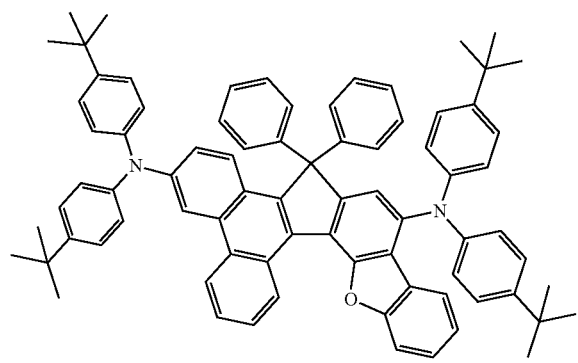
<Chemical Formula 151>
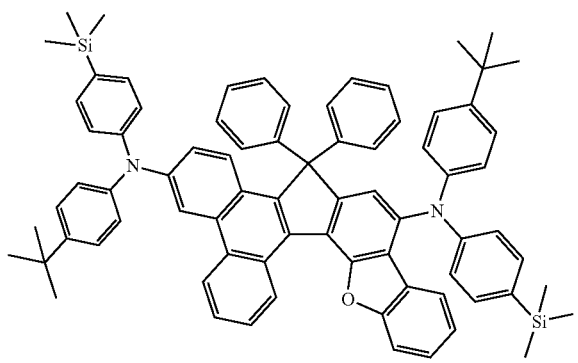
<Chemical Formula 152>
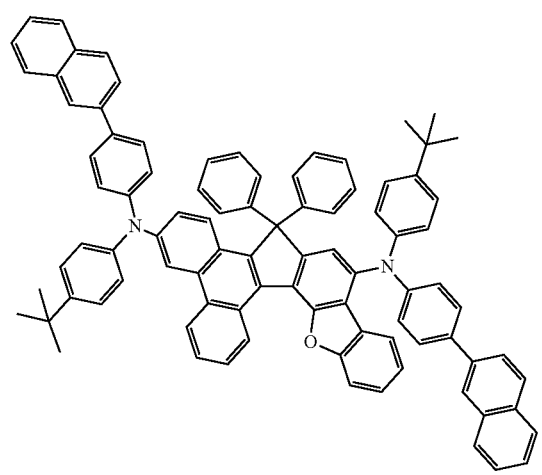
<Chemical Formula 153>
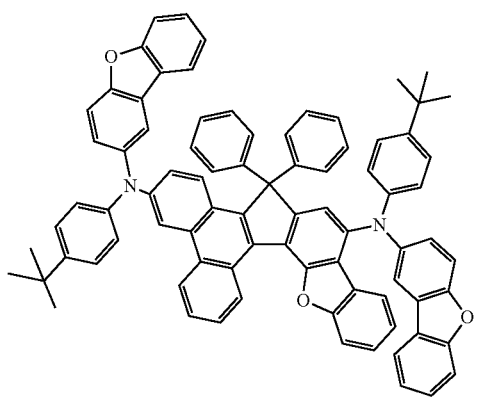
<Chemical Formula 154>
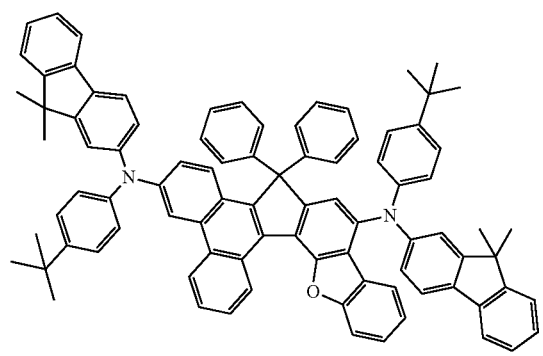
<Chemical Formula 155>
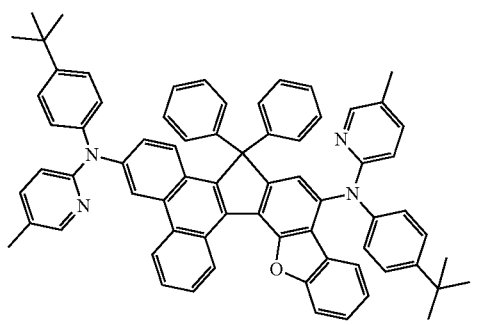
<Chemical Formula 156>
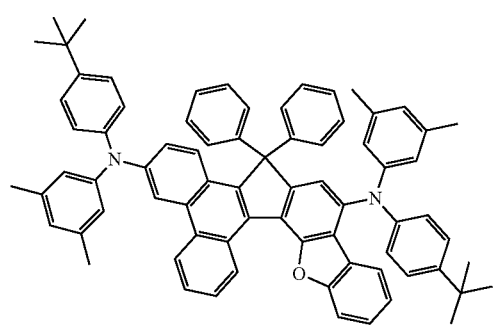
<Chemical Formula 157>
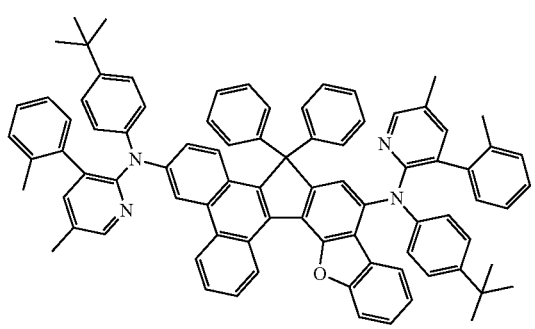

<Chemical Formula 158>
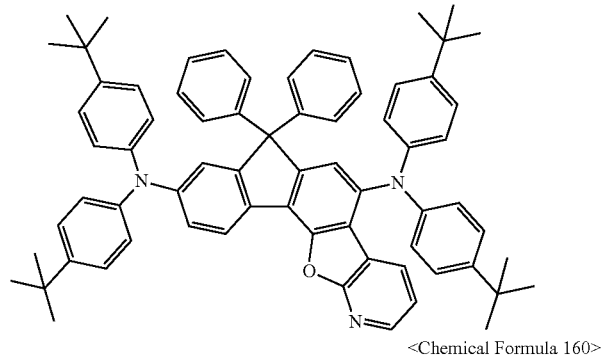
<Chemical Formula 159>
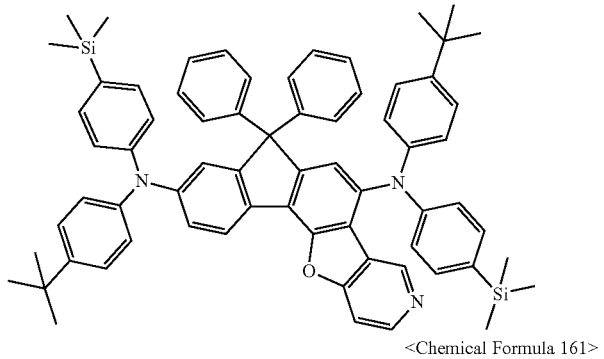
<Chemical Formula 160>
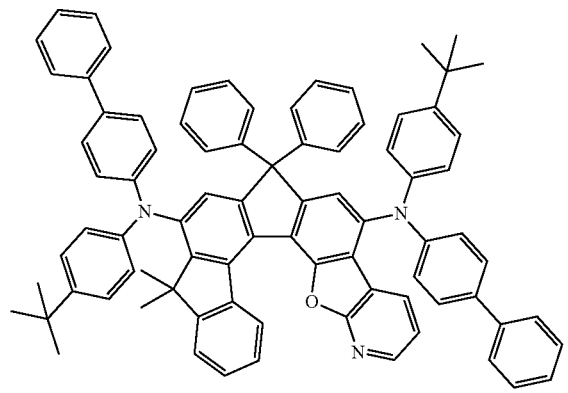
<Chemical Formula 161>
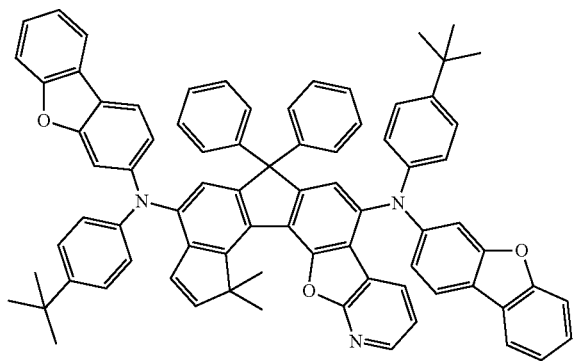
<Chemical Formula 162>
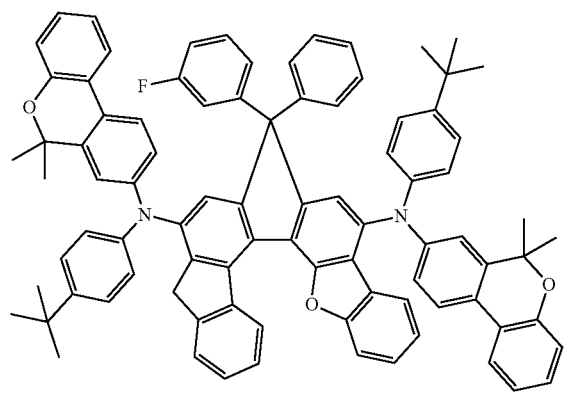
<Chemical Formula 163>
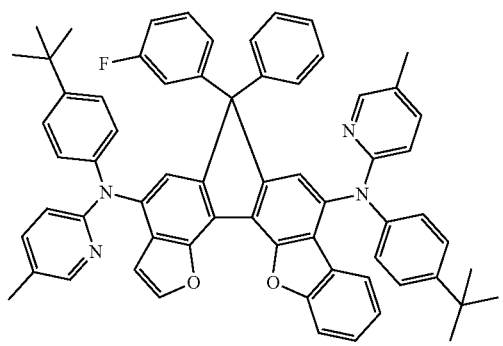
<Chemical Formula 164>
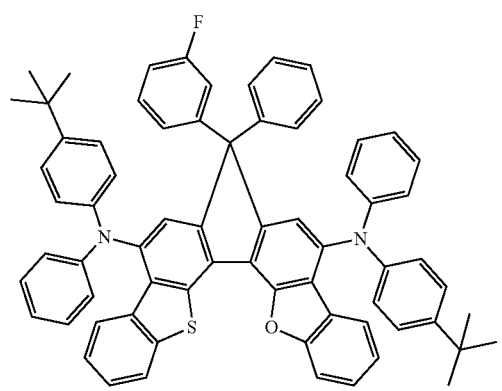
<Chemical Formula 165>
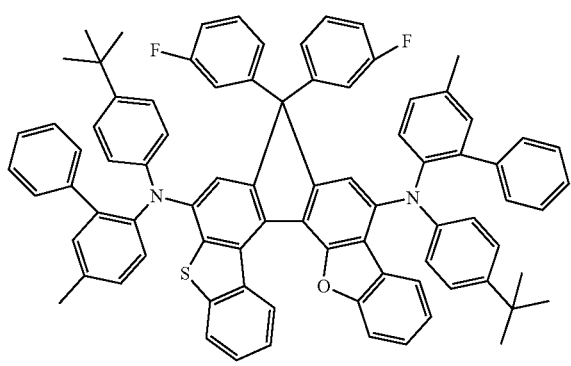

-continued
<Chemical Formula 166>
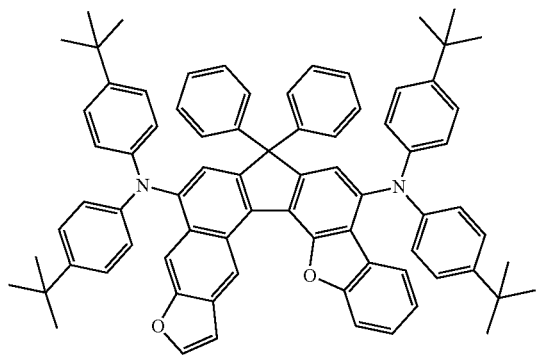
<Chemical Formula 167>
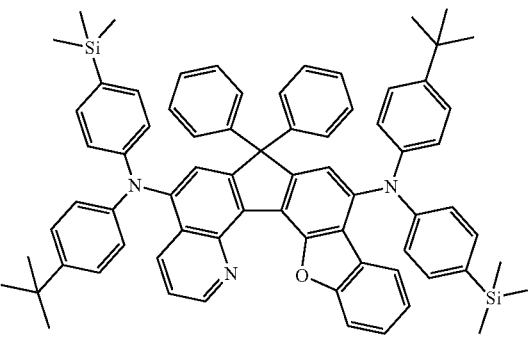
<Chemical Formula 168>
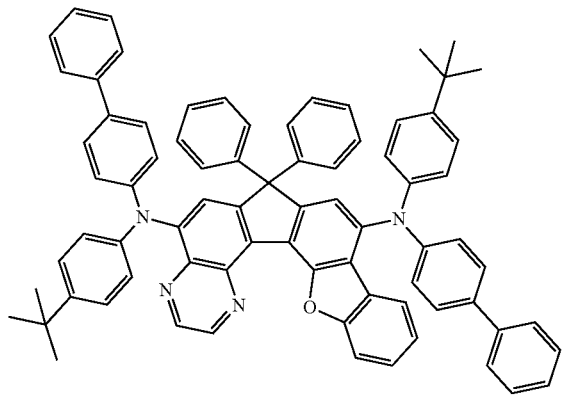
<Chemical Formula 169>
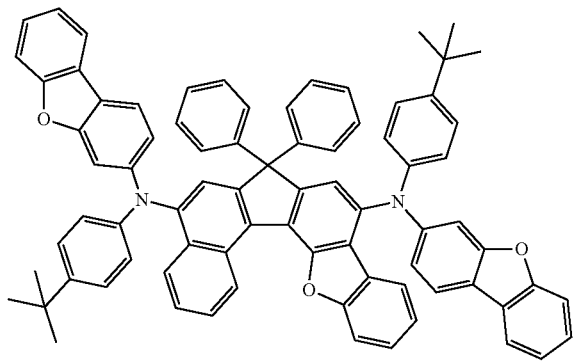
<Chemical Formula 170>
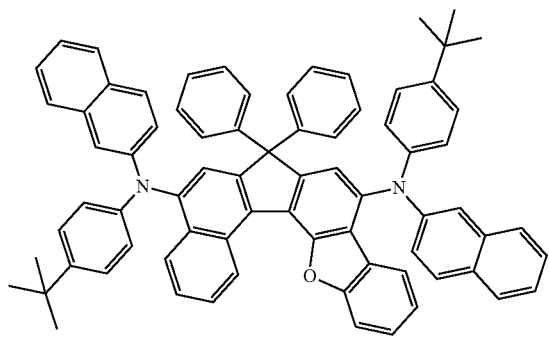
<Chemical Formula 171>
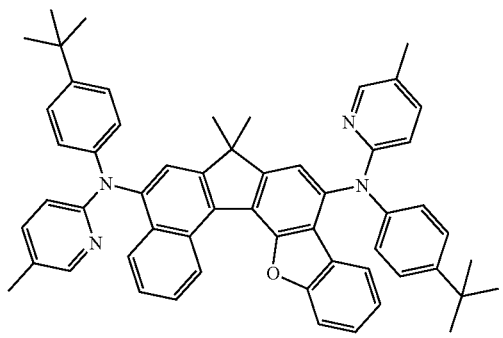
<Chemical Formula 172>
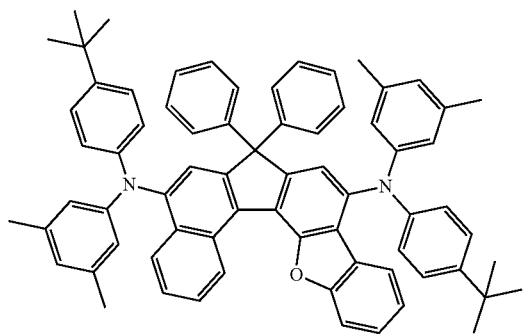
<Chemical Formula 173>
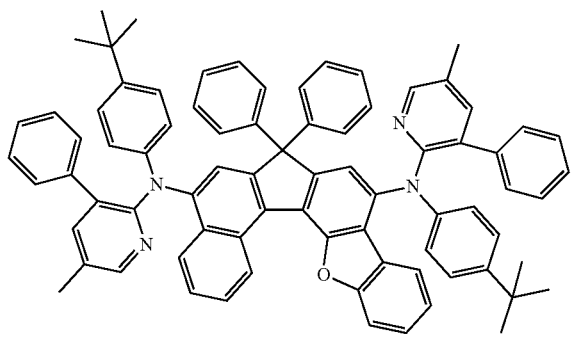

<Chemical Formula 174>
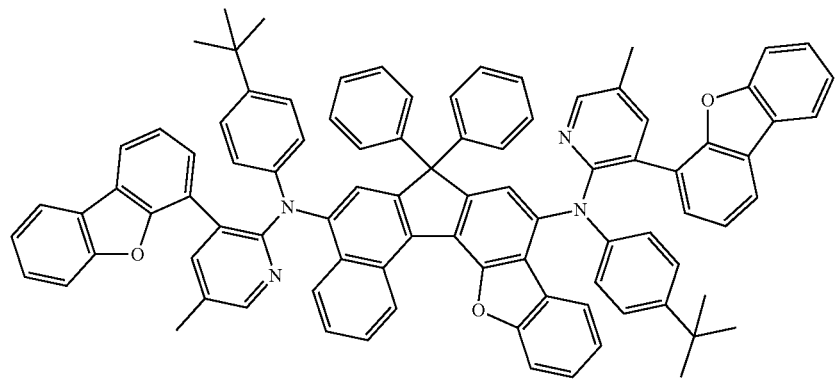
<Chemical Formula 175>
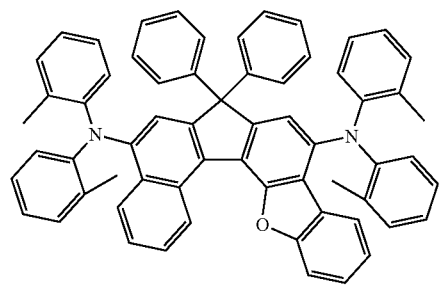
<Chemical Formula 176>
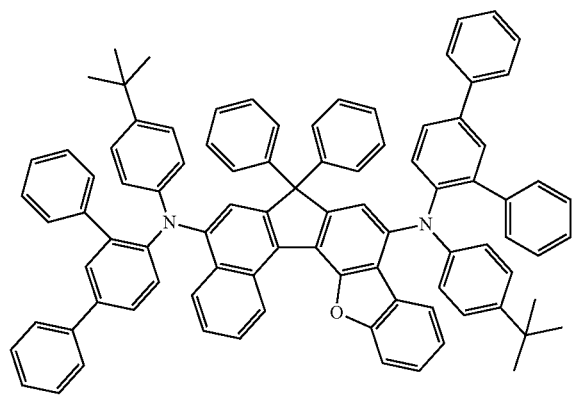
<Chemical Formula 177>
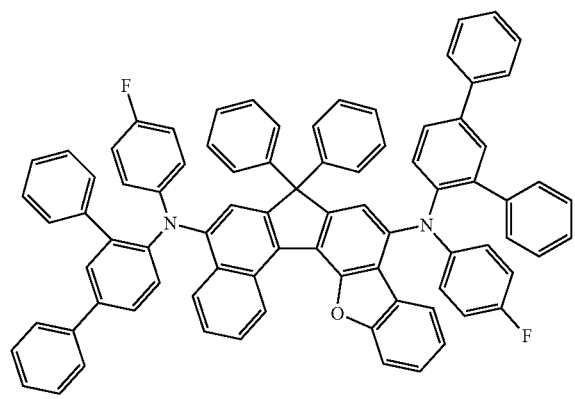
<Chemical Formula 178>
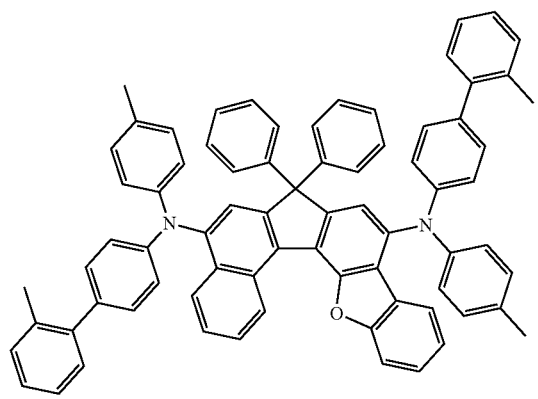
<Chemical Formula 179>
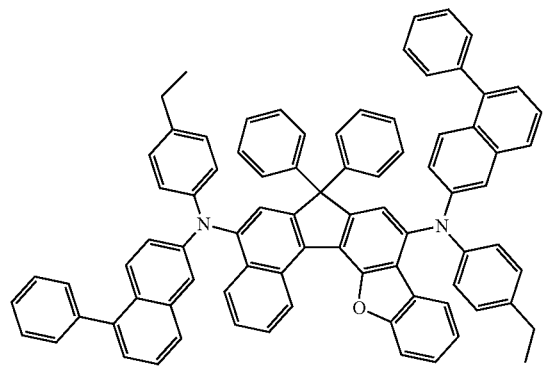
<Chemical Formula 180>
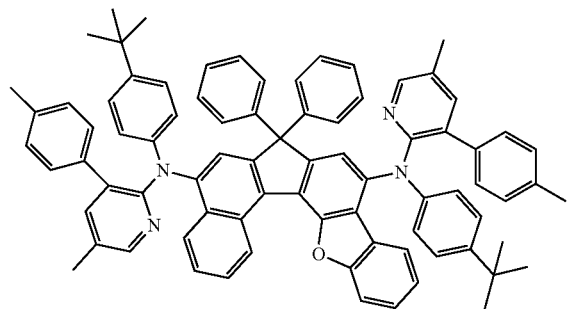

<Chemical Formula 181>
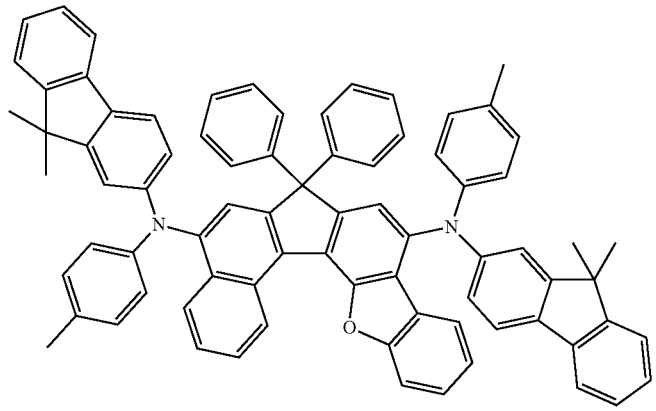
<Chemical Formula 182>
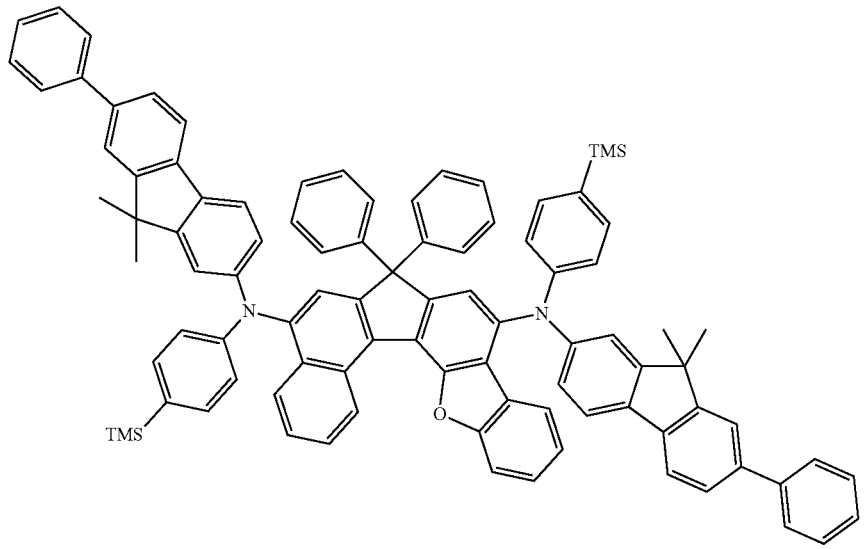
<Chemical Formula 183>
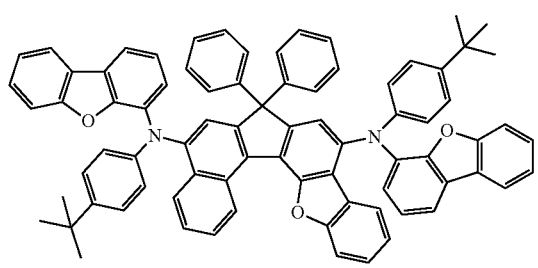
<Chemical Formula 184>
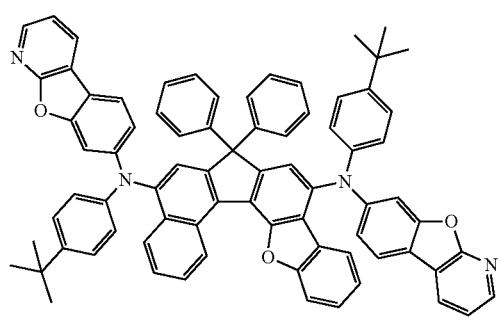
<Chemical Formula 185>
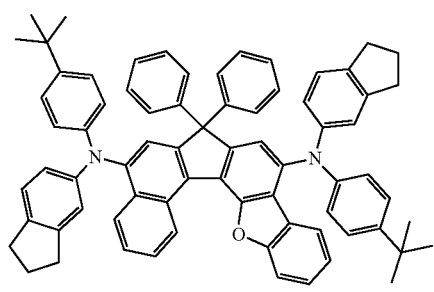
<Chemical Formula 186>
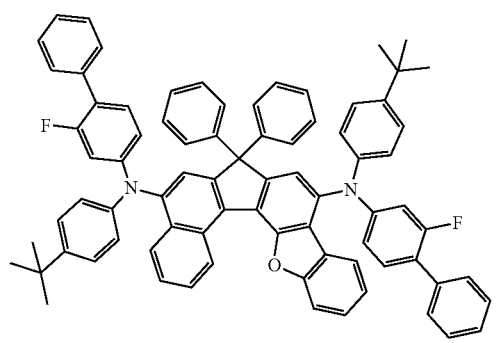

-continued
<Chemical Formula 187>
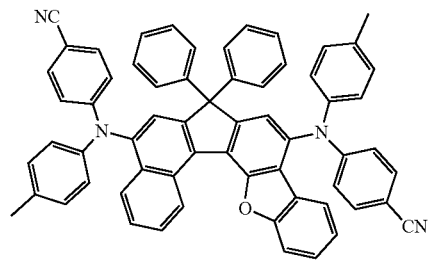
<Chemical Formula 188>
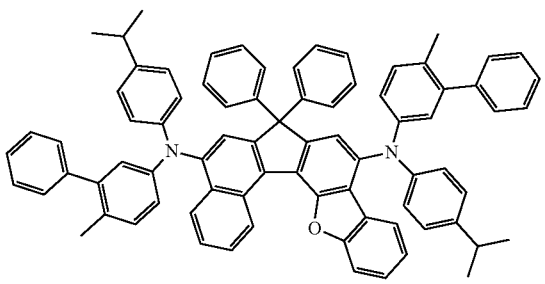
<Chemical Formula 189>
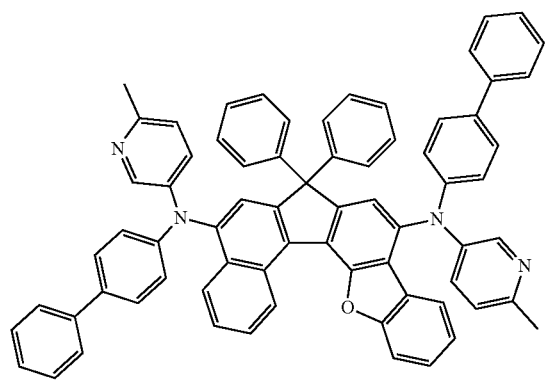
<Chemical Formula 190>
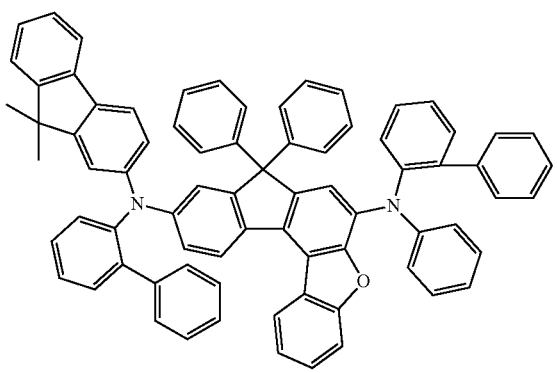
<Chemical Formula 191>
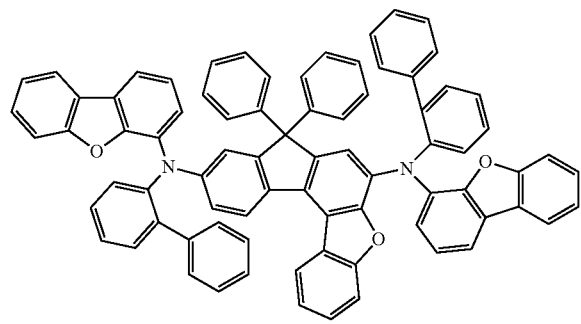
<Chemical Formula 192>
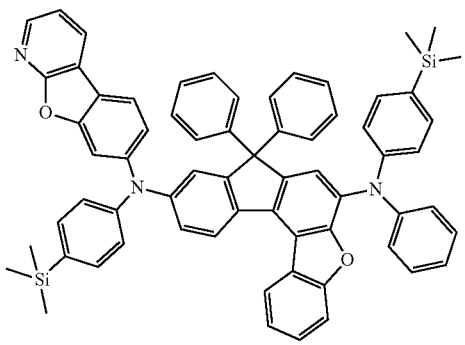
<Chemical Formula 193>
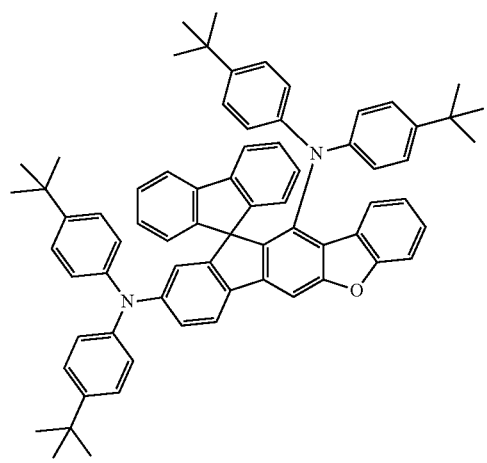
<Chemical Formula 194>
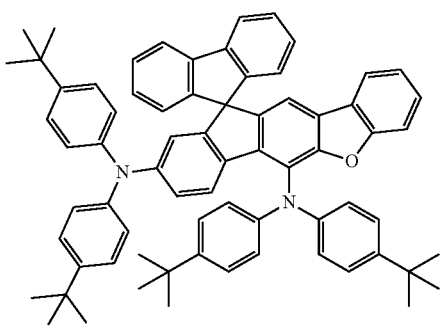

-continued
<Chemical Formula 195>
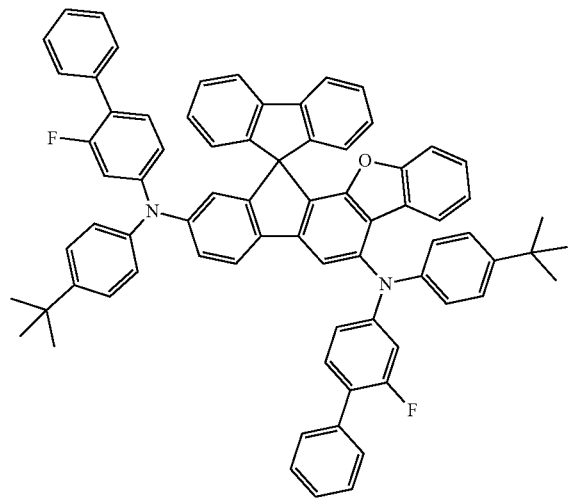
<Chemical Formula 196>
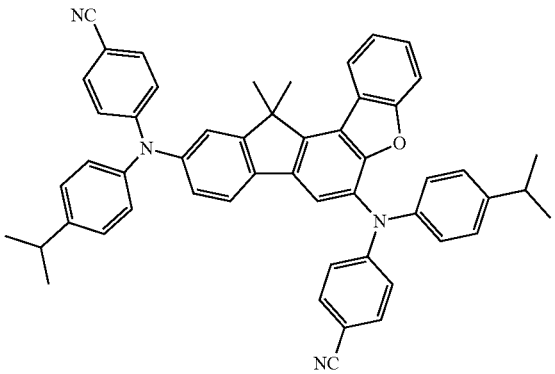
<Chemical Formula 197>
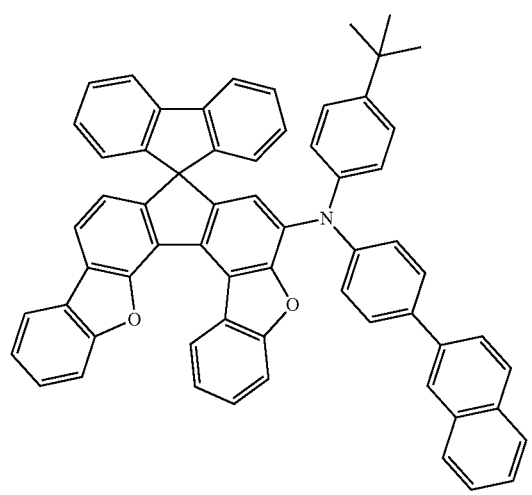
<Chemical Formula 198>
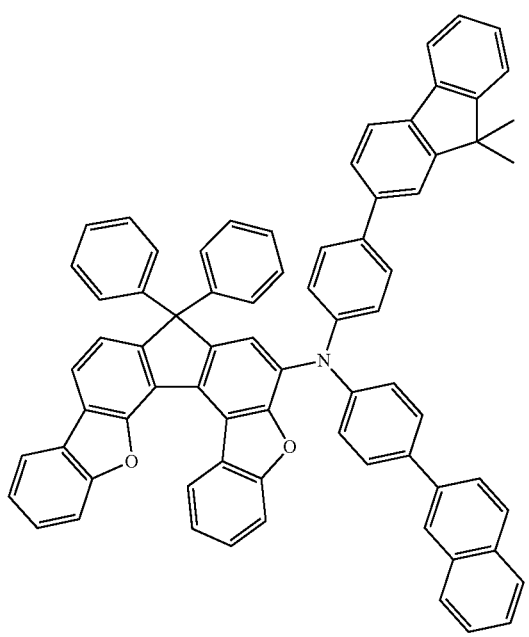

<Chemical Formula 199>
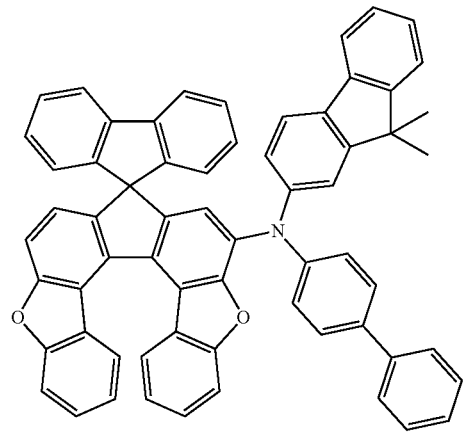
<Chemical Formula 200>
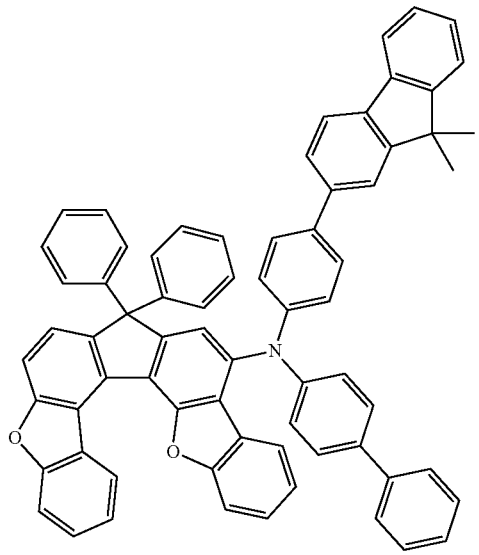
<Chemical Formula 201>
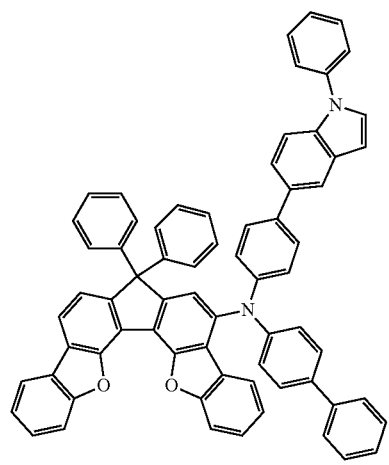
<Chemical Formula 202>
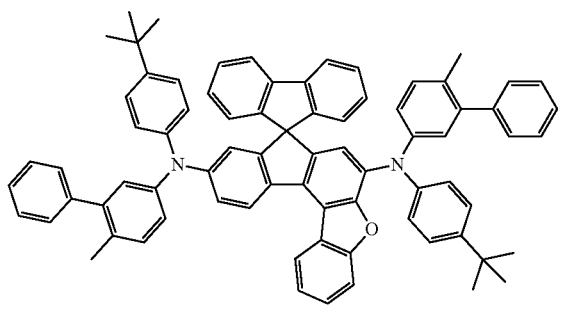
<Chemical Formula 203>
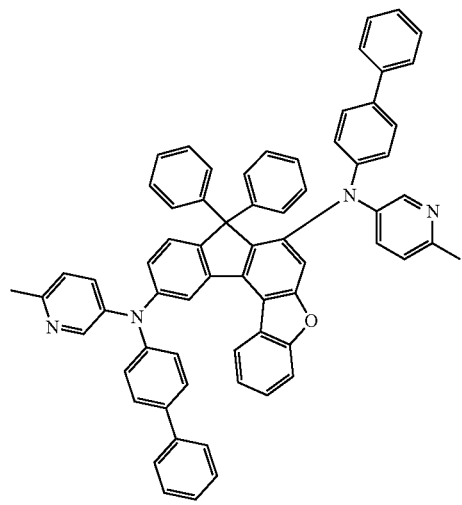
<Chemical Formula 204>
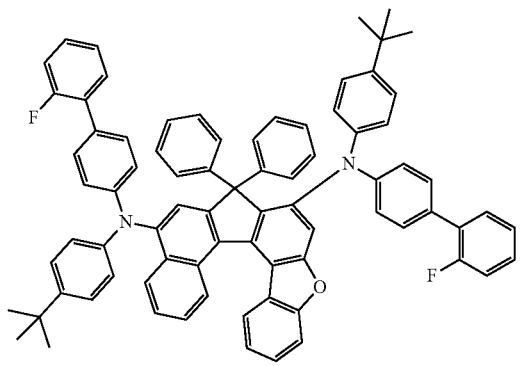

<Chemical Formula 205>
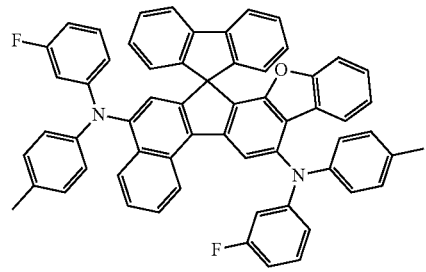
<Chemical Formula 206>
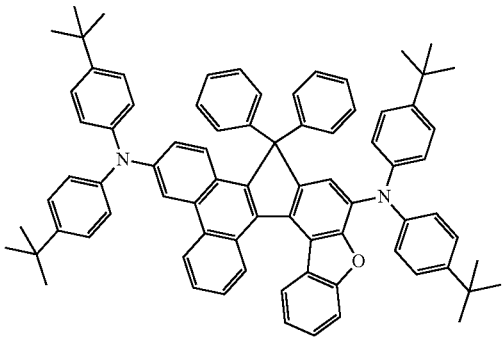
<Chemical Formula 207>
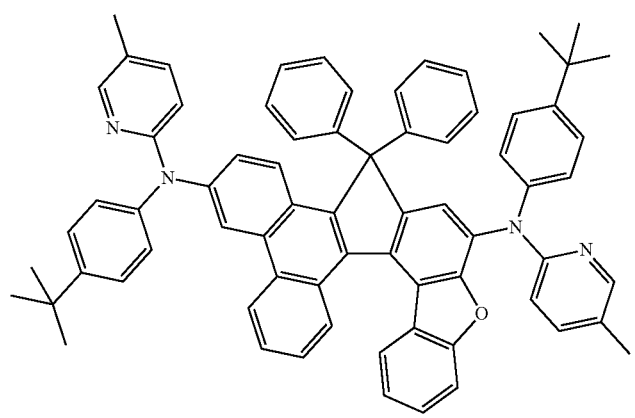
<Chemical Formula 208>
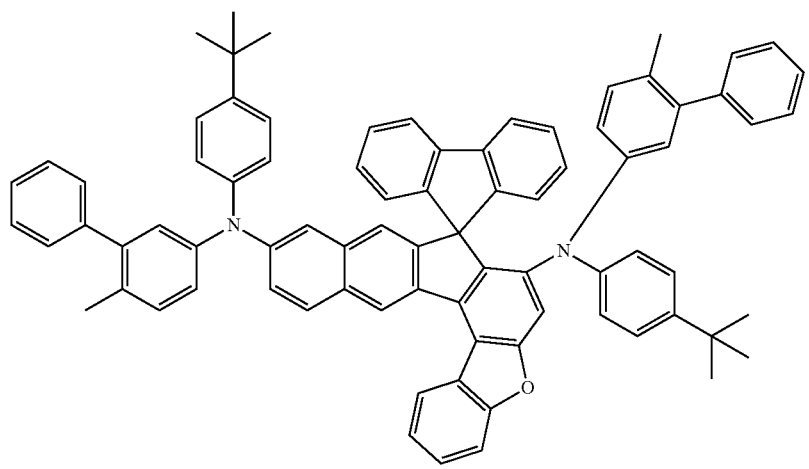
<Chemical Formula 209>
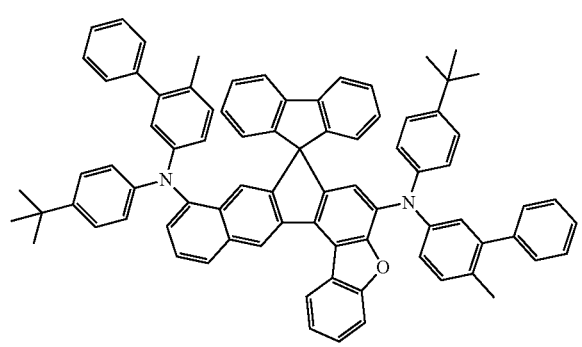
<Chemical Formula 210>
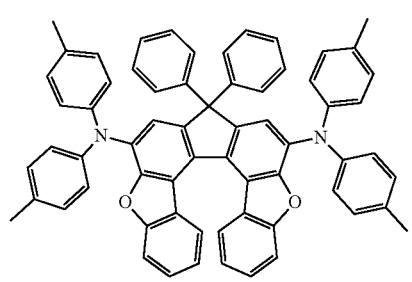

<Chemical Formula 211>
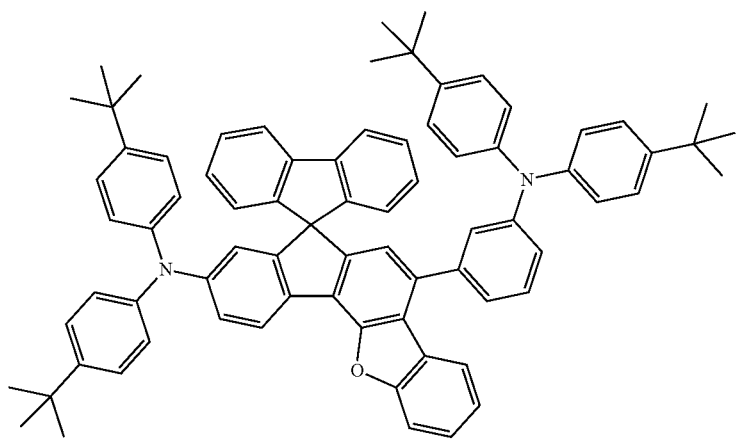
<Chemical Formula 212>
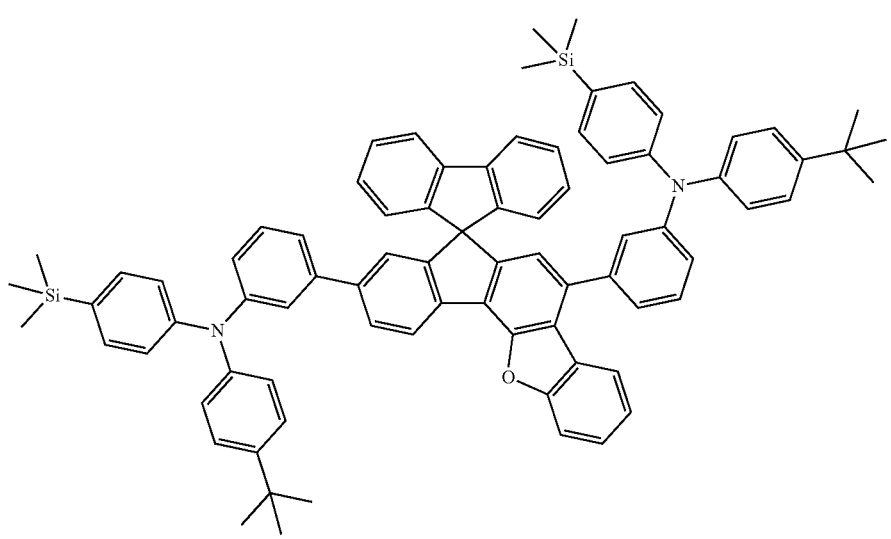
<Chemical Formula 213>
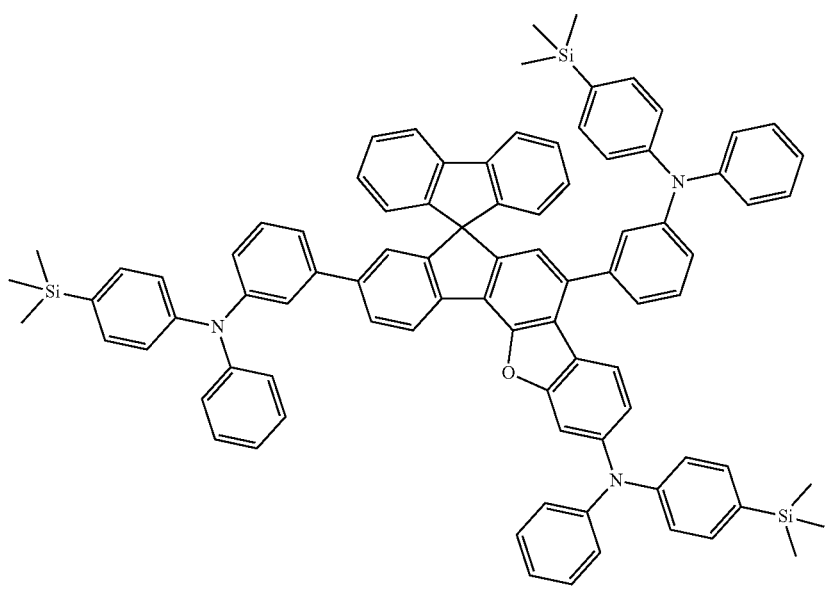

<Chemical Formula 214>
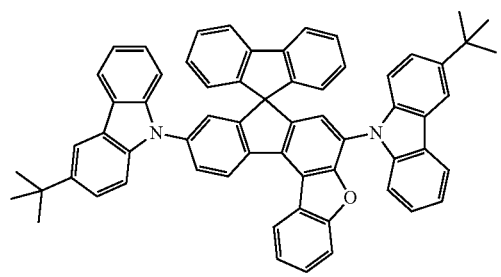
<Chemical Formula 215>
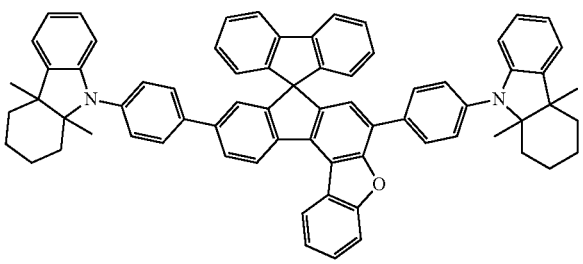
<Chemical Formula 216>
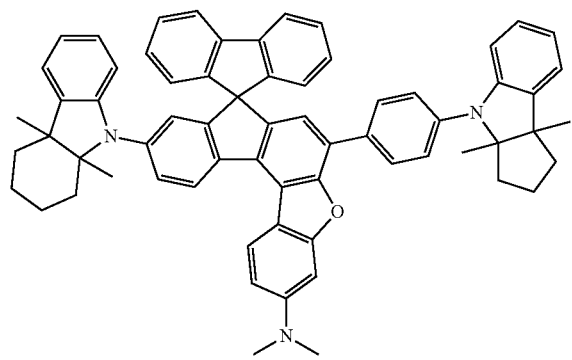
<Chemical Formula 217>
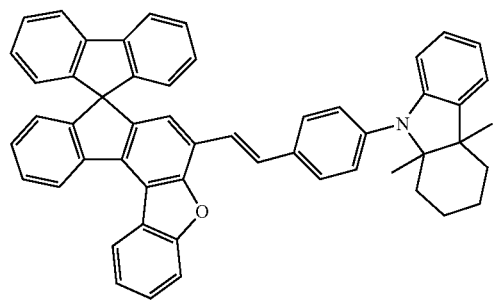
<Chemical Formula 218>
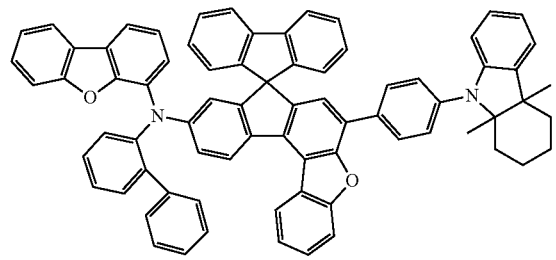
<Chemical Formula 219>
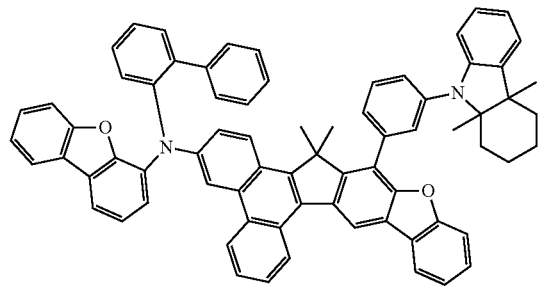
<Chemical Formula 220>
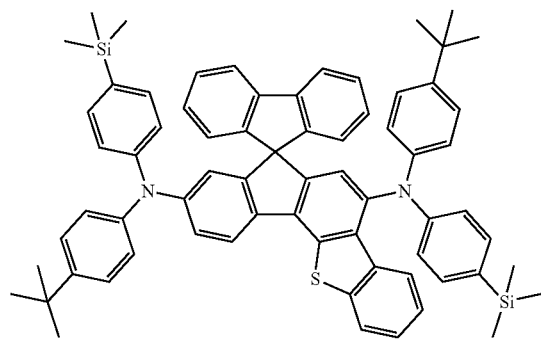
<Chemical Formula 221>
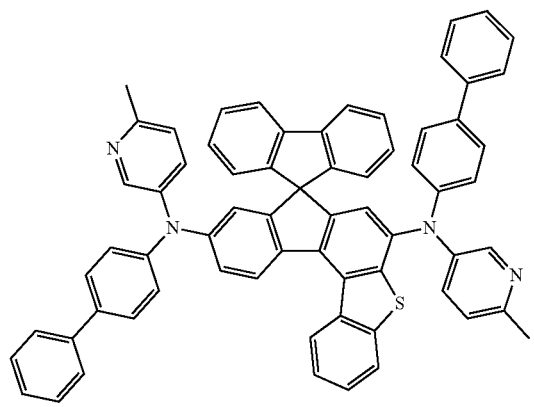

<Chemical Formula 222>
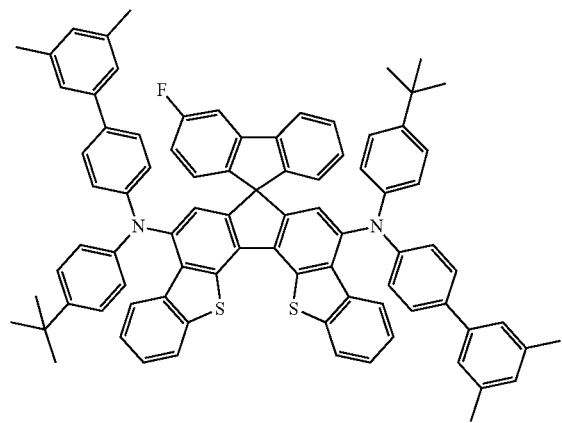
<Chemical Formula 223>
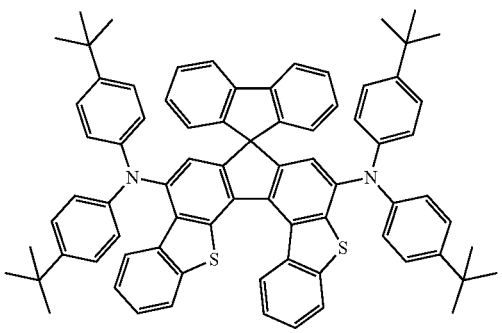
<Chemical Formula 224>
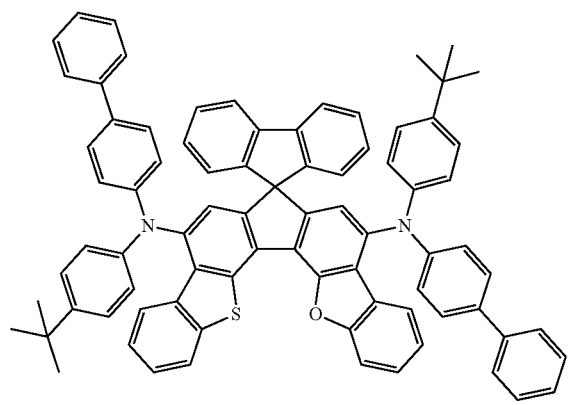
<Chemical Formula 225>
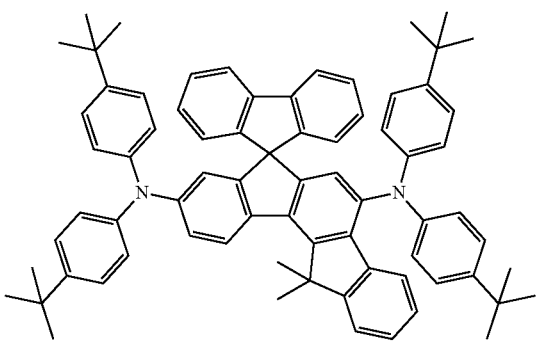
<Chemical Formula 226>
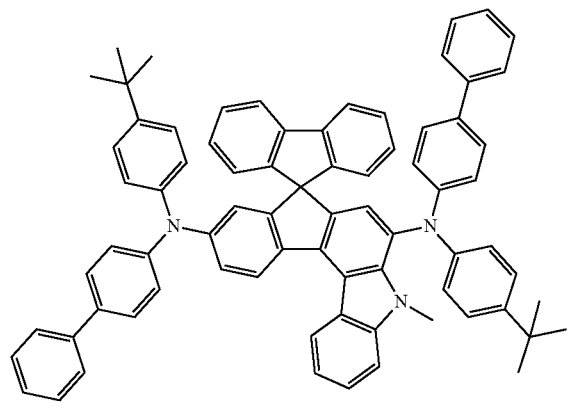
<Chemical Formula 227>
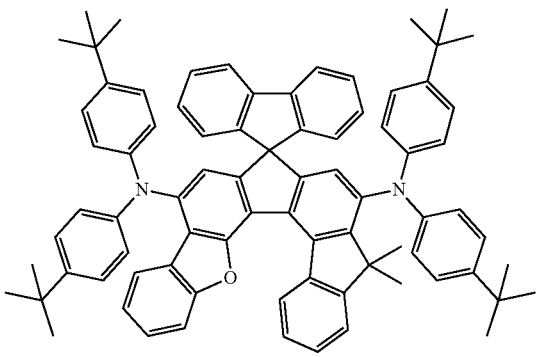

-continued
<Chemical Formula 228>
<Chemical Formula 229>
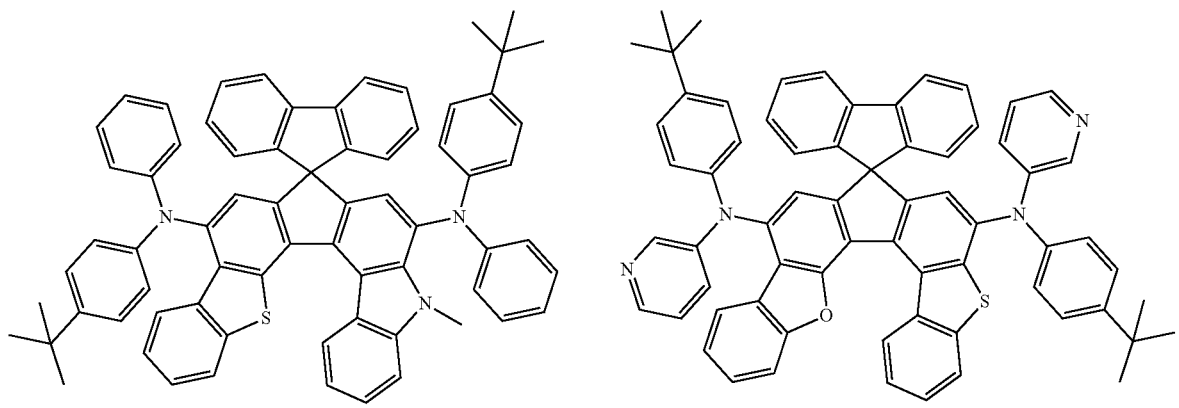
<Chemical Formula 230>
<Chemical Formula 231>
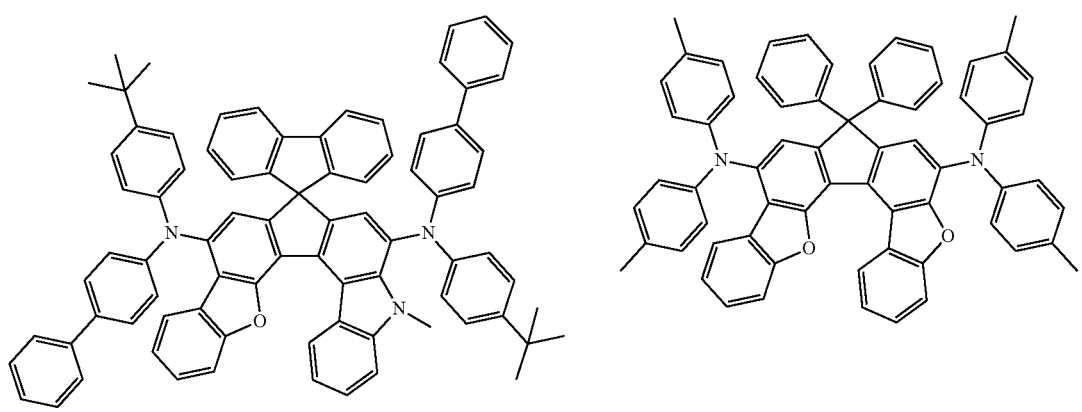
<Chemical Formula 232>
<Chemical Formula 233>
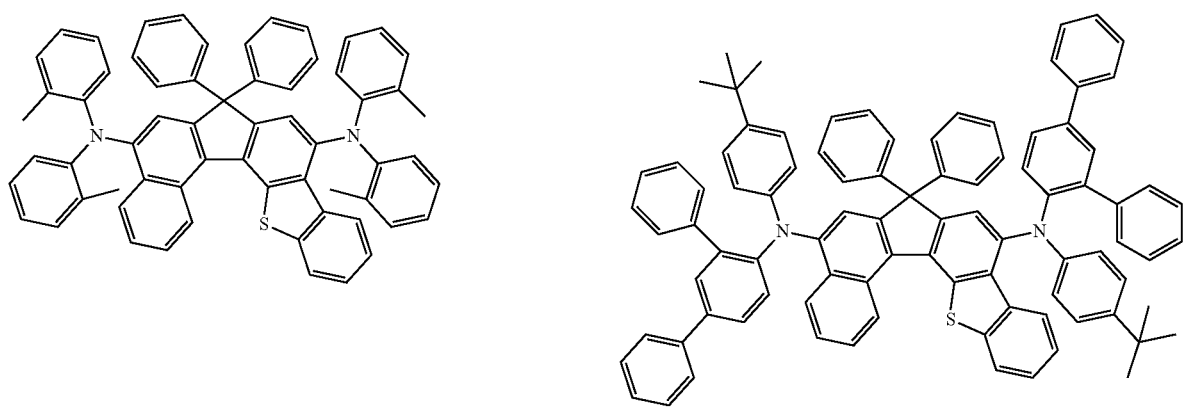

<Chemical Formula 234>
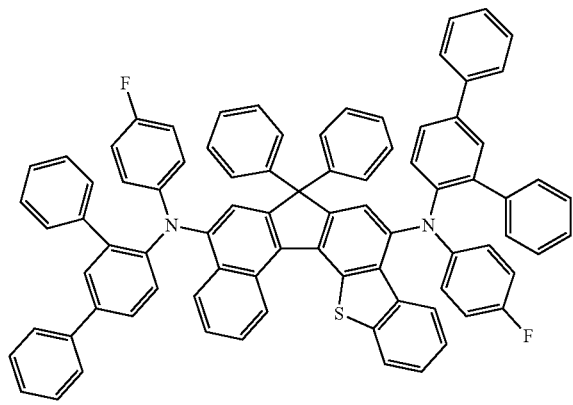
<Chemical Formula 235>
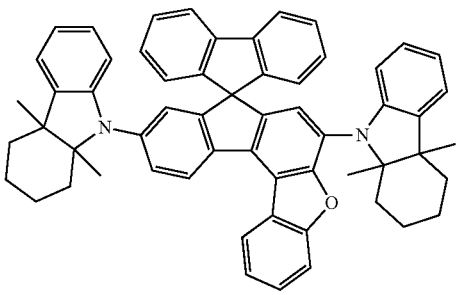
<Chemical Formula 236>
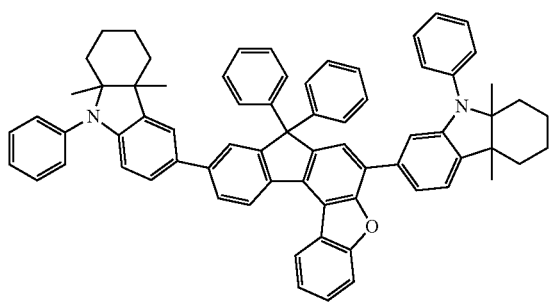
<Chemical Formula 237>
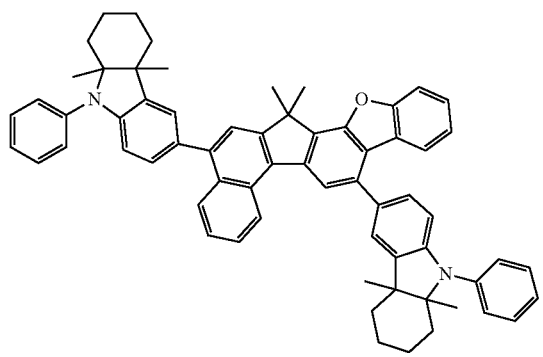
<Chemical Formula 238>
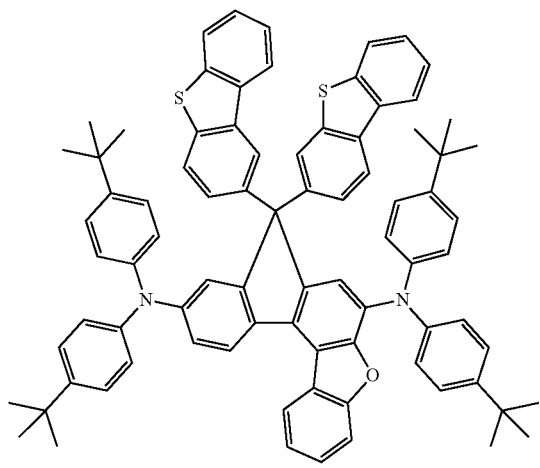
<Chemical Formula 239>
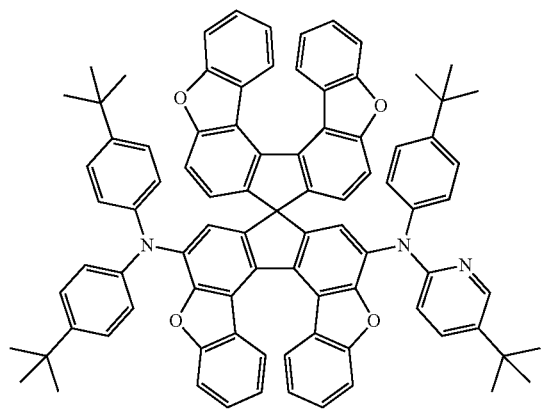
In addition, the pyrene compound represented by Chemical Formula C may be any one selected from compounds represented by Chemical Formulas 240 to Chemical Formula 284, but is not limited thereto.

<Chemical Formula 240>
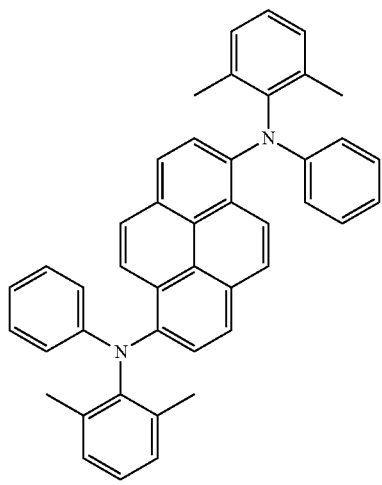
<Chemical Formula 241>
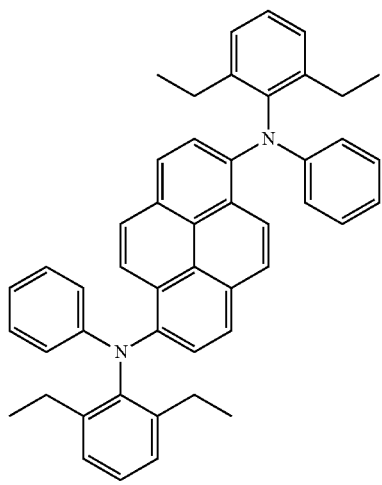
<Chemical Formula 242>
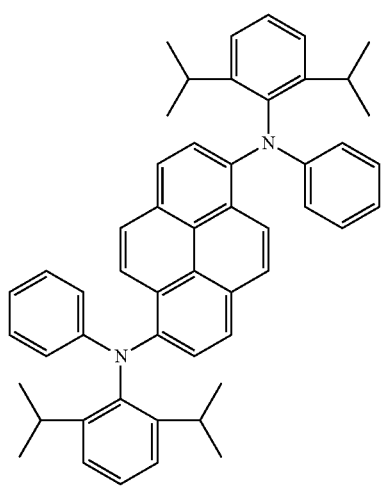
<Chemical Formula 243>
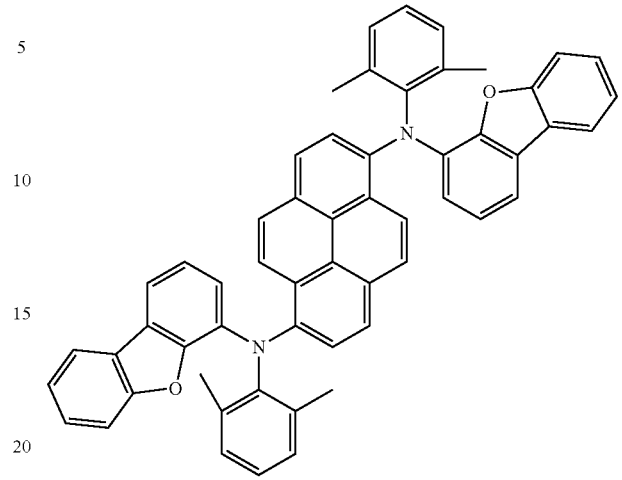
<Chemical Formula 244>
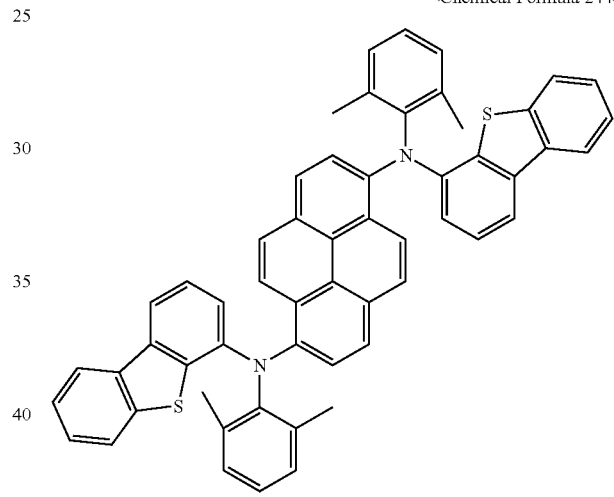
<Chemical Formula 245>
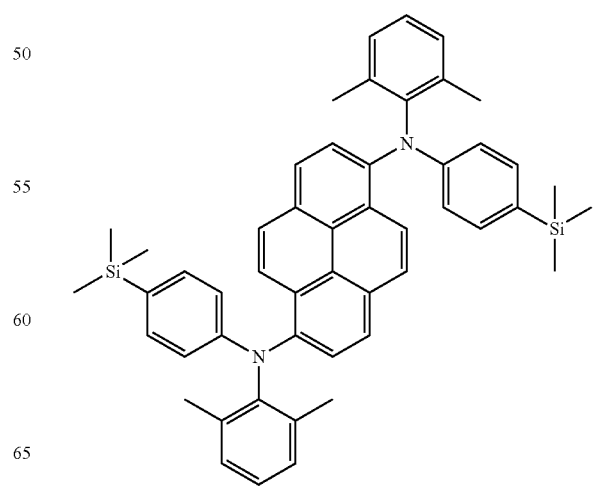

-continued
<Chemical Formula 246>
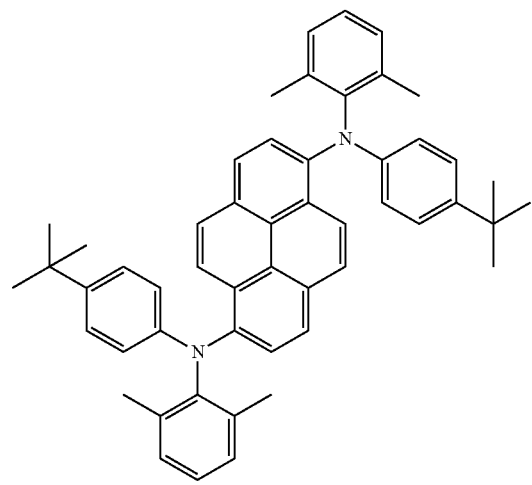
<Chemical Formula 247>
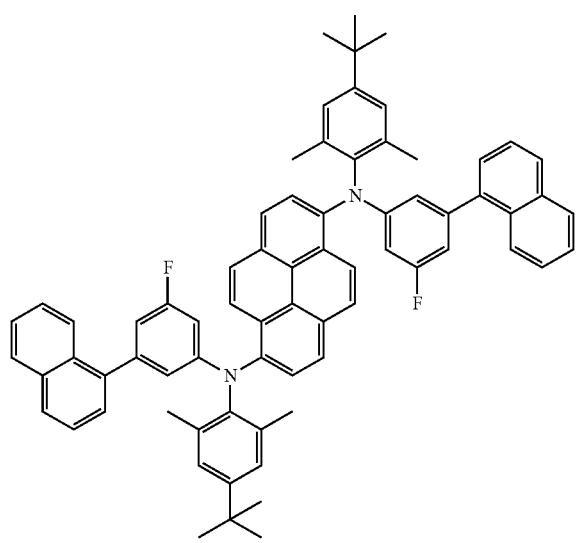
<Chemical Formula 248>
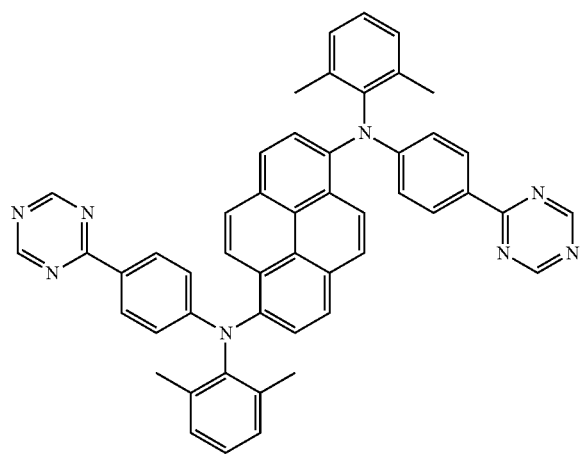
<Chemical Formula 249>
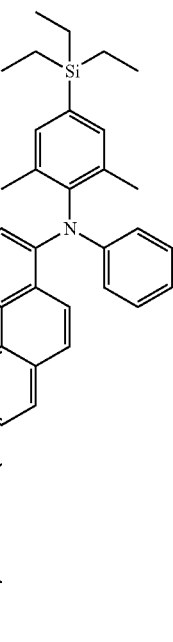
<Chemical Formula 250>
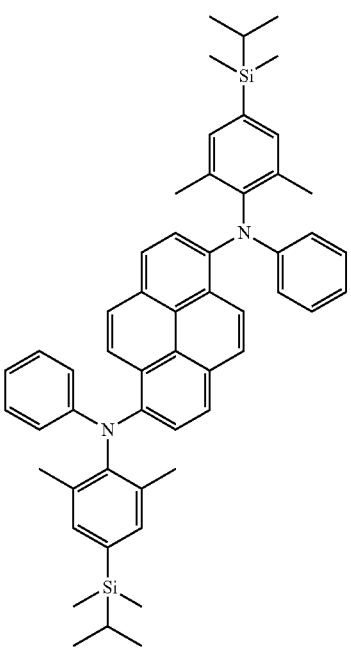

<Chemical Formula 251>
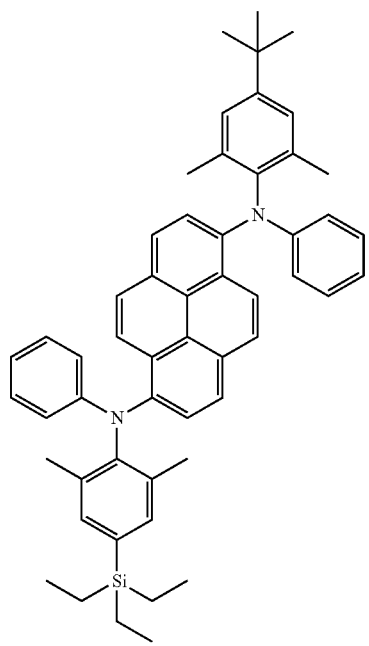
<Chemical Formula 252>
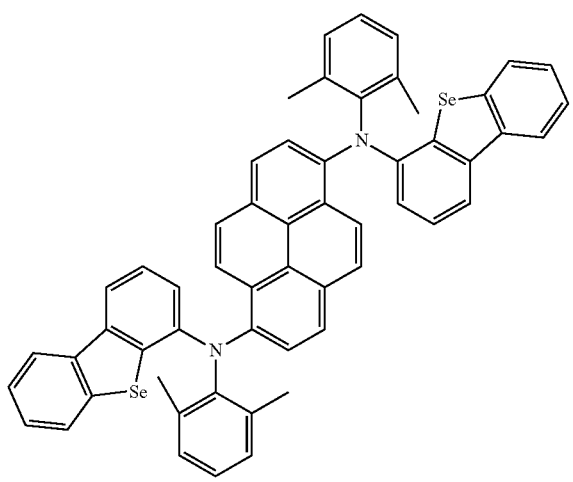
<Chemical Formula 253>
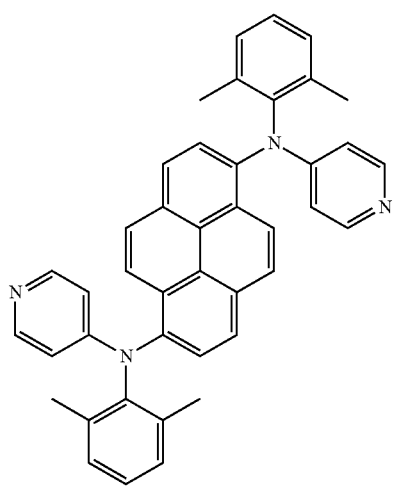
<Chemical Formula 254>
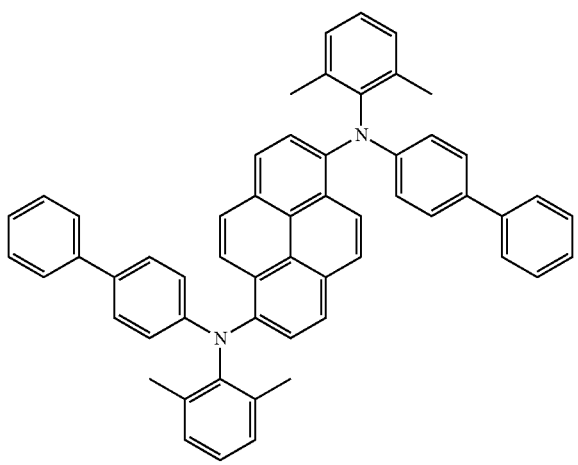
<Chemical Formula 255>
<Chemical Formula 256>
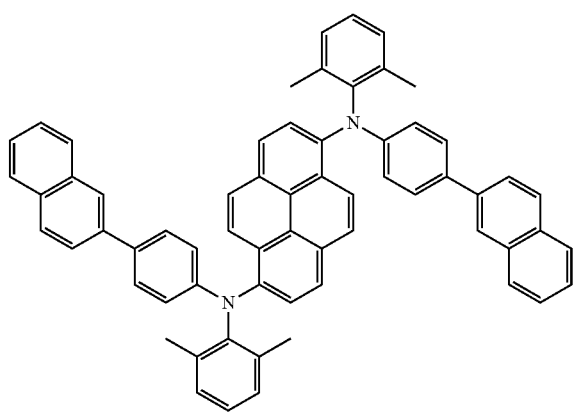

<Chemical Formula 257>
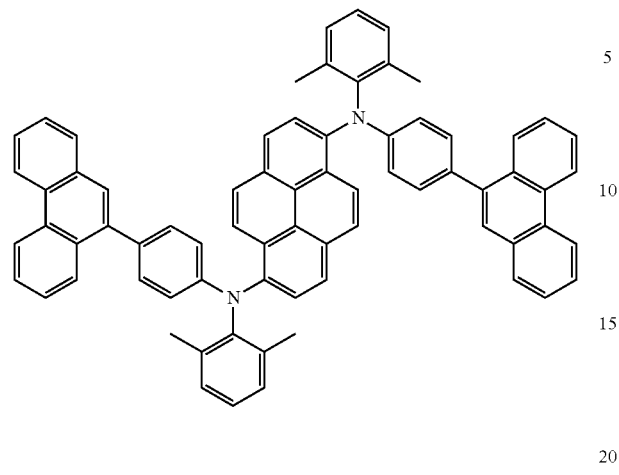
<Chemical Formula 258>
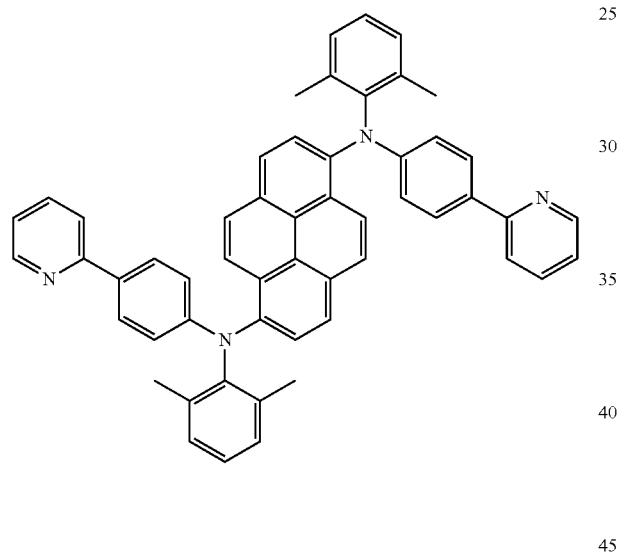
<Chemical Formula 259>
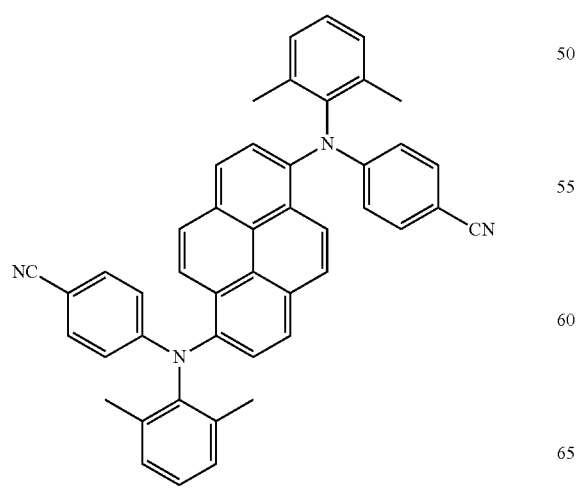
<Chemical Formula 260>
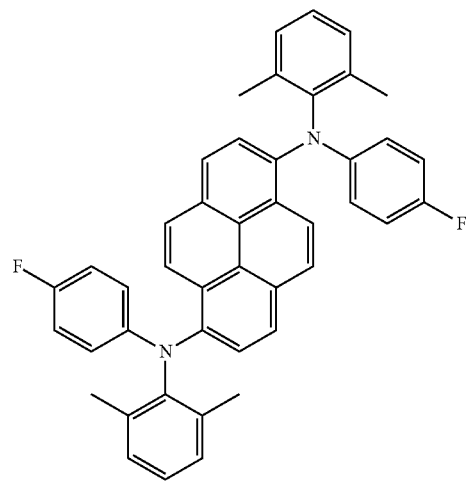
<Chemical Formula 261>
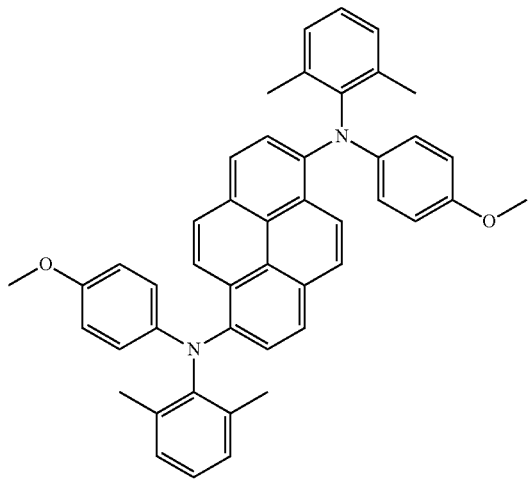
<Chemical Formula 262>
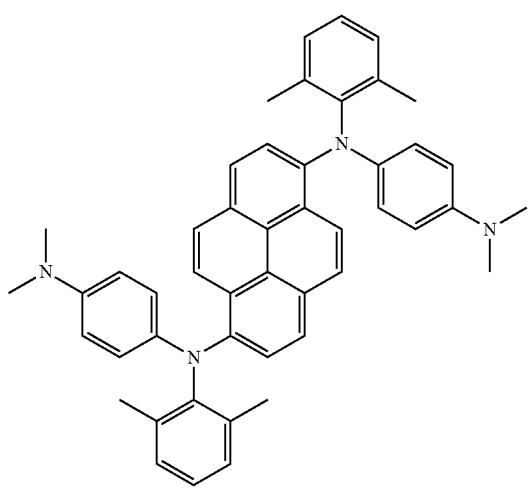

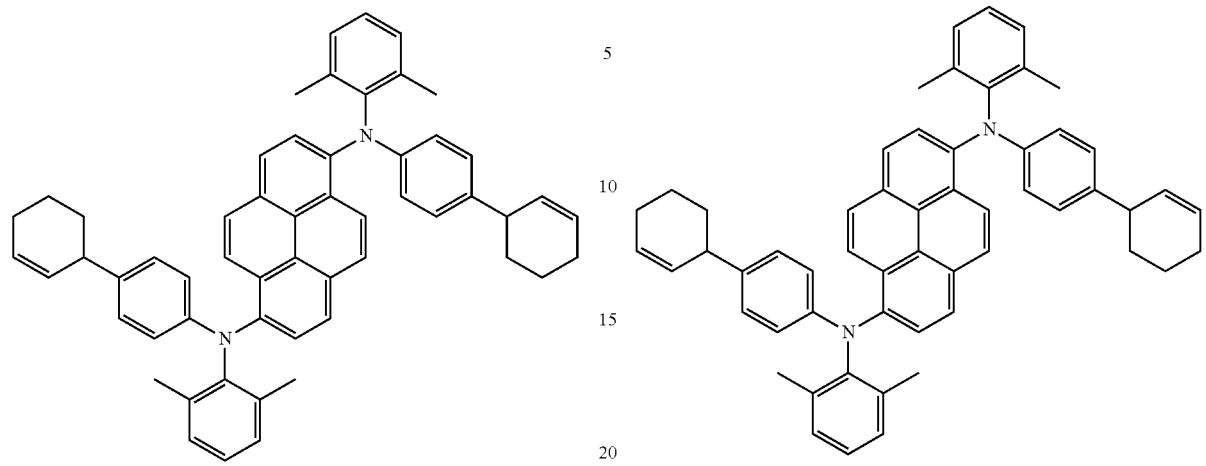
<Chemical Formula 263>
<Chemical Formula 266>
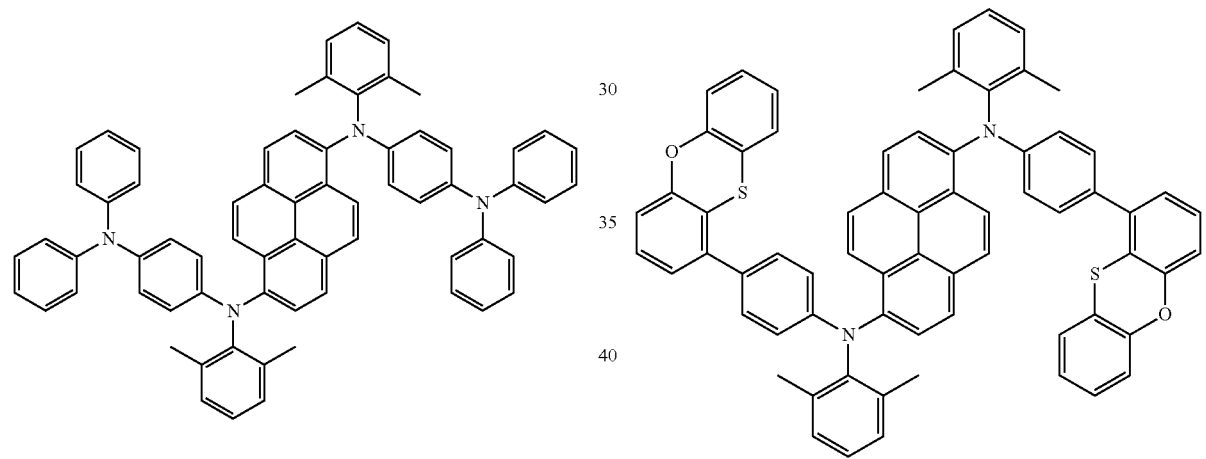
<Chemical Formula 264>
<Chemical Formula 267>
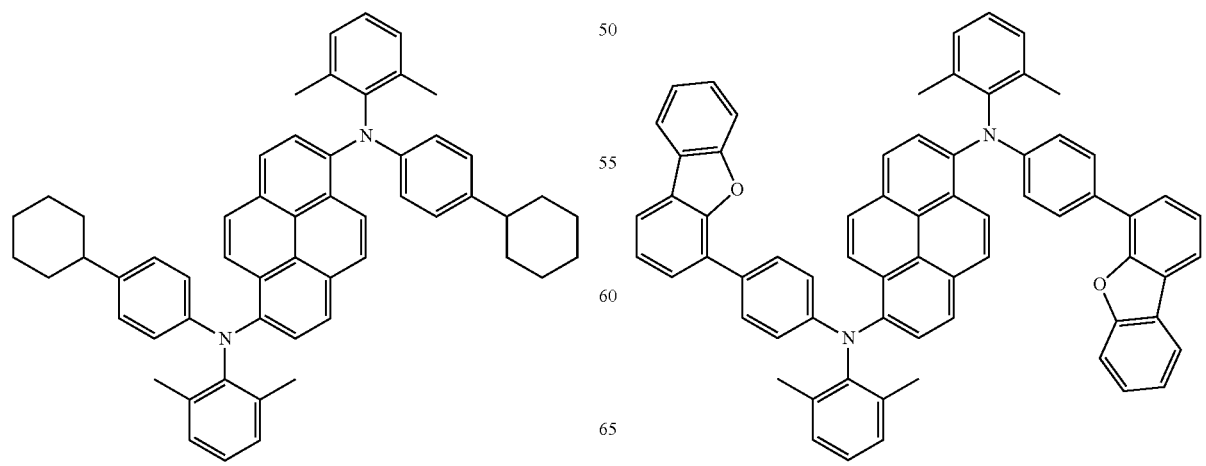
<Chemical Formula 265>
<Chemical Formula 268>

<Chemical Formula 269>
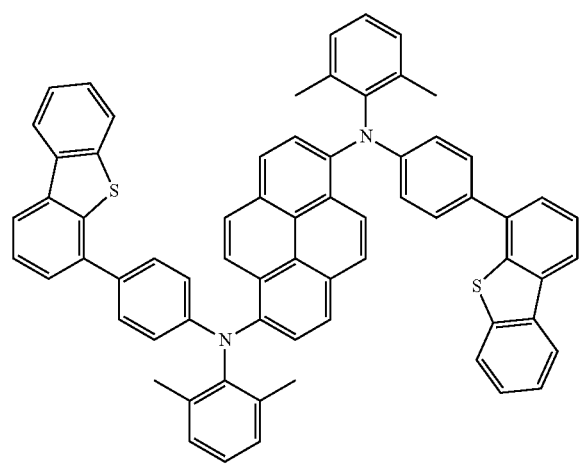
<Chemical Formula 270>
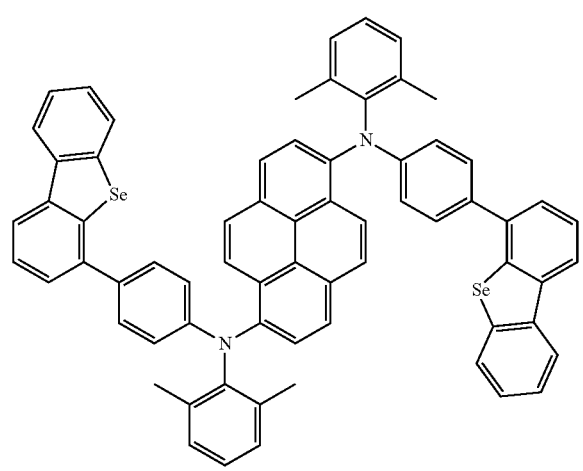
<Chemical Formula 271>
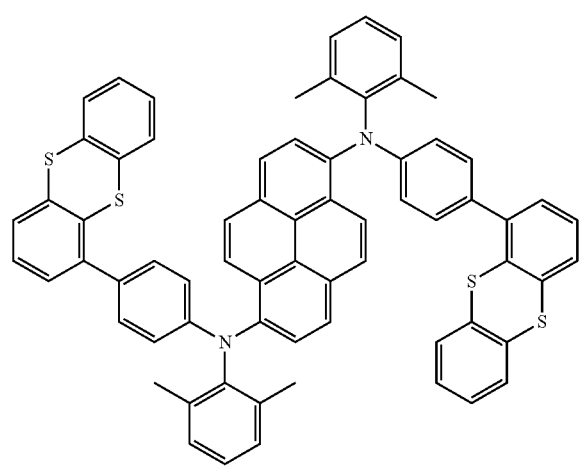
<Chemical Formula 272>
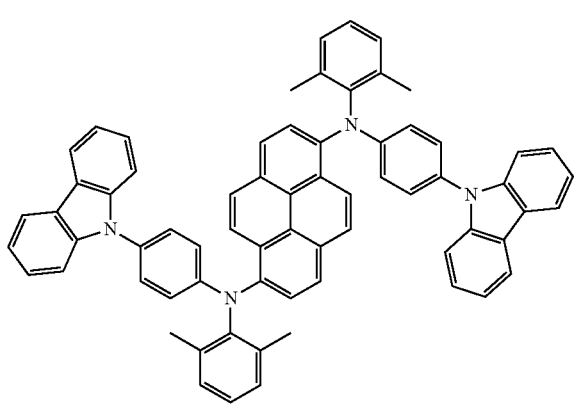
<Chemical Formula 273>
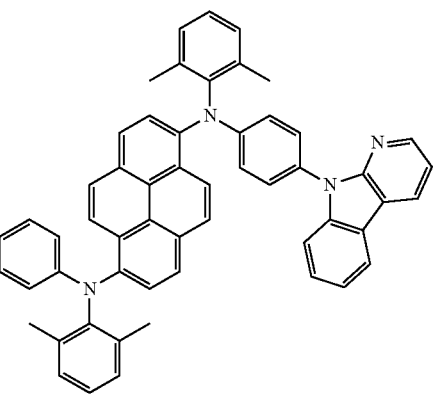
<Chemical Formula 274>
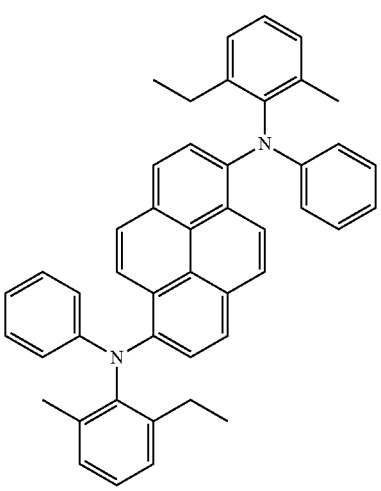

<Chemical Formula 275>
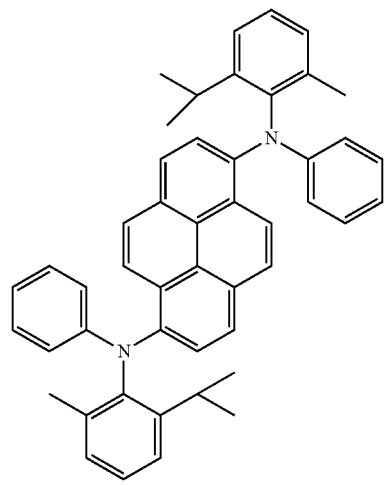
<Chemical Formula 276>
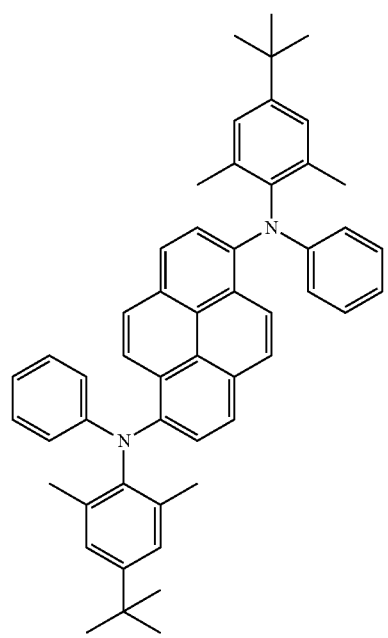
<Chemical Formula 277>
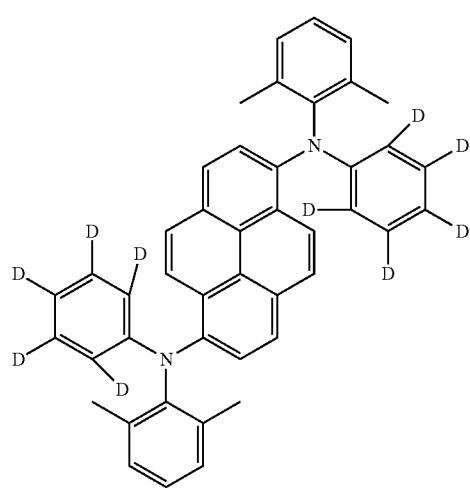
<Chemical Formula 278>
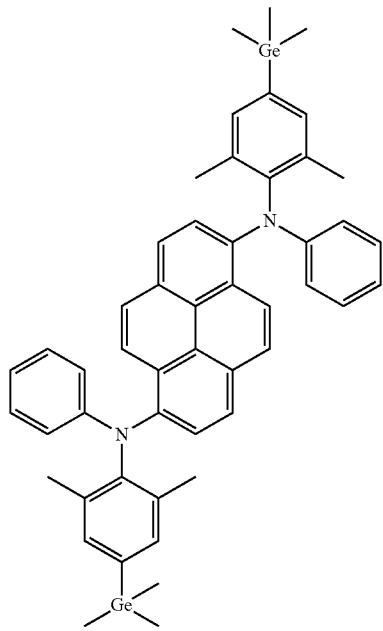
<Chemical Formula 279>
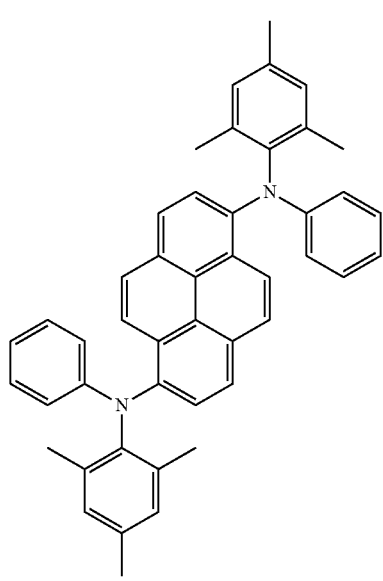

<Chemical Formula 280>
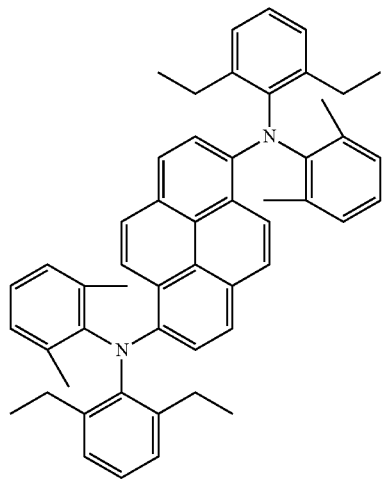
<Chemical Formula 281>
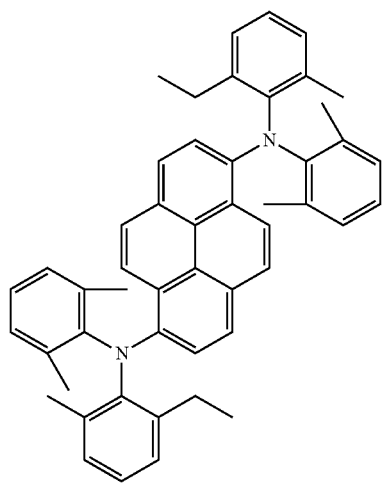
<Chemical Formula 282>
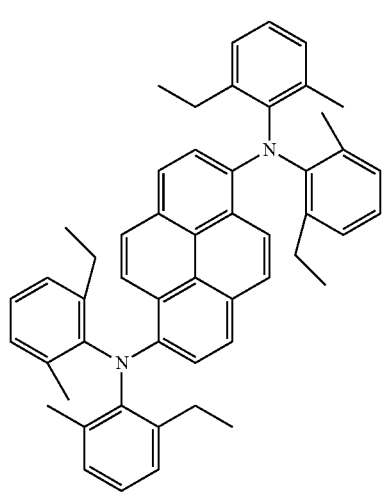
<Chemical Formula 283>
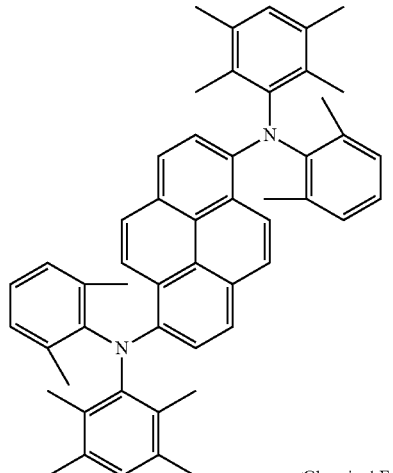
<Chemical Formula 284>
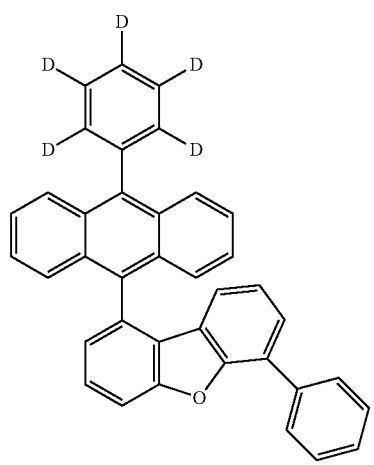
In addition, the anthracene compound represented by Chemical Formula D may be any one selected from among, but not limited to, the following Compounds 1 to 30:
<Compound 1>

<Compound 2>
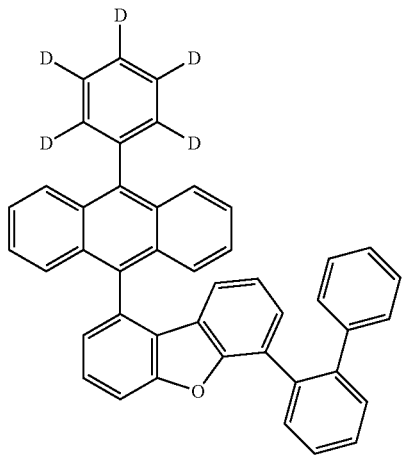
<Compound 3>
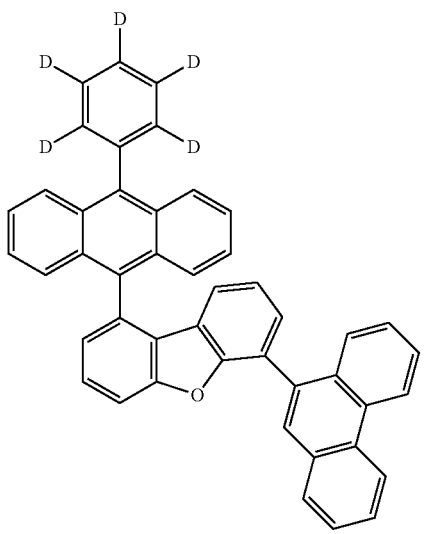
<Compound 4>
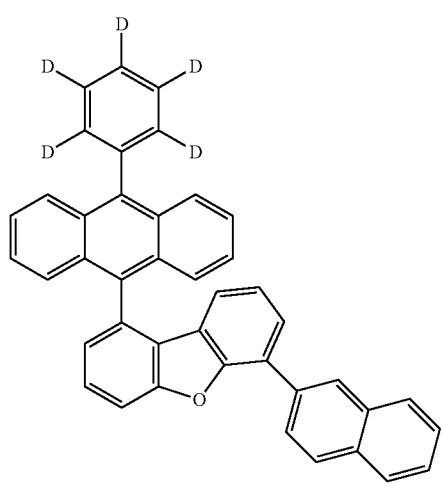
<Compound 5>
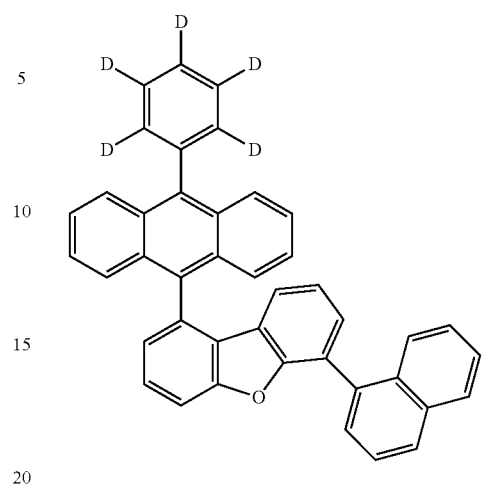
<Compound 6>
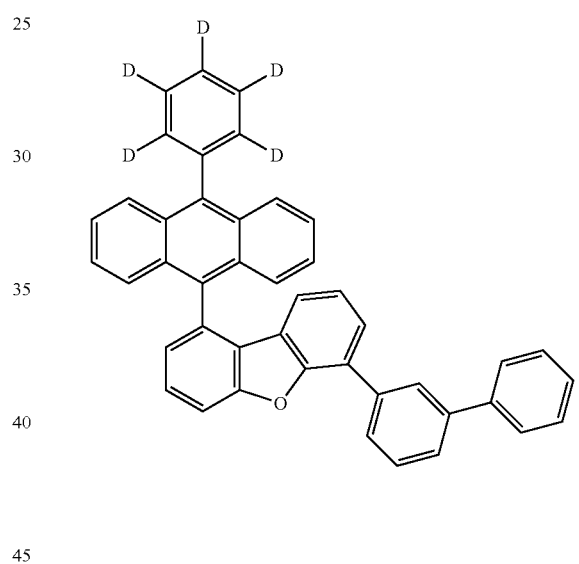
<Compound 7>
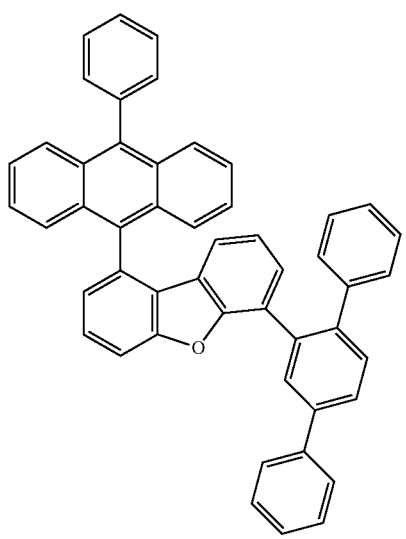

<Compound 8>
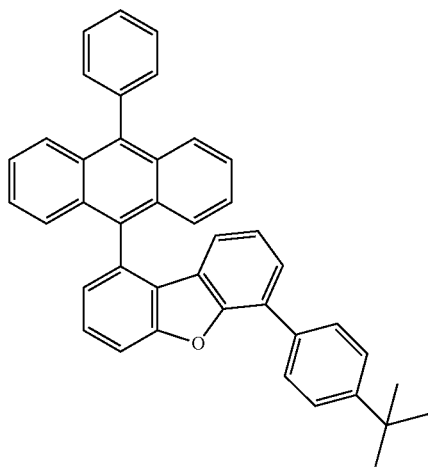
<Compound 11>
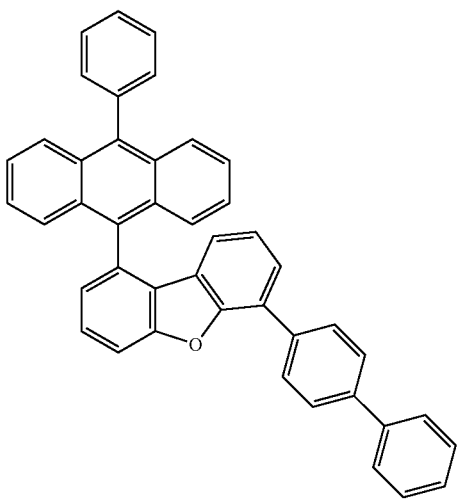
<Compound 9>
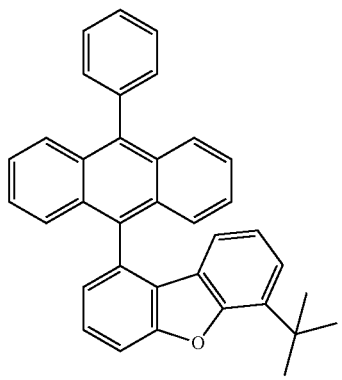
<Compound 12>
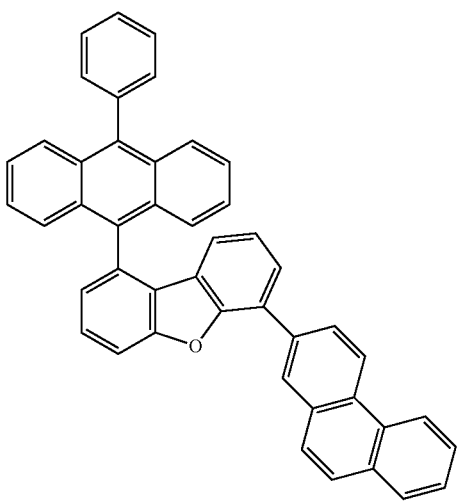
<Compound 10>
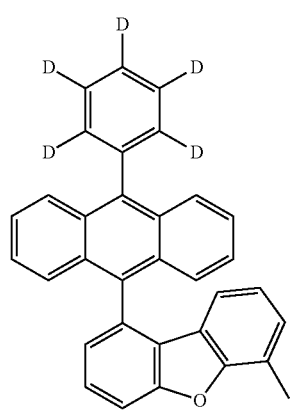
<Compound 13>
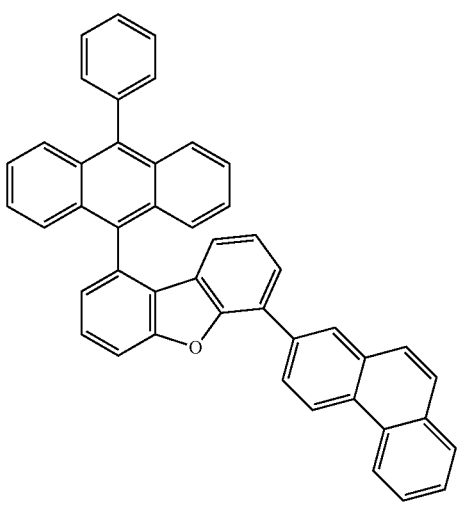

<Compound 14>
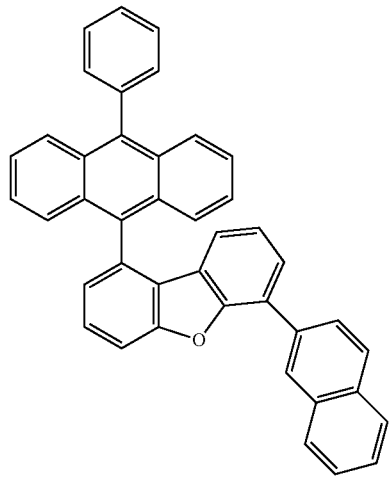
<Compound 15>
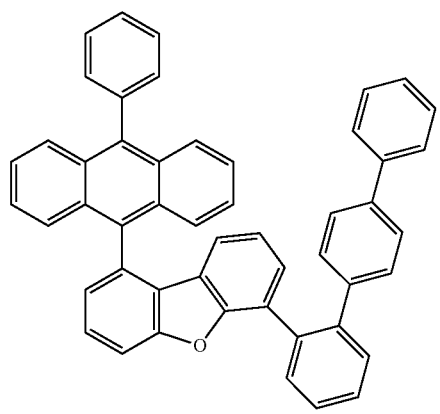
<Compound 16>
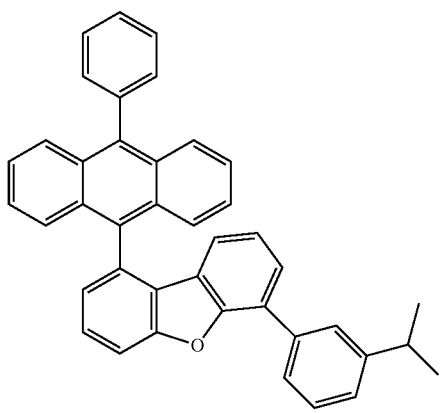
<Compound 17>
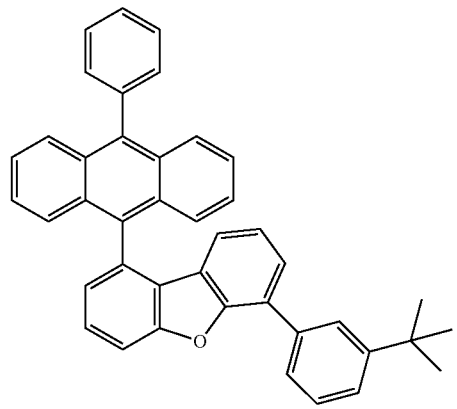
<Compound 18>
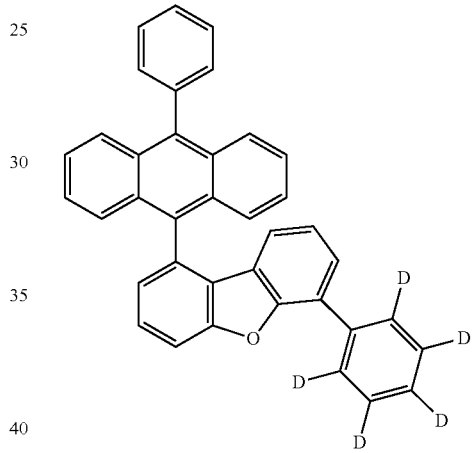
<Compound 19>
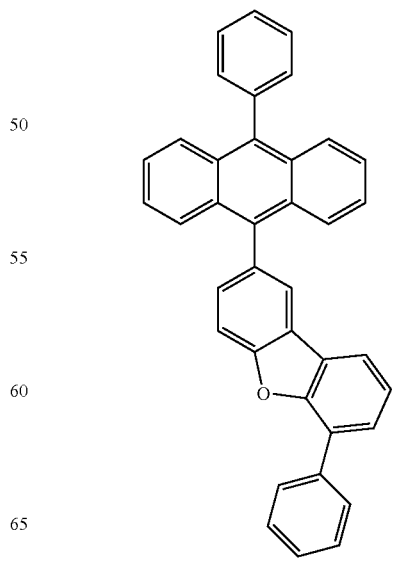

<Compound 20>
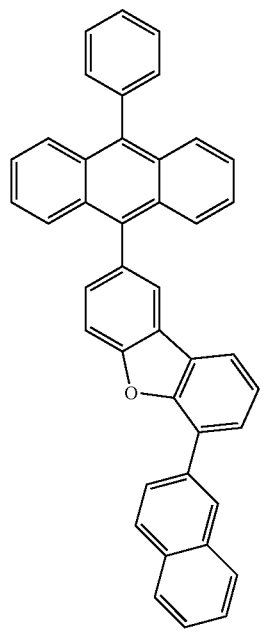
<Compound 21>
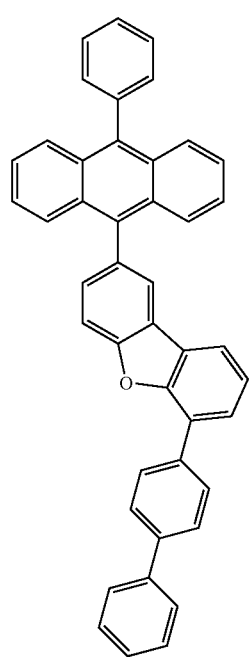
<Compound 22>
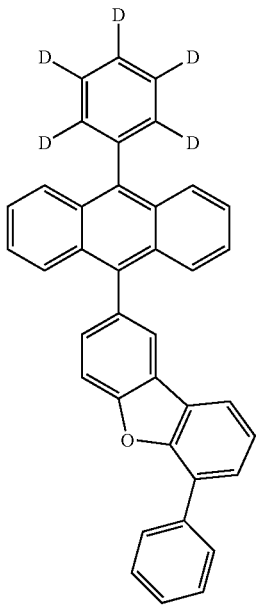
<Compound 23>
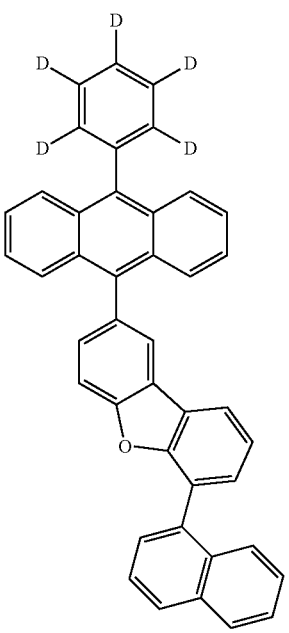

<Compound 24>
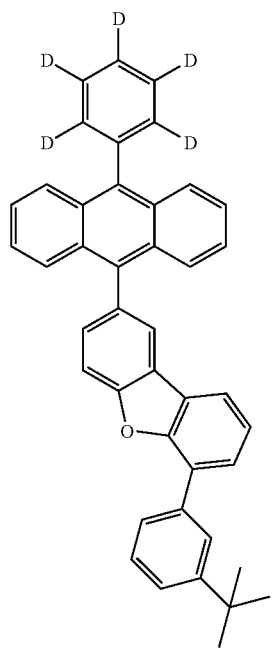
<Compound 25>
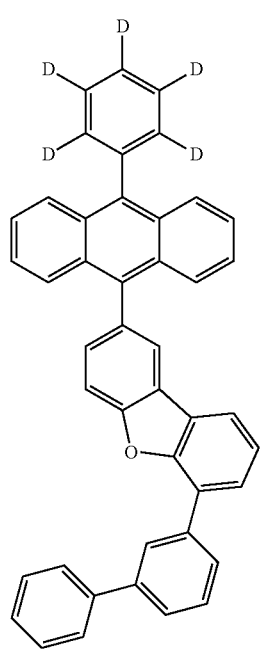
<Compound 26>
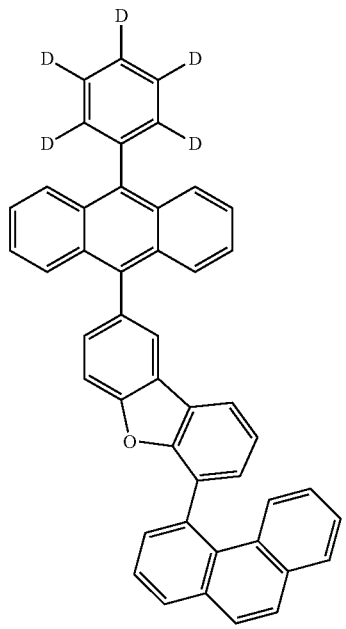
<Compound 27>
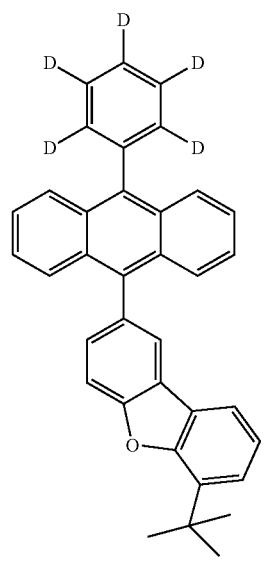
<Compound 28>
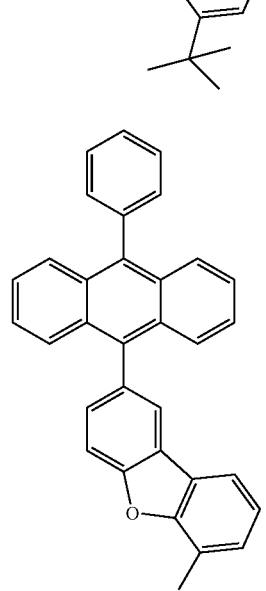

<Compound 29>

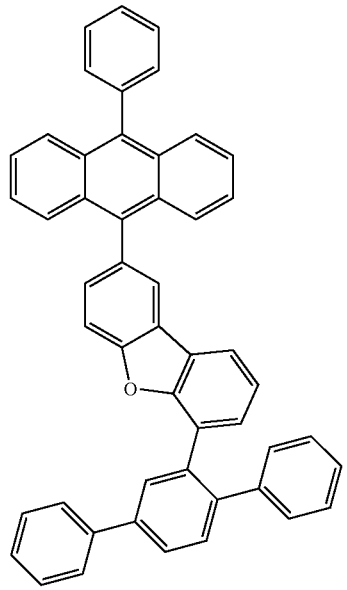

<Compound 30>

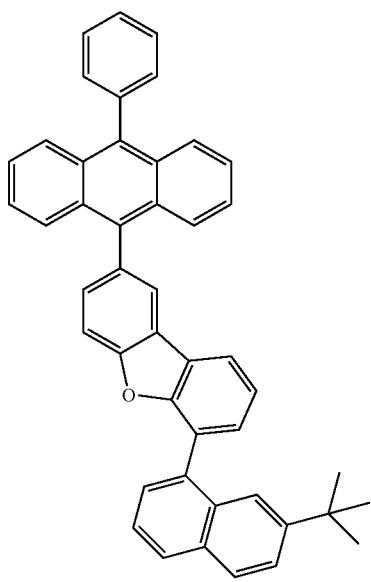

compound falling within the scope of the present disclosure or two or more different compounds falling within the scope of the present disclosure.

The amount of the dopant in the light-emitting layer may range from about 0.01 to about 20 weight parts, based on 100 weight parts of the host, but is not limited thereto.

In addition to the above-mentioned dopants and hosts, the light-emitting layer may further include various hosts and dopant materials.

Selection of an appropriate amine compound represented by Chemical Formula A or B and an appropriate pyrene compound represented by Chemical Formula C as respective dopants, and an appropriate compound represented by one of Chemical Formula D as a host in the light-emitting layer can impart high light emission efficiency to the light-emitting diode of the present disclosure.

According to some particular embodiments of the present disclosure, the organic light-emitting diode may comprise at least one selected from among a hole injection layer, a hole transport layer, a functional layer capable of both hole injection and hole transport, an electron transport layer, and an electron injection layer, in addition to the light-emitting layer.

A material for use in the electron transport layer functions to stably carry the electrons injected from the electron injection electrode (cathode), and may be an electron transport material known in the art. Examples of the electron transport material known in the art include quinoline derivatives, particularly, tris(8-quinolinorate)aluminum (Alq3), TAZ, Balq, beryllium bis(benzoquinolin-10-olate) (Bebq2), ADN, Compound 201, Compound 202, BCP, and oxadiazole derivatives such as PBD, BMD, BND, etc., but are not limited thereto.

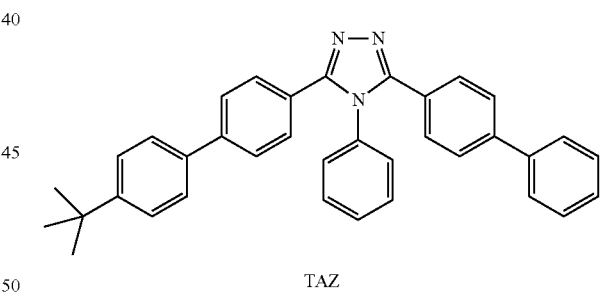

TAZ

In accordance with more particular embodiments thereof, the present disclosure addresses an organic light-emitting diode, comprising a first electrode, a second electrode facing the first electrode, and a light-emitting layer interposed therebetween, wherein the light-emitting layer contains an amine compound represented by Chemical Formula A or B and a pyrene compound represented by Chemical Formula C as respective dopants, and an anthracene compound represented by Chemical Formula D as a host.

As used herein, the expression "(the organic layer) . . . comprising at least one organic compound" is construed to mean that the organic layer may comprise one organic

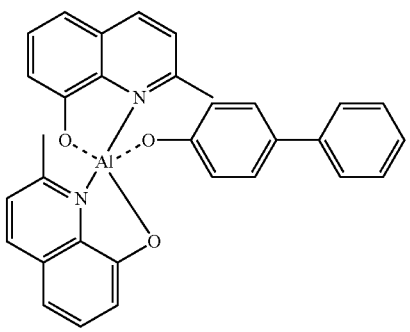

BAlq

-continued

<Compound 201>

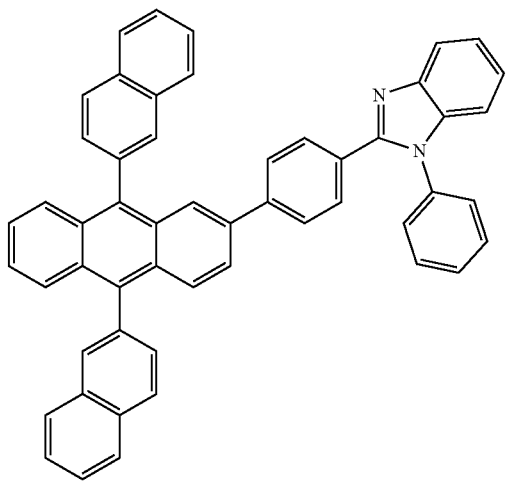

<Compound 202>

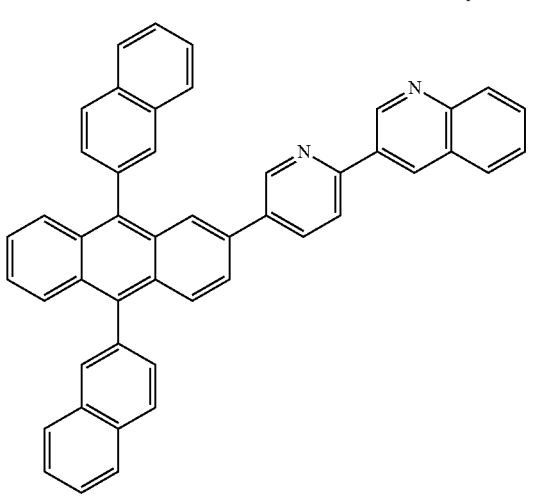

<BCP>

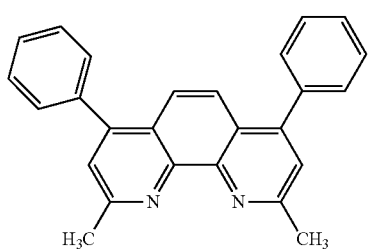

PBD

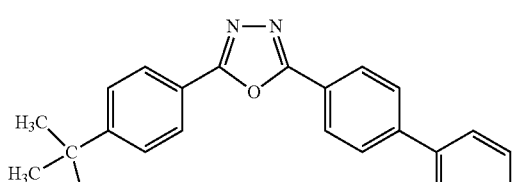

-continued

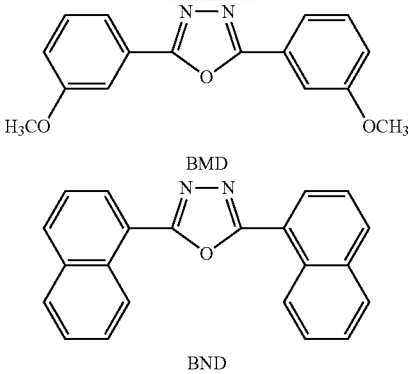

BMD

BND

Below, the organic light-emitting diode of the present disclosure is explained with reference to FIG. 1.

FIG. 1 is a schematic cross-sectional view of the structure of an present disclosure. The organic light-emitting diode comprises an anode 20, a hole transport layer 40, an organic light-emitting layer 50, an electron transport layer 60, and a cathode 80, and optionally a hole injection layer 30 or an electron injection layer 70. In addition, one or two intermediate layers may be further formed in the organic light-emitting diode, or a hole barrier layer or an electron barrier layer may also be employed.

Reference is made to FIG. 1 with regard to the fabrication of the organic light-emitting diode of the present disclosure. First, a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, and ease of handling. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied on the anode electrode 20 by thermal deposition in a vacuum or by spin coating to form a hole injection layer 30. Subsequently, thermal deposition in a vacuum or by spin coating may also be conducted to form a hole transport layer 40 with a hole transport layer material on the hole injection layer 30.

No particular limitations are imposed on the hole injection layer material, as long as it is one that is typically used in the art. For example, mention may be made of 2-TNATA [4,4',4"-tris(2-naphthylphenyl-phenylamino)-triphenylamine], NPD [N,N'-di(1-naphthyl)-N,N'-diphenylbenzidine], TPD [N,N'-diphenyl-N,N'-bis(3-methylphenyl)-1,1'-biphenyl-4,4'-diamine], or DNTPD [N,N'-diphenyl-N,N'-bis-[4-(phenyl-m-tolyl-amino)-phenyl]-biphenyl-4,4'-diamine], but is not limited thereto.

So long as it is typically used in the art, any material may be selected for the hole transport layer without particular limitation. Examples include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenyl-benzidine (a-NPD).

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the diode are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitation. Representative among hole barrier materials are BAlq, BCP, and TPBI.

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the light-emitting layer particularly ranges in thickness from 50 to 2,000 Å.

Further, one or more layers selected from among a hole injection layer, a hole transport layer, a functional layer capable of both hole injection and hole transport, an electron barrier layer, a light-emitting layer, a hole barrier layer, an electron transport layer, and an electron injection layer may be deposited using a single-molecule deposition process or a solution process. Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting the present disclosure.

EXAMPLES

I. Preparation of Dopant Compounds

Synthesis Example 1: Synthesis of Compound of Chemical Formula 1

Synthesis Example 1-(1): Synthesis of Intermediate 1-a

Intermediate 1-a was synthesized as illustrated in the following Reaction Scheme 1.

<Reaction Scheme 1>

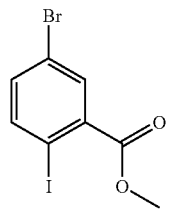

+

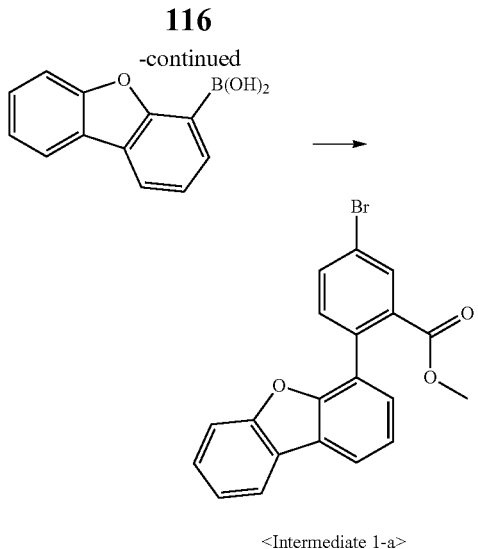

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) were stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a> (75.0 g, 60.1%).

Synthesis Example 1-(2): Synthesis of Intermediate 1-b

Intermediate 1-b was synthesized as illustrated in the following Reaction Scheme 2:

<Reaction Scheme 2>

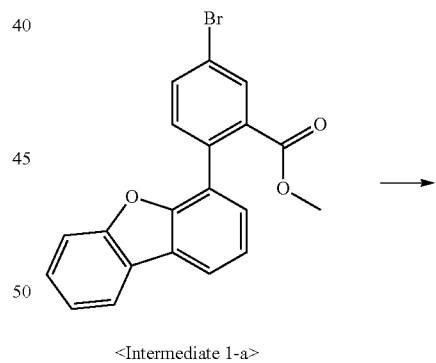

<Intermediate 1-a>

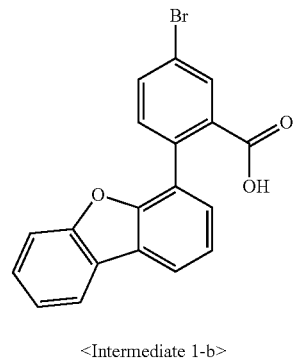

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed using thin-layer chromatography, the reaction mixture was cooled to room temperature. The chilled solution was acidified with drops of 2-N HCl, followed by stirring for 30 min. The solid thus formed was filtered and then recrystallized in dichloromethane and n-hexane to afford <Intermediate 1-b>. (14.5 g, 88.6%)

Synthesis Example 1-(3): Synthesis of Intermediate 1-c

Intermediate 1-c was synthesized as illustrated in the following Reaction Scheme 3:

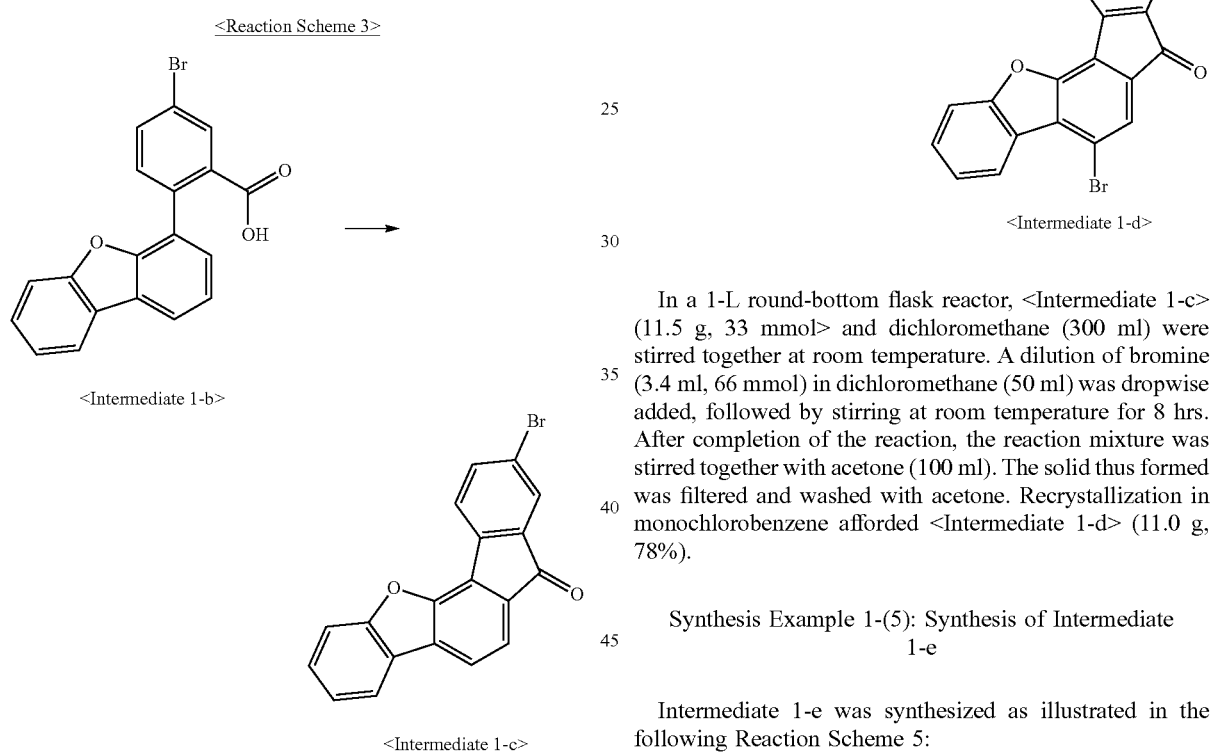

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the solid thus formed was filtered and washed with water and methanol to afford <Intermediate 1-c> (11.50 g, 83.4%).

Synthesis Example 1-(4): Synthesis of Intermediate 1-d

Intermediate 1-d was synthesized as illustrated in the following Reaction Scheme 4:

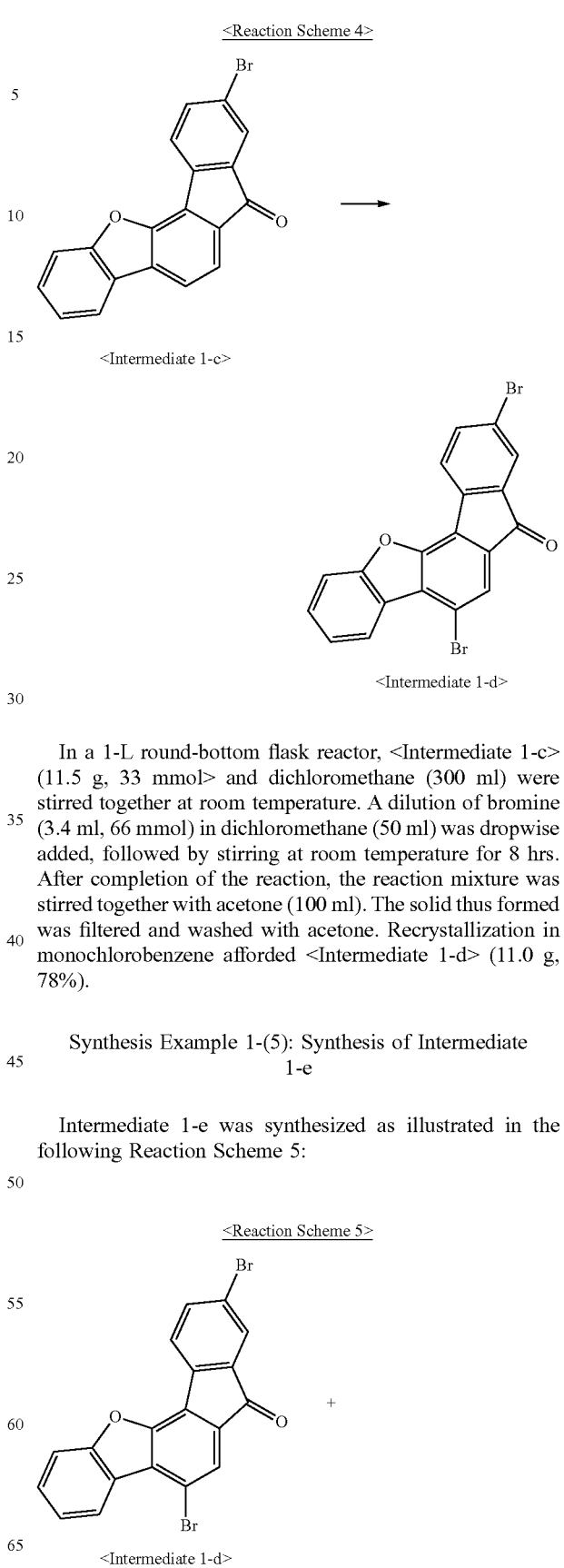

In a 1-L round-bottom flask reactor, <Intermediate 1-c> (11.5 g, 33 mmol> and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered and washed with acetone. Recrystallization in monochlorobenzene afforded <Intermediate 1-d> (11.0 g, 78%).

Synthesis Example 1-(5): Synthesis of Intermediate 1-e

Intermediate 1-e was synthesized as illustrated in the following Reaction Scheme 5:

-continued

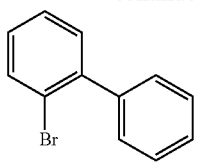

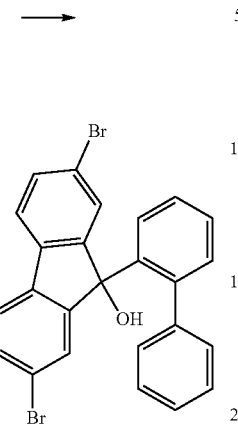

<Intermediate 1-e>

In a 250-ml round-bottom flask reactor, 2-bromobiphenyl (8.4 g, 0.036 mol) and tetrahydrofuran (110 ml) were frozen at −78° C. in a nitrogen atmosphere. At the same temperature, n-butyl lithium (19.3 ml, 0.031 mol) was dropwise added to the reaction solution, which was then stirred for 2 hrs. Thereafter, <Intermediate 1-d> (11.0 g, 0.026 mol) was added little by little to the reaction solution and stirred at room temperature. When the reaction mixture started to change color, the reaction was monitored via TLC. After the reaction was stopped with H₂O (50 ml), extraction was conducted with ethyl acetate and water. The organic layer was separated, concentrated in a vacuum, and recrystallized in acetonitrile to afford <Intermediate 1-e> (12.2 g, 81.5%).

Synthesis Example 1-(6): Synthesis of Intermediate 1-f

Intermediate 1-f was synthesized as illustrated in the following Reaction Scheme 6:

<Reaction Scheme 6>

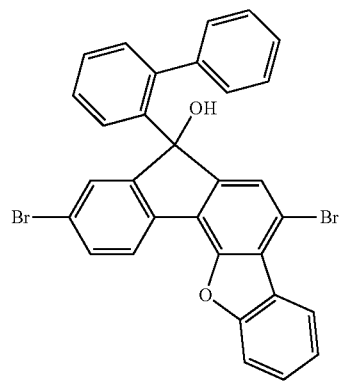

<Intermediate 1-e>

-continued

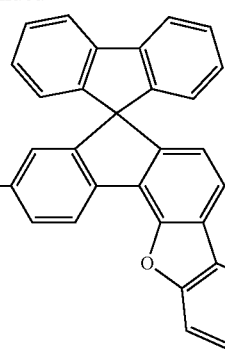

<Intermediate 1-f>

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin-layer chromatography. The reaction mixture was then cooled to room temperature and filtered. The filtrate was washed with H₂O and methanol and dissolved in monochlorobenzene. Following silica gel filtration, the fraction was concentrated and cooled to room temperature to give <Intermediate 1-f> (10.7 g, 90%).

Synthesis Example 1-(7): Synthesis of Compound of Chemical Formula 1

The compound of Chemical Formula 1 was synthesized as illustrated in the following Reaction Scheme 7:

<Reaction Scheme 7>

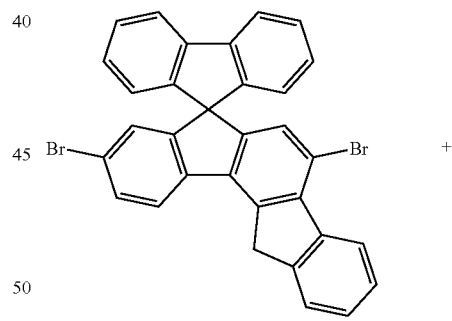

<Intermediate 1-f>

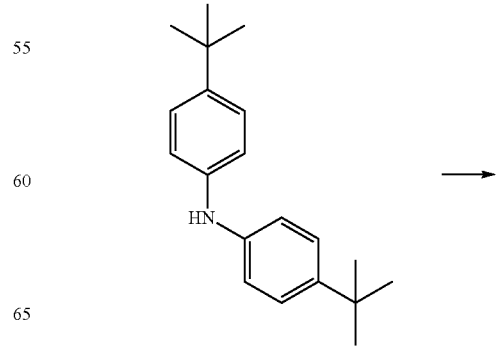

-continued

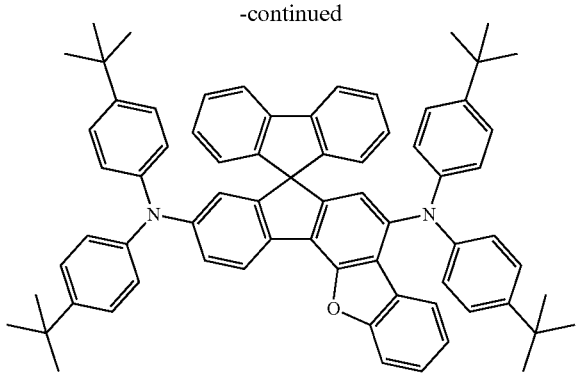

<Chemical Formula 1>

In a 250-ml round-bottom flask reactor, a mixture of <Intermediate 1-f> (5.0 g, 0.009 mol), bis(4-tert-butylphenyl)amine (6.0 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) was stirred for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 1 (3.1 g, 38%).

MS (MALDI-TOF): m/z 964.5 [M+]

Synthesis Example 2: Synthesis of Compound of Chemical Formula 33

Synthesis Example 2-(1): Synthesis of Intermediate 2-a

Intermediate 2-a was synthesized as illustrated in the following Reaction Scheme 8:

<Reaction Scheme 8>

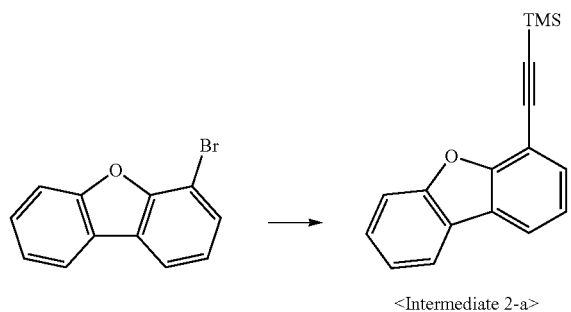

<Intermediate 2-a>

In a 2-L round bottom flask, 4-bromodibenzofuran (100.0 g, 0.405 mol), ethynyl trimethylsilane (47.7 g, 0.486 mol), [1,1'-bis(diphenylphosphino) ferrocene]dichloropalladium (9.92 g, 0.012 mol), copper iodide (2.31 g, 0.012 mol), triphenylphosphine (10.6 g, 0.040 mol), and triethylamine (700 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 2-a> (130 g, 84%).

Synthesis Example 2-(2): Synthesis of Intermediate 2-b

Intermediate 2-b was synthesized as illustrated in the following Reaction Scheme 9:

<Reaction Scheme 9>

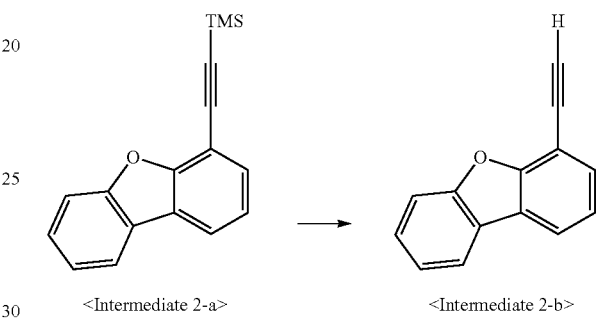

<Intermediate 2-a>          <Intermediate 2-b>

In a 2-L round-bottom flask reactor, <Intermediate 2-a> (130 g, 0.492 mol), potassium carbonate (101.9 g, 0.738 mol), methanol (650 ml), and tetrahydrofuran (650 ml) were stirred together for 2 hrs at room temperature. After completion of the reaction, heptane (500 ml) was added to terminate the reaction. The reaction mixture was filtered and the filtrate was extracted with ethyl acetate and water. The organic layer thus formed was isolated and dried over magnesium sulfate. Filtration and vacuum concentration afforded <Intermediate 2-b> as an oil (82 g, 84%).

Synthesis Example 2-(3): Synthesis of Intermediate 2-c

Intermediate 2-c was synthesized as illustrated in the following Reaction Scheme 10:

<Reaction Scheme 10>

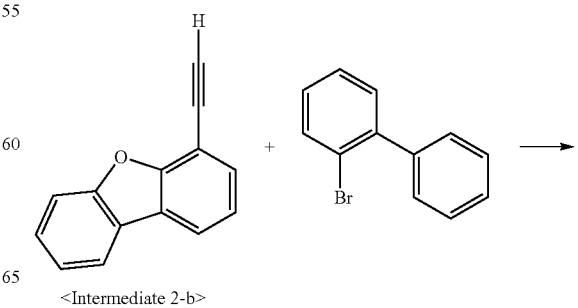

<Intermediate 2-b>

-continued

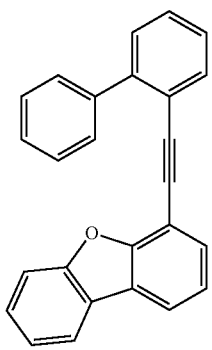

<Intermediate 2-c>

In a 2-L round-bottom flask reactor, 2-bromobiphenyl (66.0 g, 0.283 mol), <Intermediate 2-b> (65.3 g, 0.340 mol), [1,1'-bis(diphenylphosphino)ferrocene]dichloropalladium (6.94 g, 0.008 mol), copper iodide (1.62 g, 0.008 mol), triphenylphosphine (7.4 g, 0.028 mol), and triethylamine (500 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford <Intermediate 2-c> (80 g, 82%).

Synthesis Example 2-(4): Synthesis of Intermediate 2-d

Intermediate 2-d was synthesized as illustrated in the following Reaction Scheme 11:

<Reaction Scheme 11>

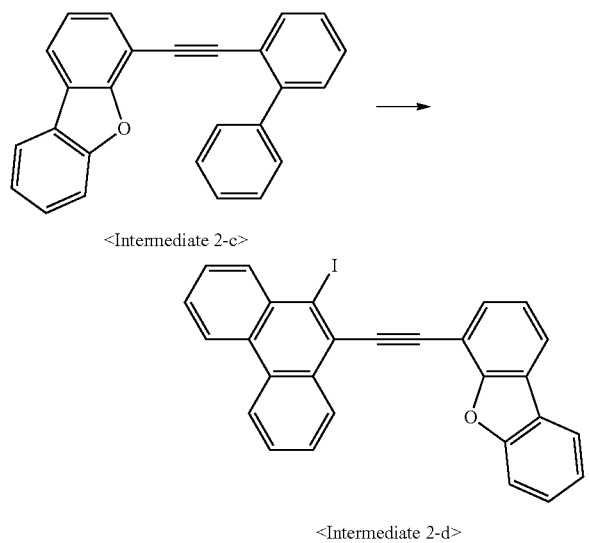

In a 2-L round-bottom flask reactor, a solution of <Intermediate 2-c> (80.0 g, 0.232 mol) in dichloromethane (960 ml) was cooled to −78° C. under a nitrogen atmosphere. Iodine monochloride (278.4 ml, 0.279 mol) was dropwise added to the chilled solution, which was then stirred at room temperature for 12 hrs. After completion of the reaction, the reaction mixture was stirred together with an aqueous saturated sodium thiosulfate solution. Following extraction with dichloromethane and water, the organic layer was isolated, concentrated in a vacuum, and washed with methanol to afford <Intermediate 2-d> as a crystal (67 g, 61.3%).

Synthesis Example 2-(5): Synthesis of Intermediate 2-e

Intermediate 2-e was synthesized as illustrated in the following Reaction Scheme 12:

<Reaction Scheme 12>

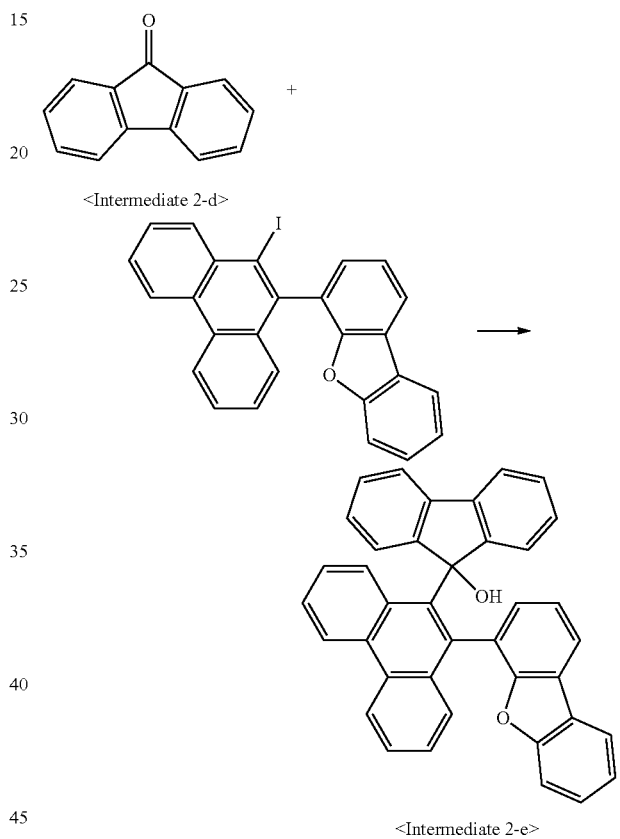

<Intermediate 2-e>

In a 500-mL round-bottom flask reactor, a solution of <Intermediate 2-d> (54.8 g, 0.117 mol) in tetrahydrofuran (150 ml) was cooled to −78° C. under a nitrogen atmosphere. At the same temperature, 1.6 M n-butyl lithium (62.4 ml, 0.1 mol) was dropwise added to the chilled solution and stirred for 1 hr. Then, a solution of 9-fluorenone (15.0 g, 0.083 mol) in tetrahydrofuran (50 ml) was dropwise added before stirring at room temperature for 8 hrs. After completion of the reaction, extraction was performed with ethyl acetate and water. The organic layer thus formed was isolated and dried over magnesium sulfate. Vacuum concentration subsequent to filtration afforded <Intermediate 2-e> as an oil (33.2 g, 76%).

Synthesis Example 2-(6): Synthesis of Intermediate 2-f

Intermediate 2-f was synthesized as illustrated in the following Reaction Scheme 13:

<Reaction Scheme 13>

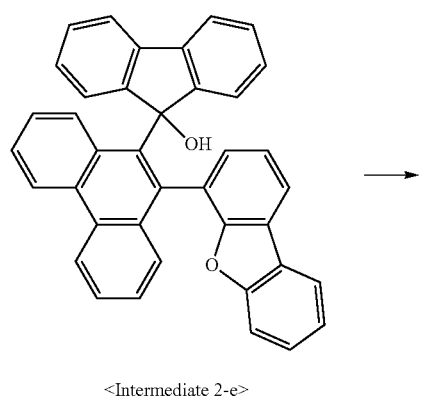

<Intermediate 2-e>

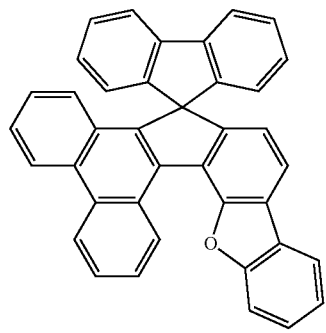

<Intermediate 2-f>

In a 1-L round-bottom flask reactor, <Intermediate 2-e> (33.3 g, 0.063 mol), acetic acid (330 ml), and sulfuric acid (3 ml) were stirred together for 3 hrs under reflux. After the completion of the reaction was confirmed using thin-layer chromatography, the reaction mixture was cooled to room temperature. The precipitates thus formed were filtered and washed with H$_2$O and methanol to afford <Intermediate 2-f> (28.6 g, 88%>.

Synthesis Example 2-(7): Synthesis of Intermediate 2-g

Intermediate 2-g was synthesized as illustrated in the following Reaction Scheme 14:

<Reaction Scheme 14>

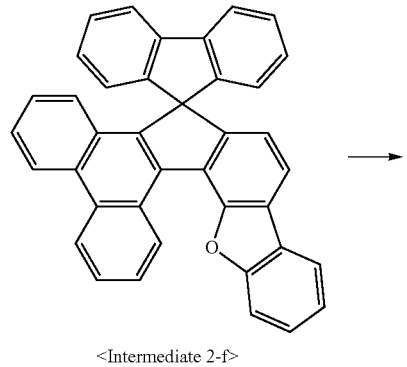

<Intermediate 2-f>

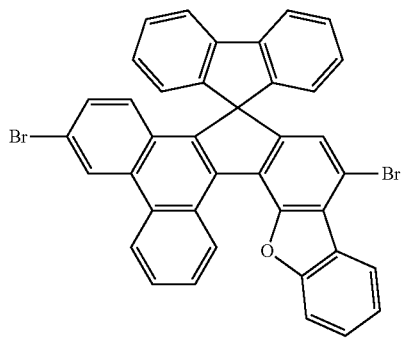

<Intermediate 2-g>

In a 1-L round-bottom flask reactor, a solution of <Intermediate 2-f> (20.0 g, 0.039 mol) in dichloromethane (200 ml) was added with drops of a dilution of bromine (6 ml, 0.118 mol) in dichloromethane (40 ml) while stirring. After completion of the reaction for 12 hrs of stirring at room temperature, the addition of methanol (100 ml) produced precipitates which were then washed with methanol. Recrystallization in 1,2-dichlorobenzene and acetone afforded <Intermediate 2-g> (16 g, 60%).

Synthesis Example 2-(8): Synthesis of Compound of Chemical Formula 33

The compound of Chemical Formula 33 was synthesized as illustrated in the following Reaction Scheme 15:

<Reaction Scheme 15>

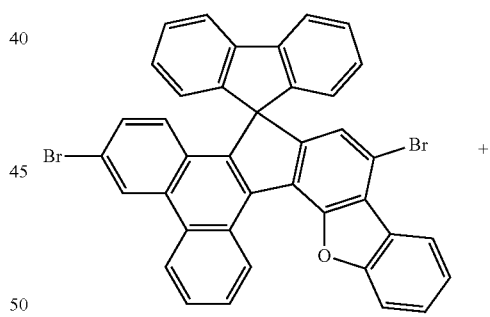

<Intermediate 2-g>

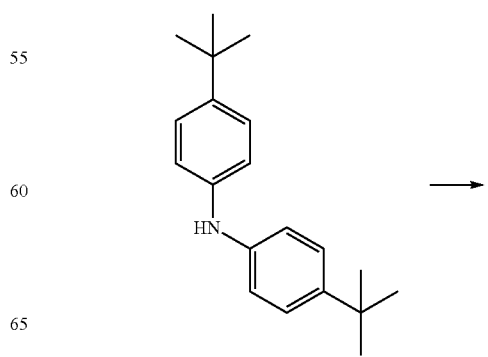

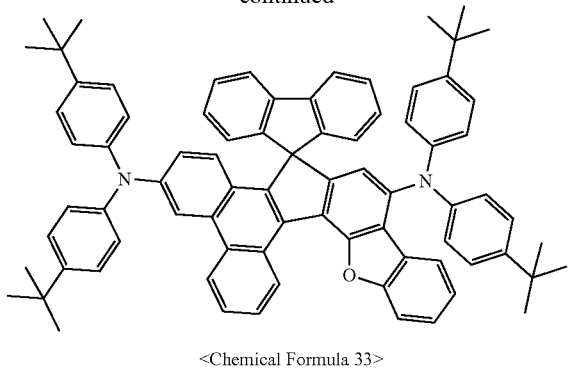

<Chemical Formula 33>

The same procedure was conducted as in Synthesis Example 1-(7), with the exception of using <Intermediate 2-g> instead of <Intermediate 1-f>, to synthesize the compound of <Chemical Formula 33> (2.5 g, 31%).

MS (MALDI-TOF): m/z 1064.5 [M$^+$]

Synthesis Example 3: Synthesis of Compound of Chemical Formula 89

Synthesis Example 3-(1): Synthesis of Intermediate 3-a

Intermediate 3-a was synthesized as illustrated in the following Reaction Scheme 16:

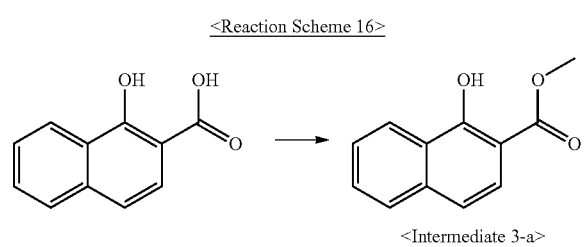

<Reaction Scheme 16>

<Intermediate 3-a>

In a 2-L round-bottom flask reactor, 1-hydroxy 2-naphthalic acid (50 g, 266 mmol), methanol (1000 ml), and sulfuric acid (100 ml) were stirred together for 100 hrs under reflux. The completion of the reaction was confirmed by TLC before the reaction mixture was cooled to room temperature. The mixture was concentrated in a vacuum and extracted with dichloromethane and water. The organic layer was isolated, dried over magnesium sulfate, and filtered. The filtrate was concentrated at a reduced pressure and crystallized in an excess of heptane to afford <Intermediate 3-a> (39 g, 72.6%).

Synthesis Example 3-(2): Synthesis of Intermediate 3-b

Intermediate 3-b was synthesized as illustrated in the following Reaction Scheme 17:

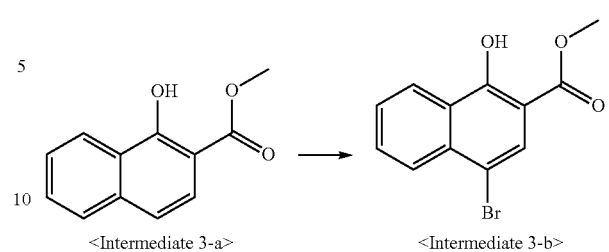

<Reaction Scheme 17>

<Intermediate 3-a>   <Intermediate 3-b>

In a 1-L round-bottom flask reactor, <Intermediate 3-a> (39.0 g, 193 mmol) was stirred together with acetic acid (390 ml) at room temperature. A dilution of acetic acid (80 ml) in bromine (11.8 ml, 231 mmol) was added dropwise thereto. The resulting reaction solution was stirred for 5 hrs at room temperature. After completion of the reaction, the precipitates thus formed were filtered and slurried in heptane to afford <Intermediate 3-b> (50 g, 90%).

Synthesis Example 3-(3): Synthesis of Intermediate 3-c

Intermediate 3-c was synthesized as illustrated in the following Reaction Scheme 18:

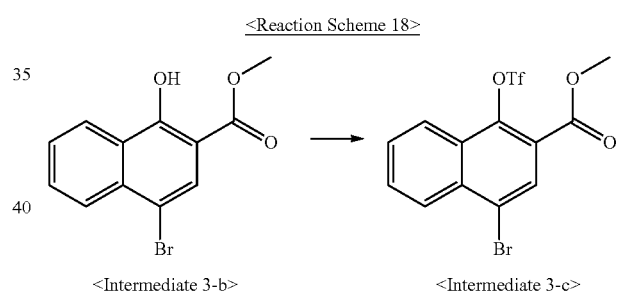

<Reaction Scheme 18>

<Intermediate 3-b>   <Intermediate 3-c>

In a 2-L round-bottom flask reactor, <Intermediate 3-b> (50 g, 178 mmol) was stirred together with dichloromethane. Under a nitrogen atmosphere, pyridine (28.1 g, 356 mmol) was added and stirred at room temperature for 20 min. The resulting solution was cooled to 0° C. and then added with drops of trifluoromethanesulfonic anhydride (65.24 g, 231 mmol) under a nitrogen atmosphere. After 3 hrs of stirring, the completion of the reaction was confirmed by TLC. Water (20 ml) was added, and the mixture was stirred for 10 min. The reaction mixture was concentrated in a vacuum, followed by purification through column chromatography to afford <Intermediate 3-c> (45 g, 61%).

Synthesis Example 3-(4): Synthesis of Intermediate 3-d

Intermediate 3-d was synthesized as illustrated in the following Reaction Scheme 19:

<Reaction Scheme 19>

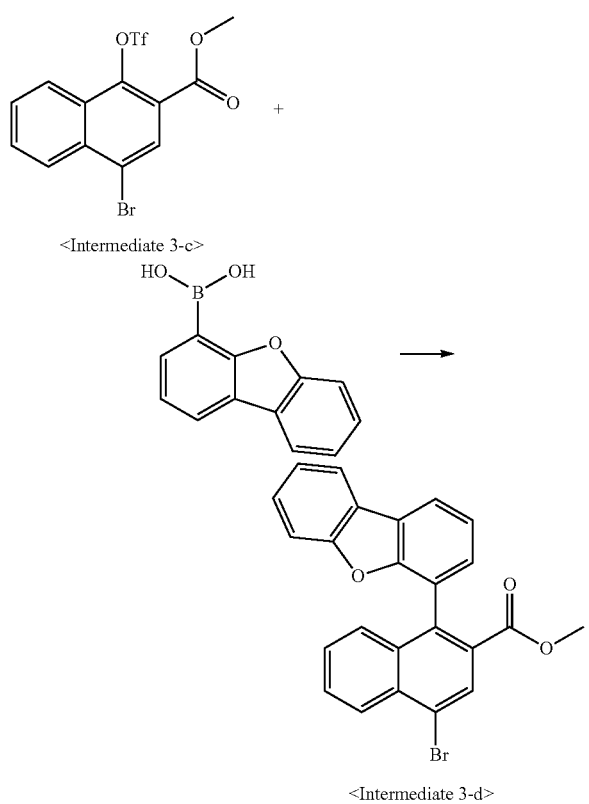

<Intermediate 3-c>

<Intermediate 3-d>

In a 1-L round-bottom flask reactor, a mixture of <Intermediate 3-c> (45.0 g, 0.109 mol), 4-dibenzoboronic acid (25.4 g, 0.120 mol), tetrakis (triphenylphosphine)palladium (2.5 g, 0.22 mmol), and potassium carbonate (30.1 g, 0.218 mol) was stirred together with toluene (300 mL), ethanol (130 mL) and water (90 mL) at 80° C. for 5 hrs. After completion of the reaction, the reaction mixture was cooled to room temperature and extracted with ethyl acetate. The organic layer was isolated and concentrated in a vacuum. Purification through column chromatography afforded Intermediate 3-d. (22.0 g, 46.1%)

Synthesis Example 3-(5): Synthesis of Intermediate 3-e

Intermediate 3-e was synthesized as illustrated in the following Reaction Scheme 20:

<Reaction Scheme 20>

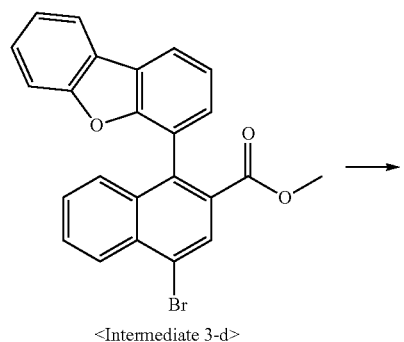

<Intermediate 3-d>

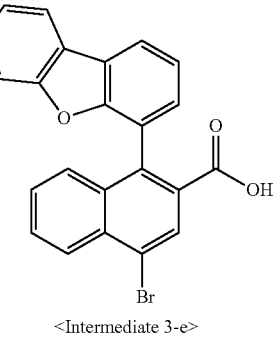

<Intermediate 3-e>

In a 1-L round-bottom flask reactor, <Intermediate 3-d> (22.0, 0.051 mol) was stirred together with sodium hydroxide (2.65 g, 0.066 mol) for 48 hrs under reflux. After completion of the reaction, the reaction mixture was cooled to room temperature. The chilled solution was acidified with drops of 2-N HCl, followed by stirring for 30 min. The solid thus formed was filtered and recrystallized in dichloromethane and n-hexane to afford Intermediate 3-e (17.6 g, 82.7%).

Synthesis Example 3-(6): Synthesis of Intermediate 3-f

Intermediate 3-f was synthesized as illustrated in the following Reaction Scheme 21:

<Reaction Scheme 21>

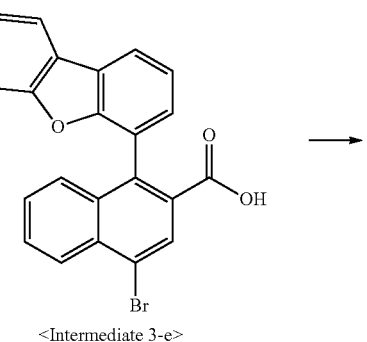

<Intermediate 3-e>

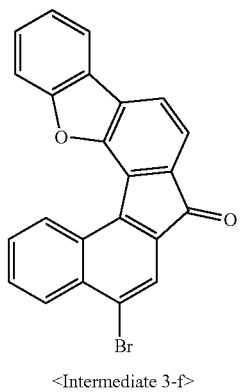

<Intermediate 3-f>

In a 500-mL round-bottom flask reactor, <Intermediate 3-e> (17.6 g, 0.042 mol) and methanesulfonic acid (170 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the precipitates thus formed were filtered and washed with water and methanol. They were dissolved in monochlorobenzene and filtered through a silica gel pad. The filtrate was concentrated by heating and recrystallized in acetone to afford Intermediate 3-f (12 g, 71%).

Synthesis Example 3-(7): Synthesis of Intermediate 3-g

Intermediate 3-g was synthesized as illustrated in the following Reaction Scheme 22:

<Reaction Scheme 22>

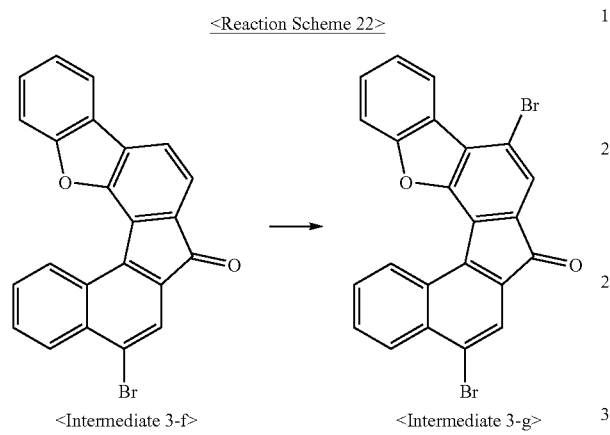

<Intermediate 3-f>     <Intermediate 3-g>

In a 1-L round-bottom flask reactor, Intermediate 3-f (12.0 g, 0.030 mol) and dichloromethane (360 ml) were stirred together at room temperature. A dilution of bromine (3.1 ml, 0.06 mol) in dichloromethane (40 ml) was dropwise added, followed by stirring at room temperature for 12 hrs. After completion of the reaction, methanol (100 ml) was added to induce the formation of precipitates. They were then filtered and washed with methanol. Recrystallization in 1,2-dichlorobenzene and acetone afforded Intermediate 3-g (10.3 g, 71.7%).

Synthesis Example 3-(8): Synthesis of Intermediate 3-h

Intermediate 3-h was synthesized as illustrated in the following Reaction Scheme 23:

<Reaction Scheme 23>

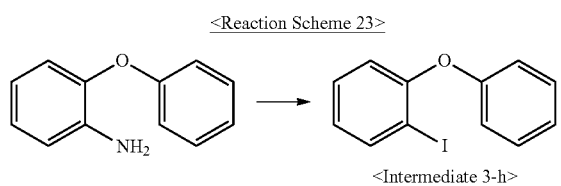 [SMILES: Nc1ccccc1Oc1ccccc1 ; Ic1ccccc1Oc1ccccc1]

<Intermediate 3-h>

In a 1-L round-bottom flask reactor, a mixture of 2-phenoxyaniline (25.0, 0.135 mol), HCl (30 ml), and water (150 ml) was cooled to 0° C. and stirred for 1 hr. At the same temperature, an aqueous solution (75 ml) of sodium nitrite (11.2 g, 0.162 mol) was added and then stirred for 1 hr. An aqueous solution (75 ml) of potassium iodide (44.8 g, 0.270 mol) was dropwise added, taking care not to increase the temperature of the reaction solution above 5° C. Stirring was continued for 5 hrs at room temperature, and after completion of the reaction, the reaction mixture was washed with an aqueous sodium thiosulfate solution and extracted with ethyl acetate and water. The organic layer was separated and concentrated in a vacuum. Purification through column chromatography gave Intermediate 5-a (22.6 g, 56.5%).

Synthesis Example 3-(9): Synthesis of Intermediate 3-i

Intermediate 3-i was synthesized as illustrated in the following Reaction Scheme 24:

<Reaction Scheme 24>

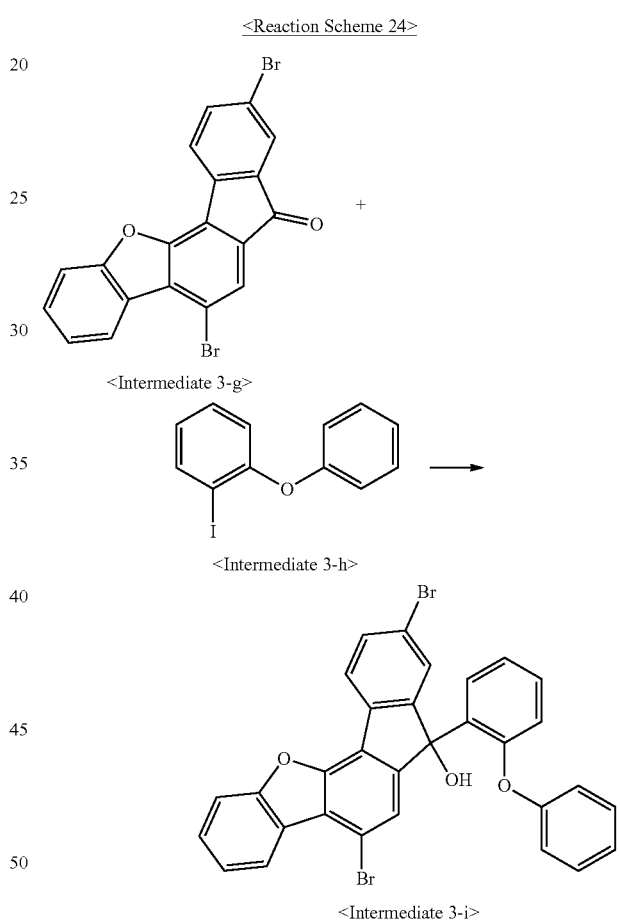

The same procedure was conducted as in Synthesis Example 1-(5), with the exception that Intermediate 3-g and Intermediate 3-h were used respectively instead of Intermediate 1-d and 2-bromobiphenyl, to synthesize Intermediate 3-i (19.6 g, 70.4%).

Synthesis Example 3-(10): Synthesis of Intermediate 3-j

Intermediate 3-j was synthesized as illustrated in the following Reaction Scheme 25:

<Reaction Scheme 25>

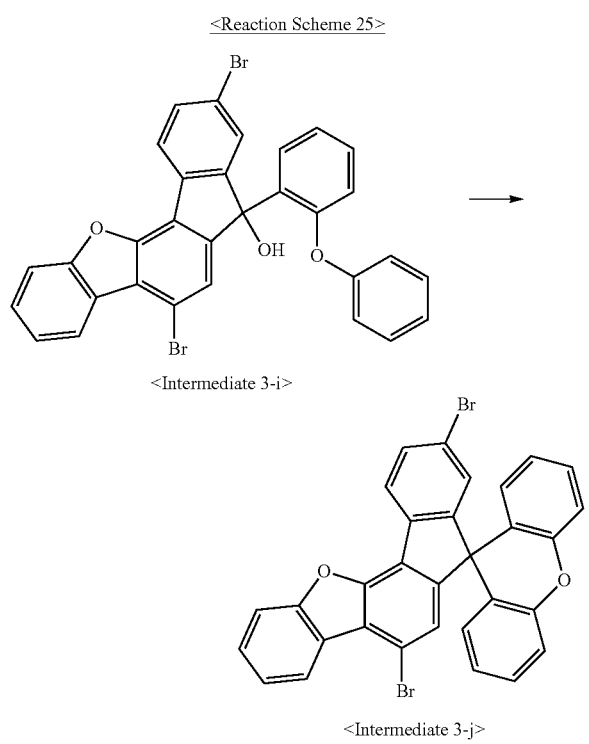

<Intermediate 3-i>

<Intermediate 3-j>

The same procedure was conducted as in Synthesis Example 1-(6), with the exception of using Intermediate 3-i instead of Intermediate 1-e, to synthesize Intermediate 3-j (14.2 g, 74.7%).

Synthesis Example 3-(11): Synthesis of Compound of Chemical Formula 89

The compound of Chemical Formula 89 was synthesized as illustrated in the following Reaction Scheme 26:

<Reaction Scheme 26>

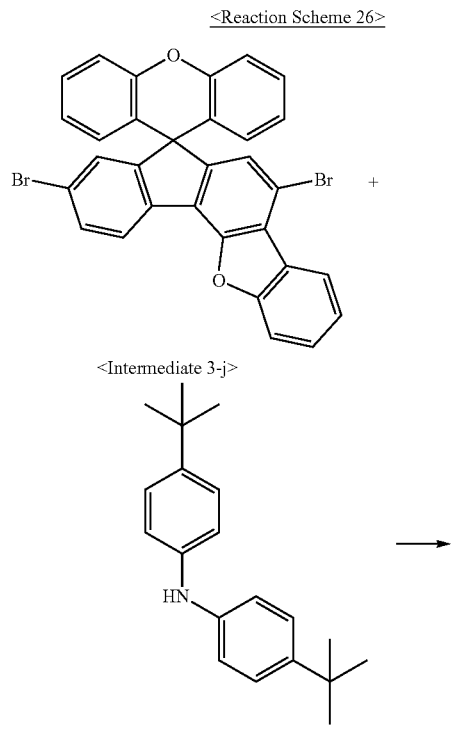

<Intermediate 3-j>

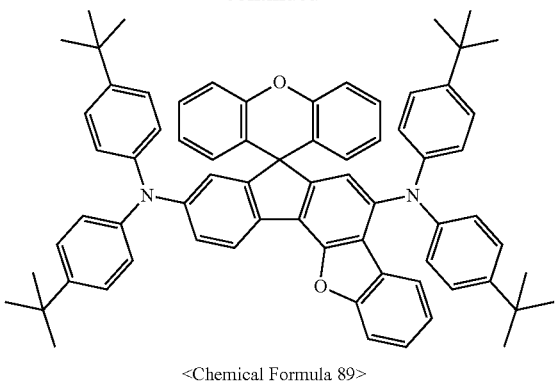

<Chemical Formula 89>

The same procedure was conducted as in Synthesis Example 1-(7), with the exception that Intermediate 3-j and 1,1'-(4-methylphenyl-4-tert-butylphenyl)amine were used respectively instead of Intermediate 1-f and bis(4-tert-butylphenyl)amine, to synthesize the compound of Chemical Formula 23 (2.4 g, 28%).

MS (MALDI-TOF): m/z 980.5 [M$^+$]

Synthesis Example 4: Synthesis of Compound of Chemical Formula 97

Synthetic Example 4-(1): Synthesis of Intermediate 4-a

Intermediate 4-a was synthesized as illustrated in the following Reaction Scheme 27:

<Reaction Scheme 27>

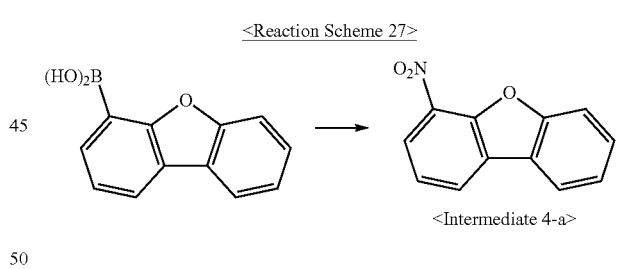

<Intermediate 4-a>

In a 2-L round-bottom flask reactor, 4-dibenzoboronic acid (85.0 g, 0.401 mol), bismuth (III) nitrate pentahydrate (99.2 g, 0.200 mol), and toluene (400 ml) were stirred together at 70° C. for 3 hrs under a nitrogen atmosphere. After completion of the reaction, the reaction mixture was cooled to room temperature, and the precipitates thus formed were filtered and washed with toluene to afford Intermediate 4-a (61.5 g, 72%).

Synthetic Example 4-(2): Synthesis of Intermediate 4-b

Intermediate 4-b was synthesized as illustrated in the following Reaction Scheme 28:

<Reaction Scheme 28>

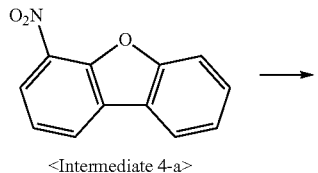

<Intermediate 4-a>

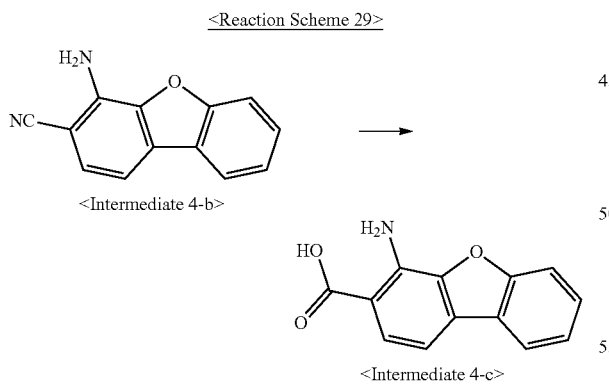

In a 2-L round-bottom flask reactor, ethyl cyanoacetate (202.9 g, 1.794 mol) and dimethylformamide (500 ml) were placed. Potassium hydroxide (67.10 g, 1.196 mol) and potassium cyanide (38.95 g, 0.598 mol) were added thereto, followed by dimethyl formamide (200 ml). The reaction solution was stirred at room temperature. Intermediate 4-a (127.5 g, 0.737 mol) was added little by little to the reaction solution, followed by stirring at 50° C. for 72 hrs. After completion of the reaction, an aqueous sodium hydroxide solution (25%, 200 ml) was added to the reaction solution, which was then stirred for 3 hrs under reflux and cooled to room temperature. Extraction was performed using ethyl acetate and water. The organic layer was isolated and concentrated in a vacuum. Purification through column chromatography afforded Intermediate 4-b (20.0 g, 16%).

Synthetic Example 4-(3): Synthesis of Intermediate 4-c

Intermediate 4-c was synthesized as illustrated in the following Reaction Scheme 29:

In a 2-L round-bottom flask reactor, Intermediate 4-b (20.0 g, 0.096 mol), ethanol (600 ml), and an aqueous potassium hydroxide solution (142.26 g, 2.53 mol, 170 ml) were stirred together for 12 hrs under reflux. After completion of the reaction, the reaction mixture was cooled to room temperature and acidified with 6-N HCl (400 ml). The solid thus formed was stirred for 20 min and filtered. The filtrate was washed with ethanol to afford <Intermediate 4-c> (17.0 g, 88.5%).

Synthetic Example 4-(4): Synthesis of Intermediate 4-d

Intermediate 4-d was synthesized as illustrated in the following Reaction Scheme 30:

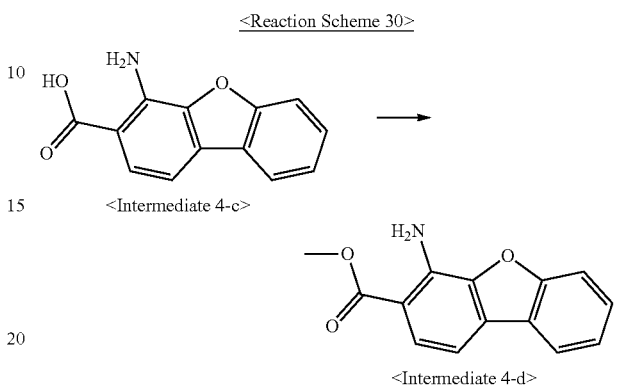

In a 2-L round-bottom flask reactor, Intermediate 4-c (17.0 g, 0.075 mol) and sulfuric acid (15 ml) were stirred together for 72 hrs under reflux. After completion of the reaction, the reaction mixture was cooled to room temperature and then extracted with ethyl acetate and water. The organic layer was isolated and washed with an aqueous sodium hydrogen carbonate, followed by concentration in a vacuum. The concentrate was crystallized in an excess of methanol and filtered to afford <Intermediate 4-d> (14.0 77.6%).

Synthetic Example 4-(5): Synthesis of Intermediate 4-e

Intermediate 4-e was synthesized as illustrated in the following Reaction Scheme 31:

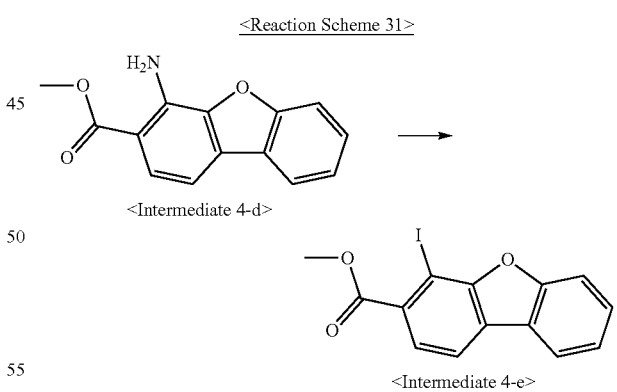

The same procedure was conducted as in Synthesis Example 3-(8), with the exception of using <Intermediate 4-d> instead of 2-phenoxyaniline, to synthesize <Intermediate 4-e> (9.1 g, 48%).

Synthetic Example 4-(6): Synthesis of Intermediate 4-f

Intermediate 4-f was synthesized as illustrated in the following Reaction Scheme 32:

Reaction Scheme 32

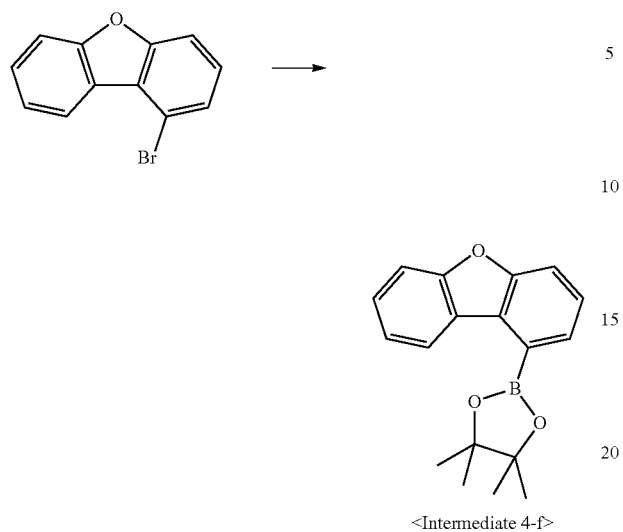

<Intermediate 4-f>

In a 500-mL round-bottom flask reactor, 1-bromodibenzofuran (20.0 g, 0.081 mmol), bis(pinacolato)diboron (26.7 g, 0.105 mol), [1,1'-bis(diphenylphosphino)ferrocene]dichloropalladium (1.3 g, 0.002 mol), potassium acetate (19.9 g, 0.202 mol), and 1,4-dioxane (200 ml) were stirred together for 10 hrs under reflux. After completion of the reaction, filtration was performed through a celite pad. The filtrate was concentrated in a vacuum, purified by column chromatography, and recrystallized in dichloromethane and heptane to afford <Intermediate 4-f> (17.0 g, 70%).

Synthetic Example 4-(7): Synthesis of Intermediate 4-g

Intermediate 4-g was synthesized as illustrated in the following Reaction Scheme 33:

Reaction Scheme 33

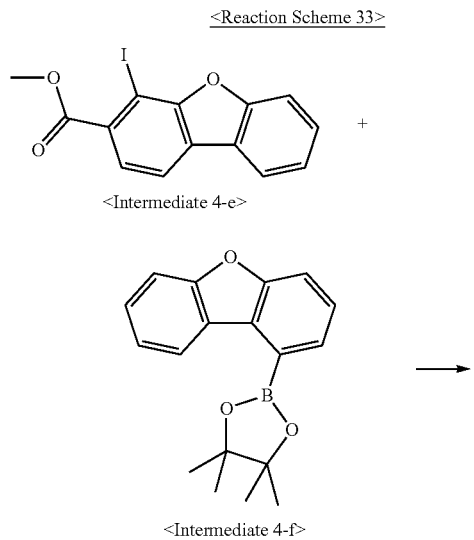

<Intermediate 4-e>

+

<Intermediate 4-f>

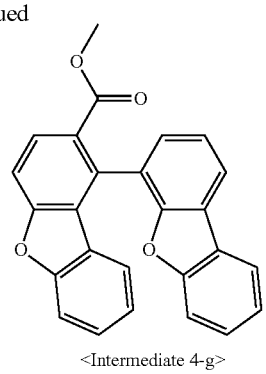

<Intermediate 4-g>

The same procedure was conducted as in Synthesis Example 1-(1), with the exception of using Intermediate 4-e and Intermediate 4-f instead of methyl 5-bromo-2-iodobenzoate and 4-dibenzofuran boronic acid, respectively, to synthesize <Intermediate>4-g (5.3 g, 52.3%).

Synthetic Example 4-(8): Synthesis of Intermediate 4-h

Intermediate 4-h was synthesized as illustrated in the following Reaction Scheme 34:

Reaction Scheme 34

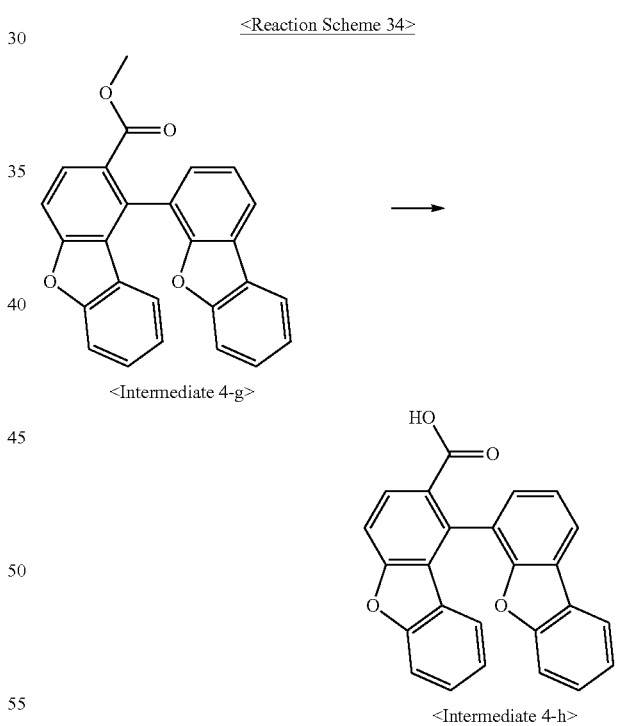

<Intermediate 4-g>

<Intermediate 4-h>

The same procedure was conducted as in Synthesis Example 1-(2), with the exception of using Intermediate 4-g instead of Intermediate 1-a, to synthesize <Intermediate 4-h> (4.5 g, 88.1%).

Synthetic Example 4-(9): Synthesis of Intermediate 4-i

Intermediate 4-i was synthesized as illustrated in the following Reaction Scheme 35:

<Reaction Scheme 35>

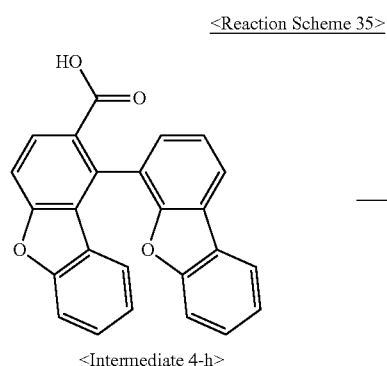

<Intermediate 4-h>

The same procedure was conducted as in Synthesis Example 1-(3), with the exception of using Intermediate 4-h instead of Intermediate 1-b, to synthesize <Intermediate 4-i> (3.8 g, 88.8%).

Synthetic Example 4-(10): Synthesis of Intermediate 4-j

Intermediate 4-j was synthesized as illustrated in the following Reaction Scheme 36:

<Reaction Scheme 36>

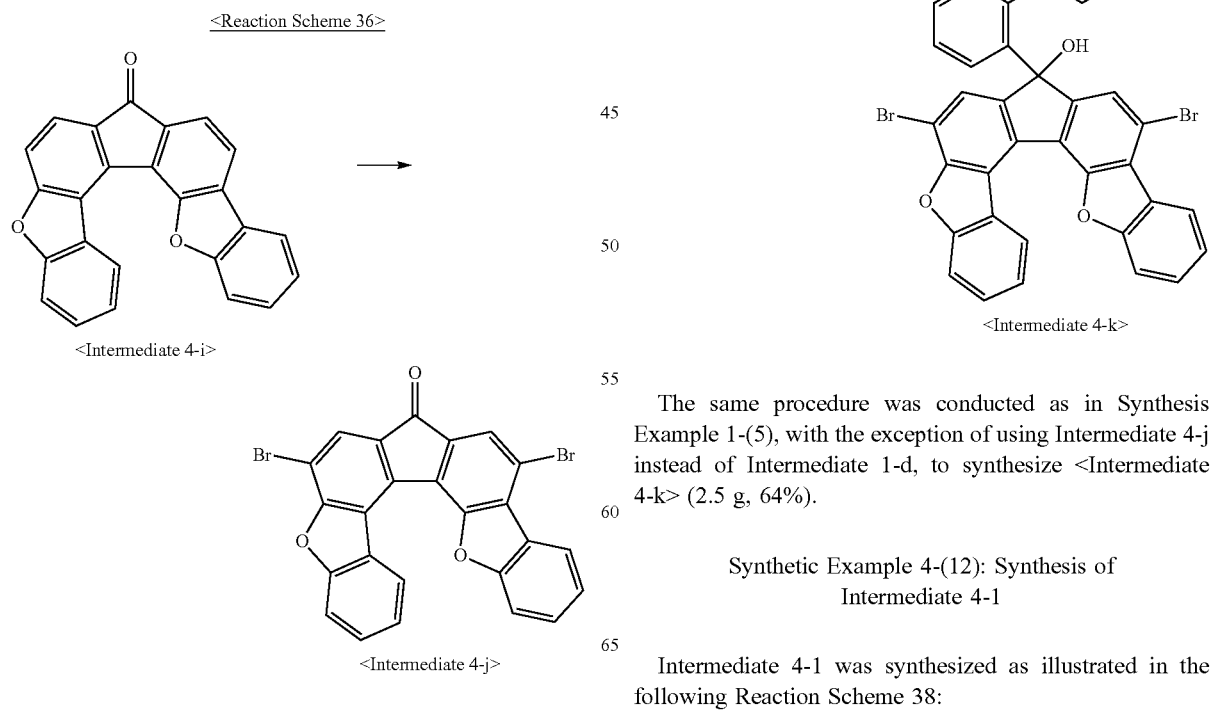

The same procedure was conducted as in Synthesis Example 1-(4), with the exception of using <Intermediate 4-i> instead of <Intermediate 1-c>, to synthesize <Intermediate 4-j> (3 g, 55%).

Synthetic Example 4-(11): Synthesis of Intermediate 4-k

Intermediate 4-k was synthesized as illustrated in the following Reaction Scheme 37:

<Reaction Scheme 37>

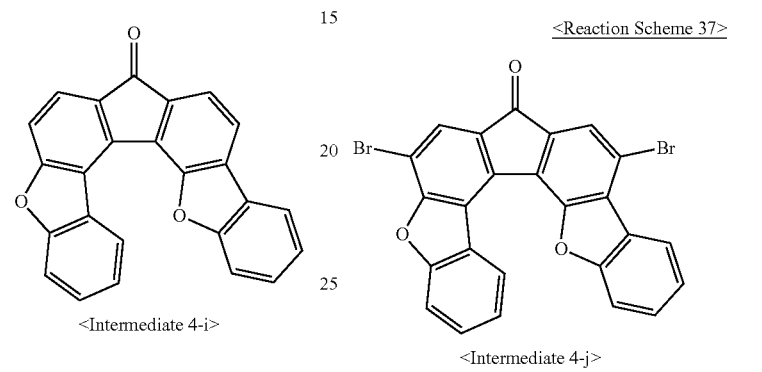

The same procedure was conducted as in Synthesis Example 1-(5), with the exception of using Intermediate 4-j instead of Intermediate 1-d, to synthesize <Intermediate 4-k> (2.5 g, 64%).

Synthetic Example 4-(12): Synthesis of Intermediate 4-l

Intermediate 4-l was synthesized as illustrated in the following Reaction Scheme 38:

<Reaction Scheme 38>

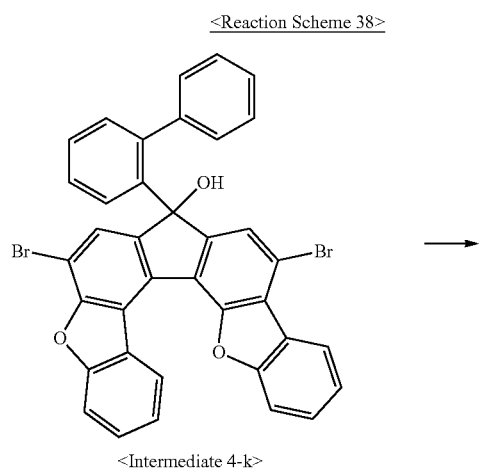

<Intermediate 4-k>

↓

<Intermediate 4-l>

The same procedure was conducted as in Synthesis Example 1-(6), with the exception of using Intermediate 4-k instead of Intermediate 1-e, to afford <Intermediate 4-l> (2.2 g, 90.4%).

Synthetic Example 4-(13): Synthesis of Intermediate 4-m

Intermediate 4-m was synthesized as illustrated in the following Reaction Scheme 39:

<Reaction Scheme 39>

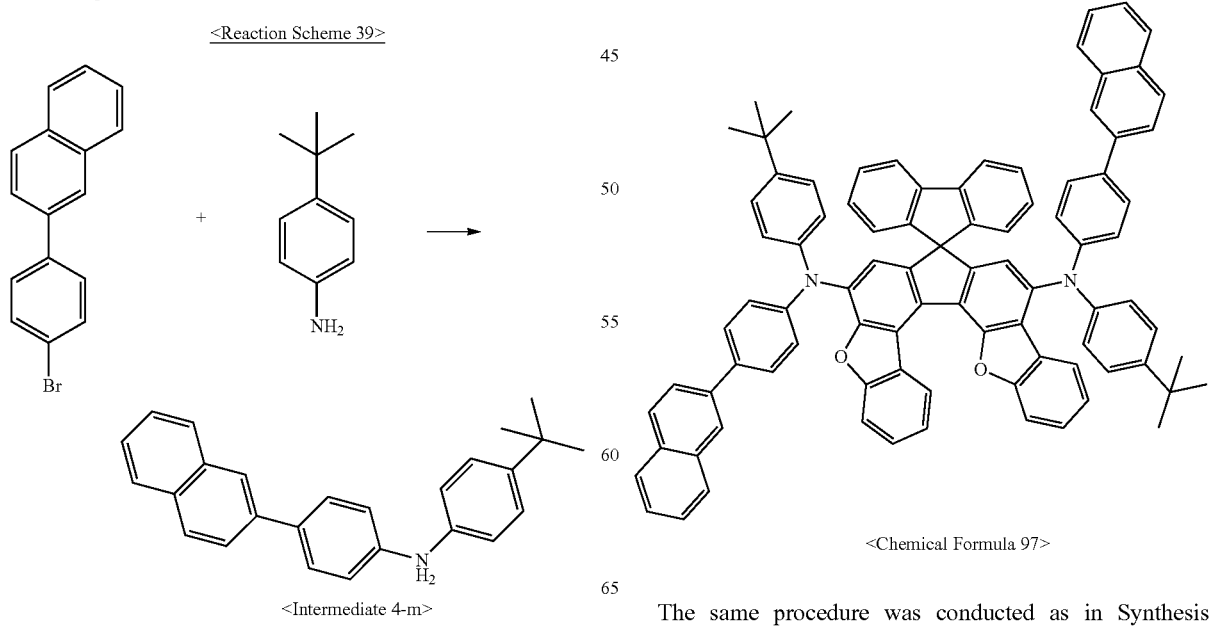

<Intermediate 4-m>

In a 250-ml round-bottom flask reactor, 1-bromo-4-(2-naphthyl)benzene (10.0 g, 0.035 mol), 4-tert-butyl aniline (5.8 g, 0.039 mol), tris(dibenzylidene acetone)dipalladium (0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together for 3 hrs under reflux. After completion of the reaction, the reaction mixture was cooled to room temperature and extracted with ethyl acetate and water. The organic layer was isolated, dried over magnesium sulfate, and concentrated in a vacuum. Purification through column chromatography gave <Intermediate 4-m> (10 g, 80%).

Synthetic Example 4-(14): Synthesis of Compound of Chemical Formula 97

The compound of Chemical Formula 97 was synthesized as illustrated in the following Reaction Scheme 40:

<Reaction Scheme 40>

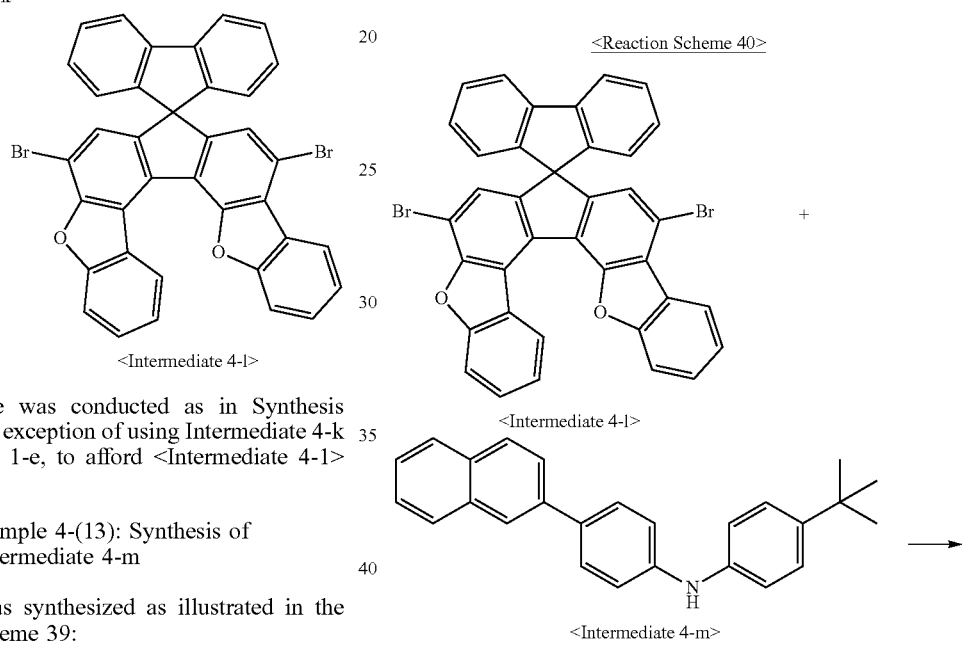

<Chemical Formula 97>

The same procedure was conducted as in Synthesis Example 1-(7), with the exception that Intermediate 4-l and Intermediate 4-m were respectively used instead of Intermediate 1-f and bis(4-tert-butylphenyl)amine, to synthesize the compound of Chemical Formula 97 (1.6 g, 38%).

MS (MALDI-TOF): m/z 1194.5 [M+]

Synthesis Example 5: Synthesis of Compound of Chemical Formula 105

Synthetic Example 5-(1): Synthesis of Intermediate 5-a

Intermediate 5-a was synthesized as illustrated in the following Reaction Scheme 41:

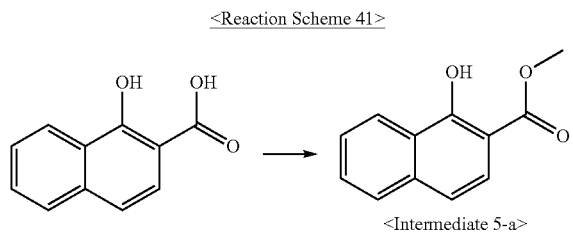

In a 2-L round-bottom flask reactor, 1-hydroxy 2-naphthalic acid (50 g, 266 mmol), methanol (1000 ml), and sulfuric acid (100 ml) were stirred together for 100 hrs under reflux. The completion of the reaction was confirmed by TLC before the reaction mixture was cooled to room temperature. The mixture was concentrated in a vacuum and extracted with dichloromethane and water. The organic layer was isolated, dried over magnesium sulfate, and filtered. The filtrate was concentrated in a vacuum and crystallized in an excess of heptane to afford <Intermediate 5-a> (39 g, 72.6%).

Synthetic Example 5-(2): Synthesis of Intermediate 5-b

Intermediate 5-b was synthesized as illustrated in the following Reaction Scheme 42:

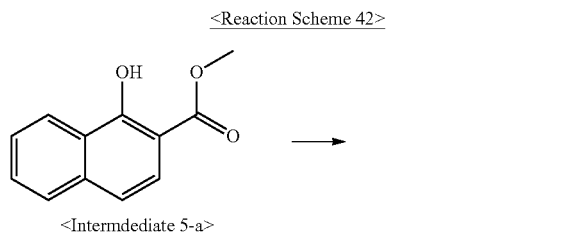

In a 1-L round-bottom flask reactor, Intermediate 5-a (39.0 g, 193 mmol) was stirred together with acetic acid (390 ml) at room temperature. A dilution of acetic acid (80 ml) in bromine (11.8 ml, 231 mmol) was added dropwise thereto. The resulting reaction solution was stirred for 5 hrs at room temperature. After completion of the reaction, the precipitates thus formed were filtered and slurried in heptane to afford <Intermediate 5-b> (50 g, 90%).

Synthetic Example 5-(3): Synthesis of Intermediate 5-c

Intermediate 5-c was synthesized as illustrated in the following Reaction Scheme 43:

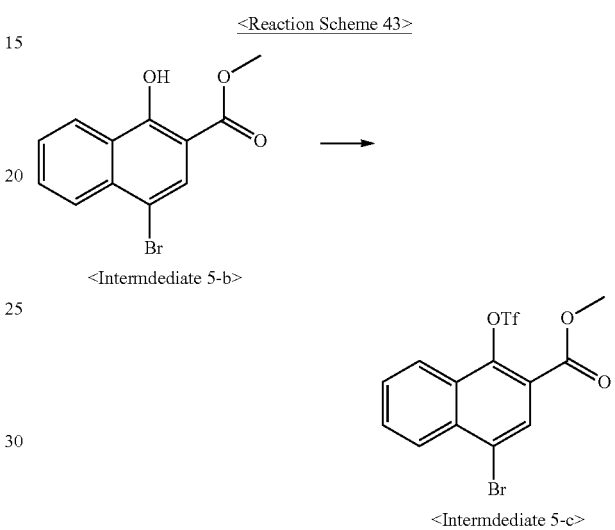

In a 2-L round-bottom flask reactor, Intermediate 5-b (50 g, 178 mmol) was stirred together with dichloromethane. Under a nitrogen atmosphere, pyridine (28.1 g, 356 mmol) was added and stirred at room temperature for 20 min. The resulting solution was cooled to 0° C. and then added with drops of trifluoromethanesulfonic anhydride (65.24 g, 231 mmol) under a nitrogen atmosphere. After 3 hrs of stirring, the completion of the reaction was confirmed by TLC. Water (20 ml) was added, and the mixture was stirred for 10 min. The reaction mixture was concentrated in a vacuum, followed by purification through column chromatography to afford <Intermediate 5-c> (45 g, 61%).

Synthetic Example 5-(4): Synthesis of Intermediate 5-d

Intermediate 5-d was synthesized as illustrated in the following Reaction Scheme 44:

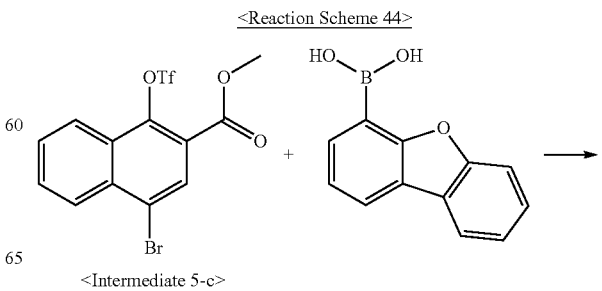

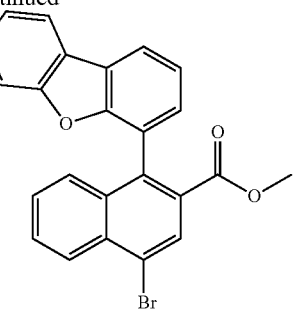

<Intermediate 5-d>

In a 1-L round-bottom flask reactor, a mixture of Intermediate 5-c (45.0 g, 0.109 mol), 4-dibenzofuran boronic acid (25.4 g, 0.120 mol), tetrakis(triphenylphosphine)palladium (2.5 g, 0.22 mmol), and potassium carbonate (30.1 g, 0.218 mol) was stirred together with toluene (300 mL), ethanol (130 mL) and water (90 mL) at 80° C. for 5 hrs. After completion of the reaction, the reaction mixture was cooled to room temperature and extracted with ethyl acetate. The organic layer was isolated and concentrated in a vacuum. Purification through column chromatography afforded <Intermediate 5-d> (22.0 g, 46.1%).

Synthetic Example 5-(5): Synthesis of Intermediate 5-e

Intermediate 5-e was synthesized as illustrated in the following Reaction Scheme 45:

<Reaction Scheme 45>

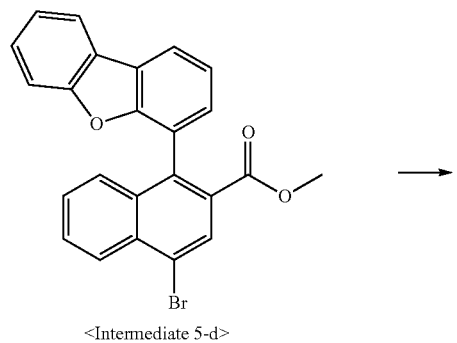

<Intermediate 5-d>

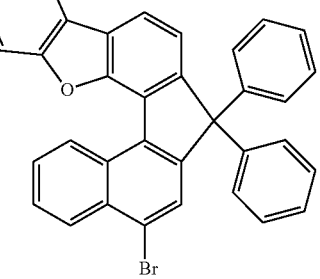

<Intermediate 5-e>

In a 500-mL round-bottom flask reactor, a mixture of bromobenzene (25.46 g, 0.163 mol) and tetrahydrofuran (170 ml) was cooled to −78° C. under a nitrogen atmosphere. N-butyl lithium (1.6 M) (95.6 ml, 0.153 mol) was dropwise added to the chilled solution, which was then stirred at the same temperature for 1 hr. Intermediate 3-d (22.0 g, 0.051 mol) was added, followed by stirring at room temperature for 3 hrs. After completion of the reaction, the reaction mixture was stirred together with water (50 ml) for 30 min. Extraction was made with ethyl acetate and water. The organic layer was isolated and concentrated in a vacuum. The concentrate was stirred together with acetic acid (200 ml) and HCl (1 ml) at 80° C. After the reaction was completed, the precipitate thus formed was filtered and washed with methanol to afford <Intermediate 5-e> (20.0 g, 73%).

Synthetic Example 5-(6): Synthesis of Intermediate 5-f

Intermediate 5-f was synthesized as illustrated in the following Reaction Scheme 46:

<Reaction Scheme 46>

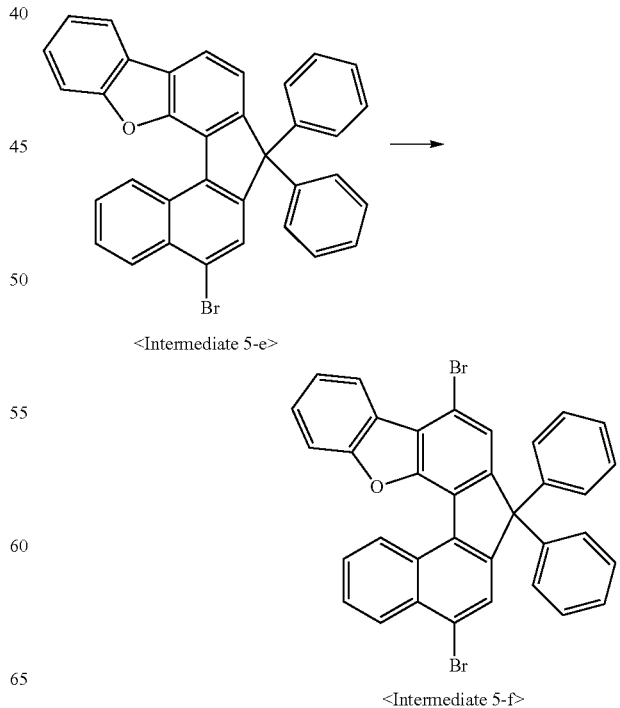

In a 1-L round-bottom flask reactor, a mixture of Intermediate 5-e (20.0 g, 0.037 mol) and chloroform (600 ml) was added with drops of a dilution of bromine (5.7 ml, 0.112 mol) in chloroform (40 ml) while stirring at room temperature for 12 hrs. After completion of the reaction, methanol (100 ml) was added to produce precipitates which were then washed with methanol. They were recrystallized in 1,2-dichlorobenzene and acetone to afford <Intermediate 5-f> (14.0 g, 61.7%).

Synthetic Example 5-(7): Synthesis of Intermediate 5-g

Intermediate 5-g was Synthesized as Illustrated in the Following Reaction Scheme 47:

<Reaction Scheme 47>

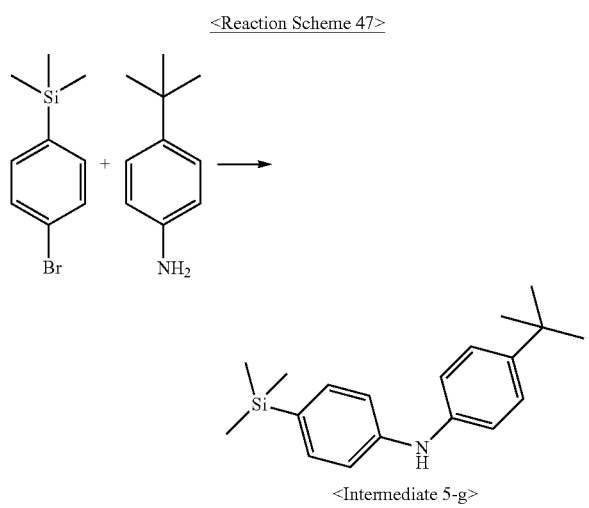

<Intermediate 5-g>

The same procedure was conducted as in Synthesis Example 4-(13), with the exception of using 1-bromo-4-(trimethylsilyl)benzene instead of 1-bromo 4-(2-naphthyl)benzene, to synthesize <Intermediate 5-g> (13.1 g, 72.1%).

Synthetic Example 5-(8): Synthesis of Compound of Chemical Formula 105

The compound of Chemical Formula 105 was synthesized as illustrated in the following Reaction Scheme 48:

<Reaction Scheme 48>

<Intermediate 5-f>

<Intermediate 5-g>

<Chemical Formula 105>

The same procedure was conducted as in Synthesis Example 1-(7), with the exception of using <Intermediate 5-f> and <Intermediate 5-g> respectively instead of Intermediate 1-f and bis(4-tert-butylphenyl)amine, to synthesize the compound of Chemical Formula 36 (3.0 g, 35%).

MS (MALDI-TOF): m/z 1048.5 [M$^+$]

Synthesis Example 6: Synthesis of Compound of Chemical Formula 240

Synthesis Example 6-(1): Synthesis of Intermediate 6-a

Intermediate 6-a was synthesized as illustrated in the following Reaction Scheme 49:

<Reaction Scheme 49>

<Intermediate 6-a>

In toluene (100 mL), a mixture of bromobenzene (8.0 g, 0.050 mol), 2,6-dimethylaniline (6.2 g, 0.050 mol), palladium acetate (0.22 g, 1 mmol), 2,2'-bis(diphenylphosphino(-1-1'-binaphthyl (1.3 g, 2 mmol), and sodium tert-butoxide (12.2 g, 0.120 mol) was fluxed for 12 hrs. After being cooled to room temperature, the reaction mixture was extracted with ethyl acetate. Column chromatography separated <Intermediate 6-a> (7.3 g, 73%).

Synthesis Example 6-(2): Synthesis of Compound of Chemical Formula 240

The compound of Chemical Formula 240 was synthesized as illustrated in the following Reaction Scheme 50:

<Reaction Scheme 50>

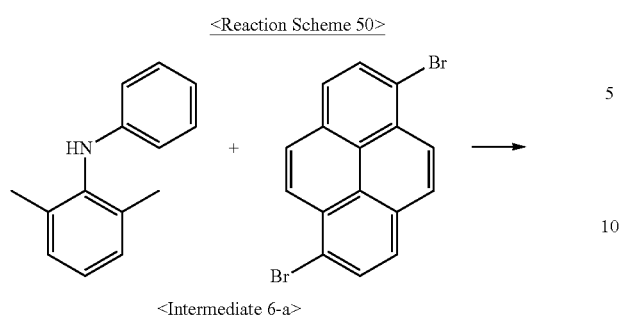

<Intermediate 6-a>

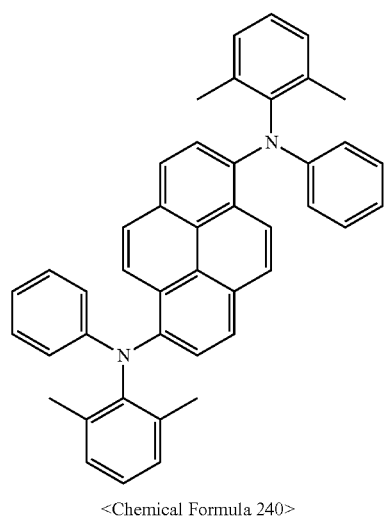

<Chemical Formula 240>

In toluene (50 ml), a mixture of 1,6-dibromopyrene (4 g, 0.011 mol), <Intermediate 6-a> (5.0 g, 0.025 mol), sodium tert-butoxide (5.3 g, 0.055 mol), palladium acetate (0.1 g, 0.44 mmol), and tri-tert-butylphosphine (0.36 g, 1.7 mmol) was fluxed for 24 hrs. After being cooled to room temperature, the reaction mixture was extracted with ethyl acetate. Column chromatography separated the compound of <Chemical Formula 240> (3.1 g, 48%).

MS (MALDI-TOF): m/z 592.29 [M$^+$]

Synthesis Example 7: Synthesis of Compound of Chemical Formula 241

Synthesis Example 7-(1): Synthesis of Intermediate 7-a

Intermediate 7-a was synthesized as illustrated in the following Reaction Scheme 51:

<Reaction Scheme 51>

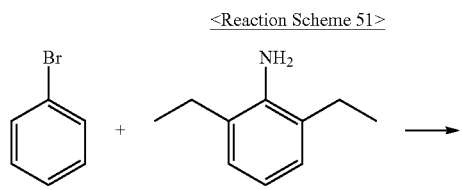

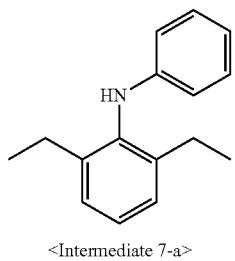

<Intermediate 7-a>

The same procedure was carried out as in Synthesis Example 7-(1), with the exception of using 2,6-diethylaniline instead of 2,6-dimethylaniline, to afford <Intermediate 7-a> (8.7 g, 75%).

Synthesis Example 7-(2): Synthesis of Compound of Chemical Formula 241

The compound of Chemical Formula 241 was synthesized as illustrated in the following Reaction Scheme 52:

<Reaction Scheme 52>

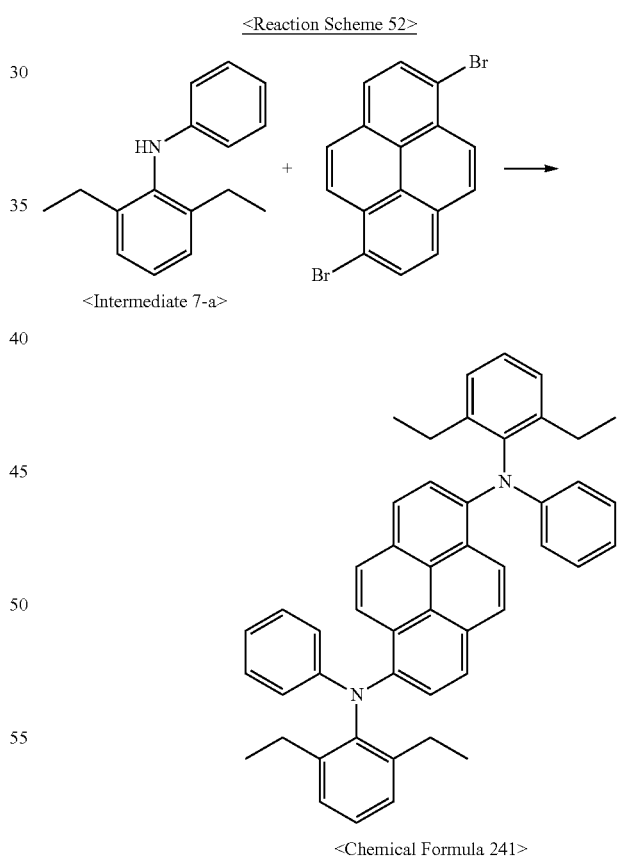

<Chemical Formula 241>

The same procedure was carried out as in Synthesis Example 6-(2), with the exception of using <Intermediate 7-a> instead of <Intermediate 6-a>, to afford the compound of Chemical Formula 241 (6.6 g, 63%).

MS (MALDI-TOF): m/z 648.35 [M$^+$]

Synthesis Example 8: Synthesis of Compound of Chemical Formula 242

Synthesis Example 8-(1): Synthesis of Intermediate 8-a

Intermediate 8-a was synthesized as illustrated in the following Reaction Scheme 53:

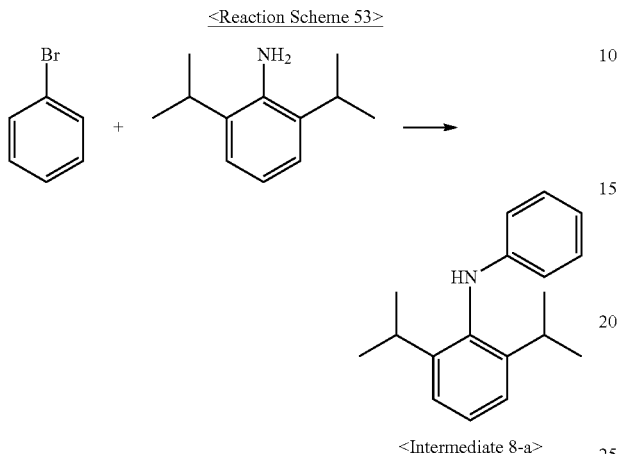

<Intermediate 8-a>

The same procedure was carried out as in Synthesis Example 6-(1), with the exception of using 2, 6-diisopropylaniline instead of 2, 6-dimethylaniline, to afford <Intermediate 8-a> (5.5 g, 75%).

Synthesis Example 8-(2): Synthesis of Compound of Chemical Formula 242

The compound of Chemical Formula 242 was synthesized as illustrated in the following Reaction Scheme 54:

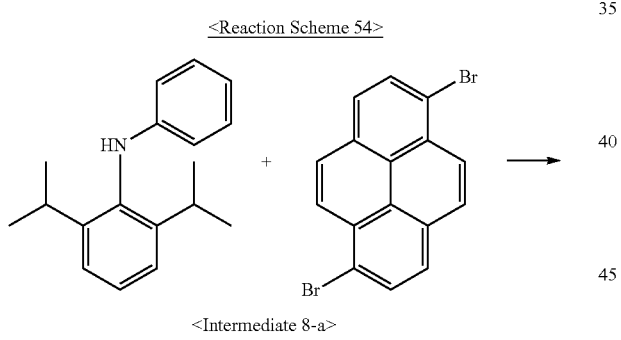

<Chemical Formula 242>

The same procedure was carried out as in Synthesis Example 6-(2), with the exception of using <Intermediate 8-a> instead of <Intermediate 6-a>, to afford the compound of <Chemical Formula 242> (4.7 g, 56%).

MS (MALDI-TOF): m/z 704.41 [M$^+$]

Synthesis Example 9: Synthesis of Compound of Chemical Formula 245

Synthetic Example 9-(1): Synthesis of Intermediate 9-a

Intermediate 9-a was synthesized as illustrated in the following Reaction Scheme 55:

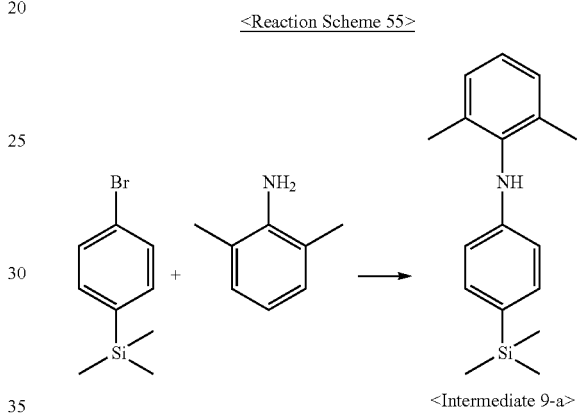

<Intermediate 9-a>

The same procedure was carried out as in Synthetic Example 6-(1), with the exception of using 1-bromo-4-trimethylsilyl benzene instead of bromobenzene, to afford <Intermediate 9-a> (6.1 g, 78%).

Synthetic Example 9-(2): Synthesis of Compound of Chemical Formula 245

The compound of Chemical Formula 245 was synthesized as illustrated in the following Reaction Scheme 56:

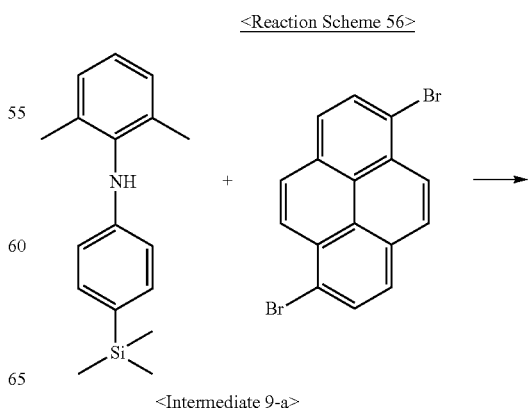

<Intermediate 9-a>

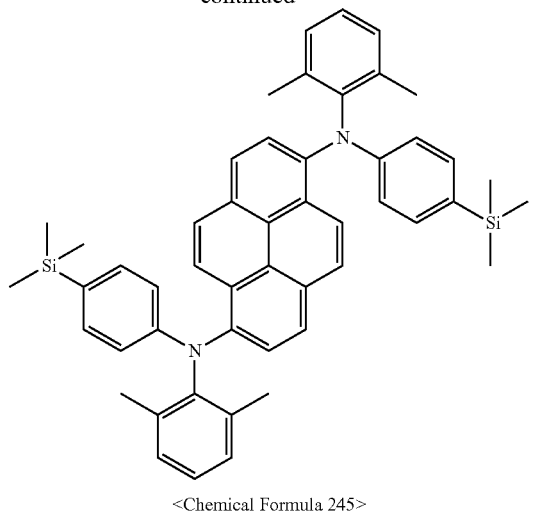

<Chemical Formula 245>

The same procedure was carried out as in Synthetic Example 6-(2), with the exception of using <Intermediate 9-a> instead of <Intermediate 6-a>, to afford the compound of <Chemical Formula 245> (3.9 g, 70%).

MS (MALDI-TOF): m/z 736.37 [$M^+$]

Synthesis Example 10: Synthesis of Compound of Chemical Formula 246

Synthetic Example 10-(1): Synthesis of Intermediate 10-a

Intermediate 10-a was synthesized as illustrated in the following Reaction Scheme 57.

<Reaction Scheme 57>

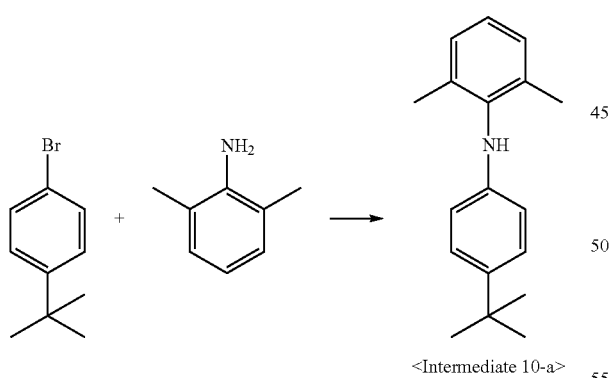

<Intermediate 10-a>

The same procedure was carried out as in Synthetic Example 6-(1), with the exception of using 1-bromo-4-tert-butylbenzene instead of bromobenzene, to afford <Intermediate 10-a> (6.6 g, 77%).

Synthetic Example 10-(2): Synthesis of Compound of Chemical Formula 246

The compound of Chemical Formula 246 was synthesized as illustrated in the following Reaction Scheme 58:

<Reaction Scheme 58>

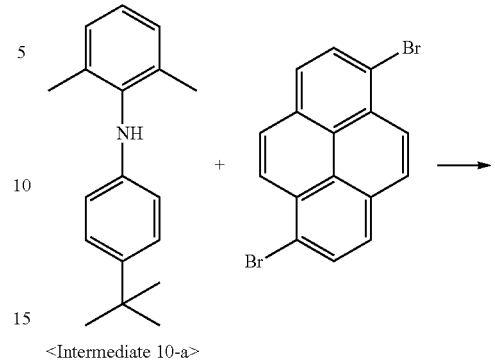

<Intermediate 10-a>

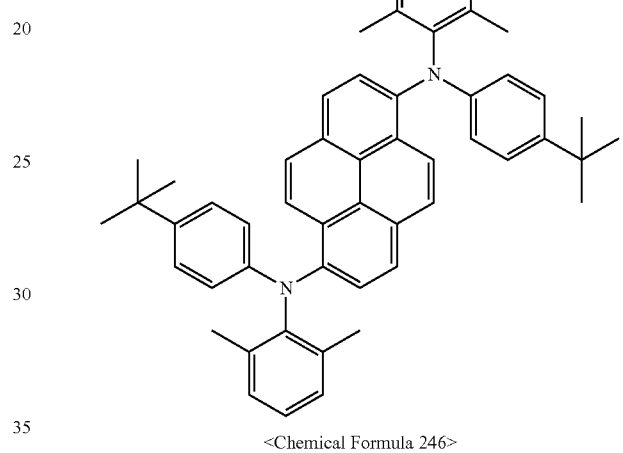

<Chemical Formula 246>

The same procedure was carried out as in Synthetic Example 6-(2), with the exception of using <Intermediate 10-a> instead of <Intermediate 6-a>, to afford the compound of <Chemical Formula 246> (5.9 g, 75%).

MS (MALDI-TOF): m/z 704.41 [$M^+$]

Synthesis Example 11: Synthesis of Compound of <Chemical Formula 247>

Synthetic Example 11-(1): Synthesis of Intermediate 11-a

Intermediate 11-a was synthesized as illustrated in the following Reaction Scheme 59:

<Reaction Scheme 59>

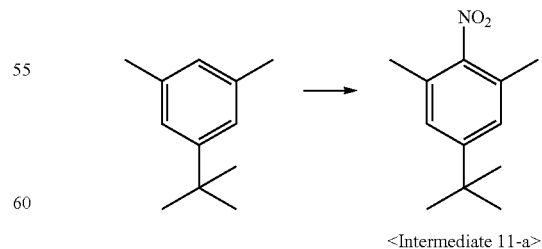

<Intermediate 11-a>

In acetic acid (60 mL), 1-tert-butyl-3,5-dimethyl benzene (15 g, 0.246 mol) was stirred, followed by dropwise adding 40 mL of a 1:1 mixture of sulfuric acid and nitric acid over 20 min thereto. The reaction mixture was heated to 45° C. and then slowly cooled to room temperature. Subsequently, the reaction mixture was poured to water and extracted with ethyl acetate. The organic layer thus formed was washed three times with a 1.0 M potassium hydroxide aqueous solution and condensed, followed by crystallization in hexane to afford <Intermediate 11-a> (27 g, 53%).

Synthetic Example 11-(2): Synthesis of Intermediate 11-b

Intermediate 11-b was synthesized as illustrated in the following Reaction Scheme 60:

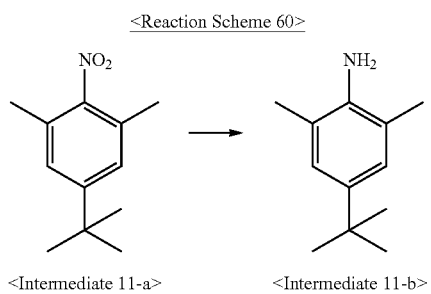

<Intermediate 11-a>      <Intermediate 11-b>

In ethanol (30 mL), <Intermediate 11-a> (15 g, 0.072 mol) and tin chloride (41 g, 0.216 mol) were fluxed together for 24. The reaction mixture was cooled to room temperature and stirred in an aqueous potassium hydroxide solution. After extraction with ethyl acetate, column chromatography separated <Intermediate 11-b> (7 g, 55%).

Synthetic Example 11-(3): Synthesis of Intermediate 11-c

Intermediate 11-c was synthesized as illustrated in the following Reaction Scheme 61:

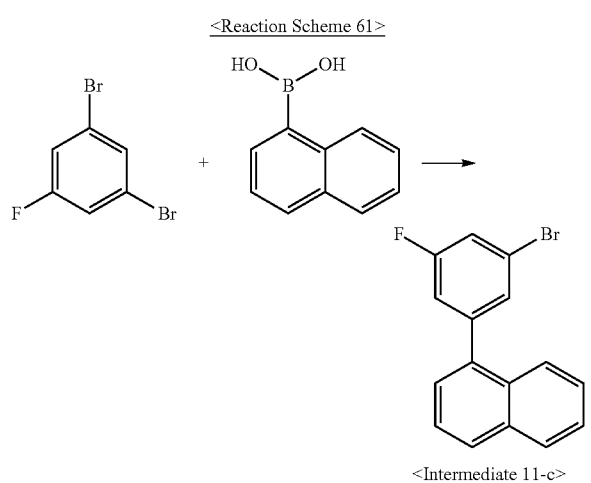

<Intermediate 11-c>

A mixture of 1,3-dibromo-5-fluorobenzene (10 g, 0.039 mol), 1-naphthyl boronic acid (6.7 g, 0.039 mol), tetrakis(triphenylphosphine) palladium (0.9 g, 0.78 mmol), and potassium carbonate (16.2 g, 0.117 mol) was fluxed for 12 hrs in toluene (150 mL) and distilled water (50 mL). The reaction mixture was cooled to room temperature and extracted with ethyl acetate, followed by column chromatography to separate <Intermediate 11-c> (8.5 g, 72%).

Synthetic Example 11-(4): Synthesis of Intermediate 11-d

Intermediate 11-d was synthesized as illustrated in the following Reaction Scheme 62:

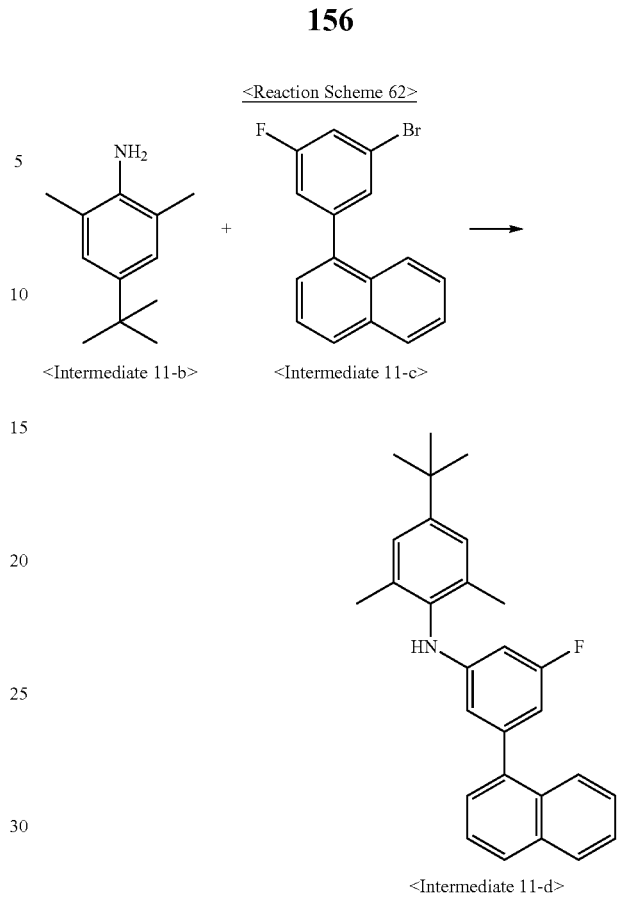

<Intermediate 11-b>      <Intermediate 11-c>

<Intermediate 11-d>

The same procedure as in Synthetic Example 6-(1), with the exception of using <Intermediate 11-b> and <Intermediate 11-c> respectively instead of 2,6-dimethylaniline and bromobenzene, was carried out to afford <Intermediate 11-d> (8.3 g, 74%).

Synthetic Example 11-(5): Synthesis of Compound of Chemical Formula 247

The compound of Chemical Formula 247 was synthesized as illustrated in the following Reaction Scheme 63:

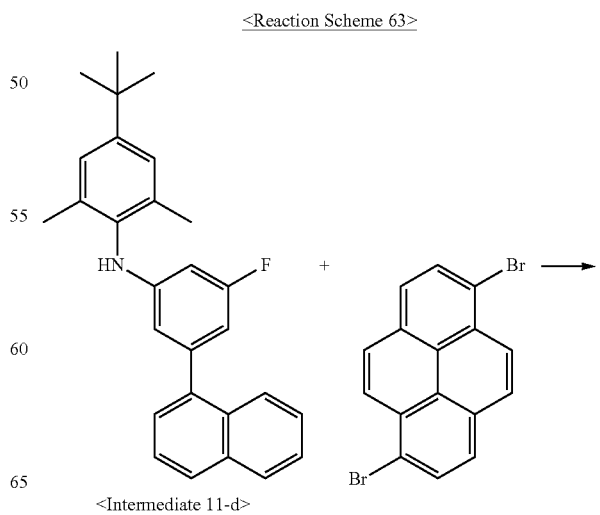

<Intermediate 11-d>

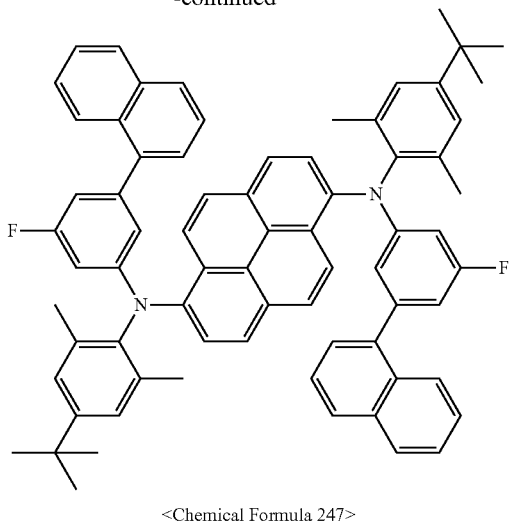

<Chemical Formula 247>

The same procedure was carried out as in Synthetic Example 6-(2), with the exception of using <Intermediate 11-d> instead of <Intermediate 6-a>, to afford the compound of <Chemical Formula 247> (11.5 g, 56%).

MS (MALDI-TOF): m/z 992.49 [M⁺]

Synthesis Example 12: Synthesis of Compound of <Chemical Formula 249>

Synthetic Example 12-(1): Synthesis of Intermediate 12-a

Intermediate 12-a was synthesized as illustrated in the following Reaction Scheme 64:

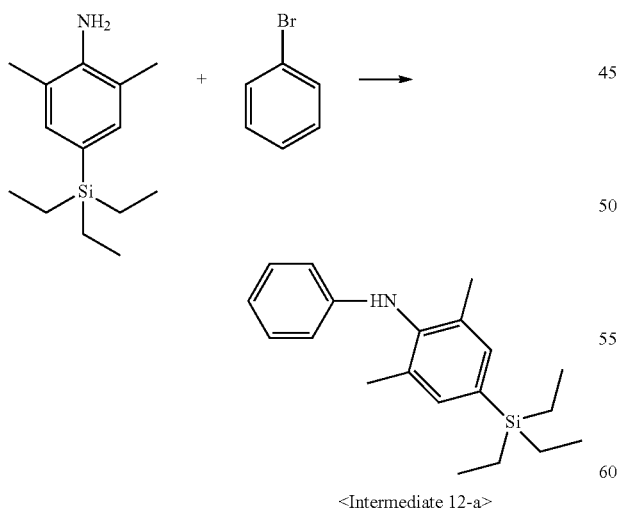

<Reaction Scheme 64>

<Intermediate 12-a>

The same procedure was carried out as in Synthetic Example 6-(1), with the exception of using 4-trimethylsilyl-2,6-dimethylaniline instead of 2,6-dimethylaniline, to afford <Intermediate 12-a> (7.4 g, 66%).

Synthetic Example 12-(2): Synthesis of Compound of Chemical Formula 249

The compound of Chemical Formula 249 was synthesized as illustrated in the following Reaction Scheme 65:

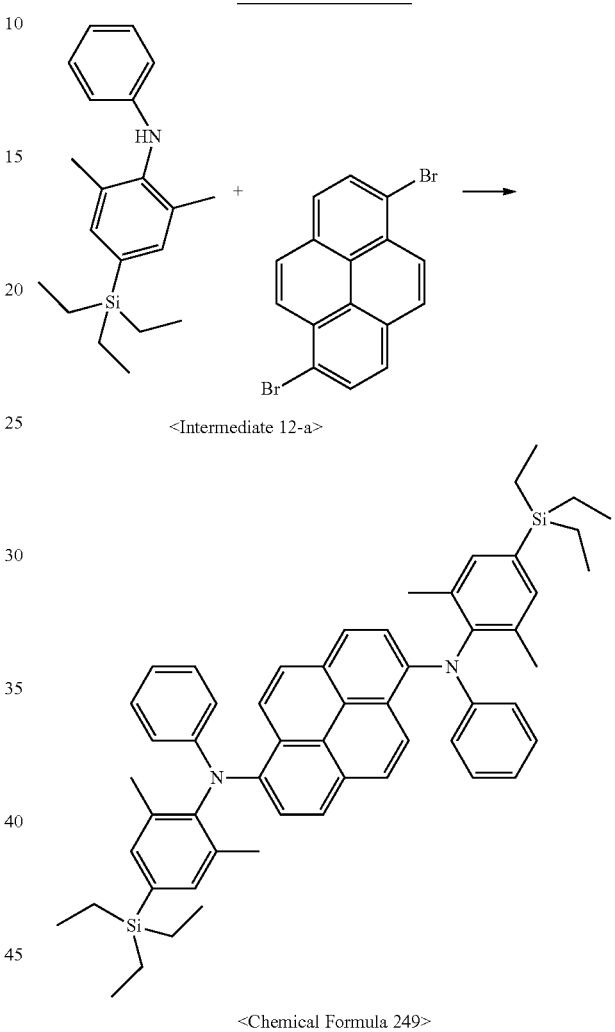

<Reaction Scheme 65>

<Intermediate 12-a>

<Chemical Formula 249>

The same procedure was carried out as in Synthetic Example 6-(2), with the exception of using <Intermediate 12-a> instead of <Intermediate 6-a>, to afford the compound of <Chemical Formula 249> (10.6 g, 58%)

MS (MALDI-TOF): m/z 820.46 [M⁺]

Synthesis Example 13: Synthesis of Compound of <Chemical Formula 250>

Synthetic Example 13-(1): Synthesis of Intermediate 13-a

Intermediate 13-a was synthesized as illustrated in the following Reaction Scheme 66:

<Reaction Scheme 66>

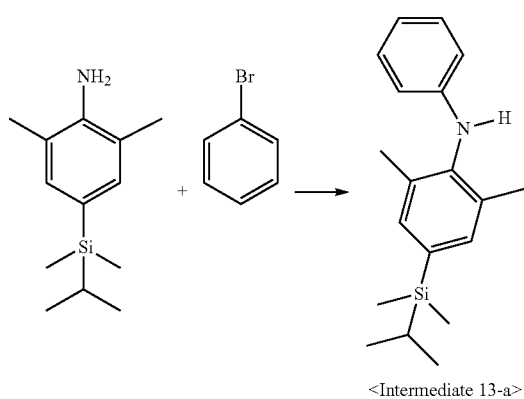

<Intermediate 13-a>

The same procedure was carried out as in Synthetic Example 6-(1), with the exception of using 4-dimethyldiisopropylsilyl-2,6-dimethylaniline instead of 2,6-dimethylaniline, to afford <Intermediate 13-a> (15.3 g, 81%).

Synthetic Example 13-(2): Synthesis of Compound of Chemical Formula 250

The compound of Chemical Formula 250 was synthesized as illustrated in the following Reaction Scheme 67:

<Reaction Scheme 67>

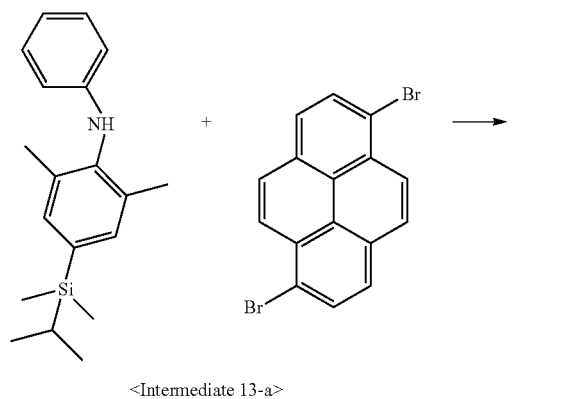

<Chemical Formula 250>

The same procedure was carried out as in Synthetic Example 6-(2), with the exception of using <Intermediate 13-a> instead of <Intermediate 6-a>, to afford <Chemical Formula 250> (9.3 g, 51%).

MS (MALDI-TOF): m/z 792.43 [M$^+$]

Synthesis Example 14: Synthesis of Compound of <Chemical Formula 251>

Synthetic Example 14-(1): Synthesis of Intermediate 14-a

Intermediate 14-a was synthesized as illustrated in the following Reaction Scheme 68:

<Reaction Scheme 68>

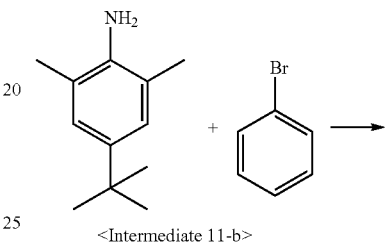

<Intermediate 11-b>

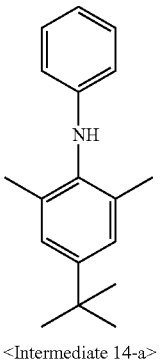

<Intermediate 14-a>

The same procedure was carried out as in Synthetic Example 6-(1), with the exception of using <Intermediate 11-b> instead of 2,6-dimethylaniline, to afford <Intermediate 14-a> (11.1 g, 79%).

Synthetic Example 14-(2): Synthesis of Intermediate 14-b

Intermediate 14-b was synthesized as illustrated in the following Reaction Scheme 69:

<Reaction Scheme 69>

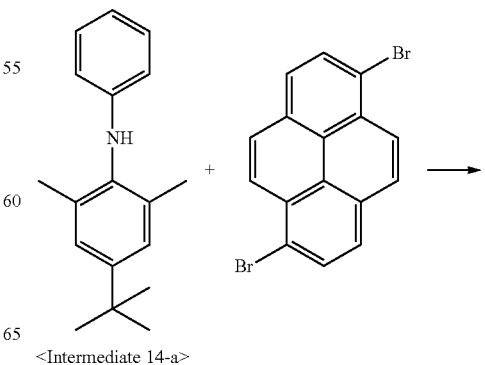

<Intermediate 14-a>

-continued

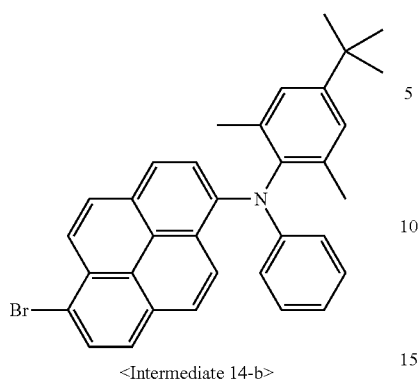

<Intermediate 14-b>

The same procedure was carried out as in Synthetic Example 6-(2), with the exception of using <Intermediate 14-a> instead of <Intermediate 6-a>, to afford <Intermediate 14-b> (6.8 g, 62%).

Synthetic Example 14-(3): Synthesis of Intermediate 14-c

Intermediate 14-c was synthesized as illustrated in the following Reaction Scheme 70:

<Reaction Scheme 70>

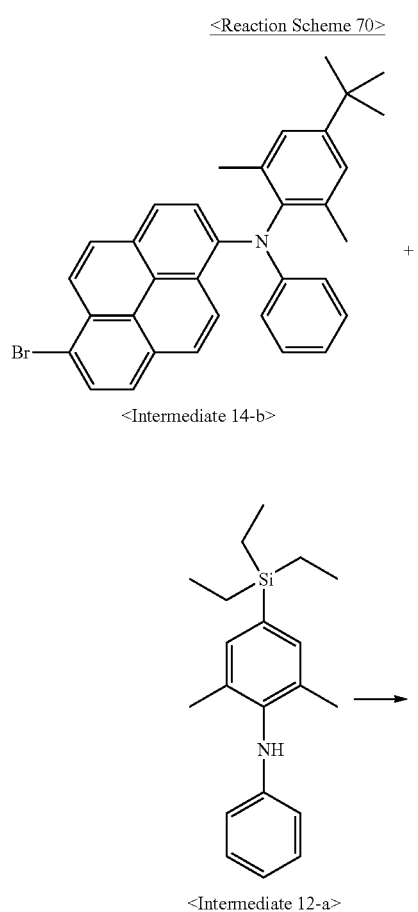

-continued

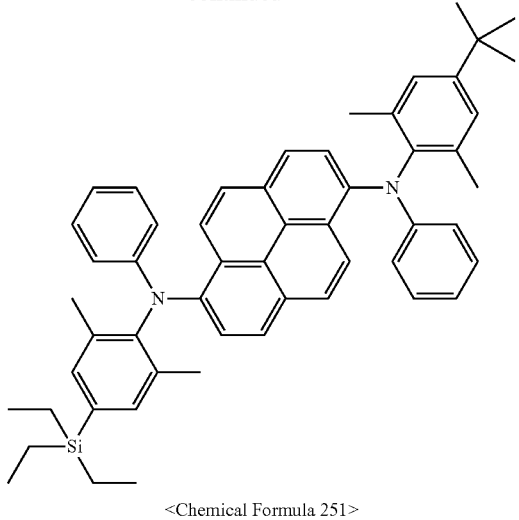

<Chemical Formula 251>

The same procedure was carried out as in Synthetic Example 6-(2), with the exception of using <Intermediate 12-a> and <Intermediate 14-b> instead of <Intermediate 6-a> and 1,6-dibromopyrene, respectively, to afford the compound of <Chemical Formula 251> (6.6 g, 47%).

MS (MALDI-TOF): m/z 762.44 [M⁺]

II. Preparation of Host Compounds

Synthesis Example 15: Synthesis of Compound 1

Synthetic Example 15-(1): Synthesis of Intermediate 15-a

Intermediate 15-a was synthesized as illustrated in the following Reaction Scheme 71:

<Reaction Scheme 71>

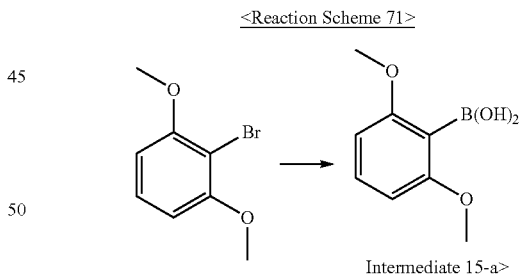

Intermediate 15-a>

In a 1-L round-bottom flask, 1-bromo-2.6-dimethoxy benzene (50 g, 230 mmol) was dissolved in tetrahydrofuran (400 ml) under a nitrogen atmosphere. The solution was cooled to −78° C. and added with drops of n-butyl lithium (167 ml, 280 mmol). Thereafter, the solution was stirred for 2 hrs at the same temperature and then overnight together with trimethyl borate (36 ml, 320 mmol) at room temperature. After completion of the reaction, drops of 2 N HCl was slowly added for acidification. Extraction was made with water and ethyl acetate, and the organic layer thus formed was isolated and dried over magnesium sulfate, followed by concentration in a vacuum and recrystallization in heptane and toluene to afford <Intermediate 15-a> (20.8 g, 50%).

Synthetic Example 15-(2): Synthesis of Intermediate 15-b

Intermediate 15-b was synthesized as illustrated in the following Reaction Scheme 72:

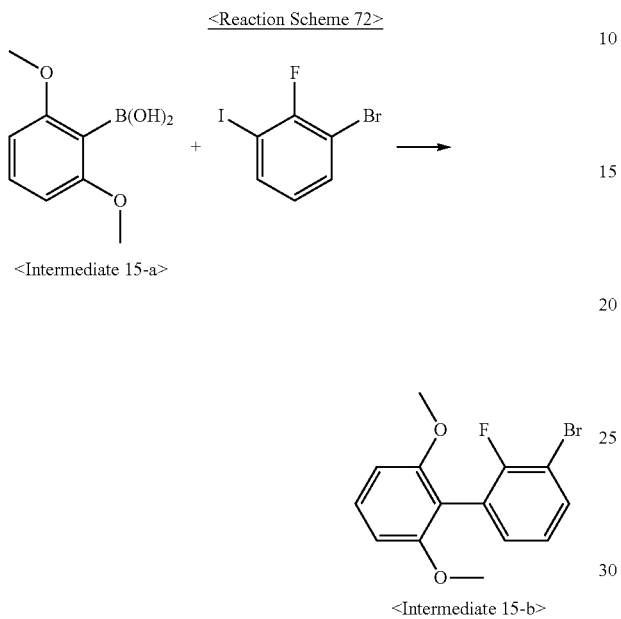

In a 500-ml round-bottom flask reactor, <Intermediate 15-a> (20.8 g, 110 mmol), 1-bromo 2-fluoro-3-iodo benzene (28.7 g, 95 mmol), tetrakis(triphenylphosphine) palladium (33 g, 29 mmol), and sodium carbonate (30.3 g, 290 mmol) were stirred together with toluene (200 ml), ethanol (60 ml) and water (60 ml) for 12 hrs. After completion of the reaction, the temperature of the reactor was decreased to room temperature, and extraction was made with ethyl acetate. The organic layer thus formed was isolated and concentrated in a vacuum, followed by column chromatography to separate <Intermediate 15-b> (22.3 g, 63%).

Synthetic Example 15-(3): Synthesis of Intermediate 15-c

Intermediate 15-c was synthesized as illustrated in the following Reaction Scheme 73:

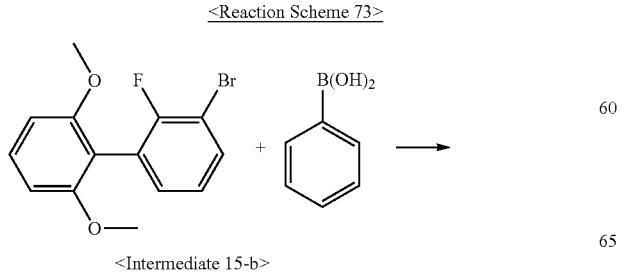

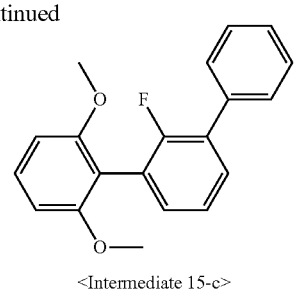

In a 500-ml round bottom flask reactor, <Intermediate 15-b> (22.3 g, 72 mmol), phenyl boronic acid (10.5 g, 86 mmol), tetrakis(triphenylphosphine) palladium (2.5 g, 2.2 mmol), and potassium carbonate (29.7 g, 22 mmol) were stirred overnight together with toluene (160 ml), ethanol (70 ml) and water (70 ml). After completion of the reaction, the reaction mixture was cooled to room temperature and extracted with water and ethyl acetate. The organic layer was isolated and concentrated in a vacuum, followed by recrystallization in heptane to afford <Intermediate 15-c> (16.3 g, 74%).

Synthetic Example 15-(4): Synthesis of Intermediate 15-d

Intermediate 15-d was synthesized as illustrated in the following Reaction Scheme 74:

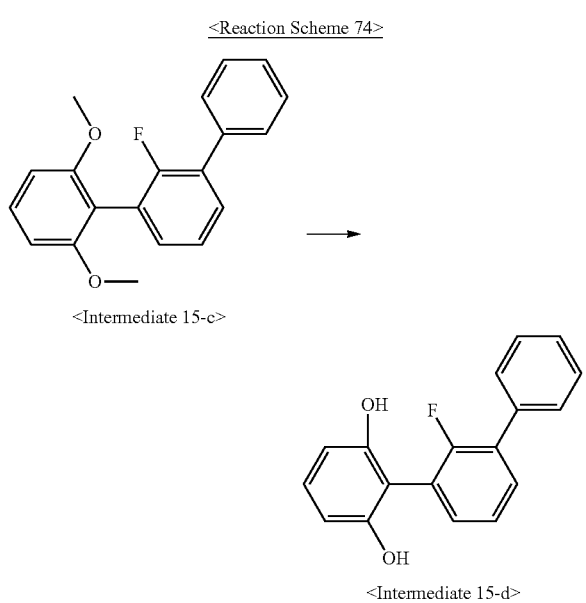

In a 500-ml round bottom flask reactor, <Intermediate 15-c> (16.3 g, 53 mmol), hydrobromic acid (48 ml, 260 mmol), and acetic acid (100 ml) were stirred together for 12 hrs. After completion of the reaction, the reaction mixture was cooled to room temperature and then stirred together with water. Extraction was made with water and ethyl acetate. The organic layer thus formed was isolated, concentrated in a vacuum, recrystallized in heptane, filtered and dried to afford <Intermediate 15-d> (14 g, 95%).

Synthetic Example 15-(5): Synthesis of Intermediate 15-e

Intermediate 15-e was synthesized as illustrated in the following Reaction Scheme 75:

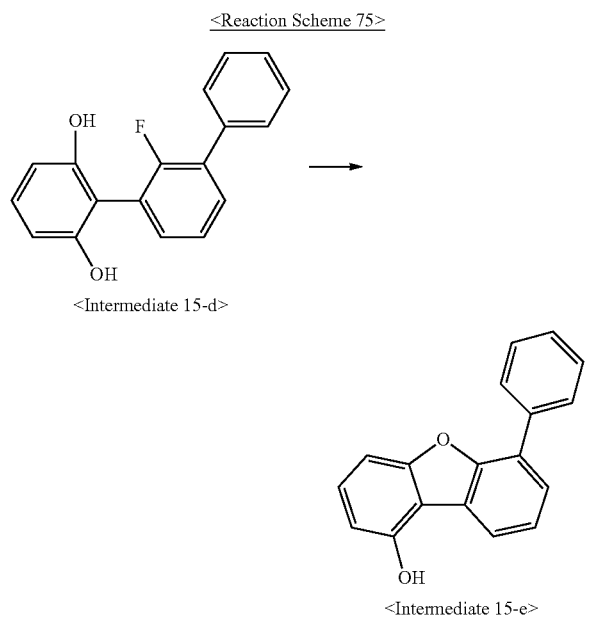

<Reaction Scheme 75>

<Intermediate 15-d>

<Intermediate 15-e>

In a 500-ml round bottom flask reactor, <Intermediate 15-d> (14 g, 50 mmol), potassium carbonate (20.7 g, 150 mmol), and N-methyl-2-pyrrolidone (112 ml) was stirred together for 12 hrs. After completion of the reaction, the reaction mixture was cooled to room temperature and extracted with water and ethyl acetate. The organic layer was isolated and concentrated in a vacuum, followed by recrystallization in heptane to afford <Intermediate 15-e> (10.5 g, 81%).

Synthetic Example 15-(6): Synthesis of Intermediate 15-f

Intermediate 15-f was synthesized as illustrated in the following Reaction Scheme 76:

<Reaction Scheme 76>

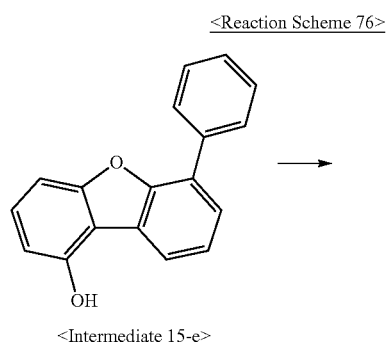

<Intermediate 15-e>

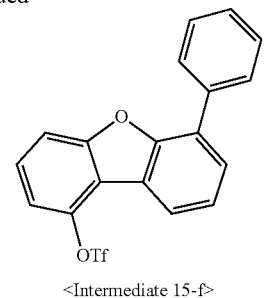

<Intermediate 15-f>

In a 500-ml round bottom flask reactor, <Intermediate 15-e> (10.5 g, 40 mmol) was dissolved in dichloromethane (136 ml) under a nitrogen atmosphere. The solution was cooled to 0° C. and added with pyridine (10 ml, 110 mmol) and then with drops of trifluoromethanesulfonyl anhydride (12.7 g, 68 mmol) at the same temperature. The reaction mixture was stirred at room temperature for 12 hrs and then together with water (20 ml). Extraction was made with water and dichloromethane. The organic layer thus formed was isolated and concentrated in a vacuum, followed by recrystallization in heptane to afford <Intermediate 15-f> (7.5 g, 47%).

Synthetic Example 15-(7): Synthesis of Compound 1

Compound 1 was synthesized as illustrated in the following Reaction Scheme 77:

<Reaction Scheme 77>

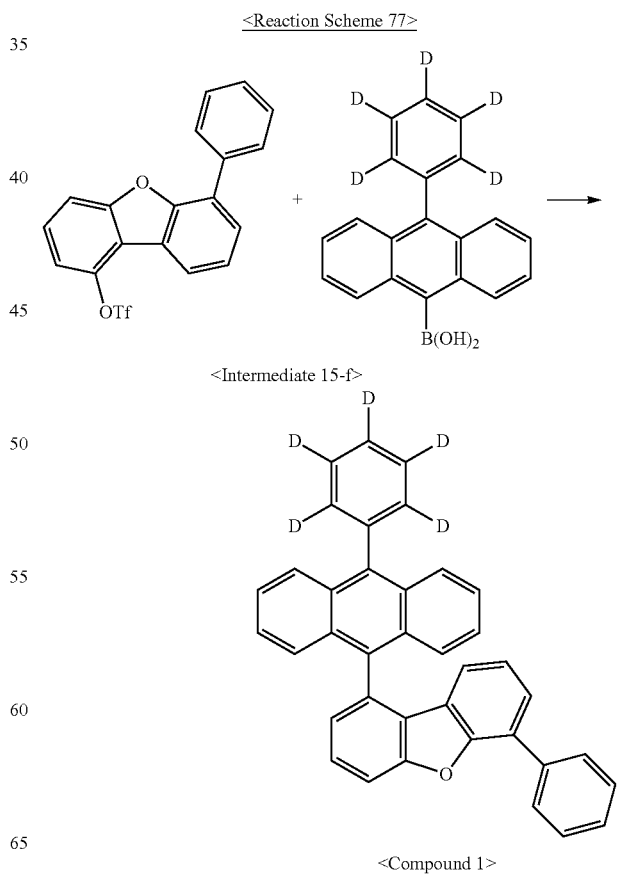

<Intermediate 15-f>

<Compound 1>

In a 250-ml round bottom flask reactor, <Intermediate 15-f> (7.5 g, 19 mmol), 10-phenyl(d5)-anthracene-9-boronic acid (7 g, 23 mmol), tetrakis(triphenylphosphine) palladium (0.66 g, 0.6 mmol), and potassium carbonate (7.9 g, 57 mmol) were stirred together with toluene (53 ml), ethanol (23 ml) and water (23 ml) for 12 hrs. After completion of the reaction, the reaction mixture was cooled to room temperature and added with methanol. The organic layer was isolated, concentrated in a vacuum, and recrystallized in toluene and acetone to afford Compound 1 (6 g, 63%).

MS (MALDI-TOF): m/z 501.21 [M+]

Synthesis Example 16: Synthesis of Compound 4

Synthetic Example 16-(1): Synthesis of Compound 4

Compound 4 was synthesized as illustrated in the following Reaction Scheme 78:

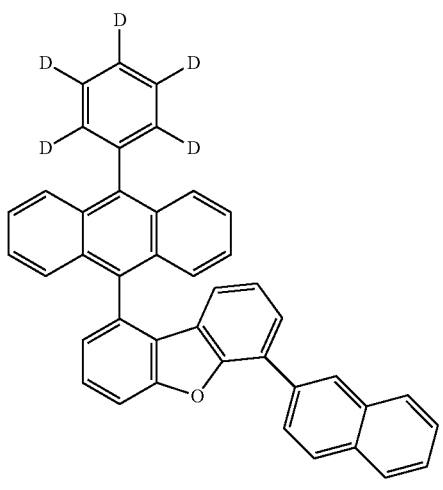

<Reaction Scheme 78>

<Compound 4>

The same procedure was carried out as in Synthetic Example 15-(3), with the exception of using naphthalene-2-boronic acid instead of phenyl boronic acid, to afford Compound 4 (23 g, 57%).

MS (MALDI-TOF): m/z 551.23 [M+]

Synthesis Example 17: Synthesis of Compound 5

Synthetic Example 17-(1): Synthesis of Compound 5

Compound 5 was synthesized as illustrated in the following Reaction Scheme 79:

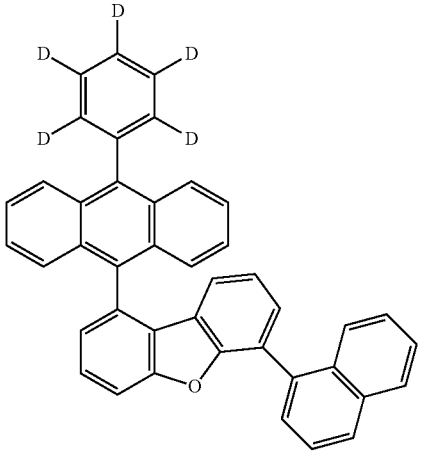

<Reaction Scheme 79>

<Compound 5>

The same procedure was carried out as in Synthetic Example 15-(3), with the exception of using 1-naphthyl boronic acid instead of phenyl boronic acid, to afford Compound 5 (18 g, 41%).

MS (MALDI-TOF): m/z 551.23 [M+]

Synthesis Example 18: Synthesis of Compound 10

Synthetic Example 18-(1): Synthesis of Intermediate 18-a

Intermediate 18-a was synthesized as illustrated in the following Reaction Scheme 80:

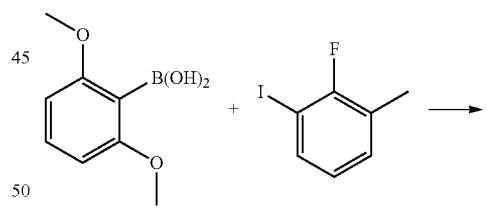

<Reaction Scheme 80>

<Intermediate 15-a>

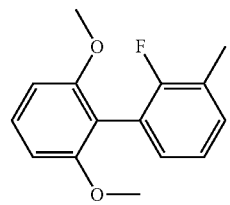

<Intermediate 18-a>

The same procedure was carried out as in Synthetic Example 15-(2), with the exception of using 2-fluoro-1-iodo benzene instead of 1-bromo-2-fluoro-3-iodo benzene, to afford <Intermediate 18-a> (22.3 g, 63%).

Synthetic Example 18-(2): Synthesis of Intermediate 18-b

Intermediate 18-b was synthesized as illustrated in the following Reaction Scheme 81:

<Reaction Scheme 81>

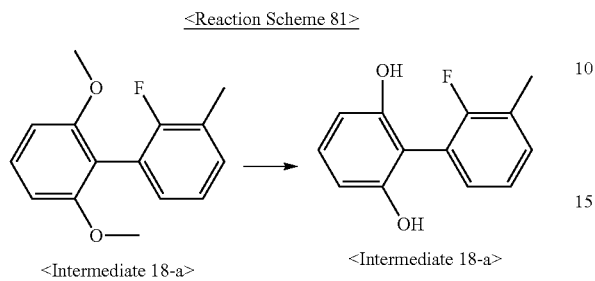

<Intermediate 18-a>   <Intermediate 18-a>

The same procedure was carried out as in Synthetic Example 15-(4), with the exception of using <Intermediate 18-a> instead of <Intermediate 15-c>, to afford <Intermediate 18-b> (16 g, 59%).

Synthetic Example 18-(3): Synthesis of Intermediate 18-c

Intermediate 18-c was synthesized as illustrated in the following Reaction Scheme 82:

<Reaction Scheme 82>

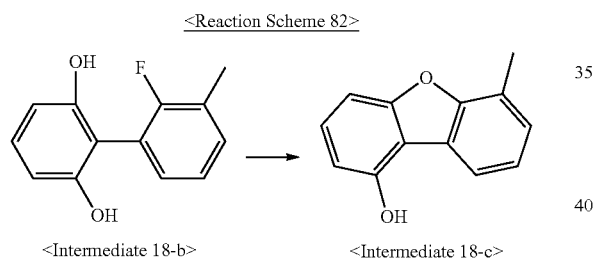

<Intermediate 18-b>   <Intermediate 18-c>

The same procedure was carried out as in Synthetic Example 15-(5), with the exception of using <Intermediate 18-b> instead of <Intermediate 15-d>, to afford <Intermediate 18-c> (19.9 g, 71%).

Synthetic Example 18-(4): Synthesis of Intermediate 18-d

Intermediate 18-d was synthesized as illustrated in the following Reaction Scheme 83:

<Reaction Scheme 83>

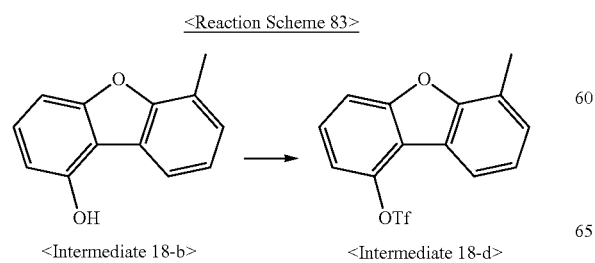

<Intermediate 18-b>   <Intermediate 18-d>

The same procedure was carried out as in Synthetic Example 15-(6), with the exception of using <Intermediate 18-c> instead of <Intermediate 15-e>, to afford <Intermediate 18-d> (17.7 g, 74%).

Synthetic Example 18-(5): Synthesis of Compound 10

Compound 10 was synthesized as illustrated in the following Reaction Scheme 84:

<Reaction Scheme 84>

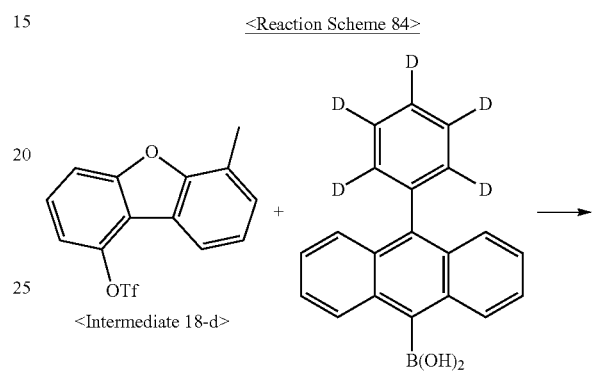

<Intermediate 18-d>

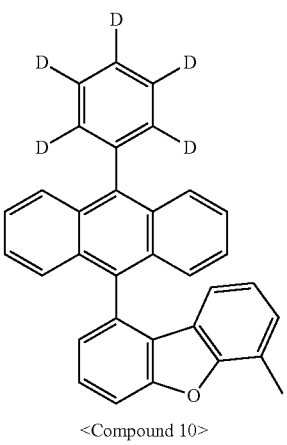

<Compound 10>

The same procedure was carried out as in Synthetic Example 15-(7), with the exception of using <Intermediate 18-d> instead of <Intermediate 15-f>, to afford Compound 10 (11.7 g, 49%).

MS (MALDI-TOF): m/z 439.20 [M+]

Synthesis Example 19: Synthesis of Compound 22

Synthetic Example 19-(1): Synthesis of Compound 22

Compound 22 was synthesized as illustrated in the following Reaction Scheme 85:

<Reaction Scheme 85>

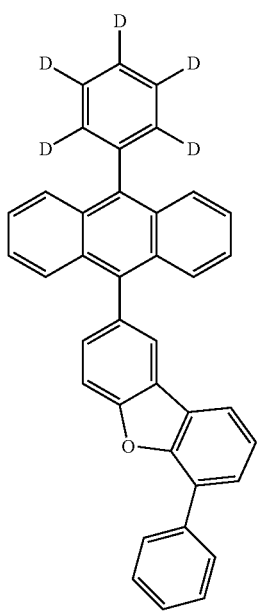

<Compound 22>

The same procedure was carried out as in Synthetic Example 15-(1), with the exception of using 2-bromo-1,4-dimethoxybenzene instead of 2-bromo-1,3-dimethoxybenzene, to afford Compound 22 (20.6 g, 51%).

MS (MALDI-TOF): m/z 501.21 [M+]

Examples 1 to 15: Fabrication of Organic Light-Emitting Diode

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were formed of HAT-CN (50 Å) and α-NPD (600 Å) in that order. A light-emitting layer (200 Å) was formed of a mixture including the host and dopant (5 wt %) of each of the compounds shown in Table 1, below. Then, [Chemical Formula E-1] and [Chemical Formula E-2] were deposited at a ratio of 1:1 to form an electron transport layer 300 Å thick, on which an electron injection layer of [Chemical Formula E-1](10 Å thick) was formed and then covered with an Al layer (1000 Å) to fabricate an organic light-emitting diode. The organic light-emitting diodes thus obtained were measured at 0.4 mA for luminescence properties.

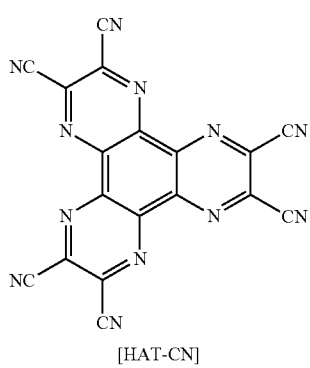

[HAT-CN]

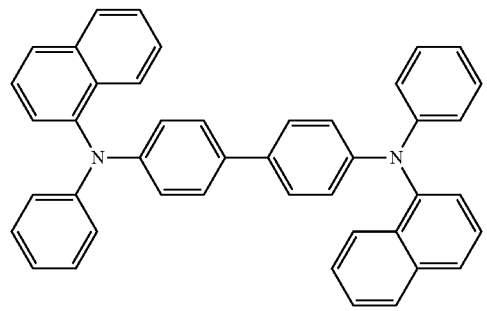

[α-NPD]

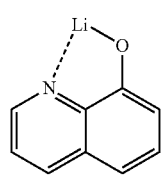

[Chemical Formula E-1]

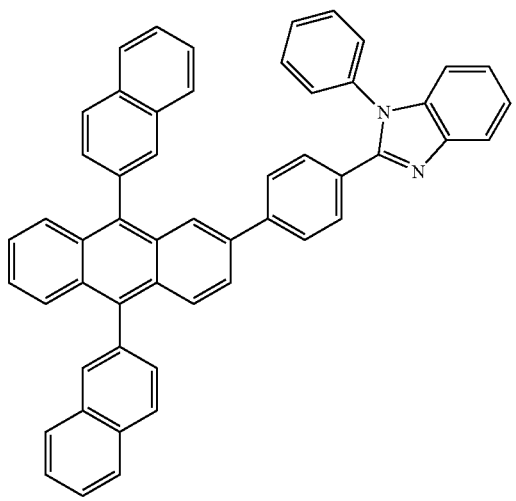

[Chemical Formula E-2]

Comparative Examples 1 to 8

Organic light-emitting diodes were fabricated in the same manner as in Examples 1 to 15, with the exception that one of [BH1] to [BH4] was used, instead of the compounds used in Examples 1 to 15, as hosts and that the compounds listed in Table 1, below was used as dopants. The structures of [BH1] to [BH4] are as follows.

[BH 1]

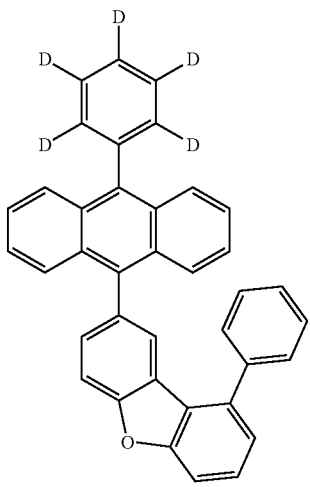

[BH 2]

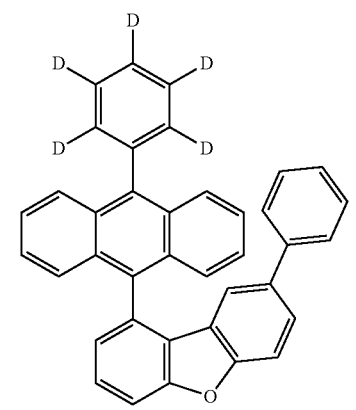

[BH 3]

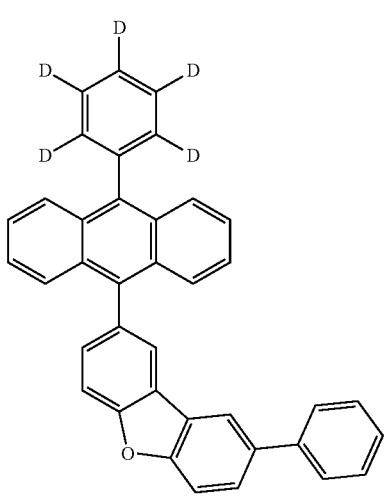

-continued

[BH 4]

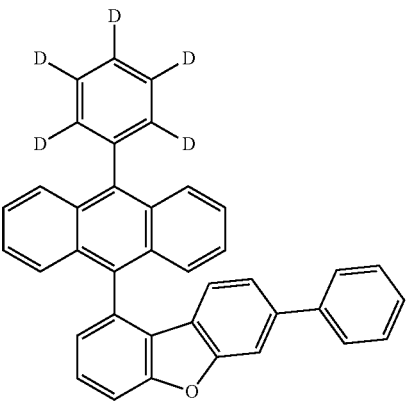

Comparative Examples 9 to 12

Organic light-emitting diodes were fabricated in the same manner as in Examples 1 to 15, with the exception that [BD1] or [BD2] was used, instead of the compounds used in Examples 1 to 15, as a dopant and that the compounds listed in Table 1, below was used as hosts. The structures of [BD1] and [BD2] are as follows.

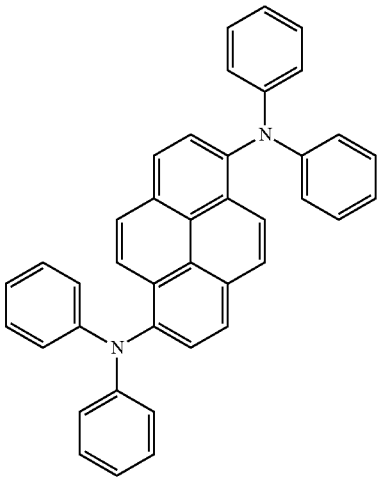

[BD 1]

[BD 2]

4, 4, 'bis[2-(4-N, N-diphenylaminophenyl)vinyl]biphenyl

The organic light-emitting diodes fabricated in Examples 1 to 15 and Comparative Examples 1 to 12 were measured for color coordinates and efficiency, and the results are summarized in Table 1, below.

TABLE 1

|  | Host | Dopant | Cd/A | CIEx | CIEy |
|---|---|---|---|---|---|
| C. Example 1 | BH 1 | Chemical Formula 1 | 7.4 | 0.136 | 0.112 |
| C. Example 2 | BH 2 | Chemical Formula 33 | 7.9 | 0.138 | 0.115 |
| C. Example 3 | BH 3 | Chemical Formula 89 | 8.1 | 0.136 | 0.117 |
| C. Example 4 | BH 4 | Chemical Formula 97 | 7.7 | 0.137 | 0.114 |
| C. Example 5 | BH 1 | Chemical Formula 240 | 7.5 | 0.133 | 0.121 |
| C. Example 6 | BH 2 | Chemical Formula 241 | 8.1 | 0.138 | 0.128 |
| C. Example 7 | BH 3 | Chemical Formula 247 | 7.6 | 0.136 | 0.124 |

TABLE 1-continued

| | Host | Dopant | Cd/A | CIEx | CIEy |
|---|---|---|---|---|---|
| C. Example 8 | BH 4 | Chemical Formula 250 | 7.3 | 0.134 | 0.131 |
| C. Example 9 | Cpd. 1 | BD 1 | 7.8 | 0.141 | 0.150 |
| C. Example 10 | Cpd. 4 | BD 2 | 6.4 | 0.150 | 0.182 |
| C. Example 11 | Cpd. 10 | BD 1 | 7.6 | 0.140 | 0.151 |
| C. Example 12 | Cpd. 22 | BD 2 | 6.6 | 0.148 | 0.178 |
| Example 1 | Cpd. 1 | Chemical Formula 1 | 9.7 | 0.132 | 0.109 |
| Example 2 | Cpd. 1 | Chemical Formula 33 | 9.4 | 0.138 | 0.111 |
| Example 3 | Cpd. 1 | Chemical Formula 240 | 8.9 | 0.137 | 0.120 |
| Example 4 | Cpd. 4 | Chemical Formula 33 | 9.5 | 0.135 | 0.108 |
| Example 5 | Cpd. 4 | Chemical Formula 240 | 8.8 | 0.136 | 0.122 |
| Example 6 | Cpd. 4 | Chemical Formula 241 | 8.6 | 0.138 | 0.119 |
| Example 7 | Cpd. 5 | Chemical Formula 89 | 9.4 | 0.137 | 0.108 |
| Example 8 | Cpd. 5 | Chemical Formula 242 | 9.0 | 0.136 | 0.125 |
| Example 9 | Cpd. 5 | Chemical Formula 245 | 8.9 | 0.135 | 0.121 |
| Example 10 | Cpd. 10 | Chemical Formula 97 | 9.3 | 0.136 | 0.100 |
| Example 11 | Cpd. 10 | Chemical Formula 246 | 8.9 | 0.133 | 0.124 |
| Example 12 | Cpd. 10 | Chemical Formula 247 | 9.2 | 0.134 | 0.121 |
| Example 13 | Cpd. 22 | Chemical Formula 105 | 9.2 | 0.137 | 0.104 |
| Example 14 | Cpd. 22 | Chemical Formula 250 | 9.3 | 0.132 | 0.123 |
| Example 15 | Cpd. 22 | Chemical Formula 251 | 9.1 | 0.136 | 0.118 |

As is understood from the data of Table 1, the organic light-emitting diodes according to the present disclosure exhibited far higher emission efficiency than those employing the compounds of Comparative Examples 1 to 12, thereby demonstrating their high applicability to organic electroluminescence devices.

As described hitherto, the OLED according to the present disclosure exhibits improved light emission efficiency compared to conventional organic light-emitting diodes.

What is claimed is:

1. An organic light-emitting diode, comprising:
a first electrode;
a second electrode facing the first electrode; and
a light-emitting layer interposed therebetween,
wherein the light-emitting layer contains; at least one selected from the group consisting of an amine compound represented by the following Chemical Formula A or Chemical Formula B and a pyrene compound represented by the following Chemical Formula C; and an anthracene compound represented by the following Chemical Formula D:

[Chemical Formula A]

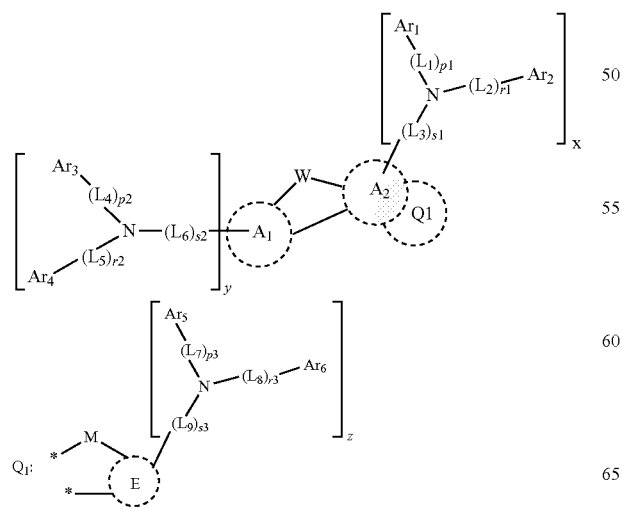

[Chemical Formula B]

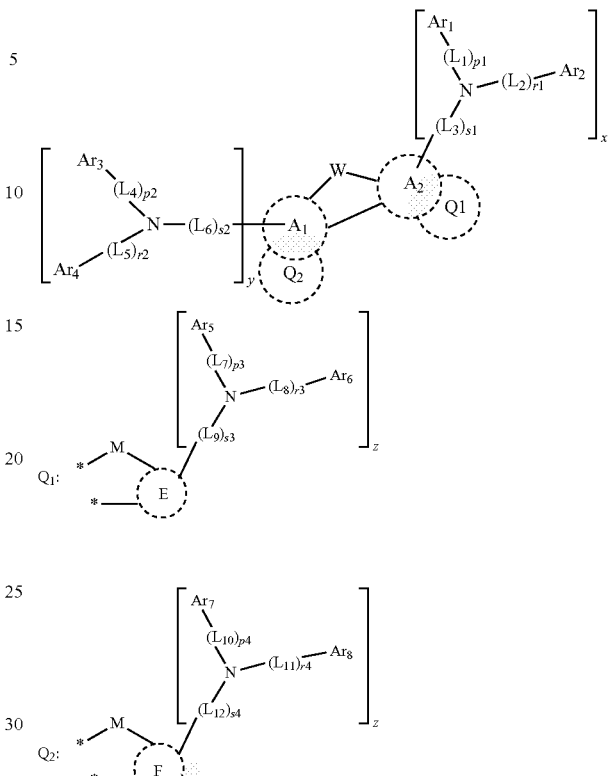

wherein, $A_1$, $A_2$, E, and F are the same or different and are each independently a substituted or unsubstituted aromatic hydrocarbon ring of 6 to 50 carbon atoms, or a substituted or unsubstituted aromatic heterocyclic ring of 2 to 40 carbon atoms, wherein two adjacent carbon atoms of the aromatic ring $A_1$ and two adjacent carbon atoms of the aromatic ring $A_2$ form a 5-membered fused ring together with W;

Linkers $L_1$ to $L_{12}$ are the same or different and are each independently selected from among a single bond, a substituted or unsubstituted arylene of 6 to 60 carbon atoms, and a substituted or unsubstituted heteroarylene of 2 to 60 carbon atoms;

W is selected from among $CR_1R_2$, $SiR_1R_2$, $GeR_1R_2$, O, S, and $NR_1$,

M is any one selected from among N—$R_3$, $CR_4R_5$, $SiR_6R_7$, $GeR_8R_9$, O, S, and Se;

$R_1$ to $R_9$, and $Ar_1$ to $Ar_8$ are same or different and are each independently any one selected from among a hydrogen, a deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted heterocycloalkyl of 2 to 30 carbon atoms a substituted or unsubstituted alkylsilyl of 1 to 30 carbon atoms, a substituted or unsubstituted arylsilyl of 6 to 30 carbon atoms, a cyano, and a halogen, with a proviso that $R_1$ and $R_2$ may be bonded to each other to form a mono- or polycyclic aliphatic or aromatic ring, which may be a heterocyclic ring bearing a heteroatom selected from among N, O, Si, and S as a ring member;

p1 to p4, r1 to r4, and s1 to s4 are each independently an integer of 1 to 3, with a proviso that when any of them is 2 or greater, the corresponding linkers may be same or different;

x is 1, and y and z are the same or different and are each independently an integer of 0 to 1;

$Ar_1$ may form a ring with $Ar_8$, $Ar_3$ may form a ring with $Ar_4$, $Ar_5$ may form a ring with $Ar_6$, and $Ar_7$ may form a ring with $Ar_5$;

two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions * of Structural Formula $Q_1$ to form a fused ring,

[Chemical Formula C]

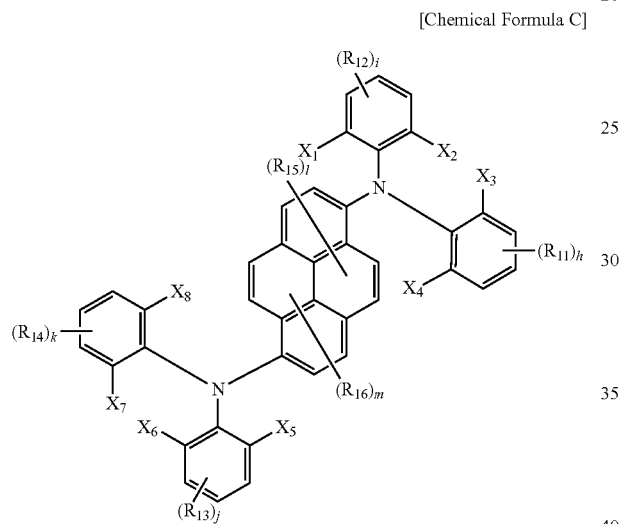

wherein, $R_{11}$ to $R_{16}$ may be same or different and are each independently any one selected from among a hydrogen, a deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, and a halogen, with a proviso that each of the unsubstituted carbon atoms of the aromatic ring moieties of $R_{11}$ to $R_{16}$ is bound with a hydrogen atom or a deuterium atom;

h, i, j, and k are each an integer of 0 to 3, with a proviso that when each of them is 2 or greater, the corresponding $R_{11}$'s to $R_{14}$'s are each same or different;

l and m are each an integer of 0 to 4, with a proviso that when each of them are 2 or greater, the corresponding $R_{15}$'s and $R_{16}$'s are each same or different;

wherein a bond may be formed between $R_{11}$ and adjacent $X_1$ or $X_2$, between $R_{12}$ and adjacent $X_3$ or $X_4$, between $R_{13}$ and adjacent $X_5$ or $X_6$, and between $R_{14}$ and adjacent $X_7$ or $X_8$, or when each of $R_{11}$ to $R_{14}$ exists in duplicate or more, individual $R_{11}$'s to $R_{14}$'s may be bonded to each other to form a mono- or polycyclic aliphatic or aromatic ring, which may be heterocyclic ring bearing a heteroatom selected from among, N, O, P, Si, and S as a ring member, wherein $X_1$ to $X_8$ may be same or different and are each independently selected from among a hydrogen, a deuterium, and a substituted or unsubstituted alkyl of 1 to 20 carbon atoms, with a proviso that at least $X_1$, $X_2$, $X_5$ and $X_6$ among $X_1$ to $X_8$ are each a substituted or unsubstituted alkyl of 1 to 20 carbon atoms,

[Chemical Formula D]

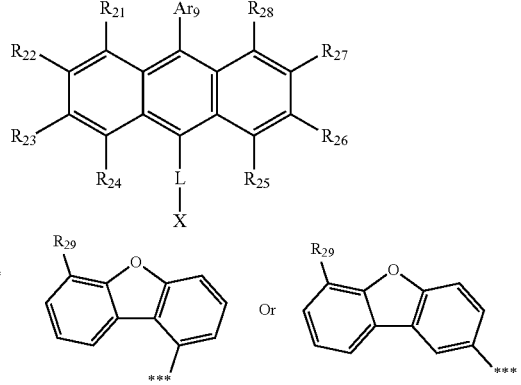

wherein, $Ar_9$ is a substituted or unsubstituted aryl of 6 to 50 carbon atoms, or a substituted or unsubstituted heteroaryl of 2 to 50 carbon atoms, $R_{21}$ to $R_{28}$ are the same or different and are each independently selected from among a hydrogen, a deuterium, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, a substituted or unsubstituted heteroaryl of 2 to 50 carbon atoms bearing O, N or S as a heteroatom, a substituted or unsubstituted silyl of 1 to 30 carbon atoms, a cyano and a halogen, $R_{29}$ is a substituted or unsubstituted aryl of 6 to 50 carbon atoms, linker L is selected from among a single bond and a substituted or unsubstituted arylene of 6 to 60 carbon atoms, "***" of X denotes a bonding site to be linked to linker L, wherein the term 'substituted' in the expression 'substituted or unsubstituted' used in Chemical Formulas A, B, C, and D means having at least one substituent selected from the group consisting of a deuterium, a cyano, a halogen, a nitro, an alkyl of 1 to 24 carbon atoms, a halogenated alkyl of 1 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkylsilyl of 1 to 24 carbon atoms, an arylsilyl of 6 to 24 carbon atoms, and an aryloxy of 6 to 24 carbon atoms.

2. The organic light-emitting diode as set forth in claim 1, wherein the light-emitting layer contains the amine compound represented by Chemical Formula A or B and the pyrene compound represented by Chemical Formula C as respective dopants, and the anthracene compound represented by Chemical Formula D as a host.

3. The organic light-emitting diode as set forth in claim 1, wherein $A_1$, $A_2$, E, and F may be same or different and are each independently a substituted or unsubstituted aromatic hydrocarbon ring of 6 to 50 carbon atoms.

4. The organic light-emitting diode as set forth in claim 3, wherein the substituted or unsubstituted aromatic hydrocarbon rings of 6 to 50 carbon atoms may be same or different and are each independently selected from among compounds represented by Structural Formulas 10 to 21,

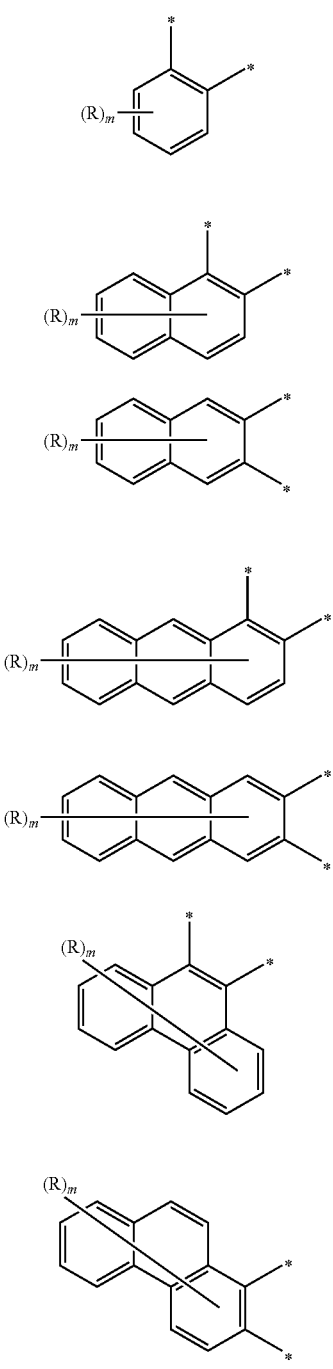

[Str. Formula 10]

[Str. Formula 11]

[Str. Formula 12]

[Str. Formula 13]

[Str. Formula 14]

[Str. Formula 15]

[Str. Formula 16]

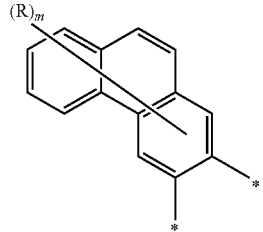

[Str. Formula 17]

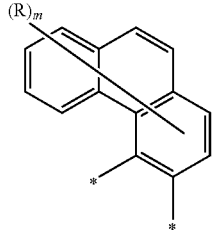

[Str. Formula 18]

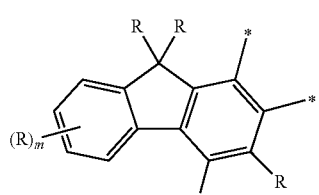

[Str. Formula 19]

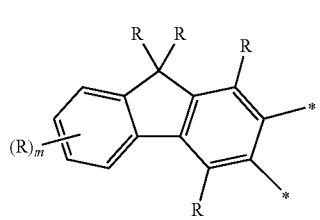

[Str. Formula 20]

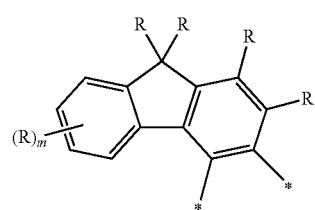

[Str. Formula 21]

wherein

"-*" denotes a bonding site for forming a 5-membered ring containing W or a bonding site for forming a 5-membered ring containing M of the structural Formula $Q_1$ and $Q_2$;

when one of the aromatic hydrocarbon rings of [Str. Formula 10] to [Str. Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring;

R's are the same or different and are each independently any one selected from among a hydrogen, a deuterium, a cyano, a halogen, a nitro, an alkyl of 1 to 24 carbon atoms, an aryl of 6 to 24 carbon atoms, a heteroaryl of 2 to 24 carbon atoms, an alkylsilyl of 1 to 24 carbon atoms, and an arylsilyl of 6 to 24 carbon atoms; and m is an integer of 1 to 8, with a proviso that when m is 2 or greater or when two or more R's exist, the corresponding R's may be same or different.

5. The organic light-emitting diode as set forth in claim 1, wherein the linkers $L_1$ to $L_{12}$ in Chemical Formulas A and B and the linker L in Chemical Formula D may be same or different and are each a single bond or any one selected from among the following Structural Formulas 22 to 30:

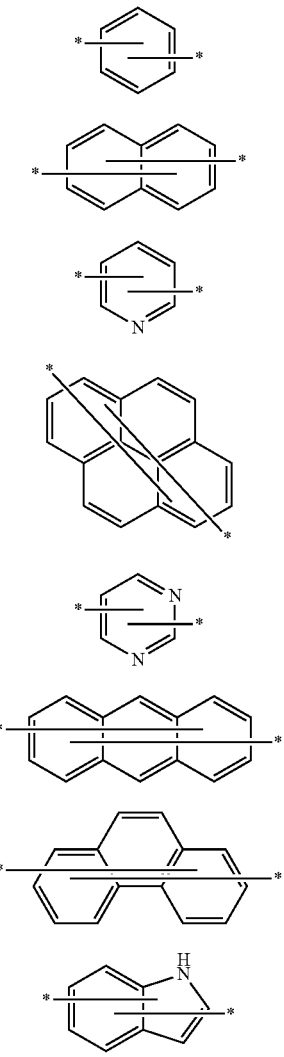

[Str. Formula 22]
[Str. Formula 23]
[Str. Formula 24]
[Str. Formula 25]
[Str. Formula 26]
[Str. Formula 27]
[Str. Formula 28]
[Str. Formula 29]

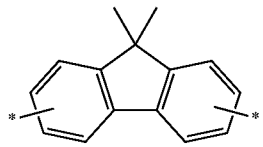

[Str. Formula 30]

wherein each of the unsubstituted carbon atoms of the aromatic ring moiety is bound with a hydrogen atom or a deuterium atom.

6. The organic light-emitting diode as set forth in claim 1, wherein h, i, j, and k in Chemical Formula C are each an integer of 0 to 2, with a proviso that when each of them is 2, corresponding $R_{11}$'s to $R_{14}$'s may be same or different.

7. The organic light-emitting diode as set forth in claim 1, wherein $R_{15}$ and $R_{16}$ in Chemical Formula C are each a hydrogen or a deuterium.

8. The organic light-emitting diode as set forth in claim 1, wherein $Ar_9$ in Chemical Formula D is represented by the following Structural Formula 31:

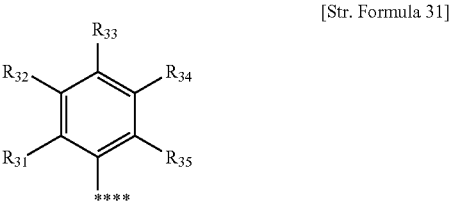

[Str. Formula 31]

wherein,
"-****" denotes a bonding site to be linked to the anthracene moiety of Chemical Formula D, and
the substituents $R_{31}$ to $R_{35}$ may be same or different and are each independently selected from among a hydrogen, a deuterium, an alkyl of 1 to 24 carbon atoms, an aryl of 6 to 24 carbon atoms, and an heteroaryl of 2 to 24 carbon atoms.

9. The organic light-emitting diode as set forth in claim 1, wherein the two amine moieties of the pyrene compound represented by Chemical Formula C are identical.

10. The organic light-emitting diode as set forth in claim 1, wherein the pyrene compound represented by Chemical Formula C is asymmetric as the two amine moieties are different.

11. The organic light-emitting diode as set forth in claim 1, wherein the amine compound represented by Chemical Formula A or B may be any one selected from among the following Chemical Formula 1 to Chemical Formula 235, Chemical Formula 238, and Chemical Formula 239:

<Chemical Formula 1>

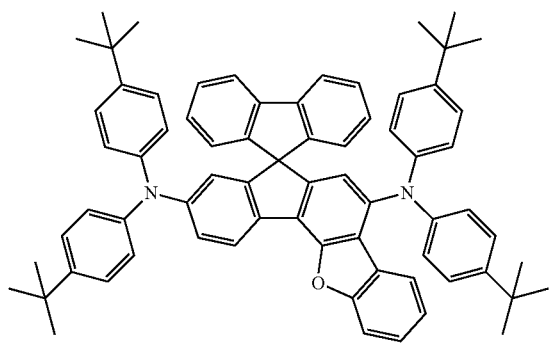

<Chemical Formula 2>

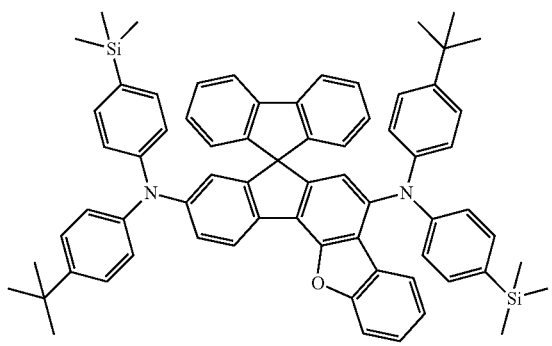

<Chemical Formula 3>
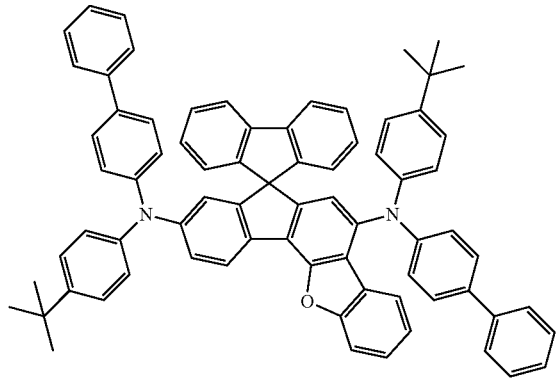
<Chemical Formula 4>
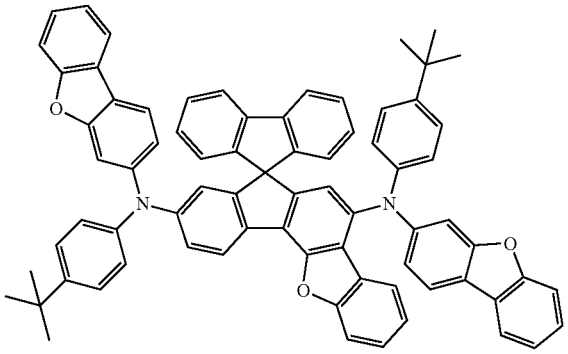
<Chemical Formula 5>
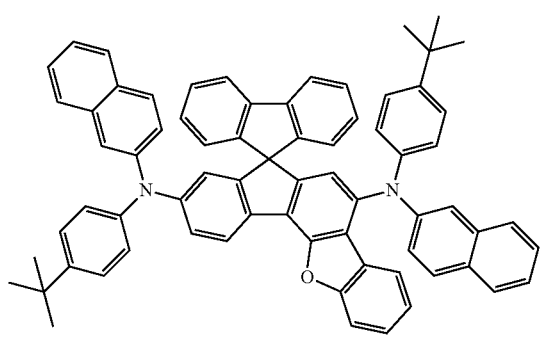
<Chemical Formula 6>
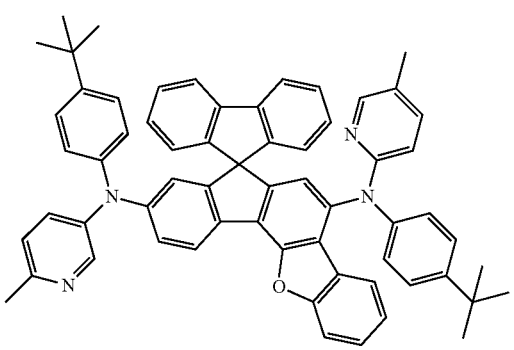
<Chemical Formula 7>
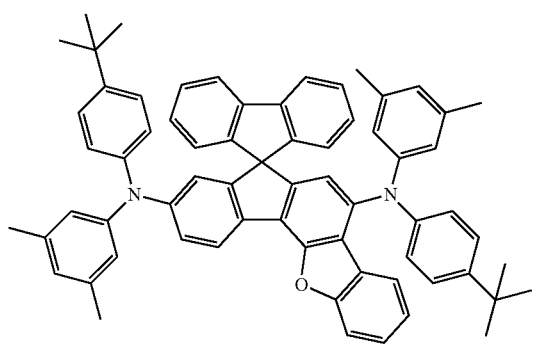
<Chemical Formula 8>
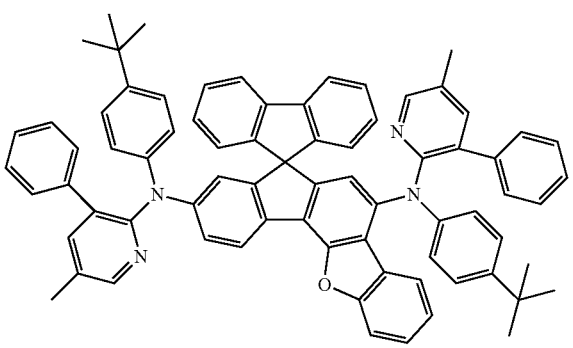
<Chemical Formula 9>
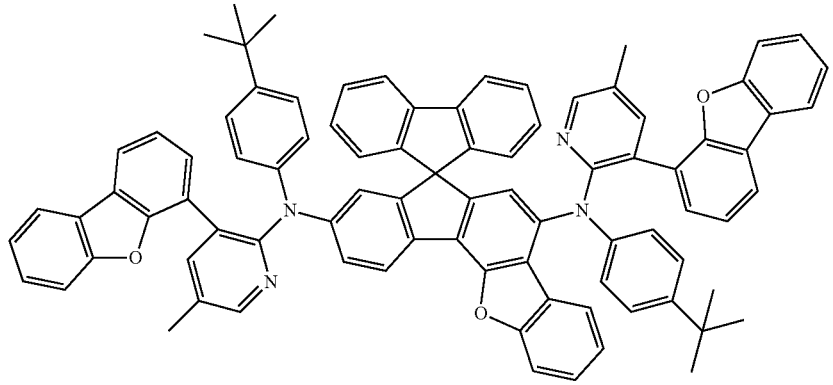

-continued
<Chemical Formula 10>
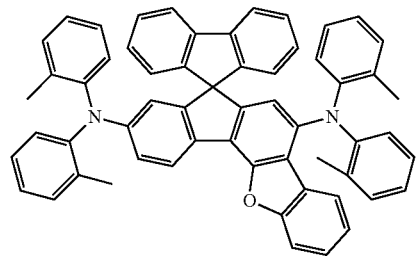
<Chemical Formula 11>
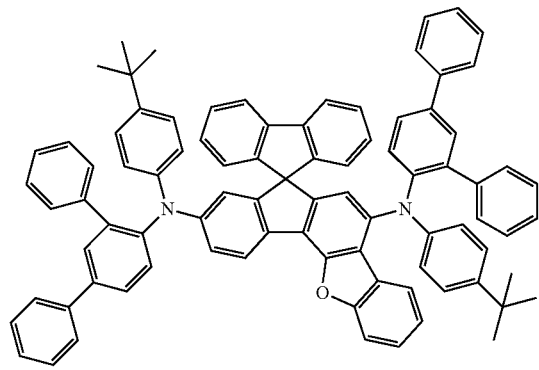
<Chemical Formula 12>
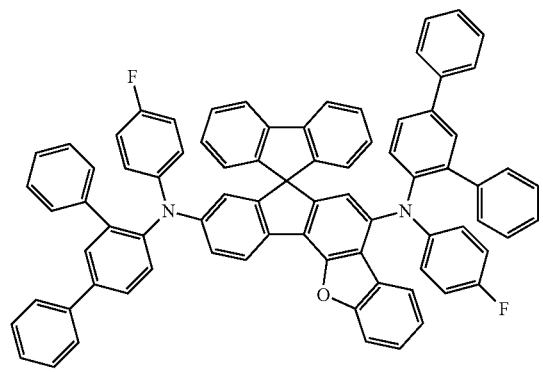
<Chemical Formula 13>
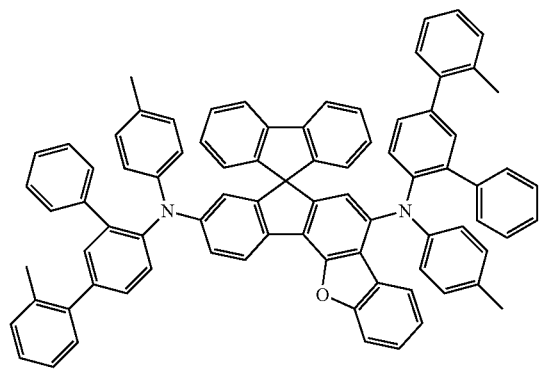
<Chemical Formula 14>
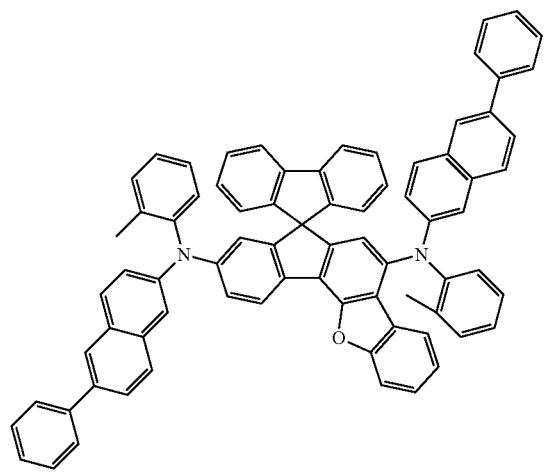
<Chemical Formula 15>
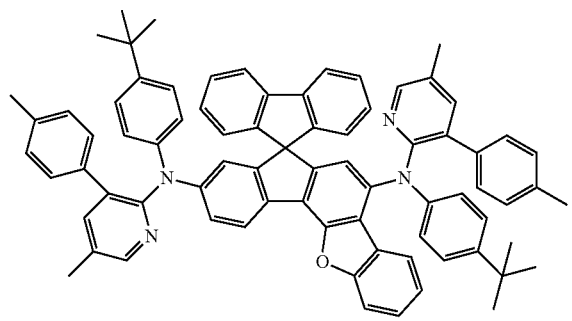

-continued
<Chemical Formula 16>
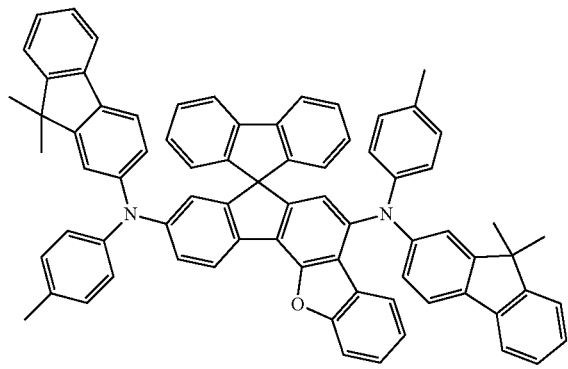
<Chemical Formula 17>
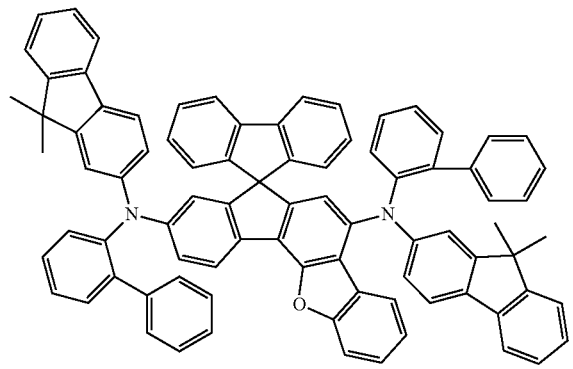
<Chemical Formula 18>
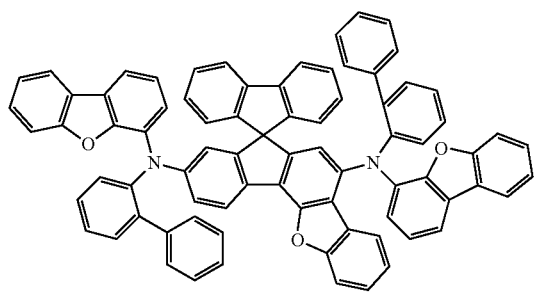
<Chemical Formula 19>
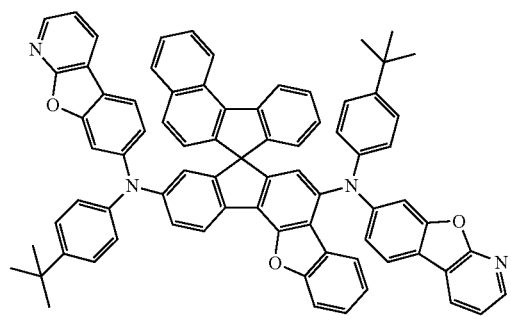
<Chemical Formula 20>
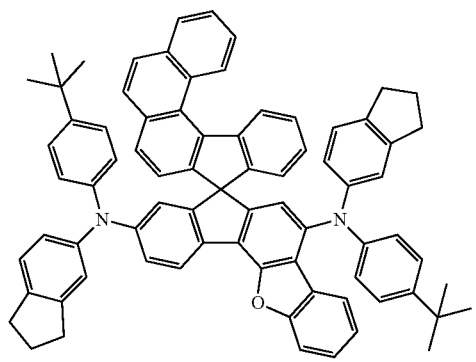
<Chemical Formula 21>
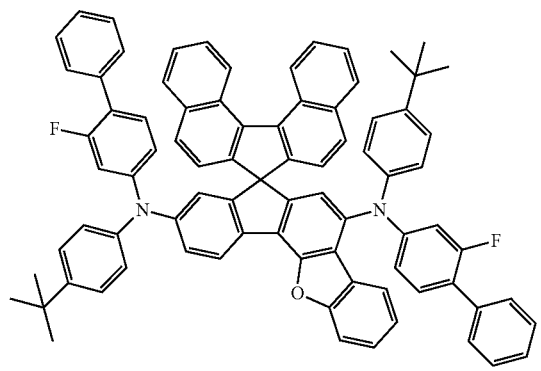
<Chemical Formula 22>
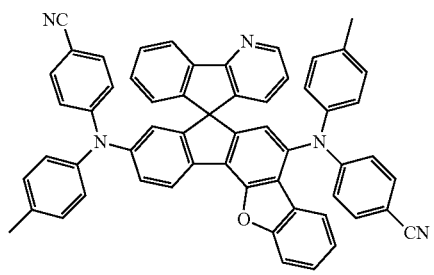
<Chemical Formula 23>
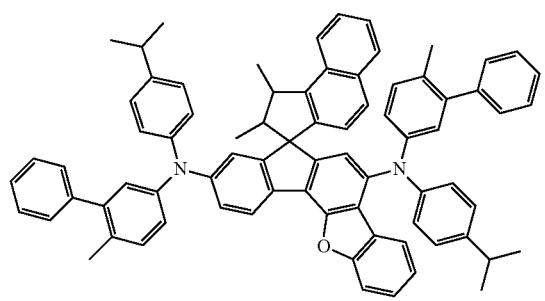

-continued
<Chemical Formula 24>
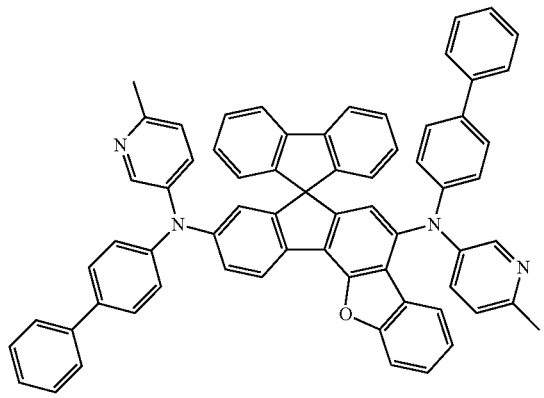
<Chemical Formula 25>
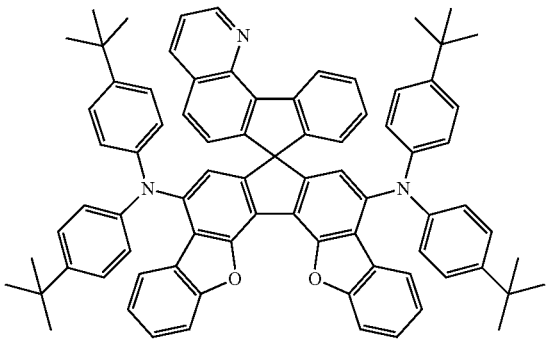
<Chemical Formula 26>
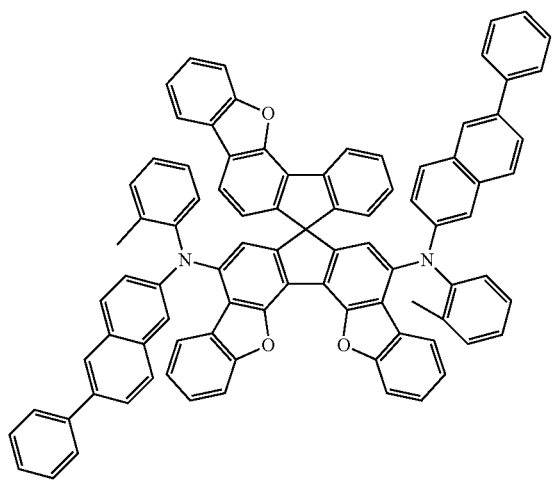
<Chemical Formula 27>
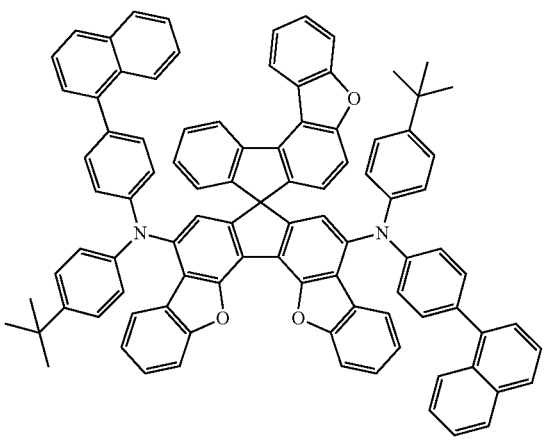
<Chemical Formula 28>
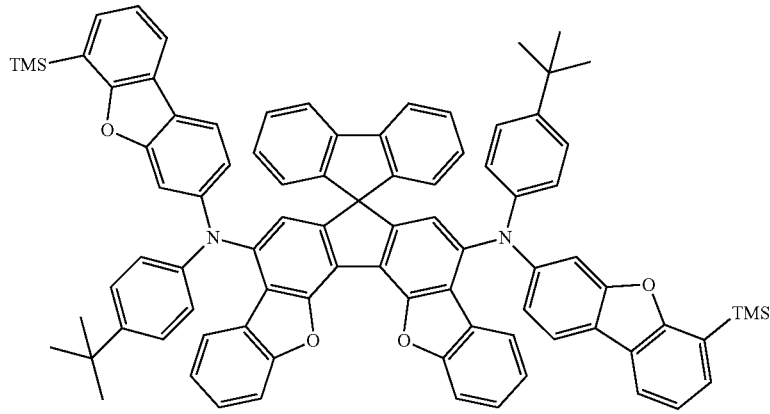
<Chemical Formula 29>
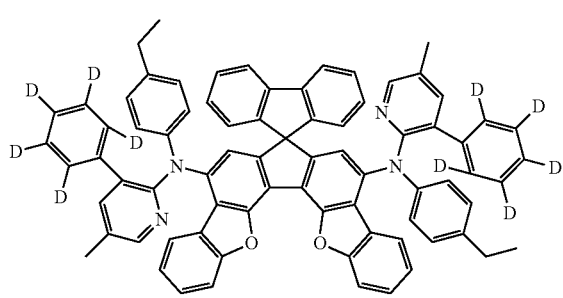
<Chemical Formula 30>
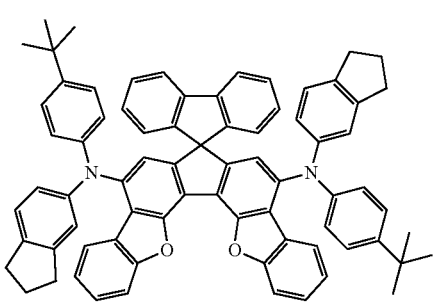

<Chemical Formula 31>
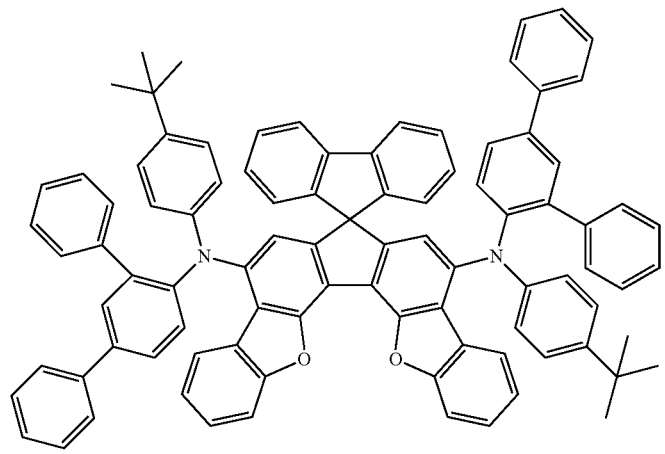
<Chemical Formula 32>
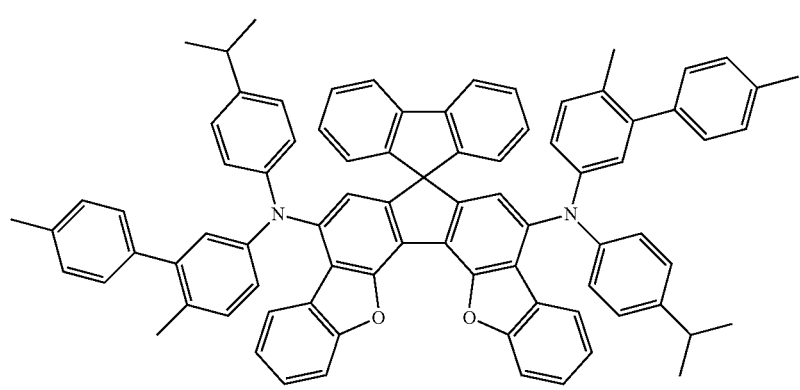
<Chemical Formula 33>
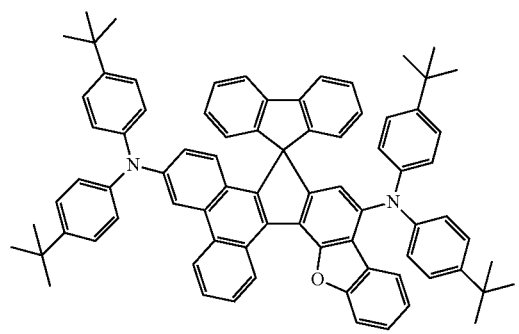
<Chemical Formula 34>
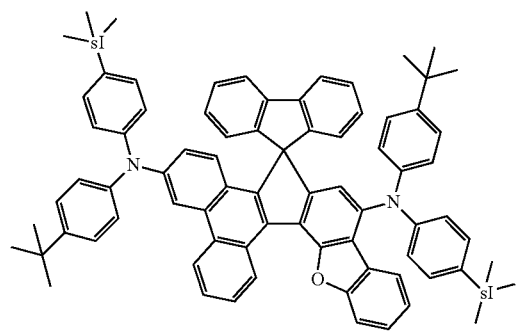

-continued
<Chemical Formula 35>
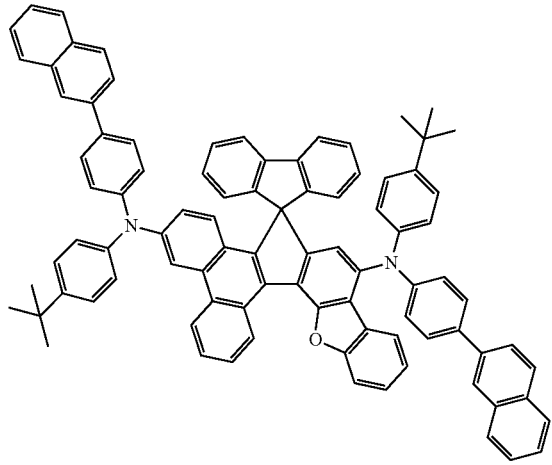
<Chemical Formula 36>
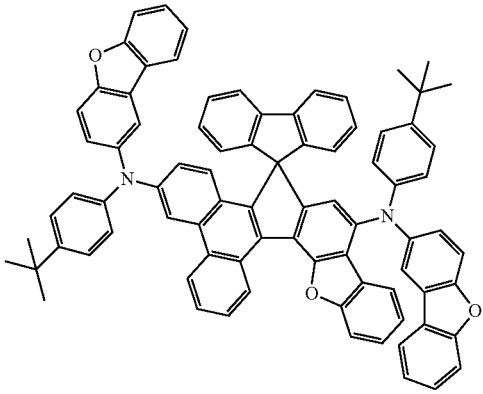
<Chemical Formula 37>
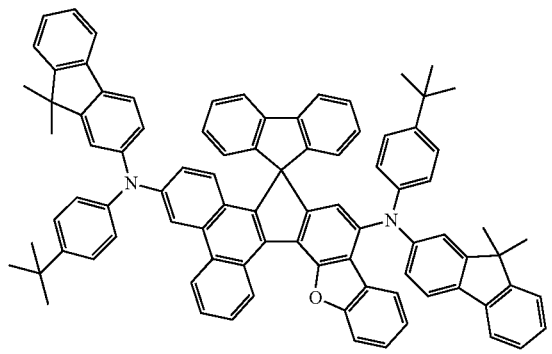
<Chemical Formula 38>
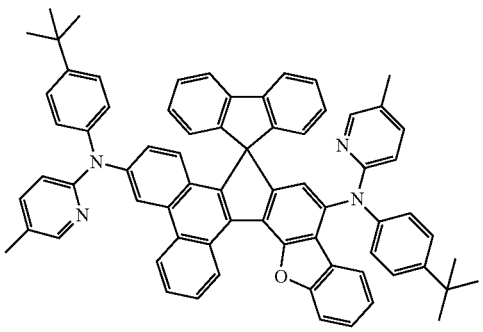
<Chemical Formula 39>
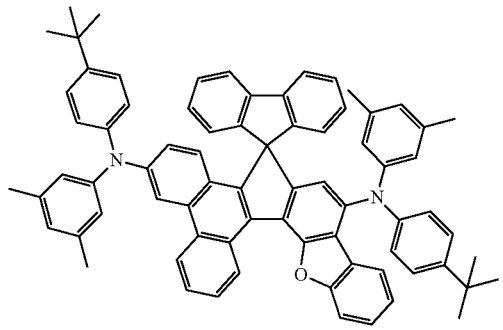
<Chemical Formula 40>
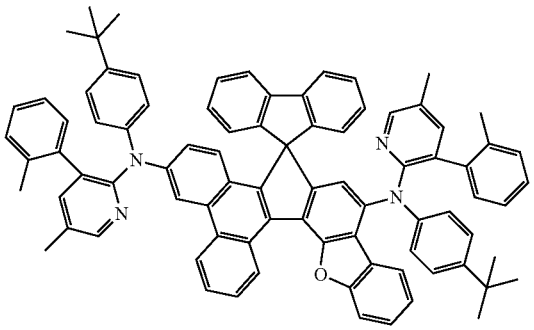
<Chemical Formula 41>
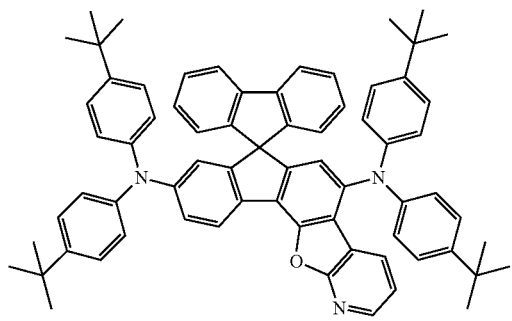
<Chemical Formula 42>
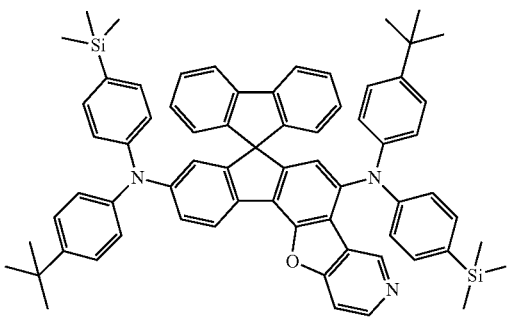

-continued
<Chemical Formula 43>
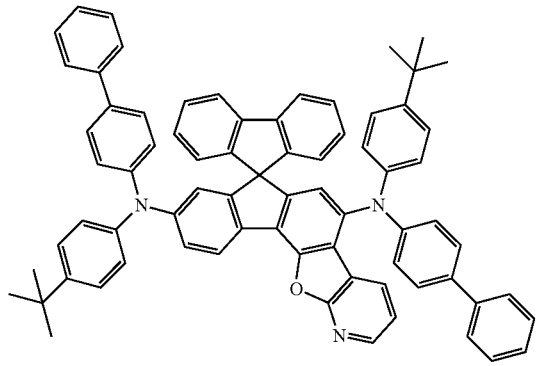
<Chemical Formula 44>
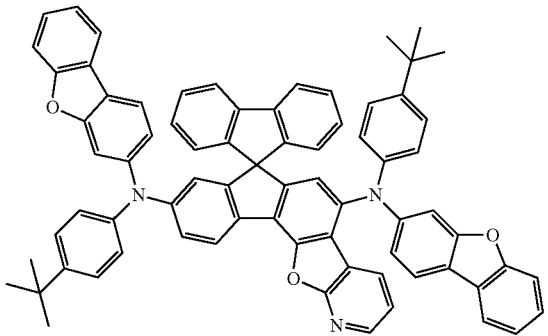
<Chemical Formula 45>
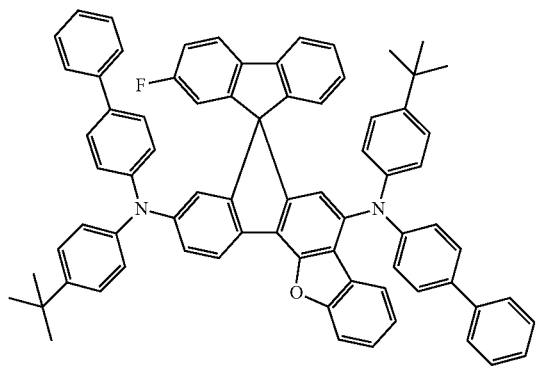
<Chemical Formula 46>
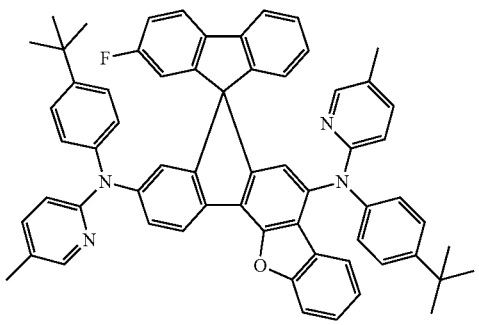
<Chemical Formula 47>
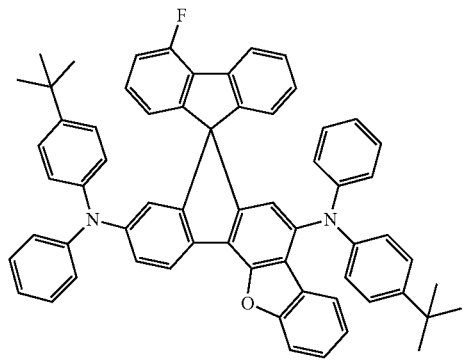
<Chemical Formula 48>
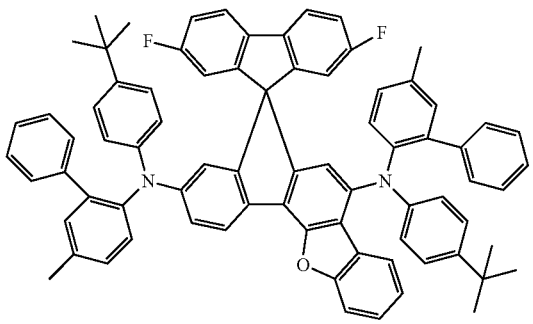
<Chemical Formula 49>
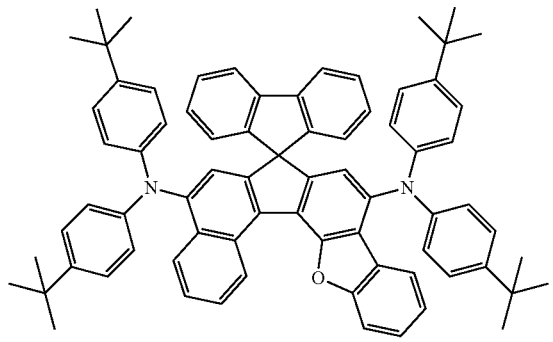
<Chemical Formula 50>
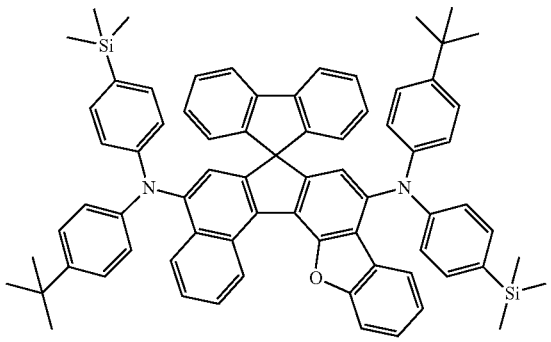

<Chemical Formula 51>
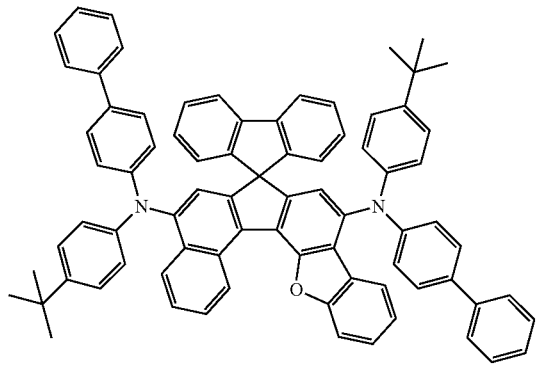
<Chemical Formula 52>
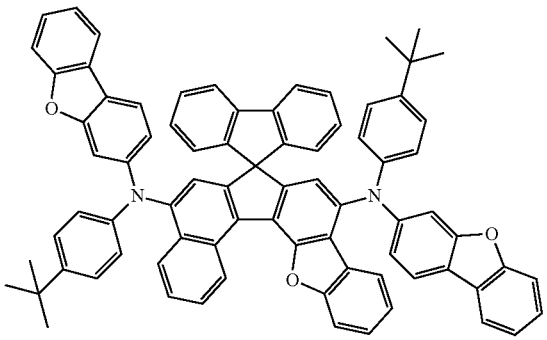
<Chemical Formula 53>
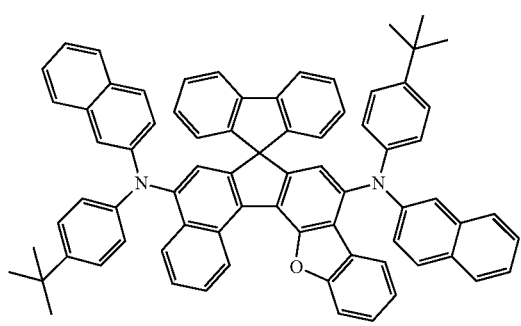
<Chemical Formula 54>
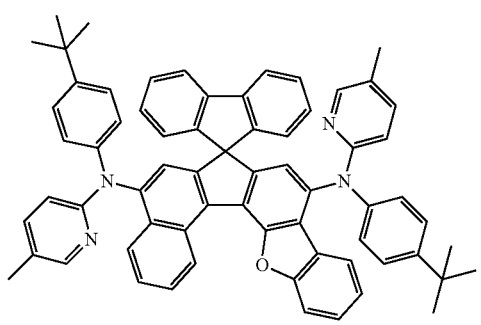
<Chemical Formula 55>
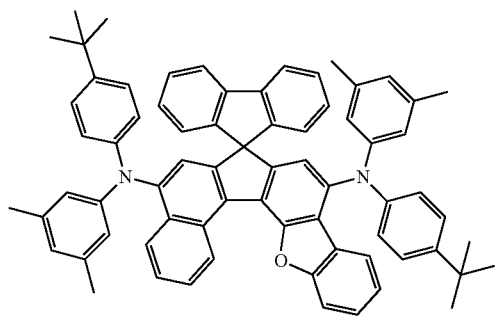
<Chemical Formula 56>
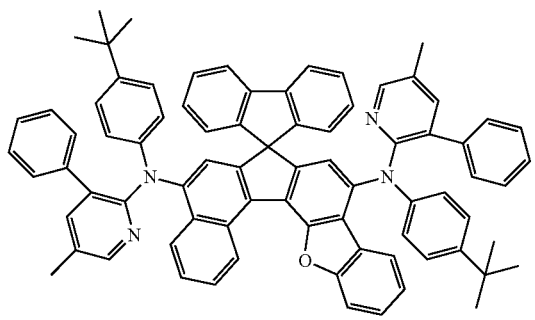
<Chemical Formula 57>
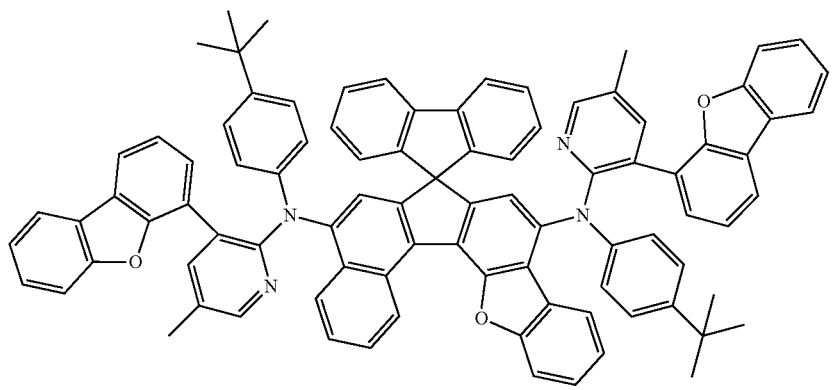

<Chemical Formula 58>
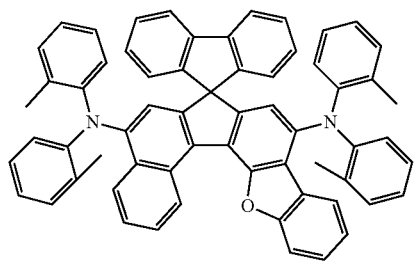
<Chemical Formula 59>
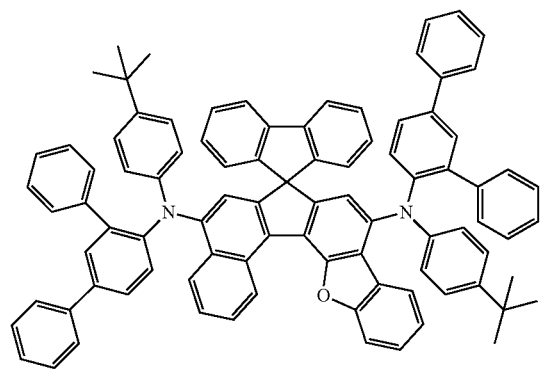
<Chemical Formula 60>
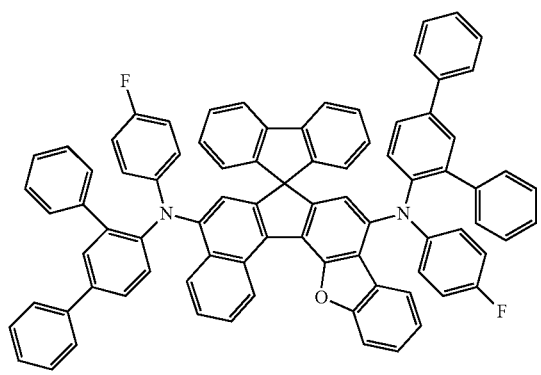
<Chemical Formula 61>
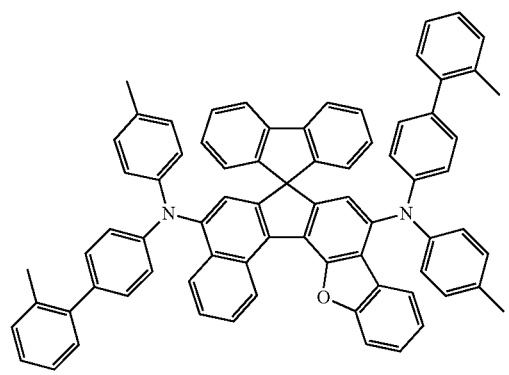
<Chemical Formula 62>
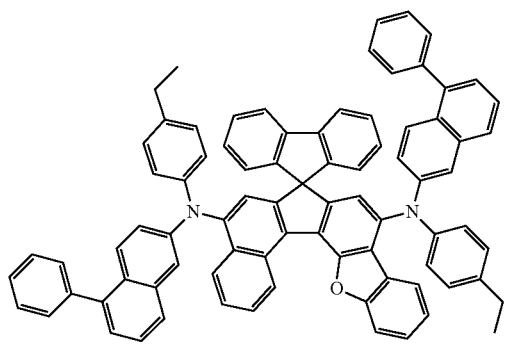
<Chemical Formula 63>
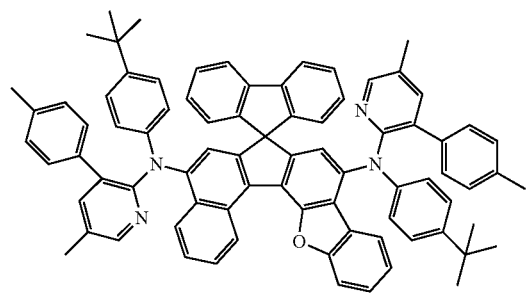
<Chemical Formula 64>
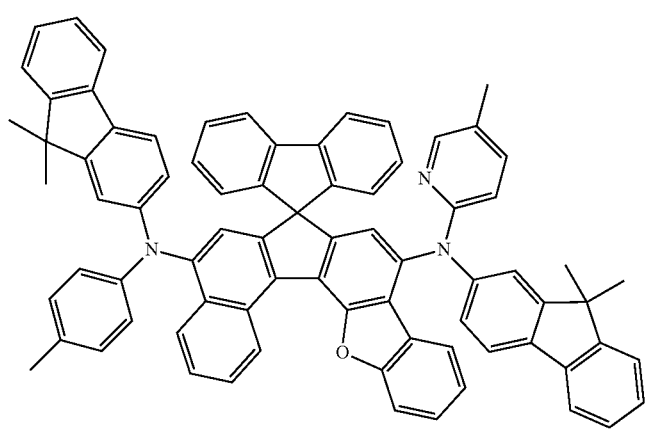

-continued
<Chemical Formula 65>
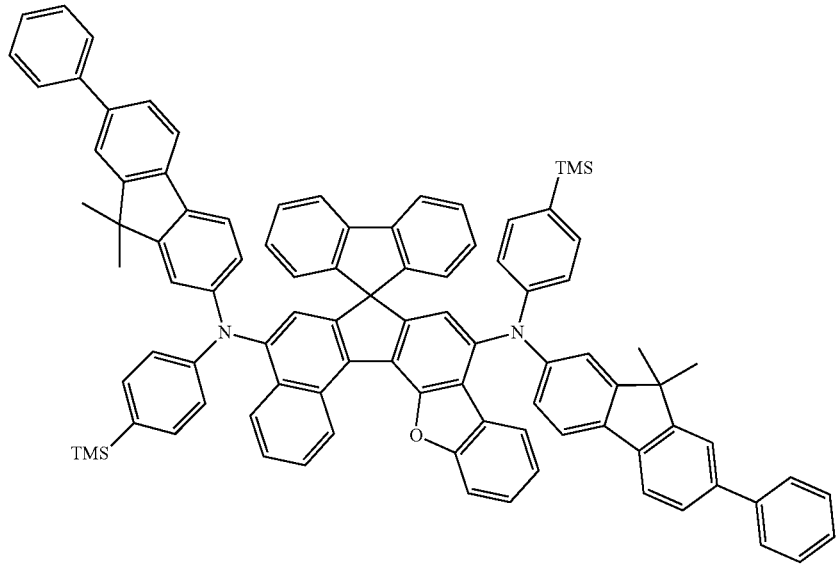
<Chemical Formula 66>
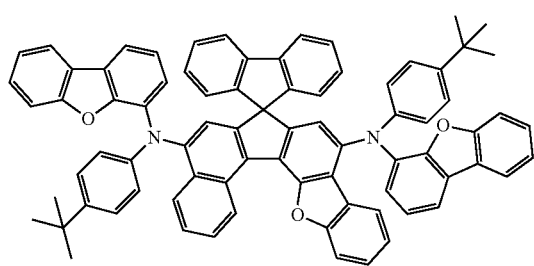
<Chemical Formula 67>
<Chemical Formula 68>
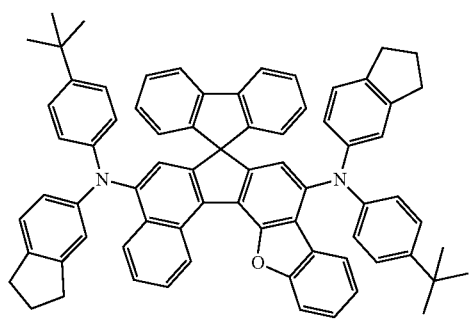
<Chemical Formula 69>
<Chemical Formula 70>
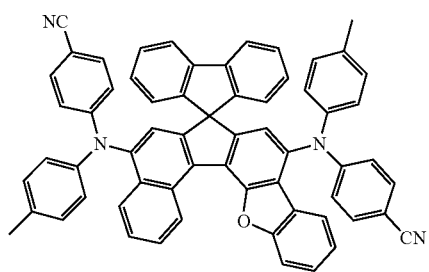
<Chemical Formula 71>

-continued
<Chemical Formula 72>
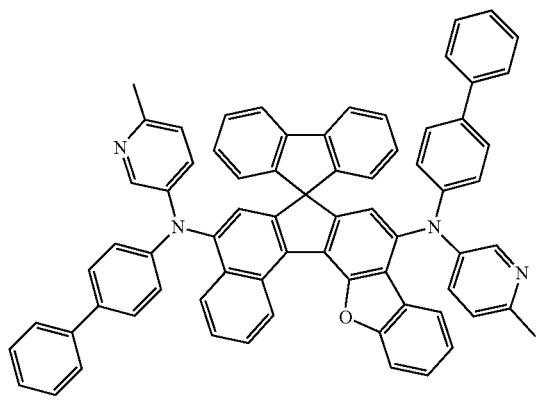
<Chemical Formula 73>
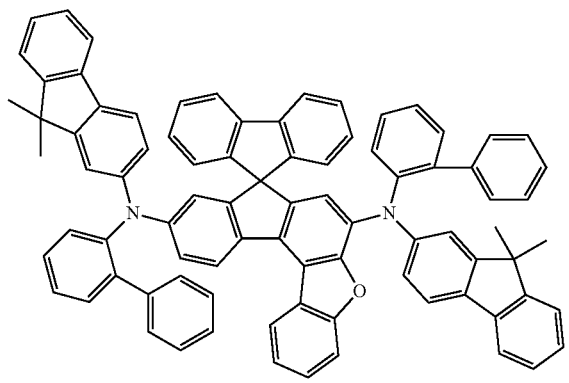
<Chemical Formula 74>
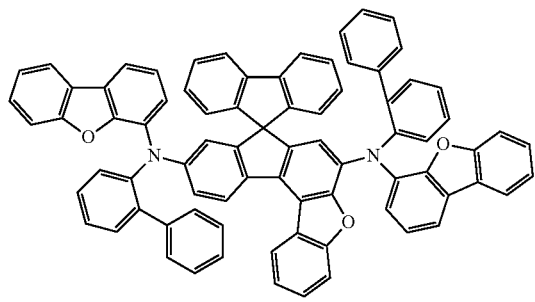
<Chemical Formula 75>
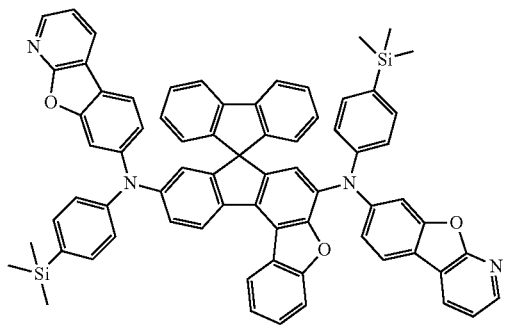
<Chemical Formula 76>
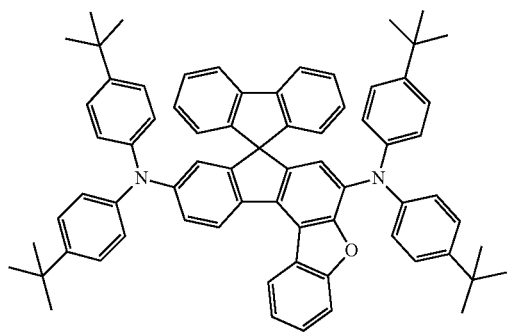
<Chemical Formula 77>
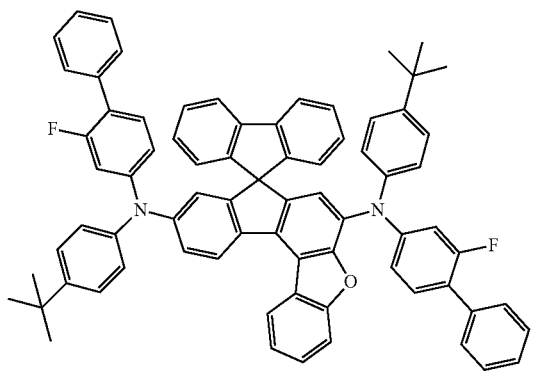
<Chemical Formula 78>
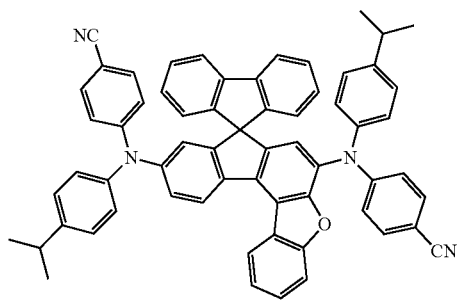
<Chemical Formula 79>
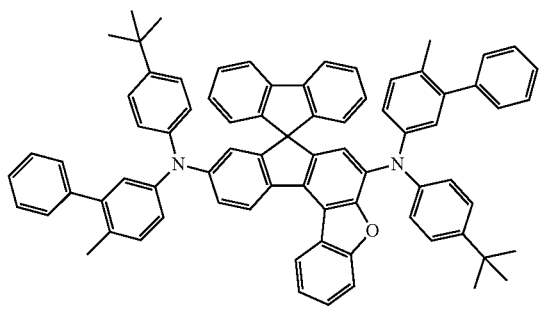

-continued
<Chemical Formula 80>
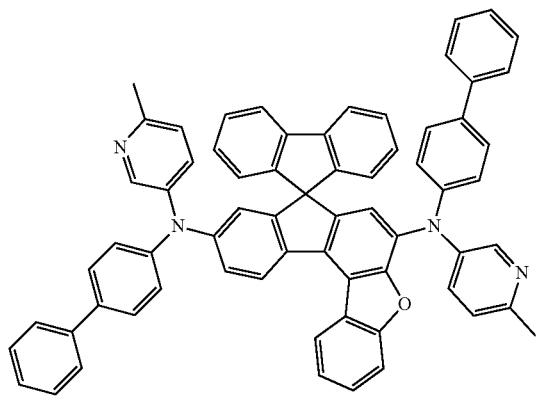
<Chemical Formula 81>
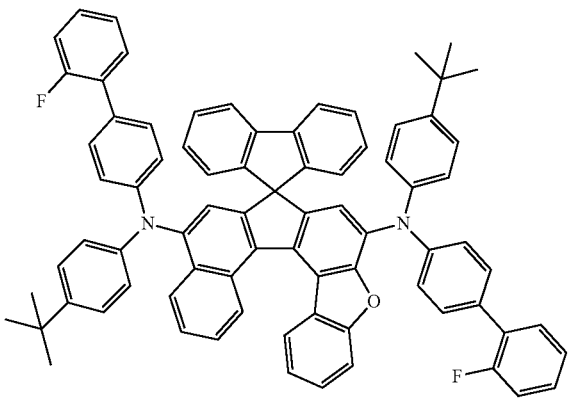
<Chemical Formula 82>
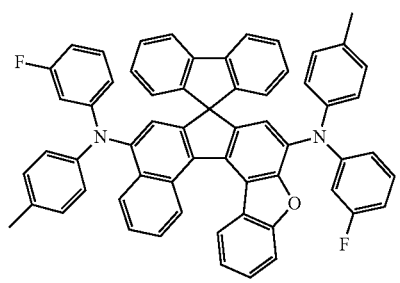
<Chemical Formula 83>
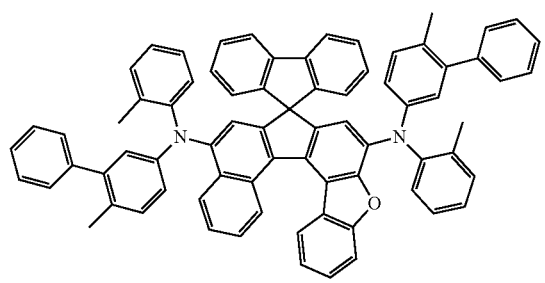
<Chemical Formula 84>
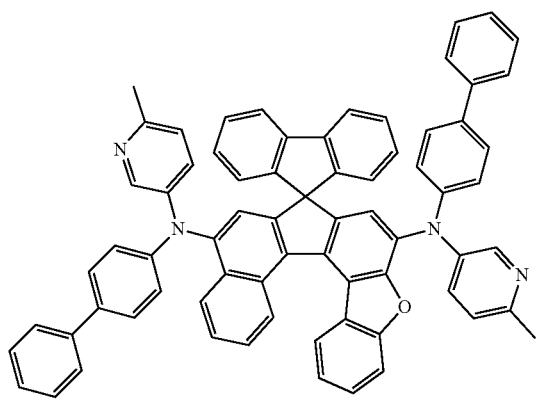
<Chemical Formula 85>
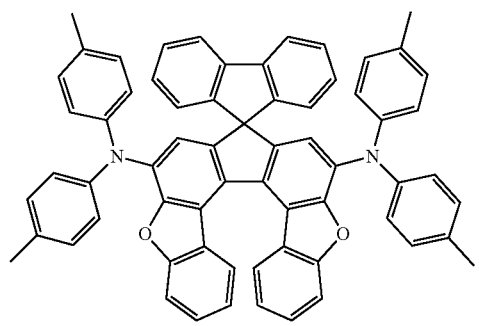
<Chemical Formula 86>
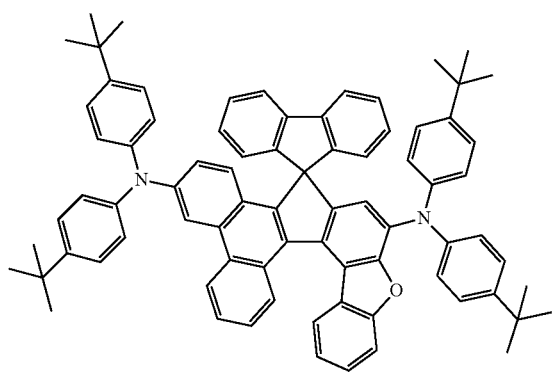
<Chemical Formula 87>
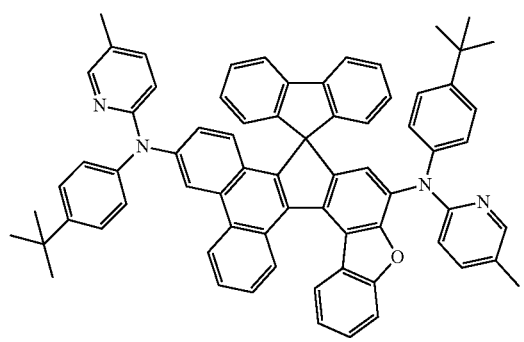

-continued
<Chemical Formula 88>
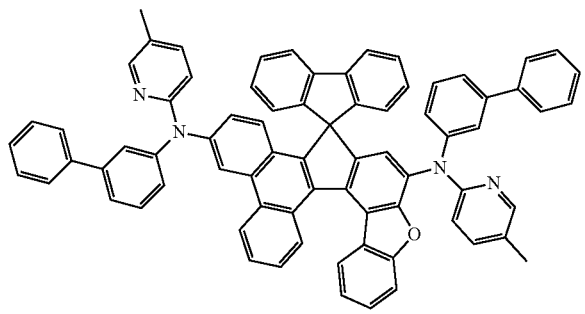
<Chemical Formula 89>
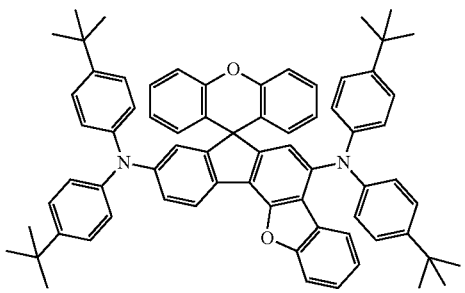
<Chemical Formula 90>
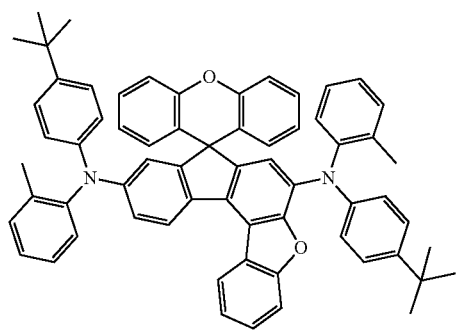
<Chemical Formula 91>
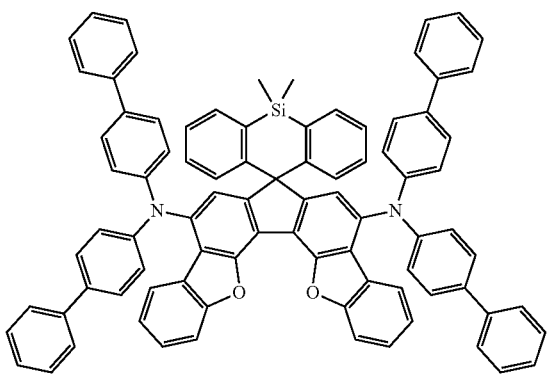
<Chemical Formula 92>
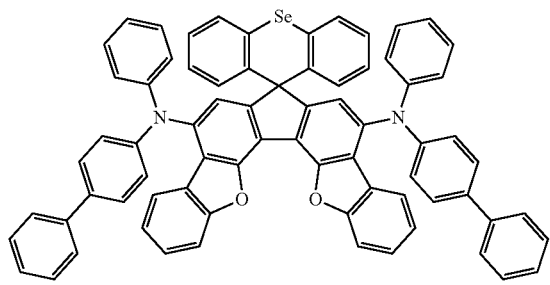
<Chemical Formula 93>
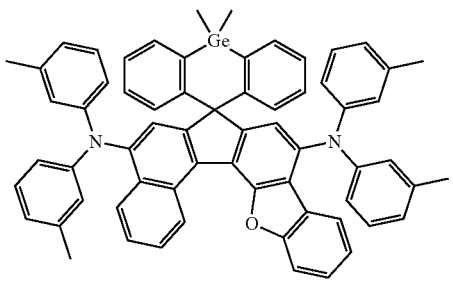
<Chemical Formula 94>
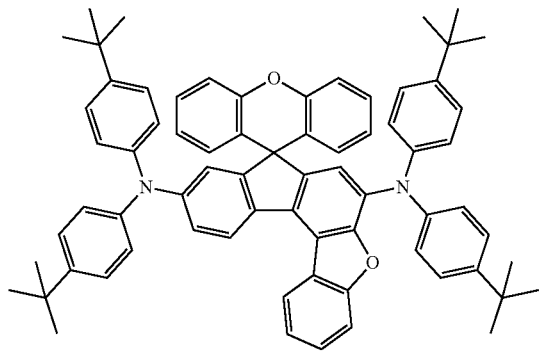
<Chemical Formula 95>
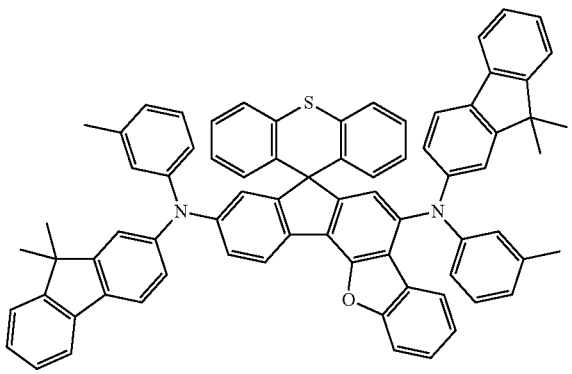

<Chemical Formula 96>
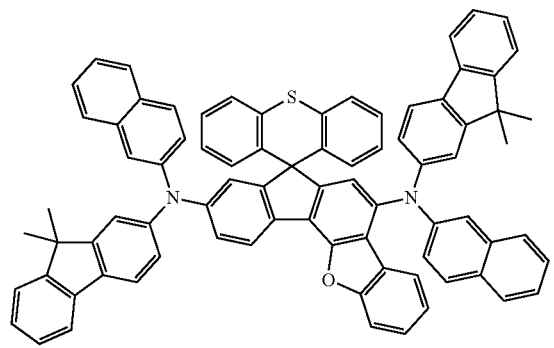
<Chemical Formula 97>
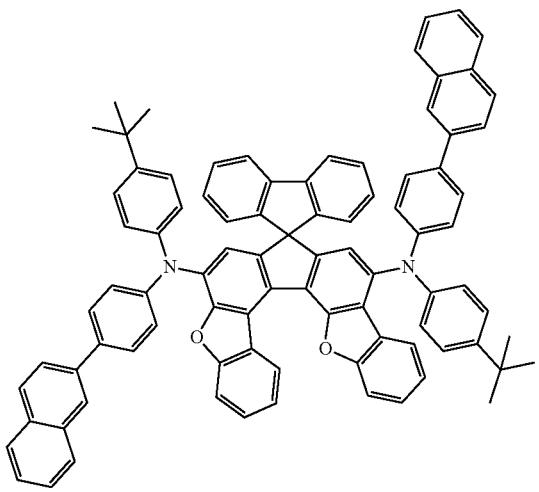
<Chemical Formula 98>
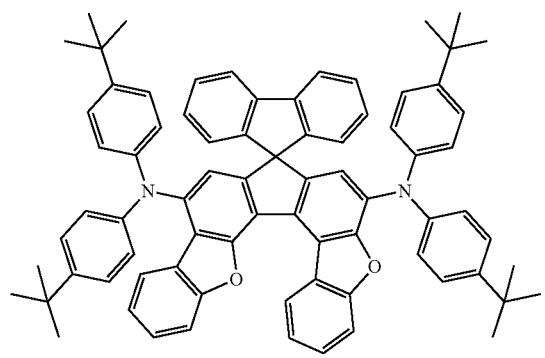
<Chemical Formula 99>
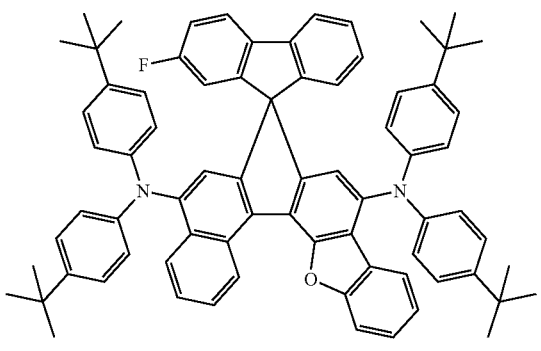
<Chemical Formula 100>
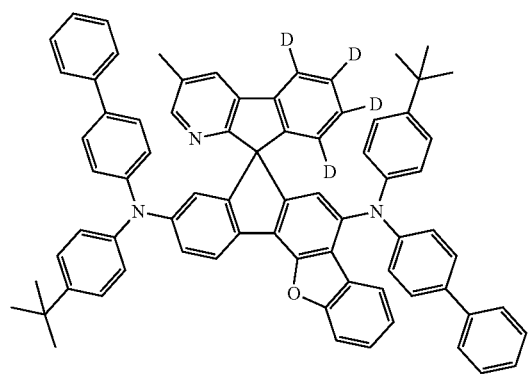
<Chemical Formula 101>
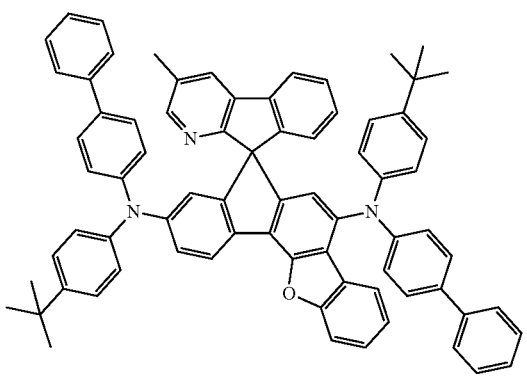

-continued
<Chemical Formula 102>
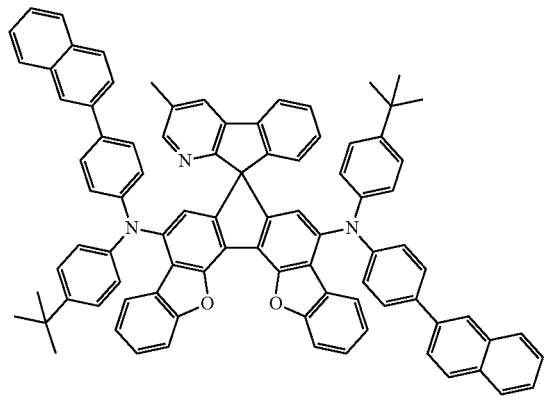
<Chemical Formula 103>
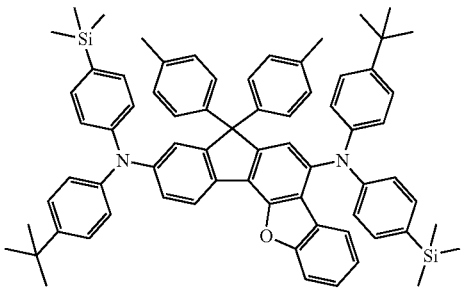
<Chemical Formula 104>
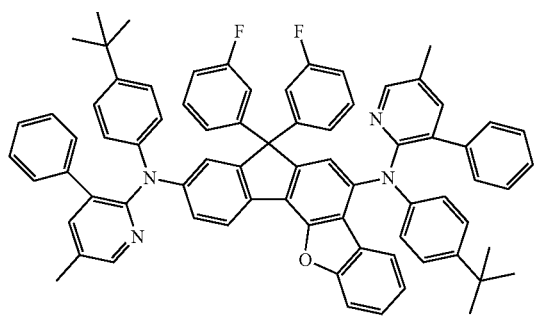
<Chemical Formula 105>
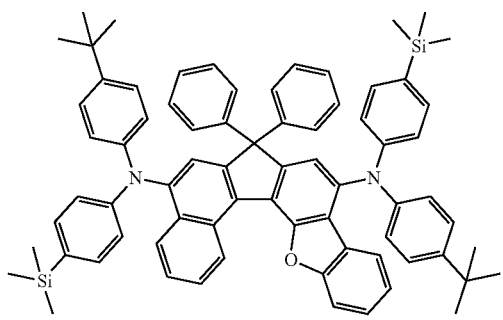
<Chemical Formula 106>
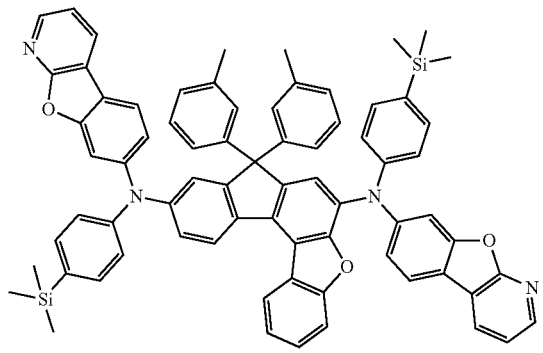
<Chemical Formula 107>
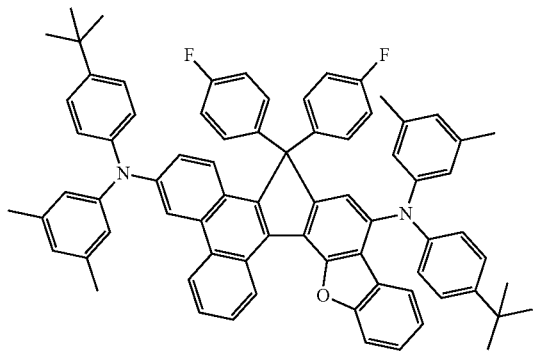
<Chemical Formula 108>
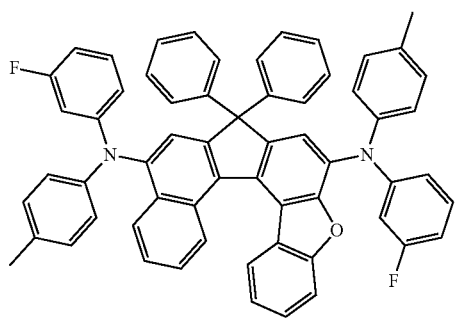
<Chemical Formula 109>
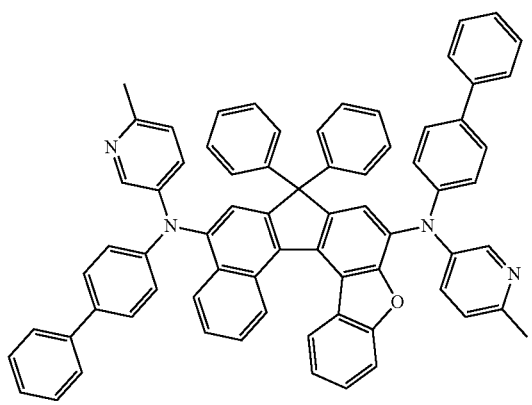

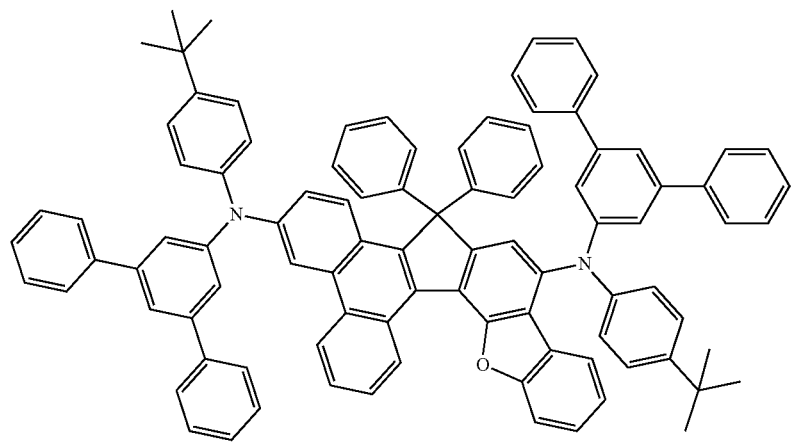
<Chemical Formula 110>
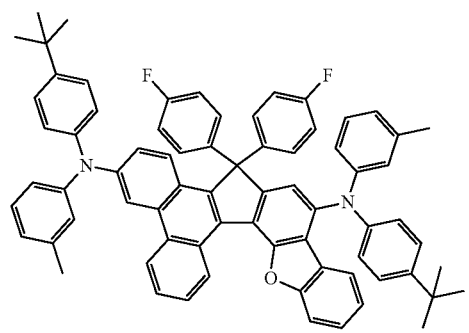
<Chemical Formula 111>
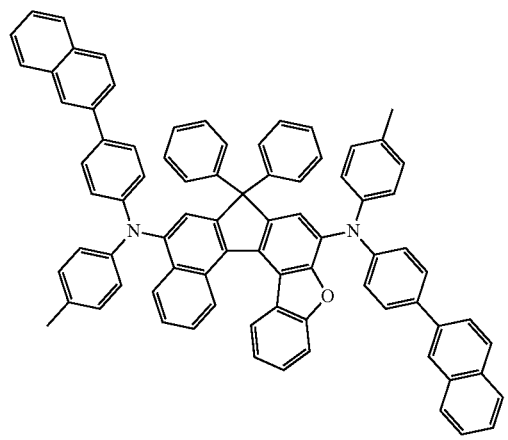
<Chemical Formula 112>
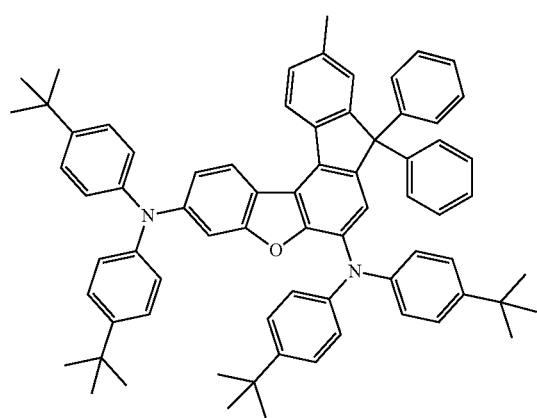
<Chemical Formula 113>
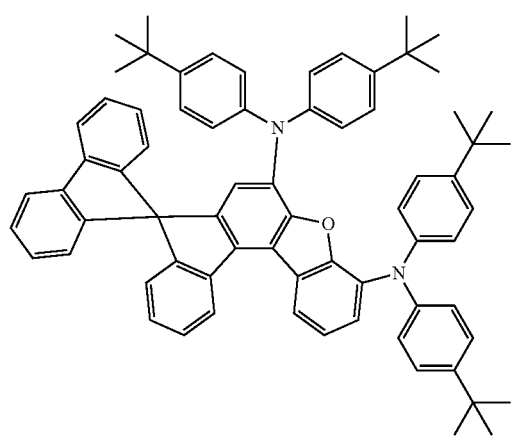
<Chemical Formula 114>

-continued
<Chemical Formula 115>
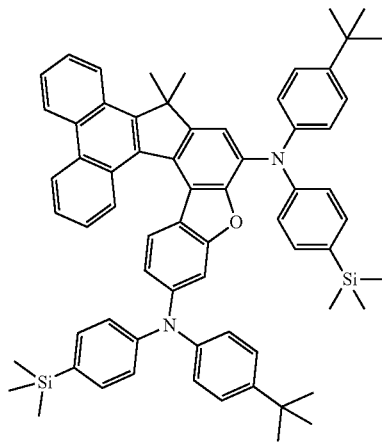
<Chemical Formula 116>
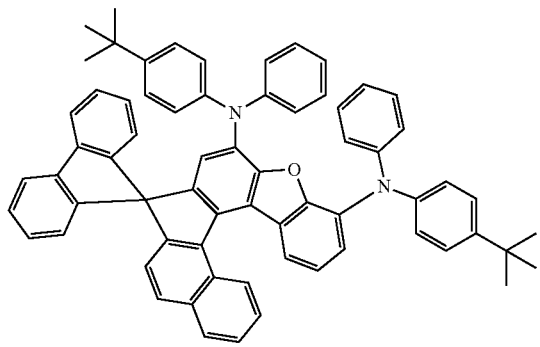
<Chemical Formula 117>
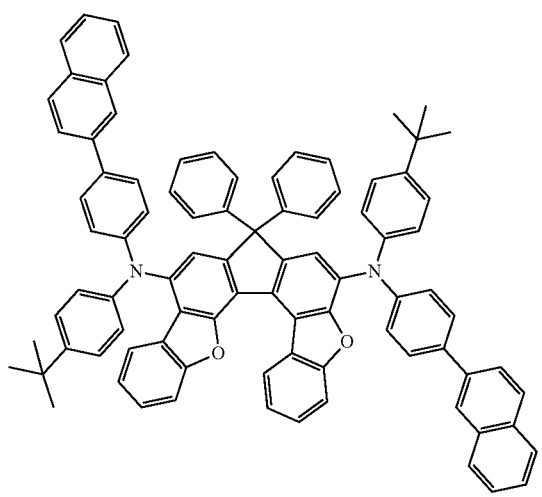
<Chemical Formula 118>
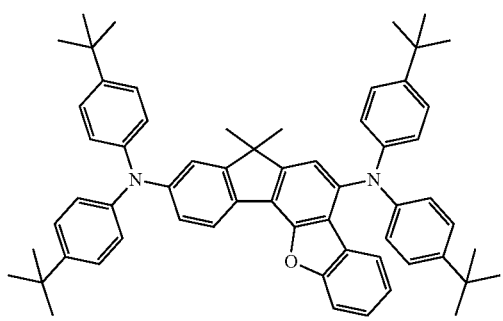
<Chemical Formula 119>
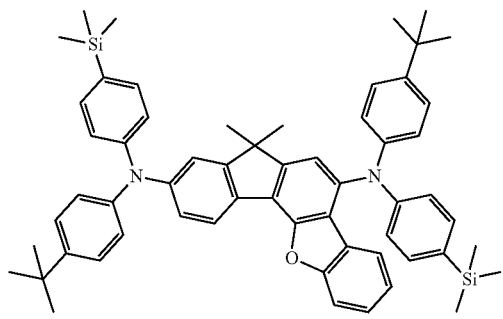
<Chemical Formula 120>
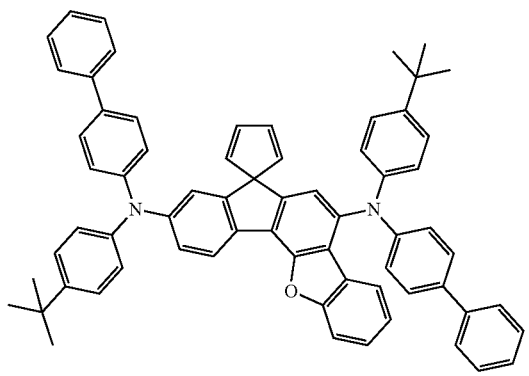

-continued
<Chemical Formula 121>
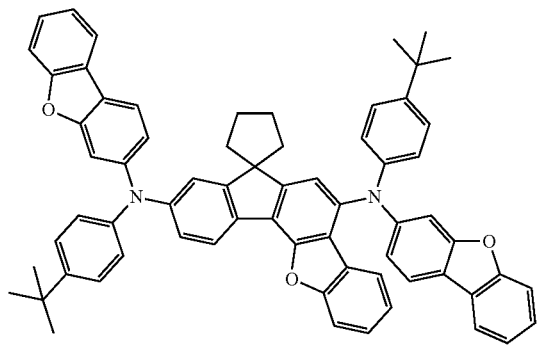
<Chemical Formula 122>
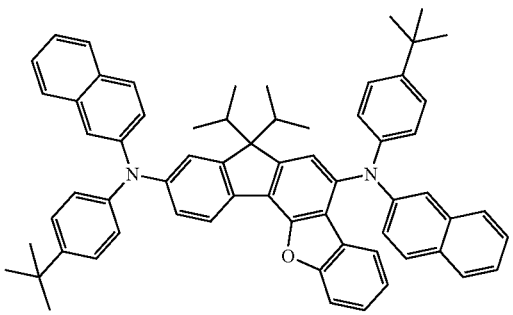
<Chemical Formula 123>
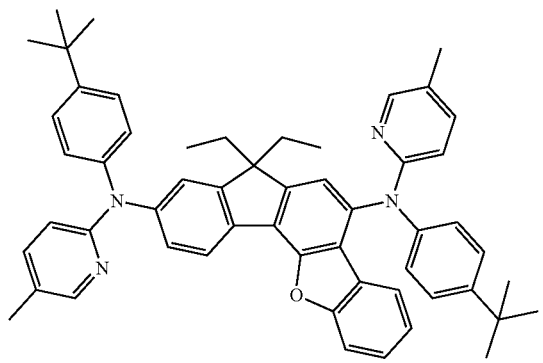
<Chemical Formula 124>
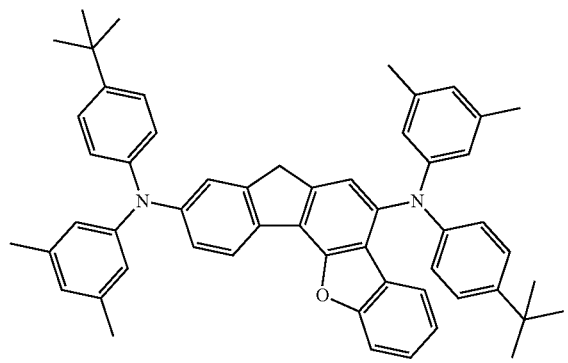
<Chemical Formula 125>
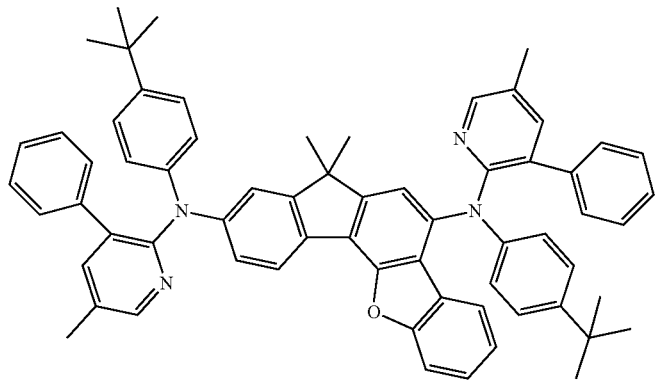
<Chemical Formula 126>
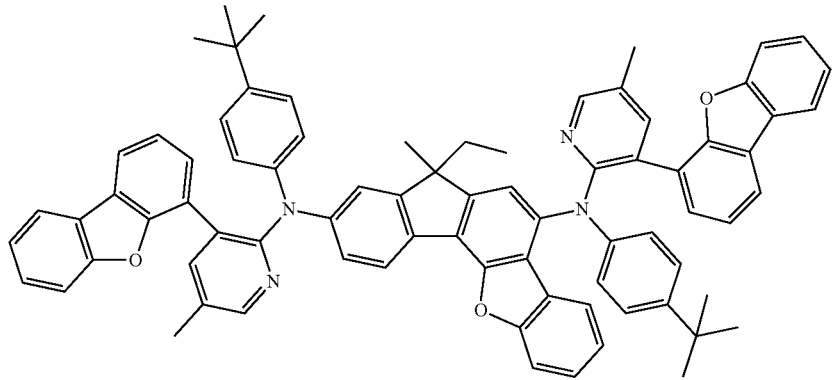

<Chemical Formula 127>
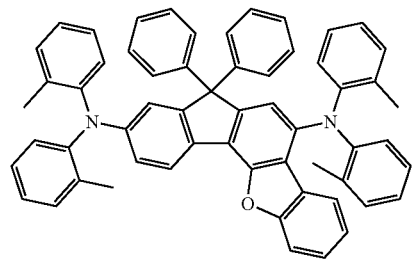
<Chemical Formula 128>
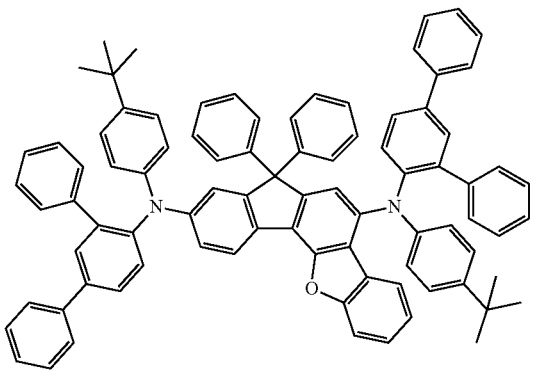
<Chemical Formula 129>
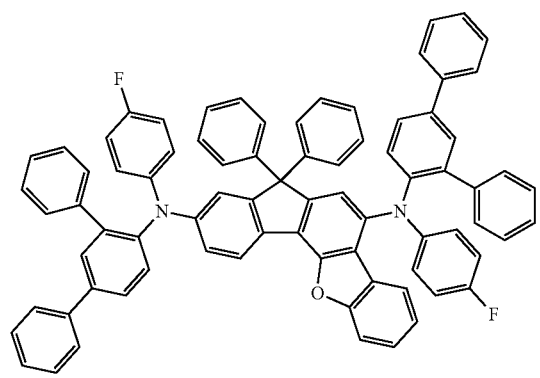
<Chemical Formula 130>
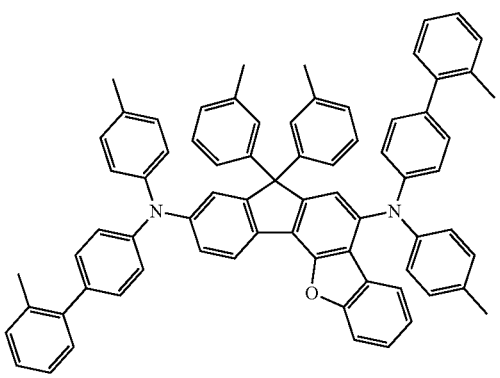
<Chemical Formula 131>
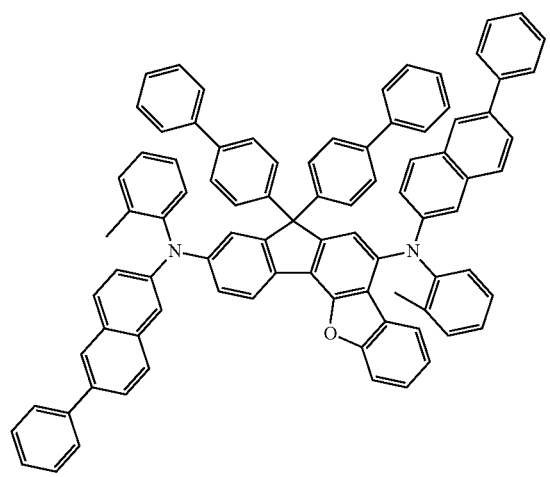
<Chemical Formula 132>
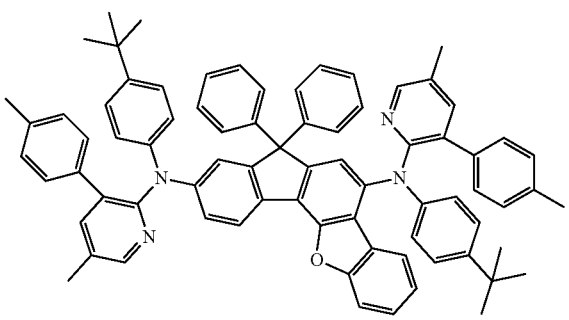

-continued
<Chemical Formula 133>
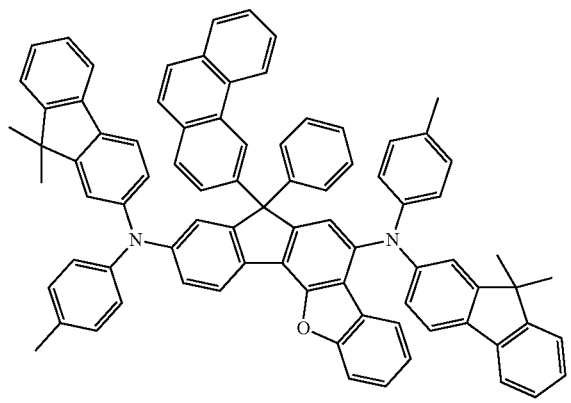
<Chemical Formula 134>
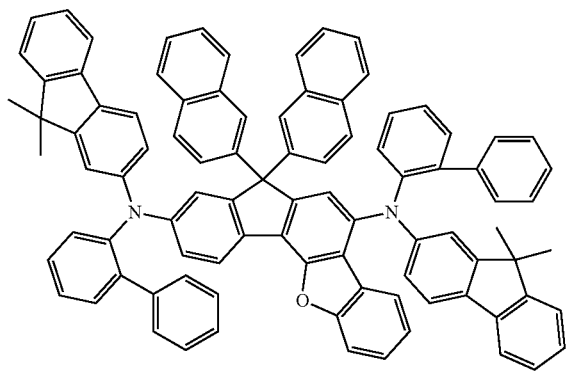
<Chemical Formula 135>
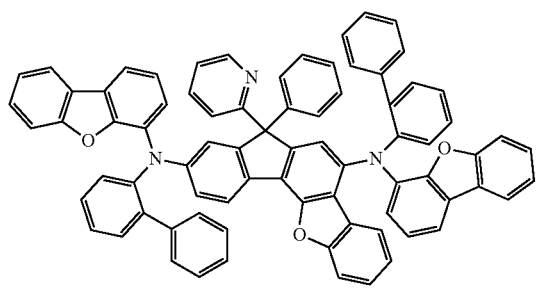
<Chemical Formula 136>
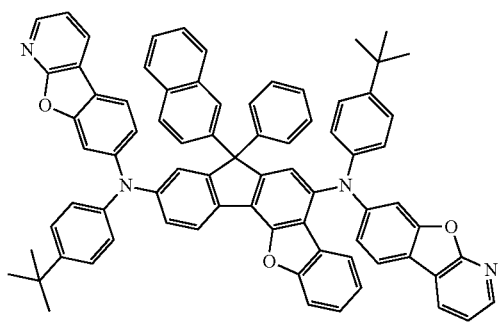
<Chemical Formula 137>
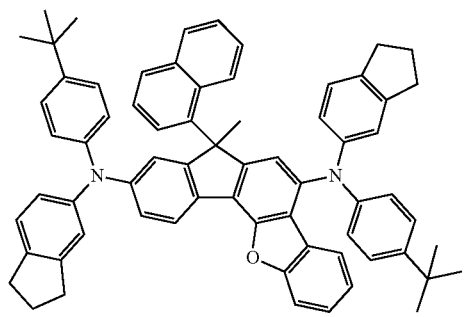
<Chemical Formula 138>
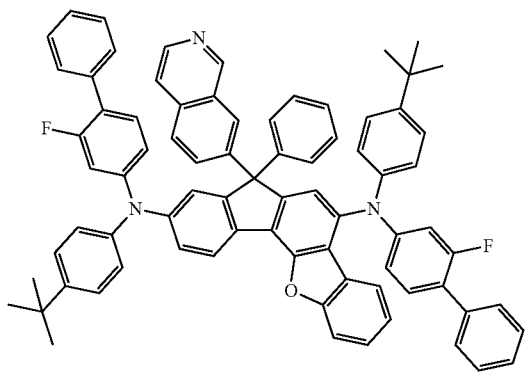
<Chemical Formula 139>
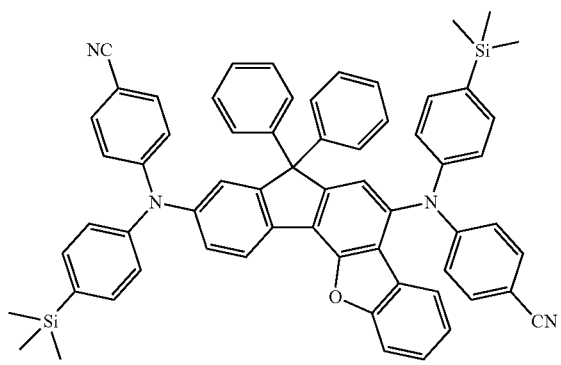
<Chemical Formula 140>
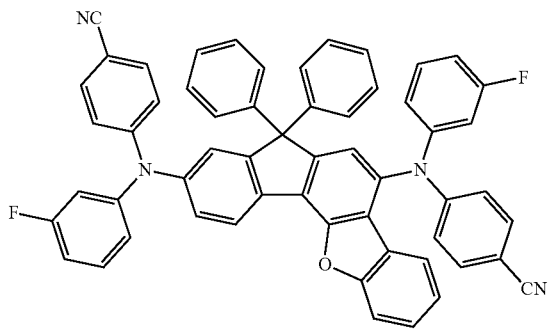

<Chemical Formula 141>
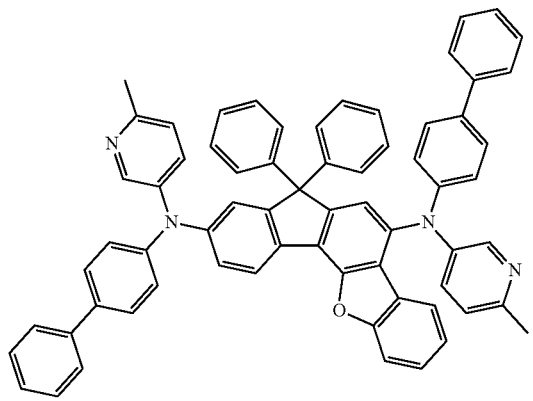
<Chemical Formula 142>
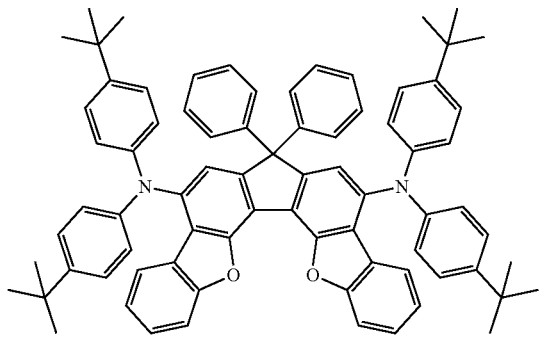
<Chemical Formula 143>
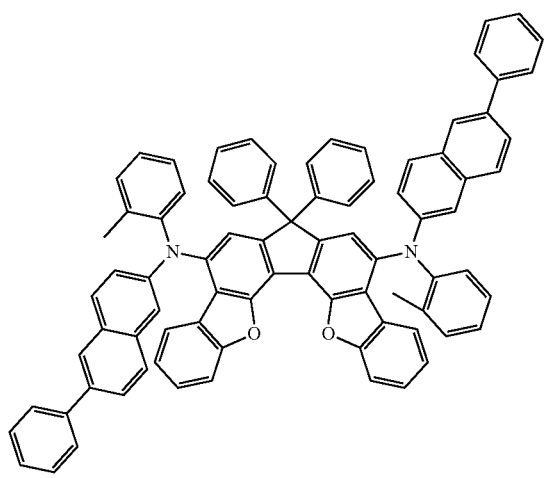
<Chemical Formula 144>
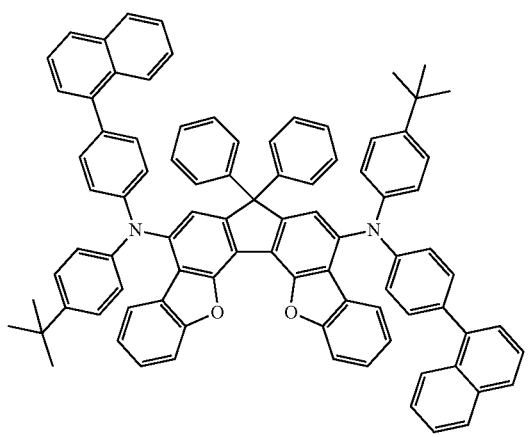
<Chemical Formula 145>
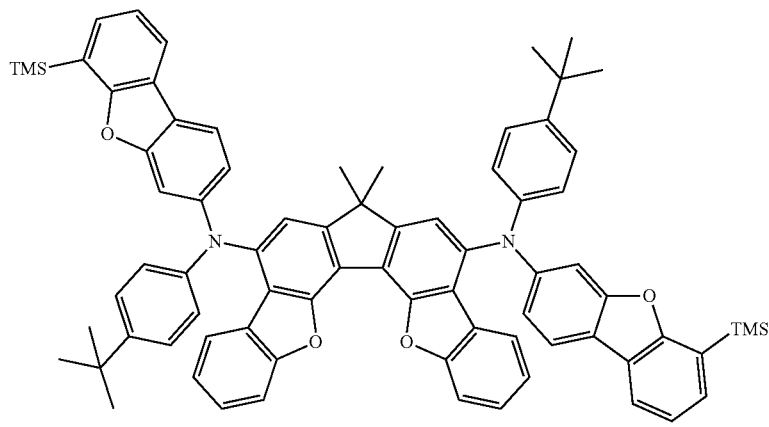
<Chemical Formula 146>
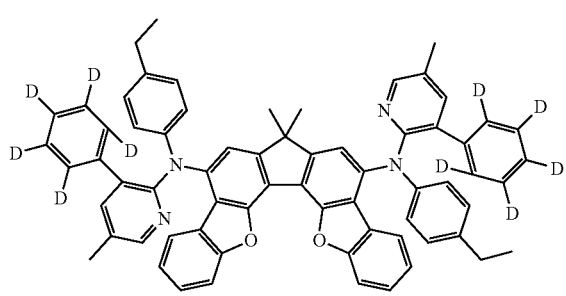
<Chemical Formula 147>
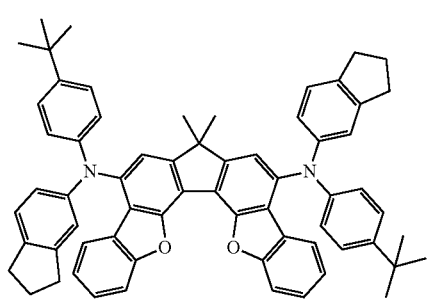

-continued
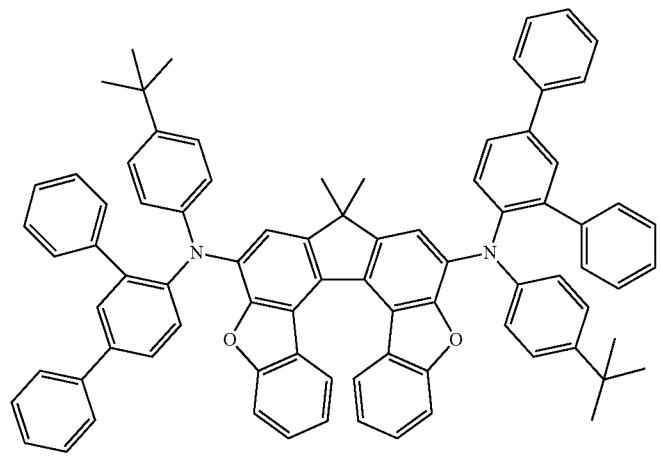
<Chemical Formula 148>
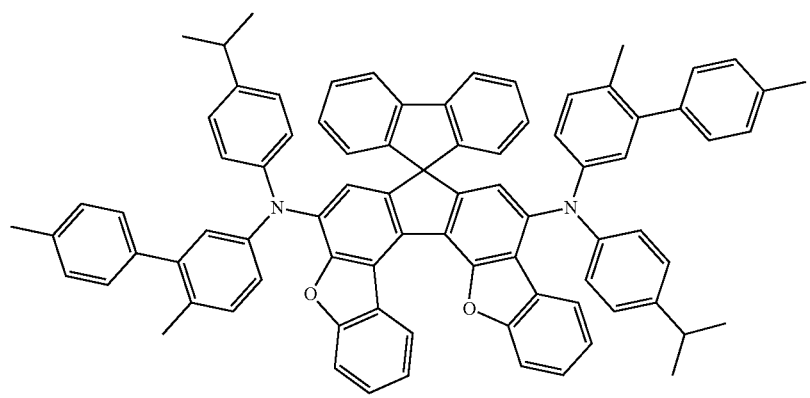
<Chemical Formula 149>
<Chemical Formula 150>
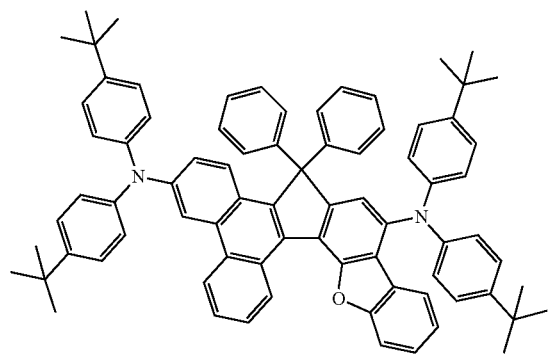
<Chemical Formula 151>
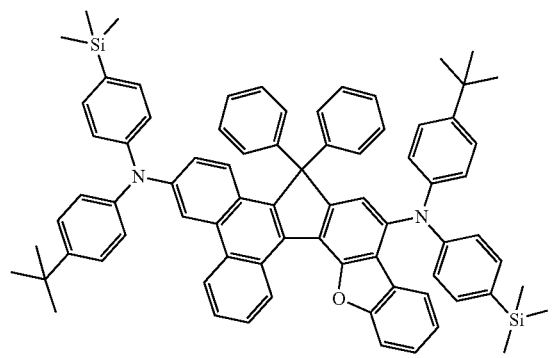

-continued
<Chemical Formula 152>
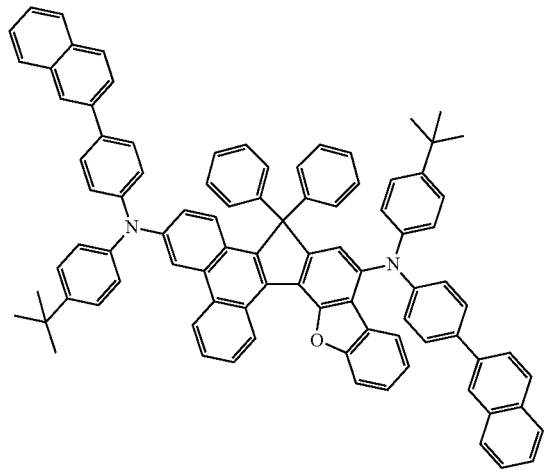
<Chemical Formula 153>
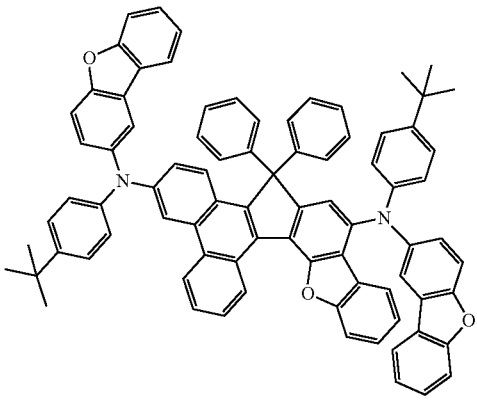
<Chemical Formula 154>
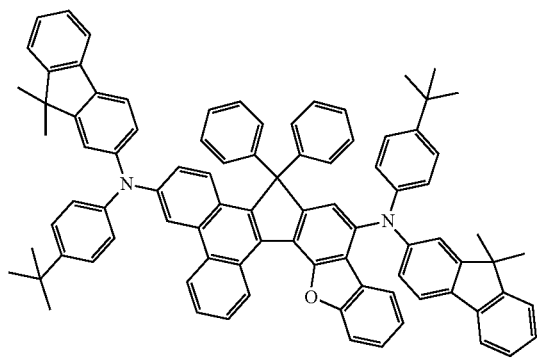
<Chemical Formula 155>
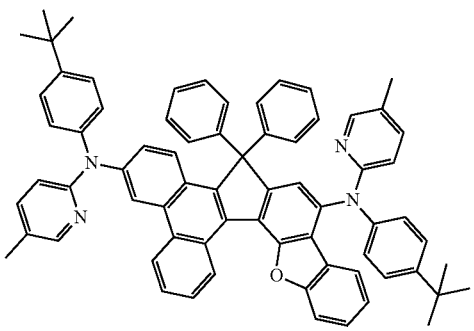
<Chemical Formula 156>
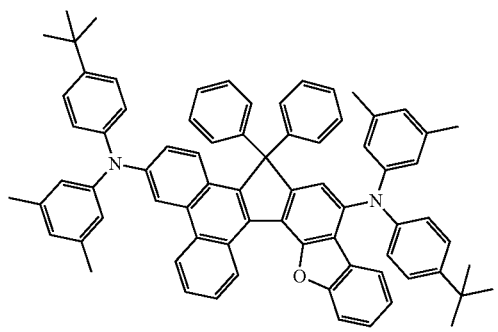
<Chemical Formula 157>
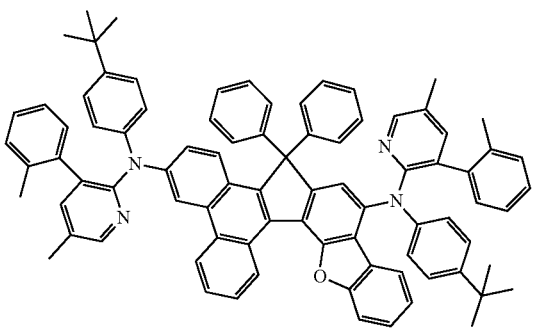
<Chemical Formula 158>
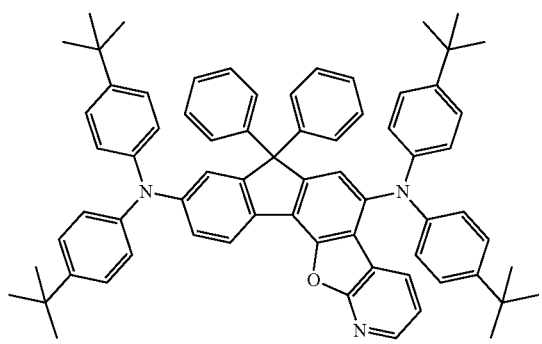
<Chemical Formula 159>
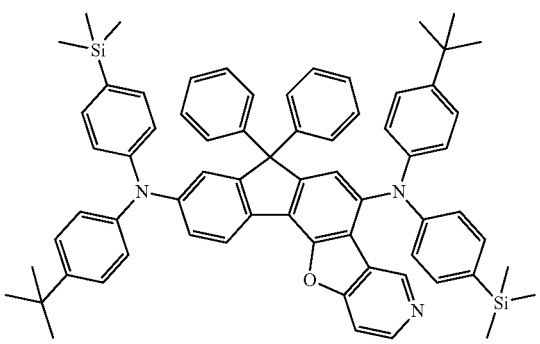

-continued
<Chemical Formula 160>
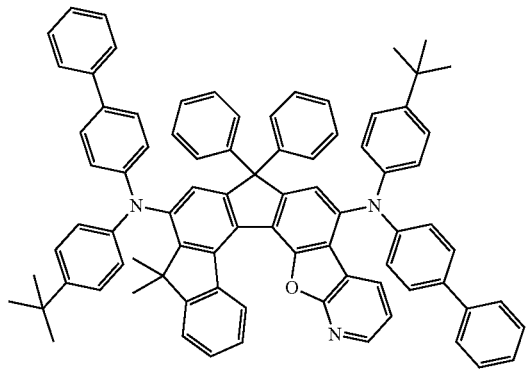
<Chemical Formula 161>
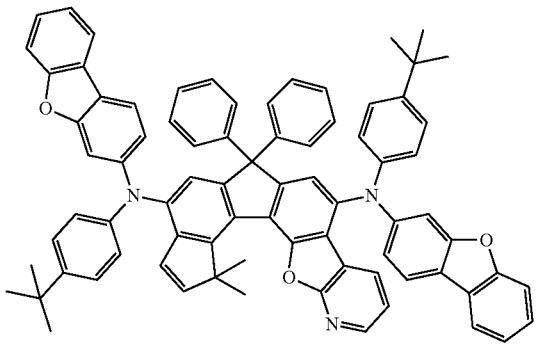
<Chemical Formula 162>
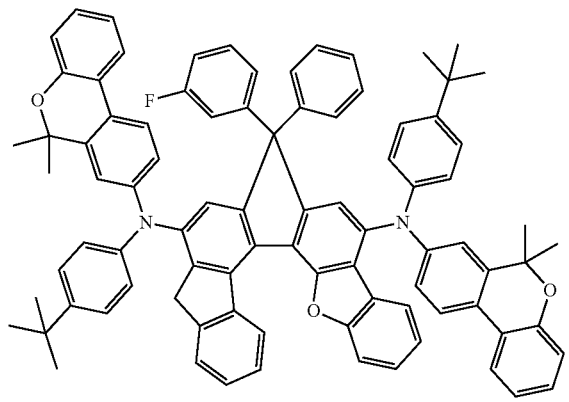
<Chemical Formula 163>
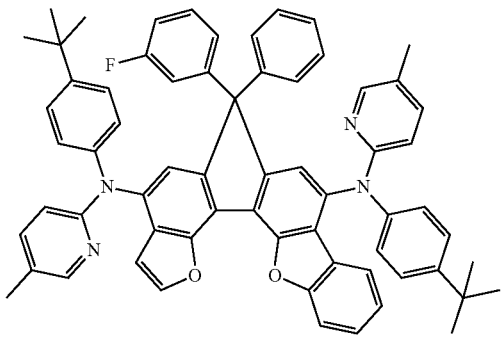
<Chemical Formula 164>
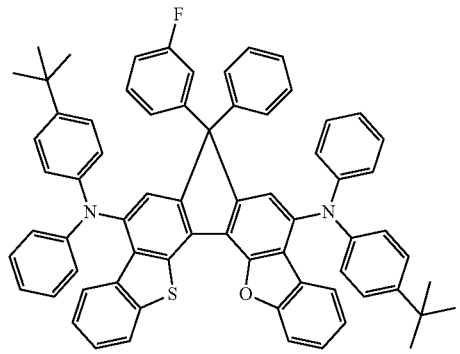
<Chemical Formula 165>
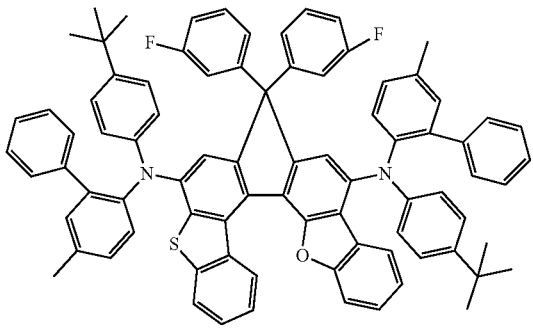
<Chemical Formula 166>
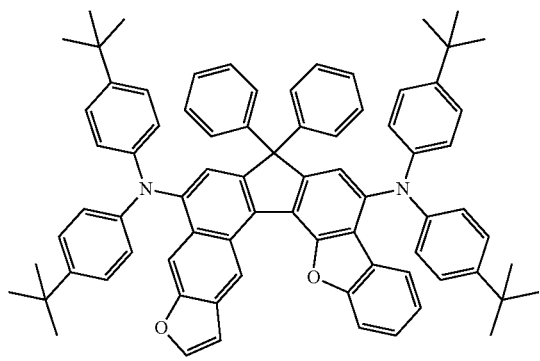
<Chemical Formula 167>
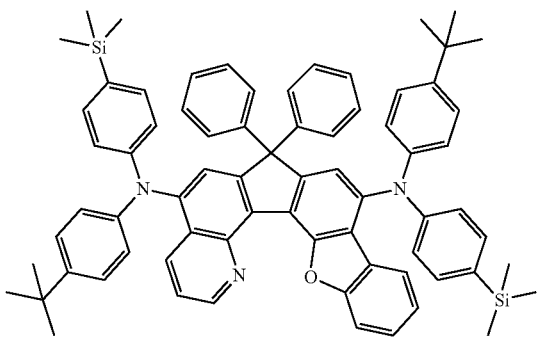

-continued
<Chemical Formula 168>
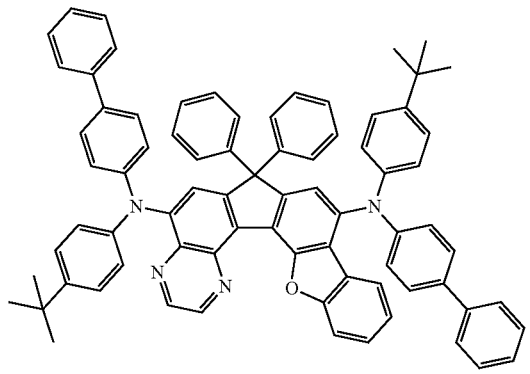
<Chemical Formula 169>
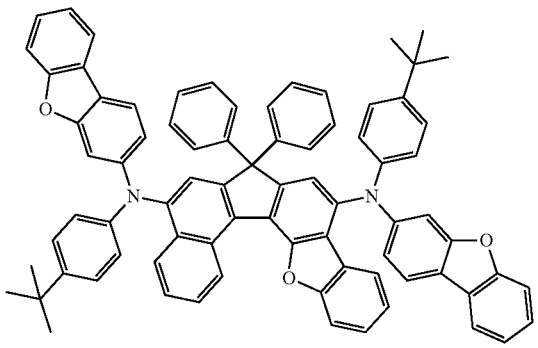
<Chemical Formula 170>
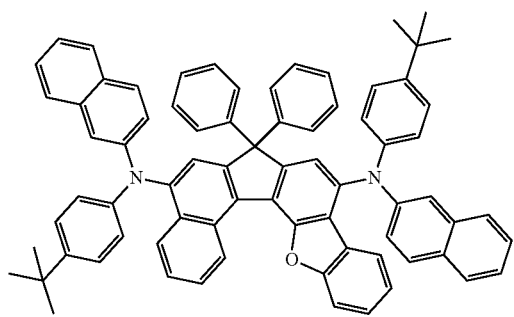
<Chemical Formula 171>
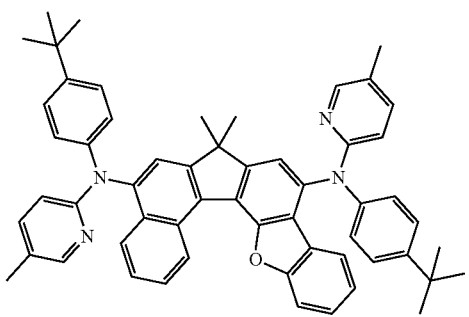
<Chemical Formula 172>
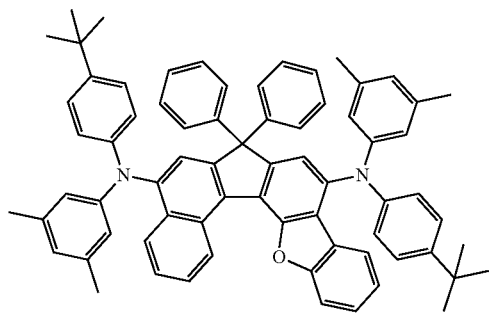
<Chemical Formula 173>
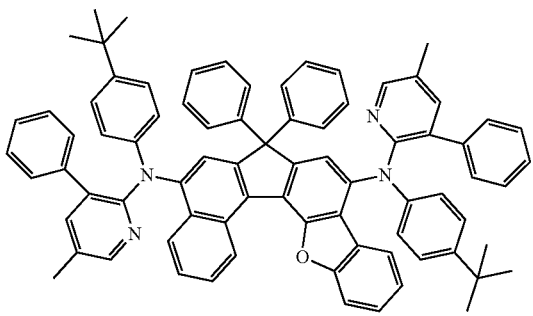
<Chemical Formula 174>
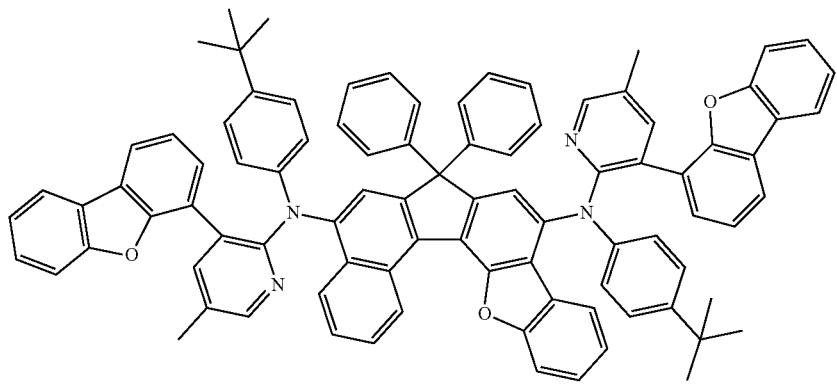

-continued
<Chemical Formula 175>
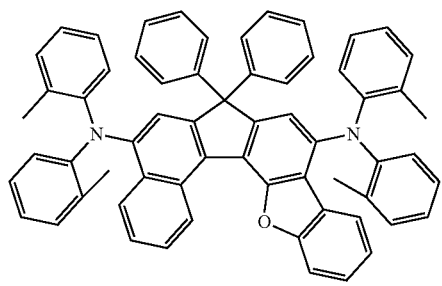
<Chemical Formula 176>
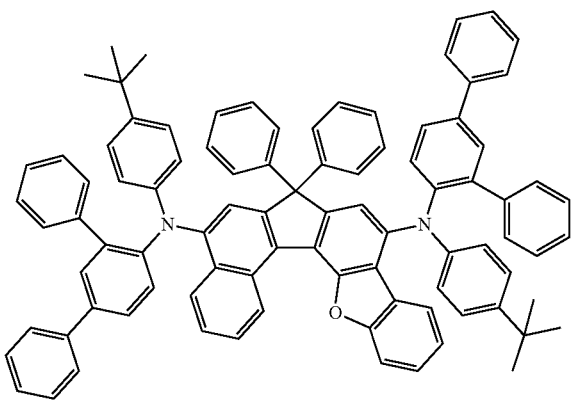
<Chemical Formula 177>
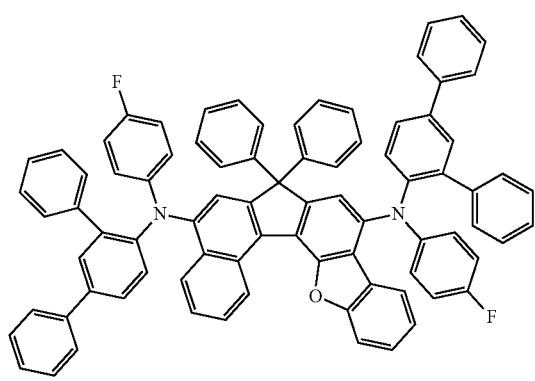
<Chemical Formula 178>
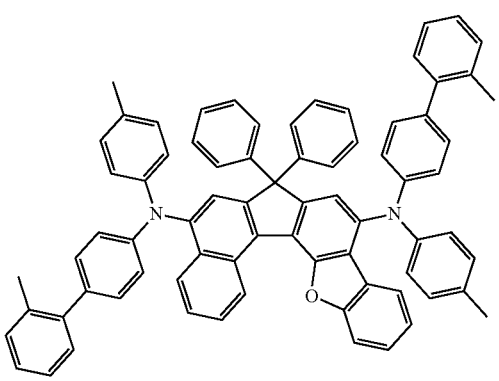
<Chemical Formula 179>
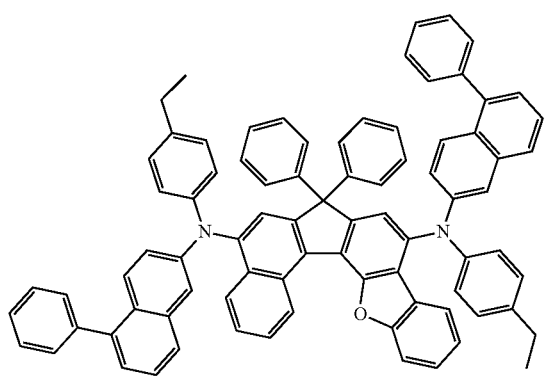
<Chemical Formula 180>
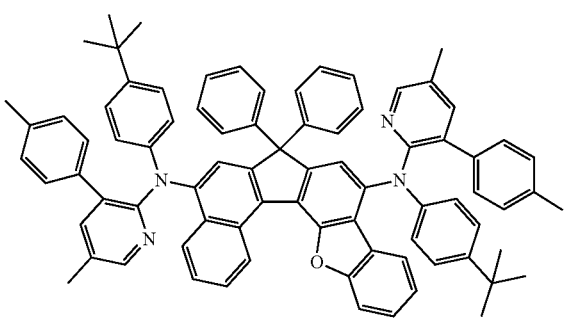
<Chemical Formula 181>
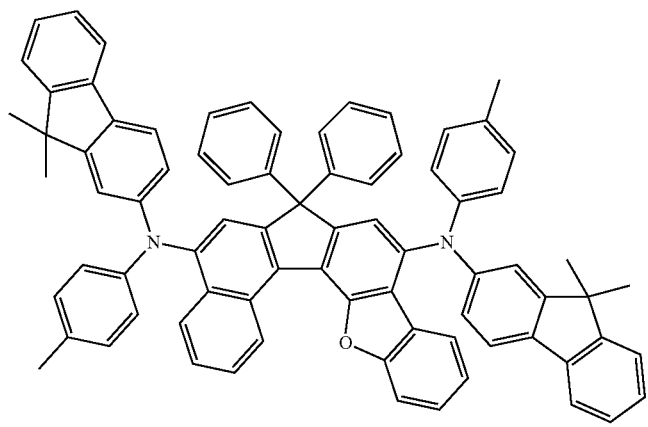

<Chemical Formula 182>
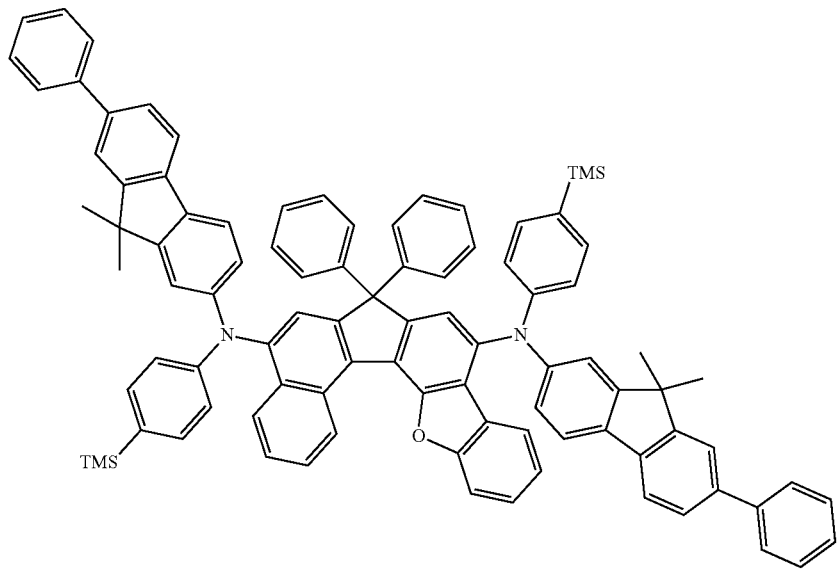
<Chemical Formula 183>
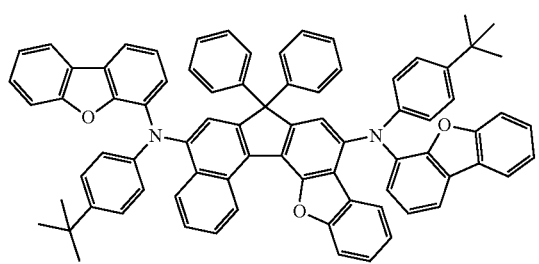
<Chemical Formula 184>
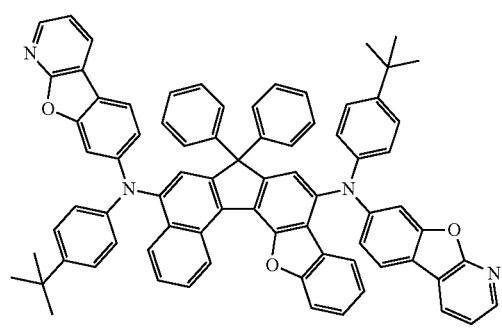
<Chemical Formula 185>
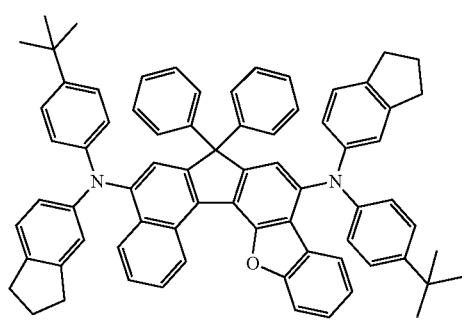
<Chemical Formula 186>
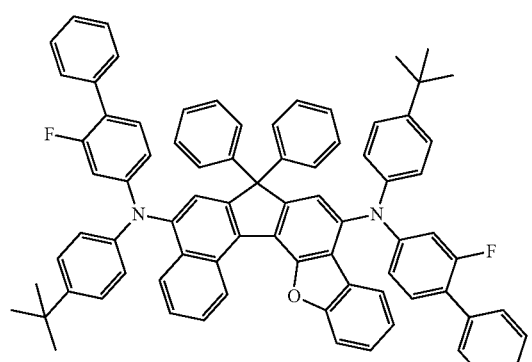
<Chemical Formula 187>
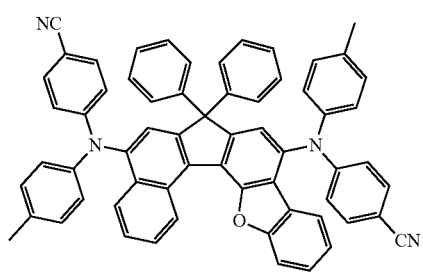
<Chemical Formula 188>
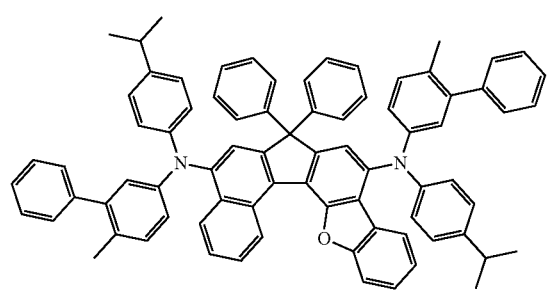

<Chemical Formula 189>
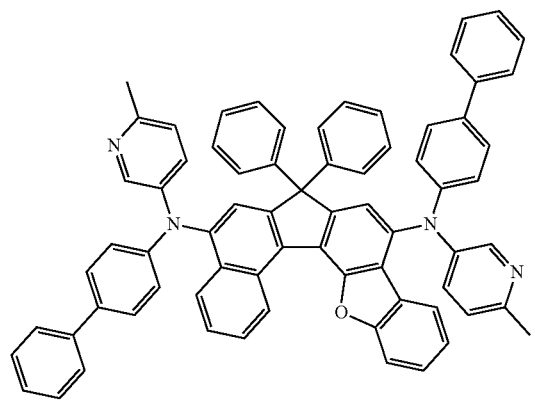
<Chemical Formula 190>
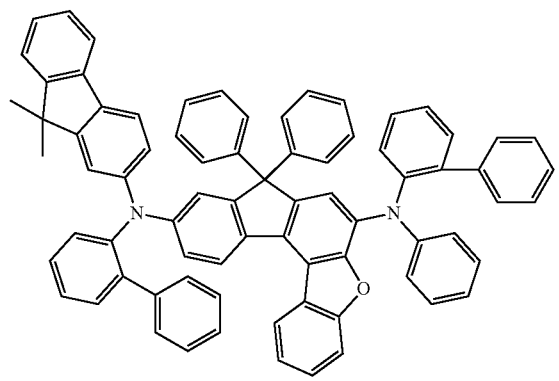
<Chemical Formula 191>
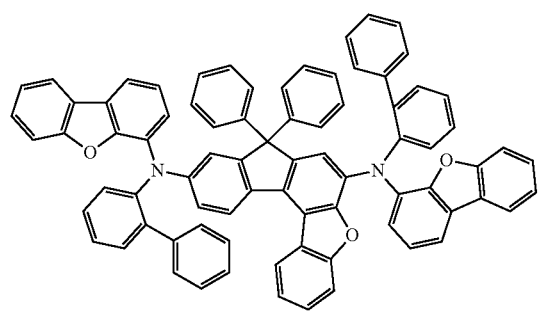
<Chemical Formula 192>
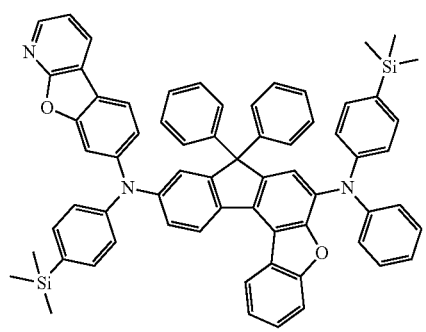
<Chemical Formula 193>
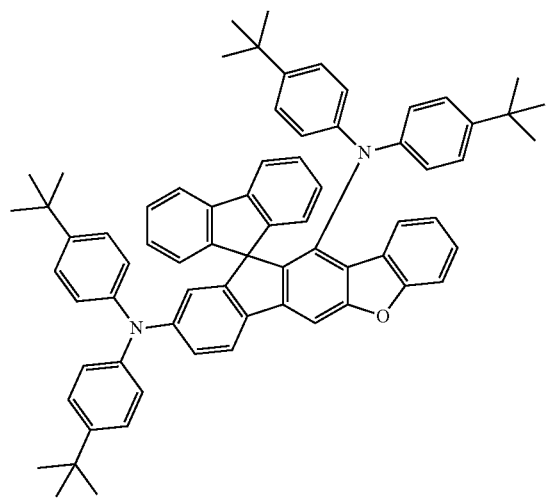
<Chemical Formula 194>
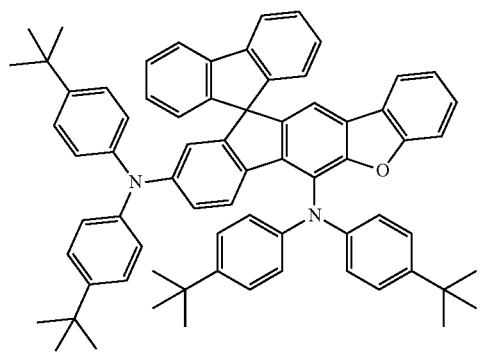

<Chemical Formula 195>
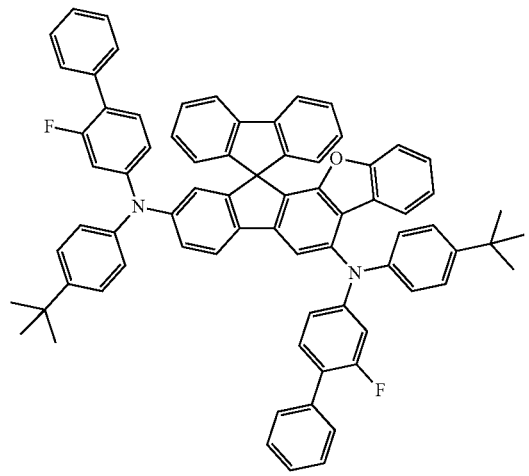
<Chemical Formula 196>
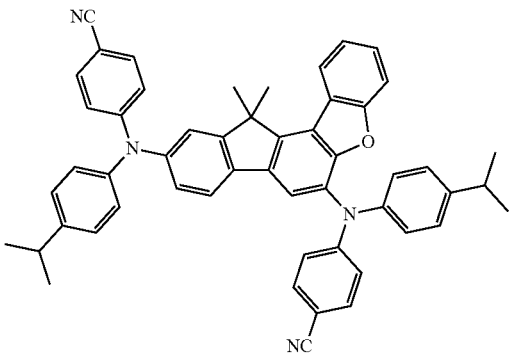
<Chemical Formula 197>
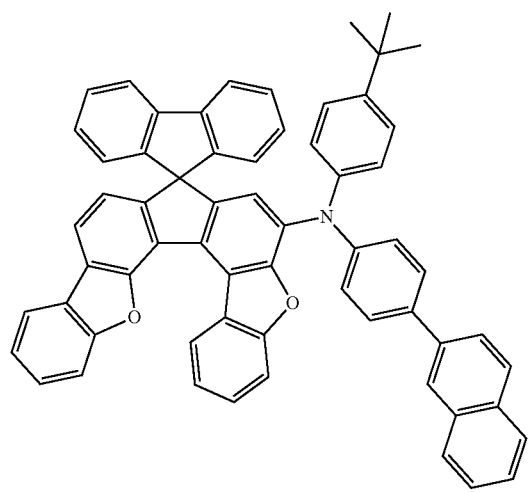
<Chemical Formula 198>
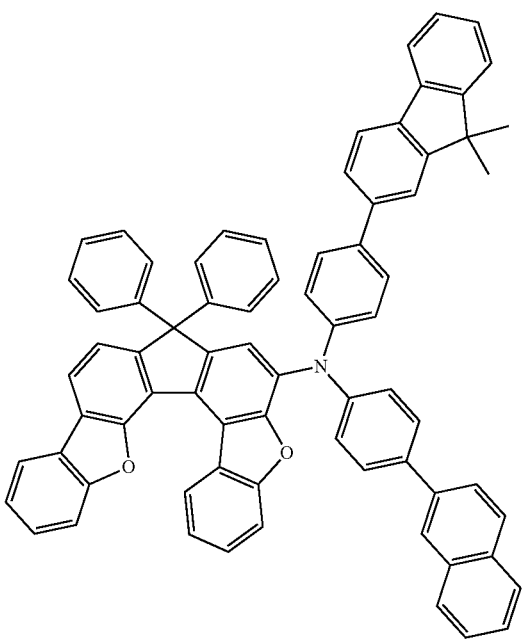

-continued
<Chemical Formula 199>
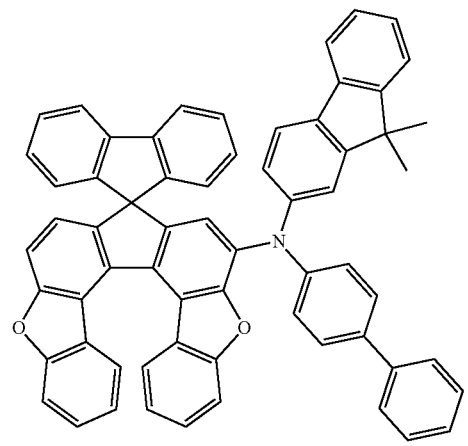
<Chemical Formula 200>
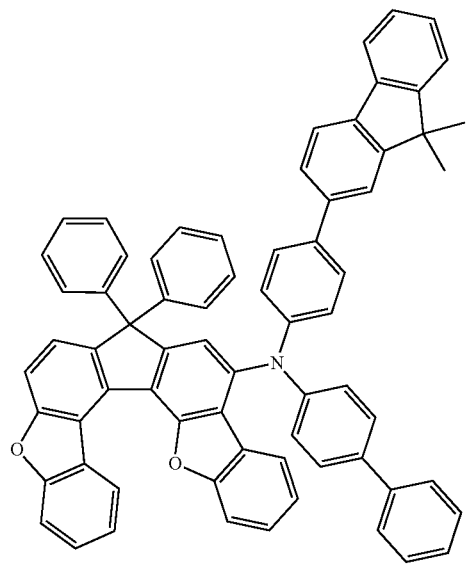
<Chemical Formula 201>
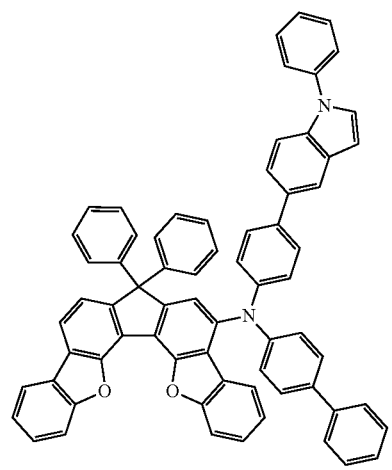
<Chemical Formula 202>
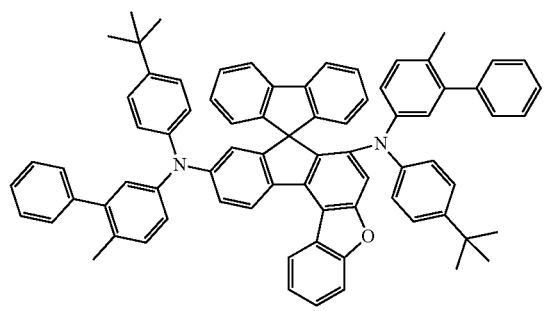
<Chemical Formula 203>
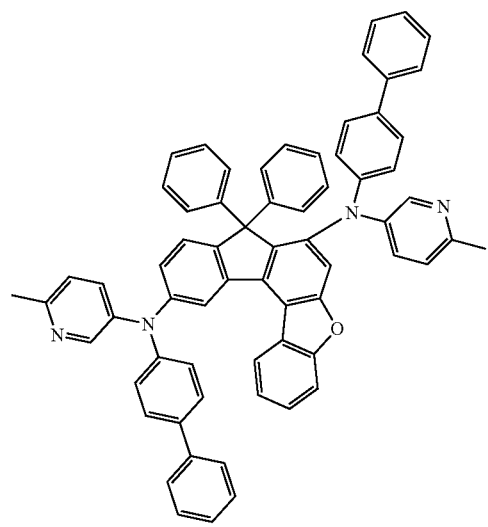
<Chemical Formula 204>
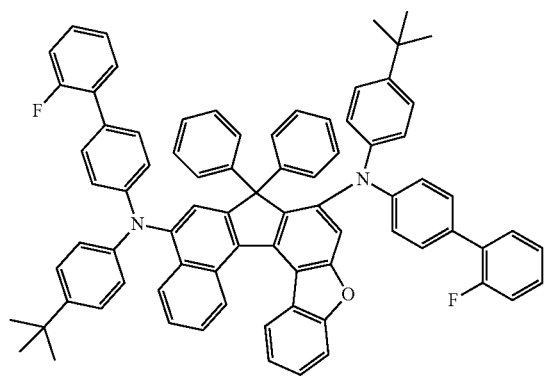

<Chemical Formula 205>
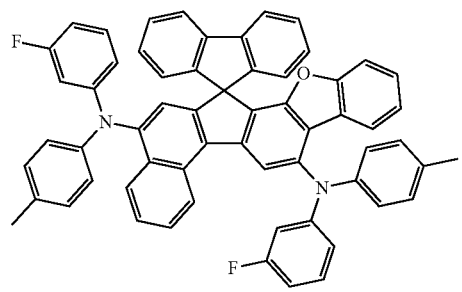
<Chemical Formula 206>
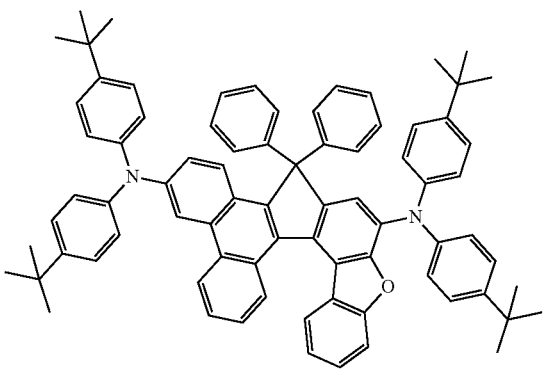
<Chemical Formula 207>
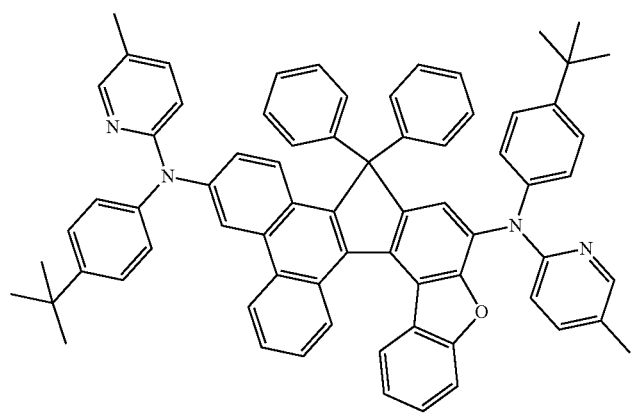
<Chemical Formula 208>
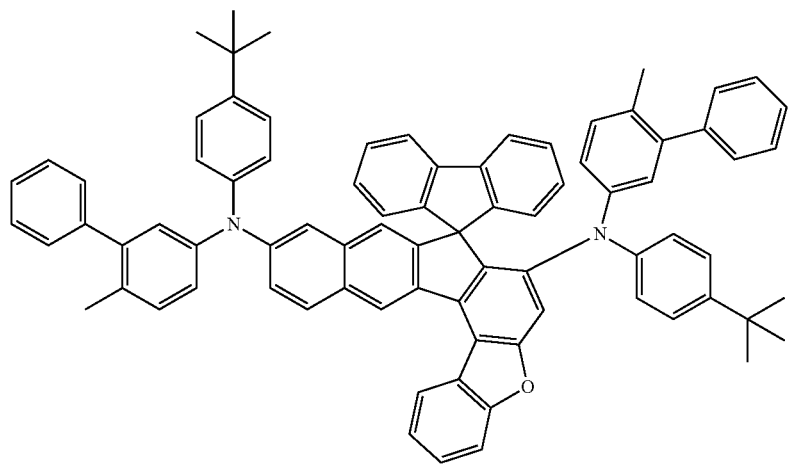
<Chemical Formula 209>
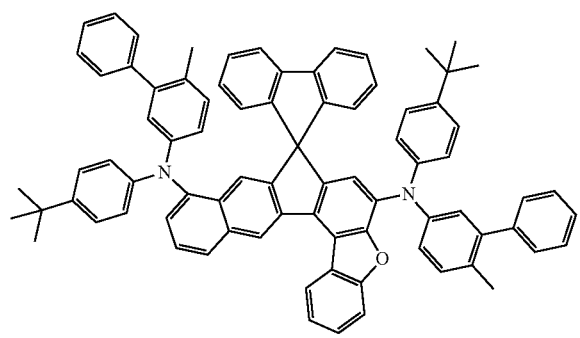
<Chemical Formula 210>
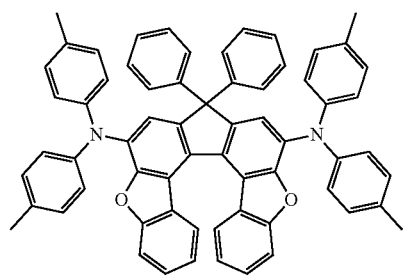

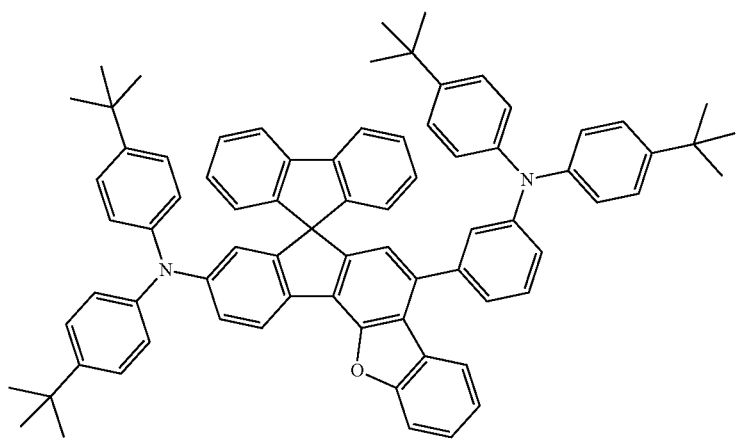
<Chemical Formula 211>
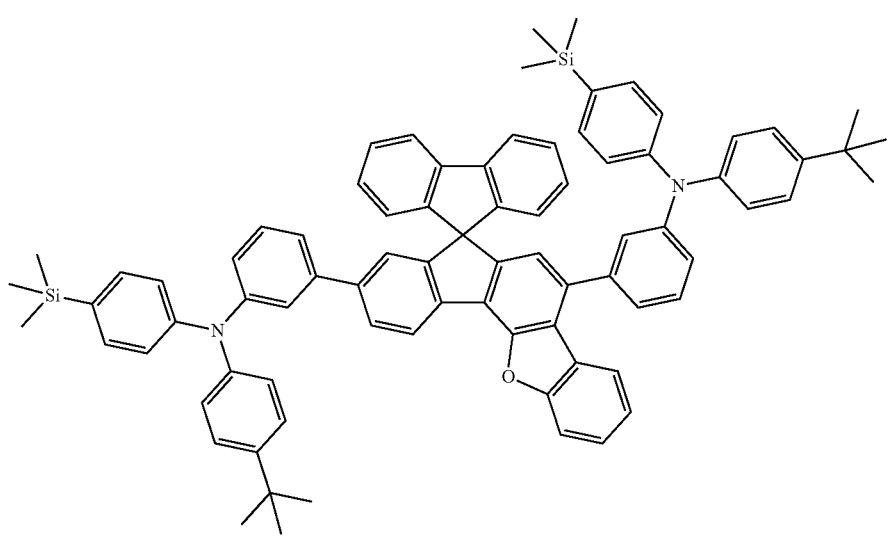
<Chemical Formula 212>
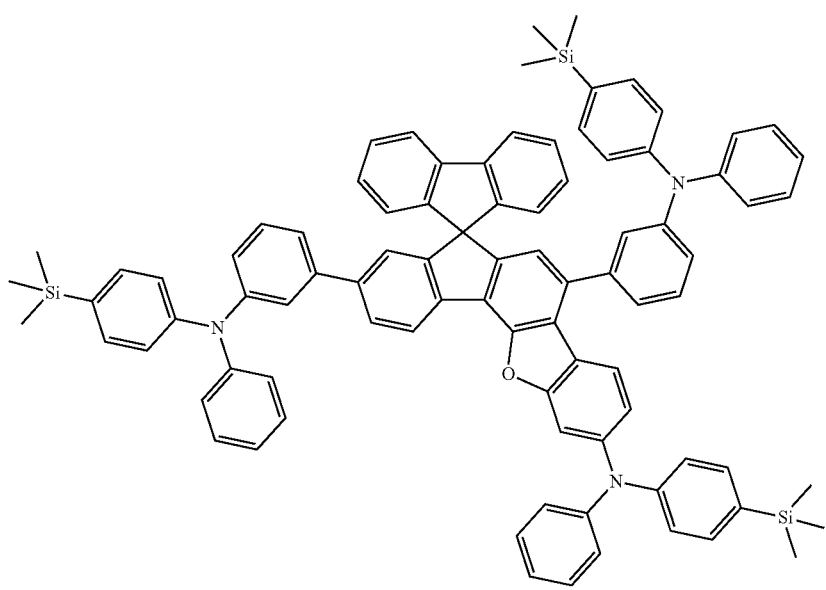
<Chemical Formula 213>

<Chemical Formula 214>
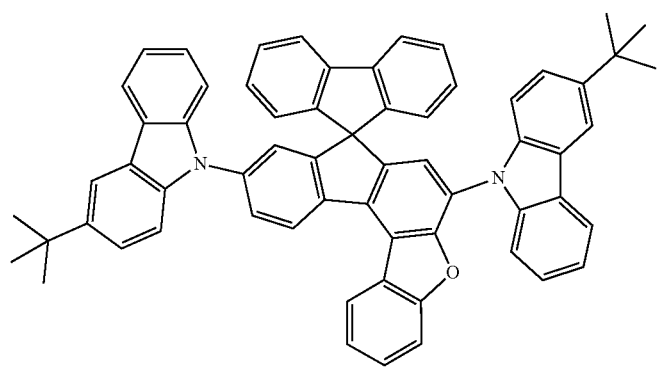
<Chemical Formula 215>
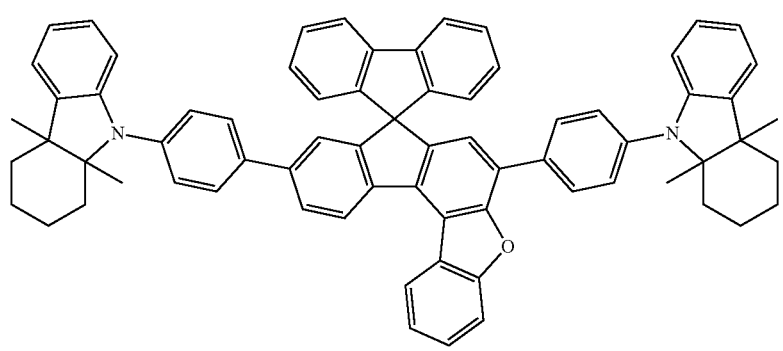
<Chemical Formula 216>
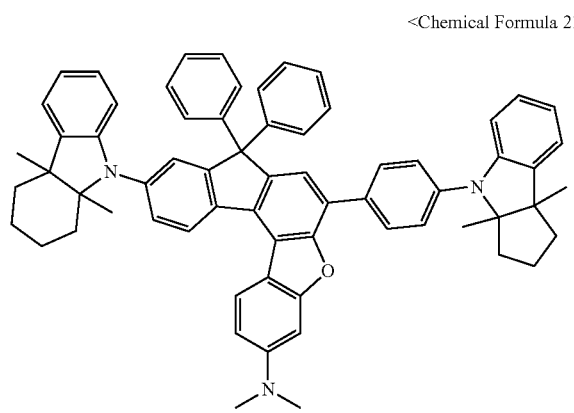
<Chemical Formula 217>
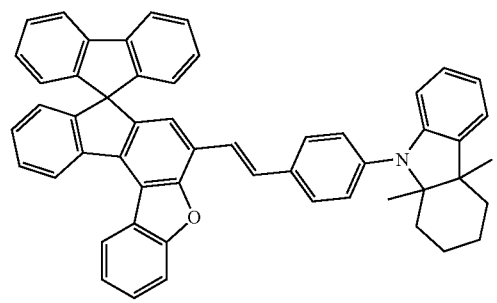
<Chemical Formula 218>
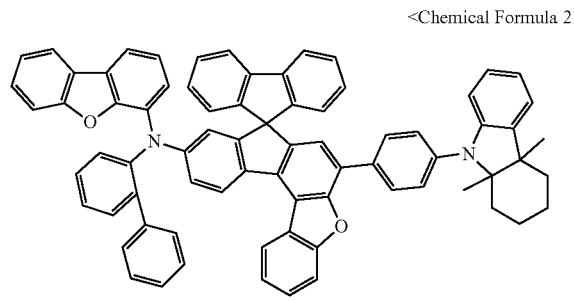
<Chemical Formula 219>
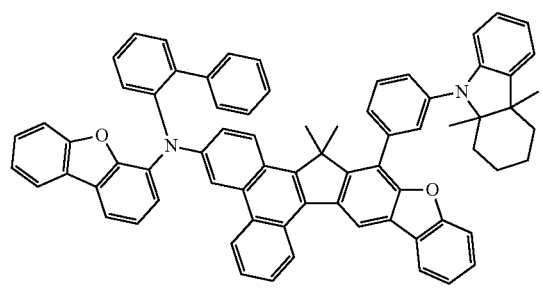

-continued
<Chemical Formula 220>
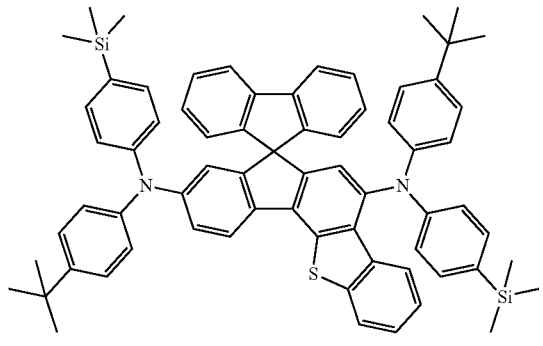
<Chemical Formula 221>
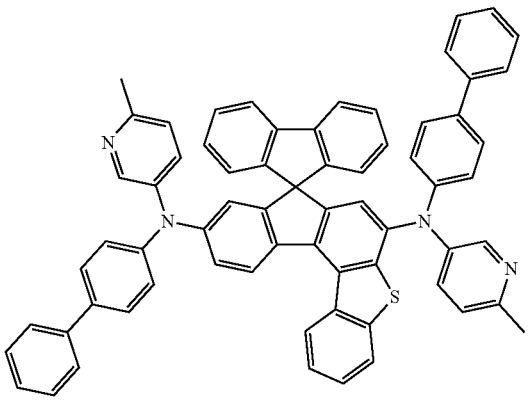
<Chemical Formula 222>
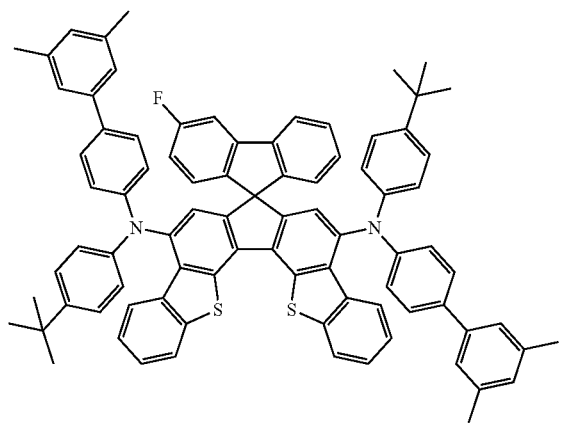
<Chemical Formula 223>
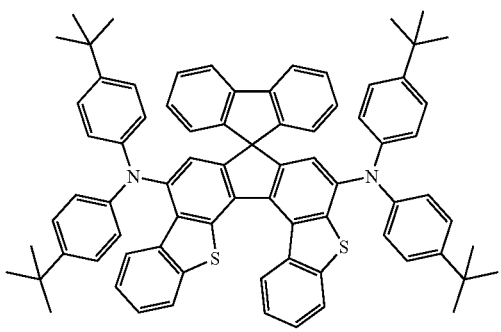
<Chemical Formula 224>
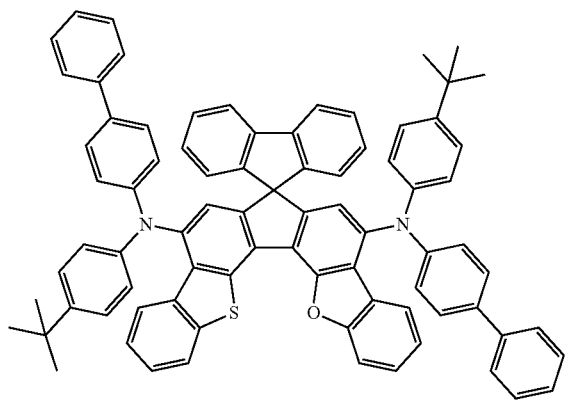
<Chemical Formula 225>
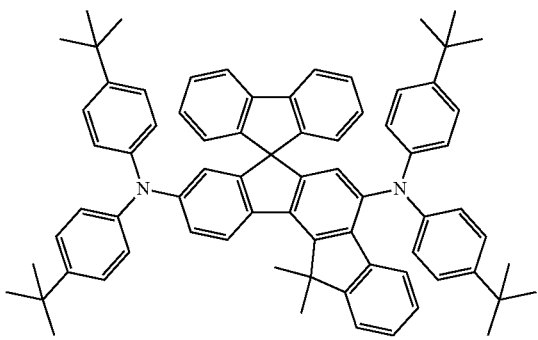

-continued
<Chemical Formula 226>
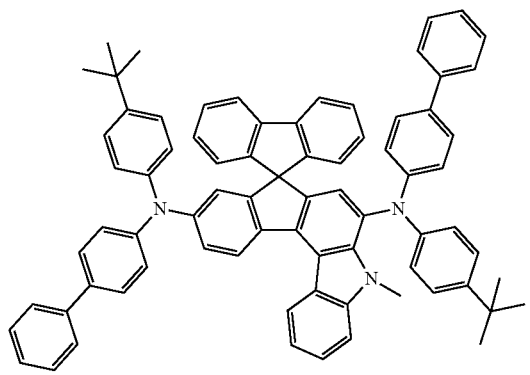
<Chemical Formula 227>
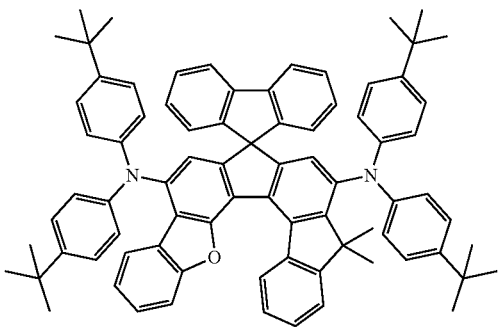
<Chemical Formula 228>
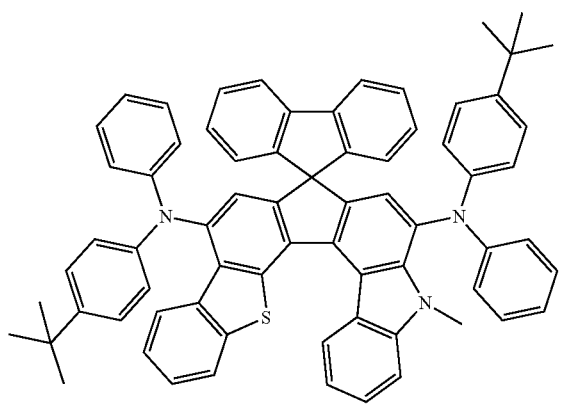
<Chemical Formula 229>
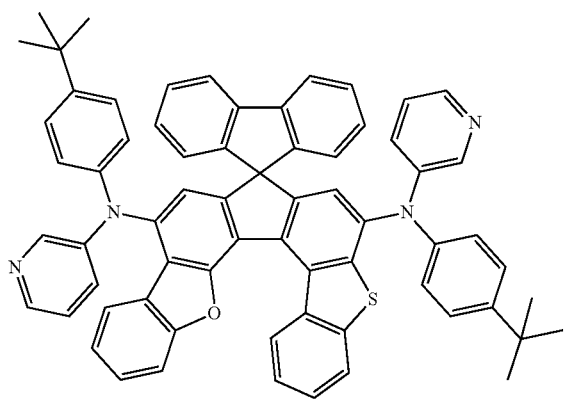
<Chemical Formula 230>
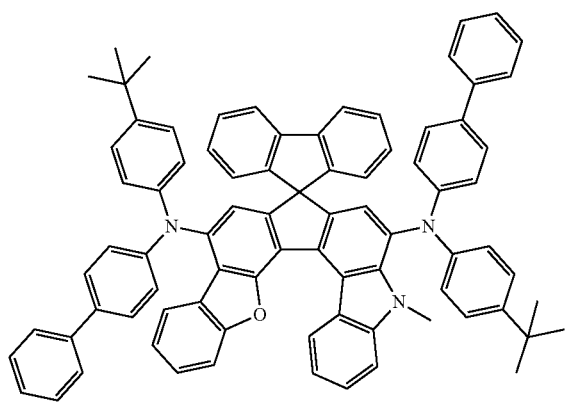
<Chemical Formula 231>
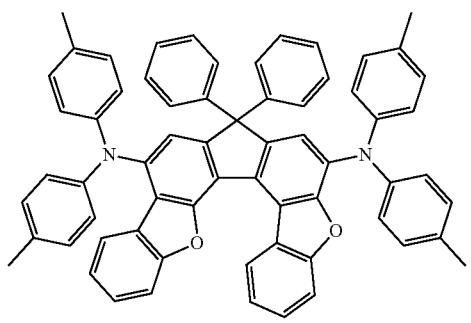
<Chemical Formula 232>
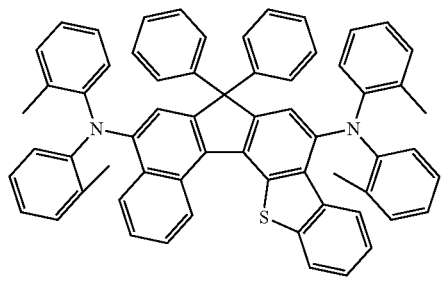
<Chemical Formula 233>
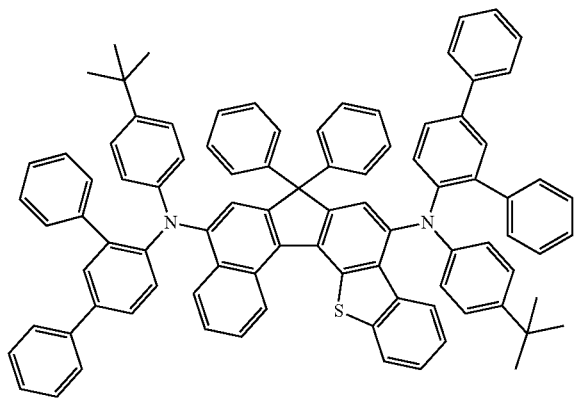

<Chemical Formula 234>
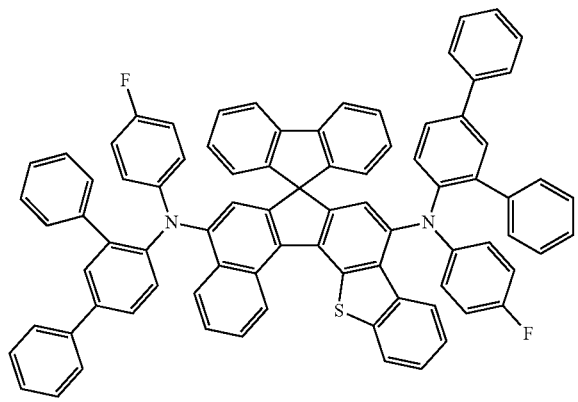
<Chemical Formula 235>
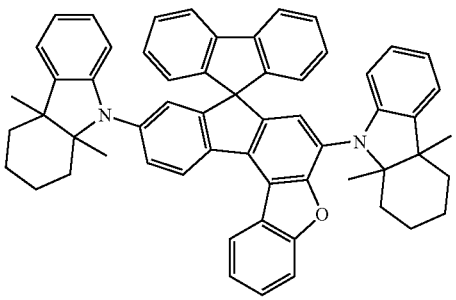
<Chemical Formula 238>
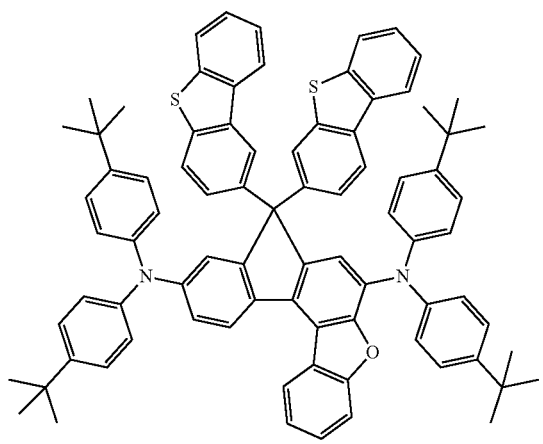
<Chemical Formula 239>
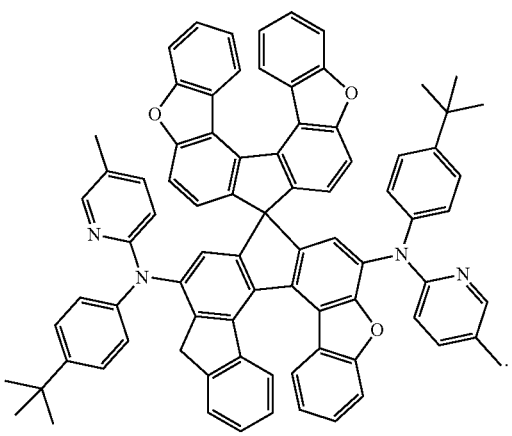
12. The organic light-emitting diode as set forth in claim 1, wherein the pyrene compound represented by Chemical Formula C is any one selected from compounds represented by Chemical Formulas 240 to Chemical Formula 284:
<Chemical Formula 240>
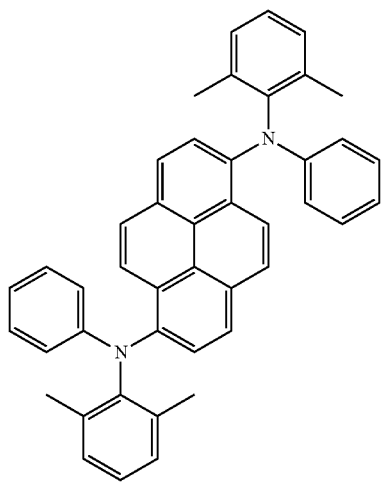
<Chemical Formula 241>
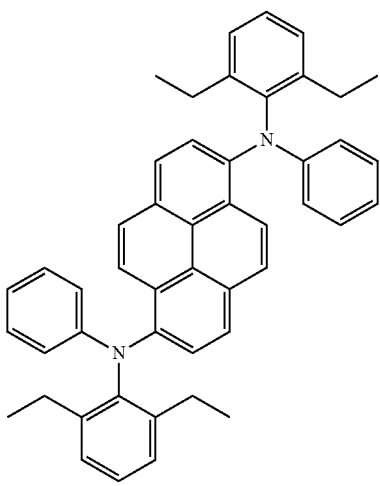

-continued
<Chemical Formula 242>
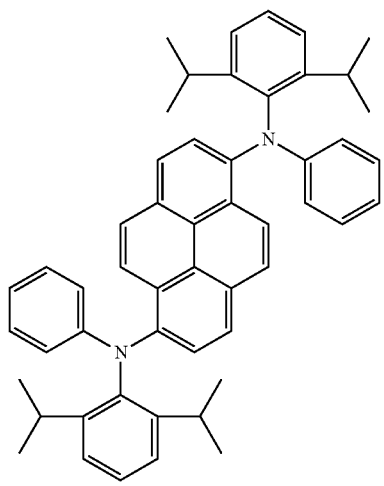
<Chemical Formula 243>
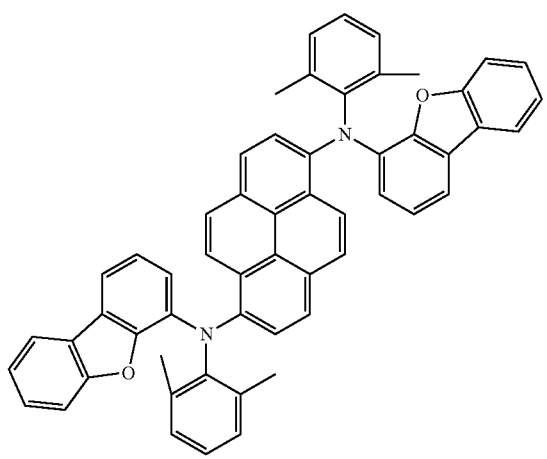
<Chemical Formula 244>
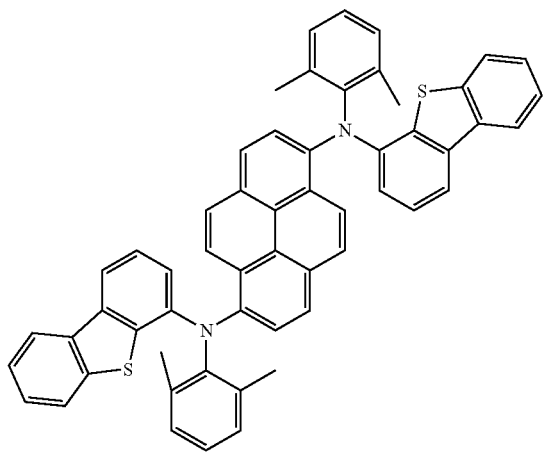
-continued
<Chemical Formula 245>
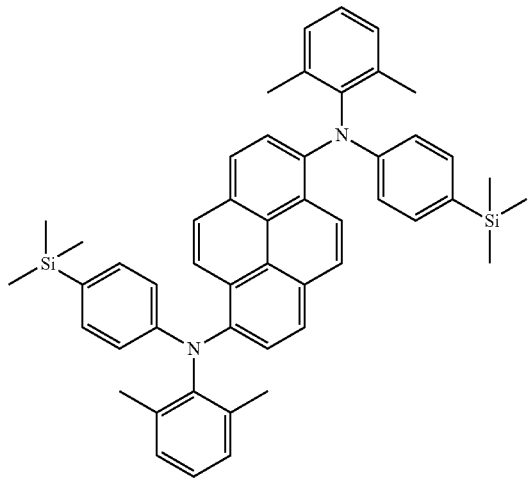
<Chemical Formula 246>
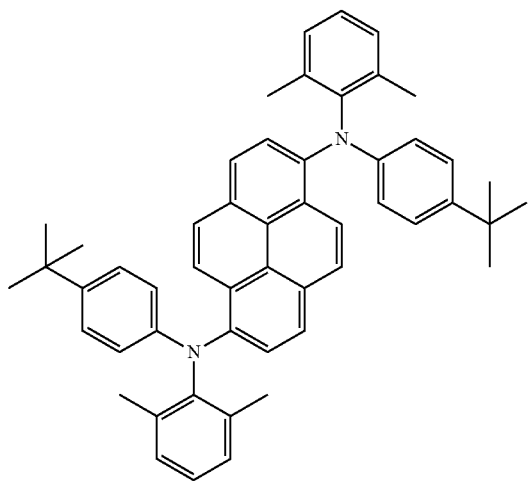
<Chemical Formula 247>
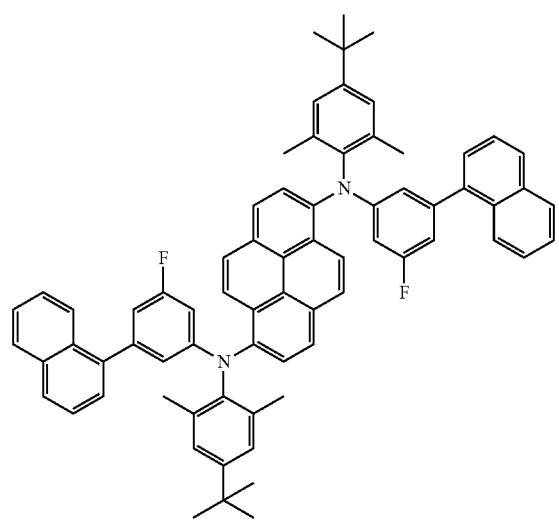

-continued
<Chemical Formula 248>
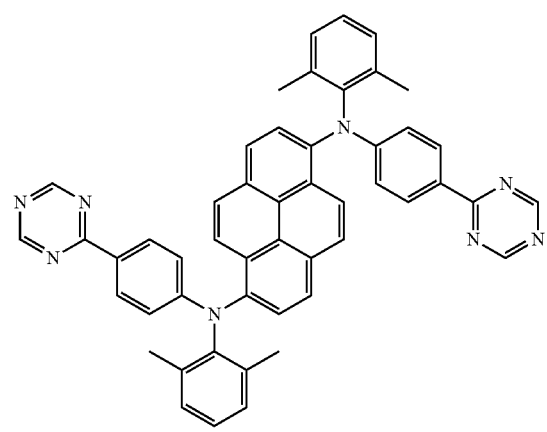
<Chemical Formula 250>
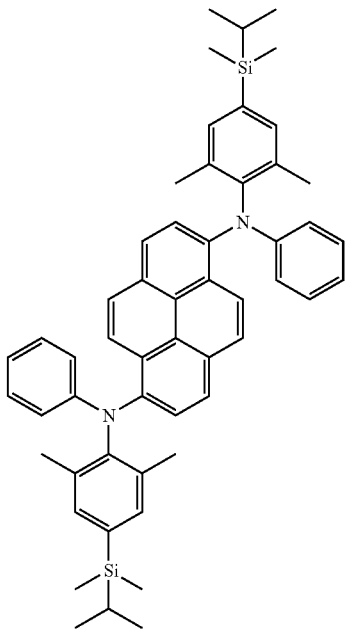
<Chemical Formula 249>
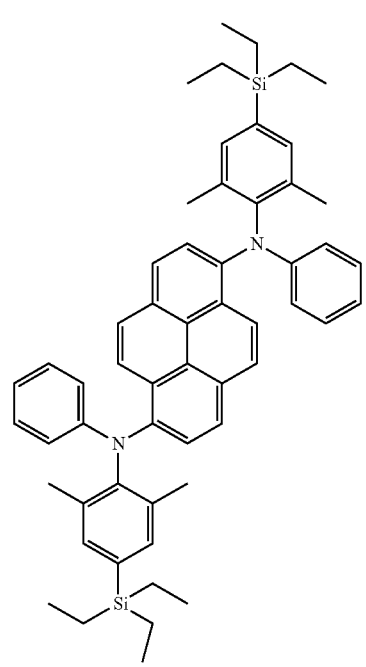
<Chemical Formula 251>
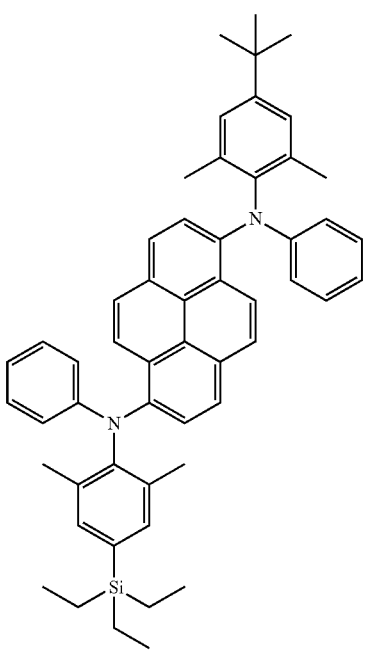

<Chemical Formula 252>
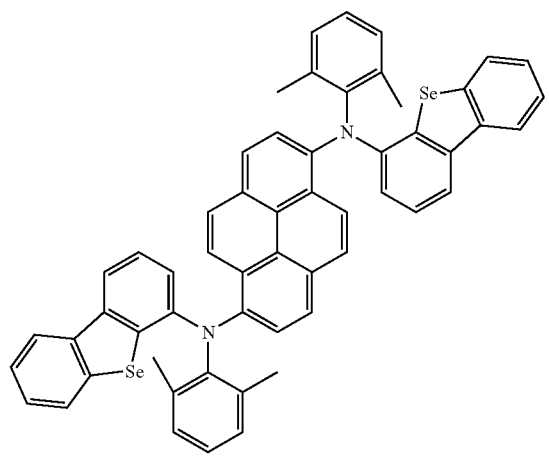
<Chemical Formula 253>
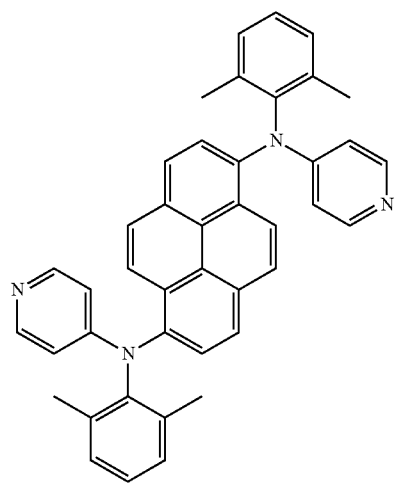
<Chemical Formula 254>
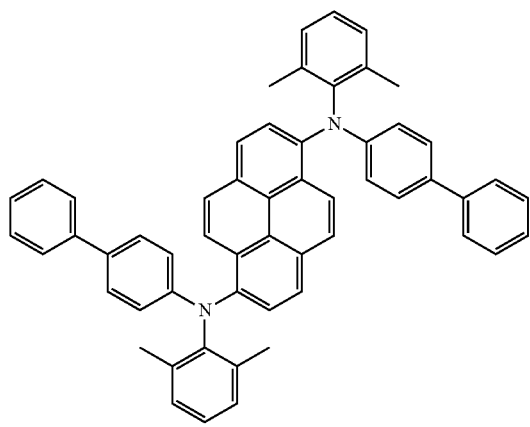
<Chemical Formula 255>
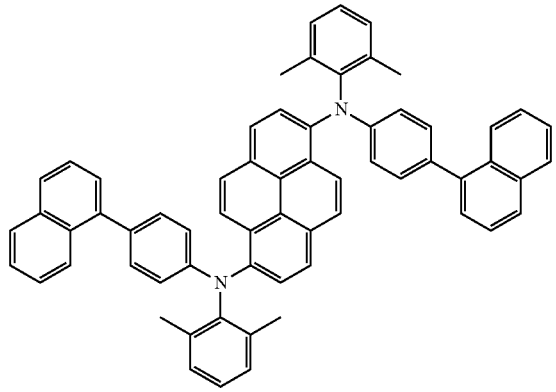
<Chemical Formula 256>
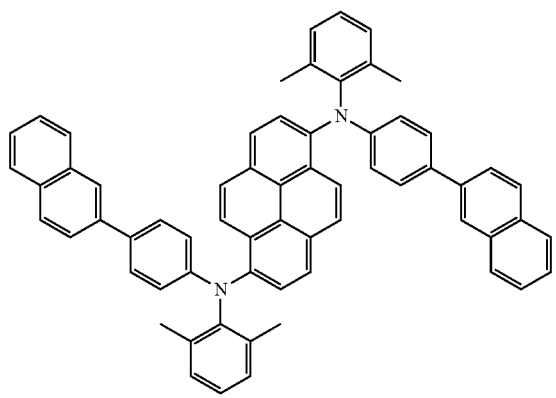
<Chemical Formula 257>
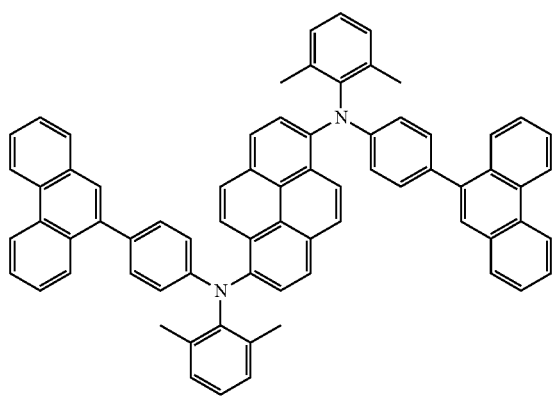

<Chemical Formula 258>
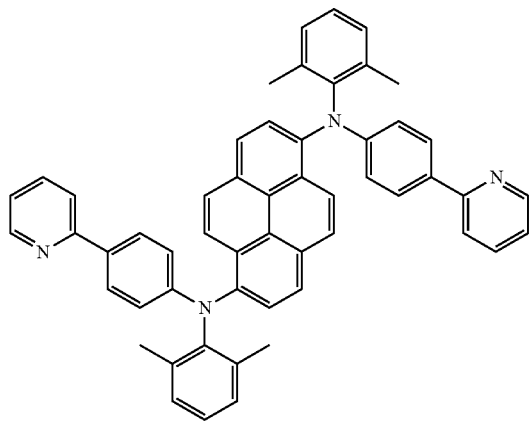
<Chemical Formula 259>
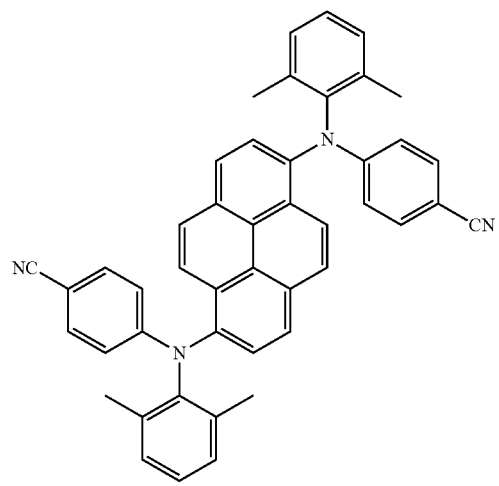
<Chemical Formula 260>
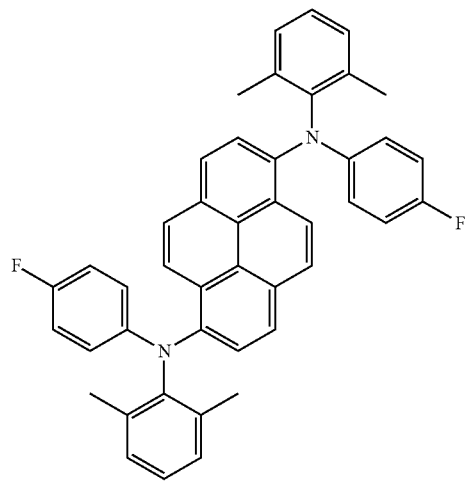
<Chemical Formula 261>
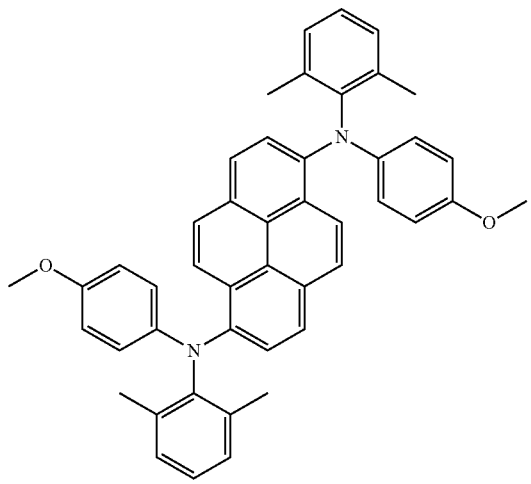
<Chemical Formula 262>
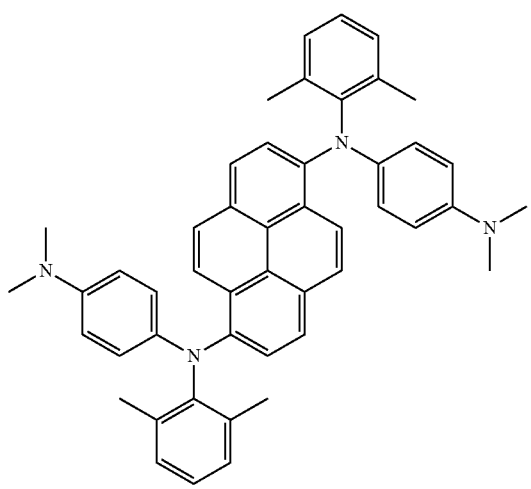
<Chemical Formula 263>
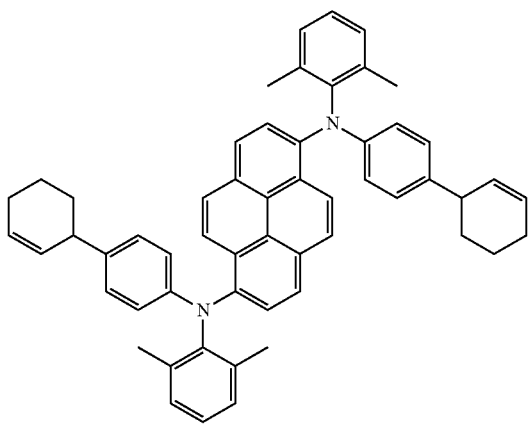

<Chemical Formula 264>
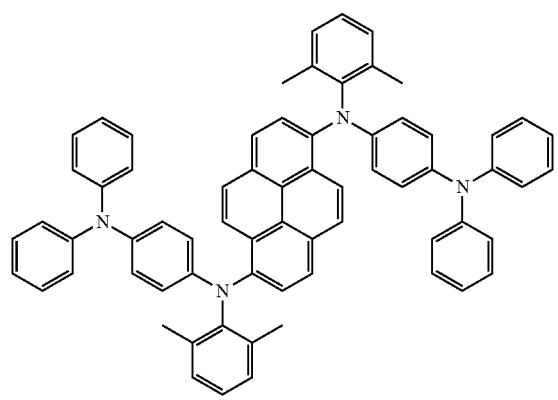
<Chemical Formula 265>
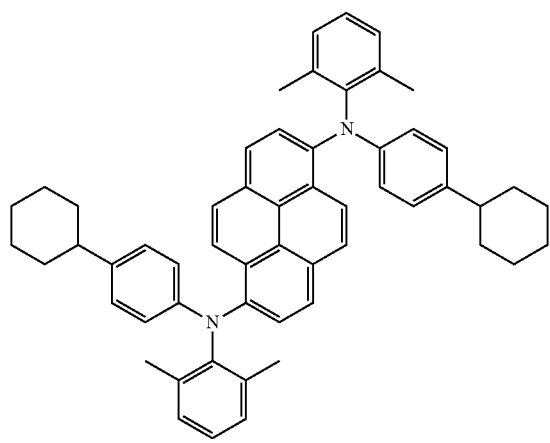
<Chemical Formula 266>
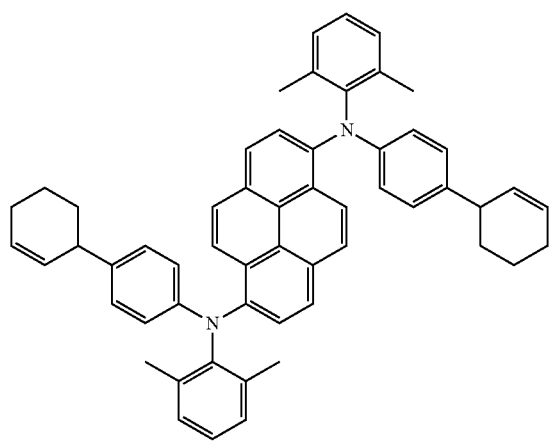
<Chemical Formula 267>
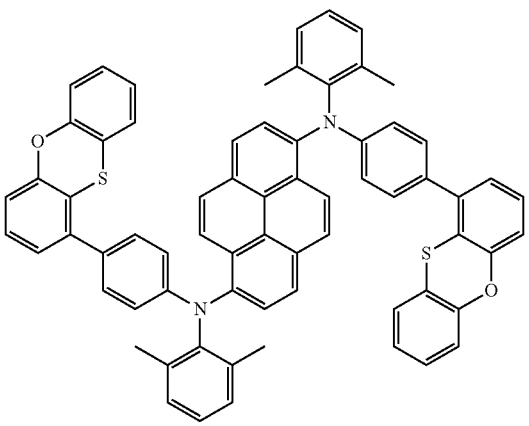
<Chemical Formula 268>
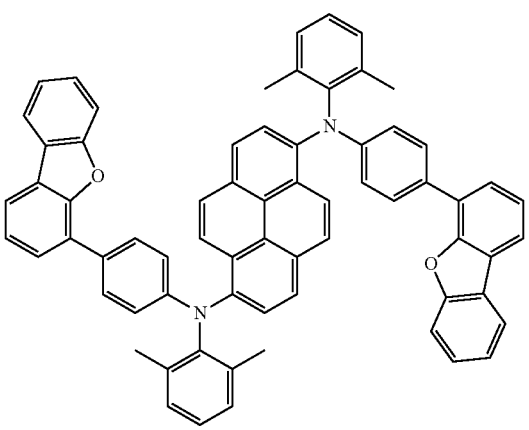
<Chemical Formula 269>
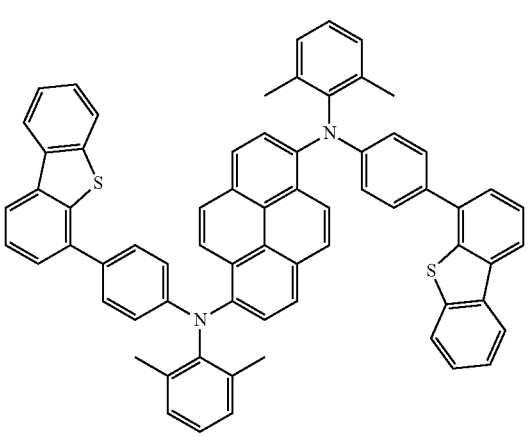

<Chemical Formula 270>
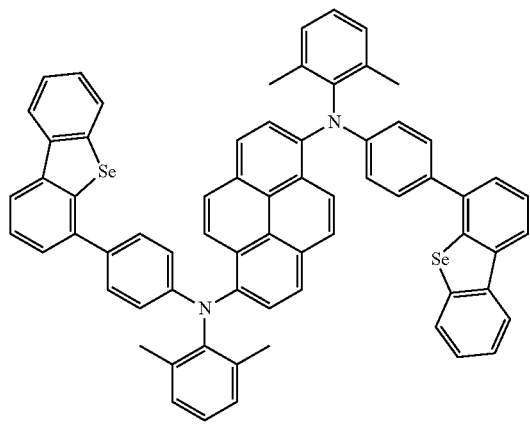
<Chemical Formula 271>
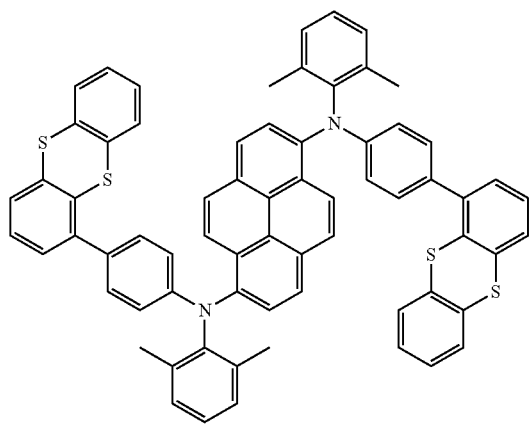
<Chemical Formula 272>
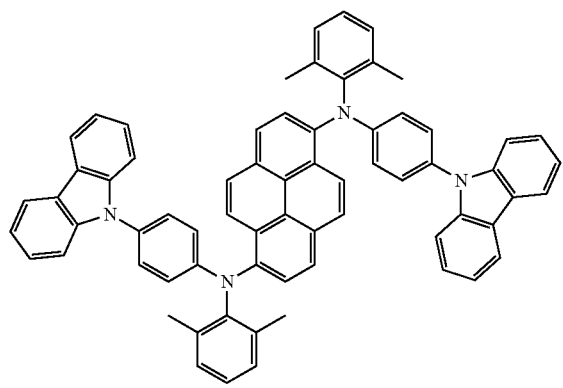
<Chemical Formula 273>
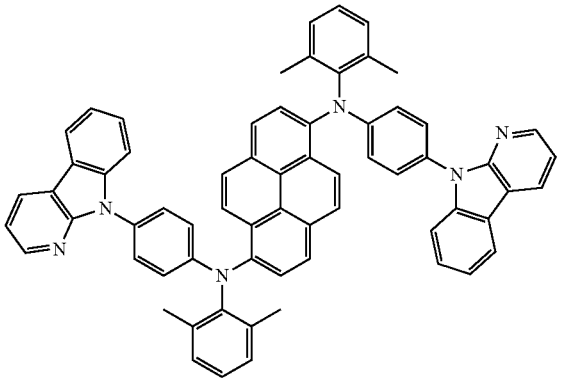
<Chemical Formula 274>
<Chemical Formula 275>
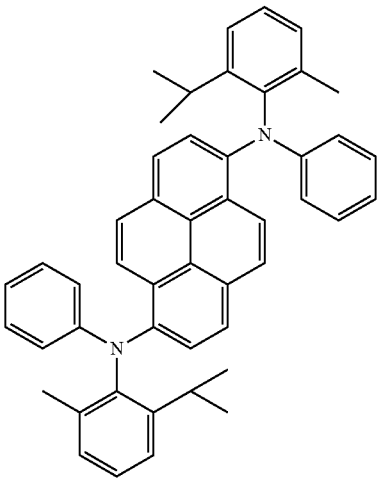

<Chemical Formula 276>
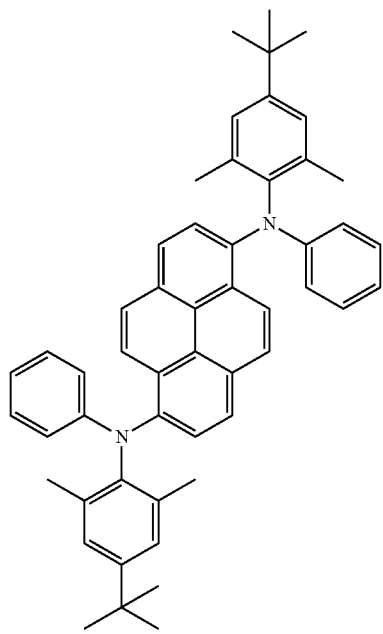
<Chemical Formula 277>
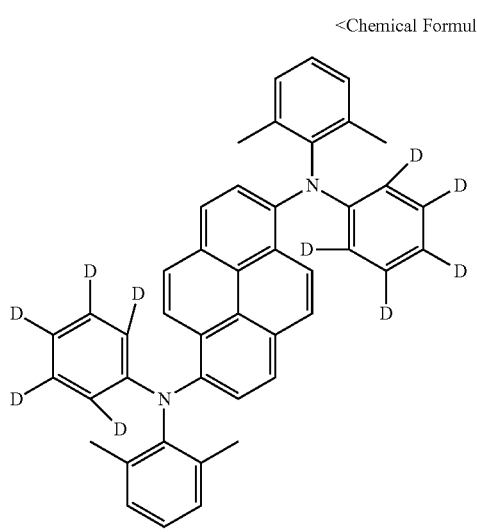
<Chemical Formula 278>
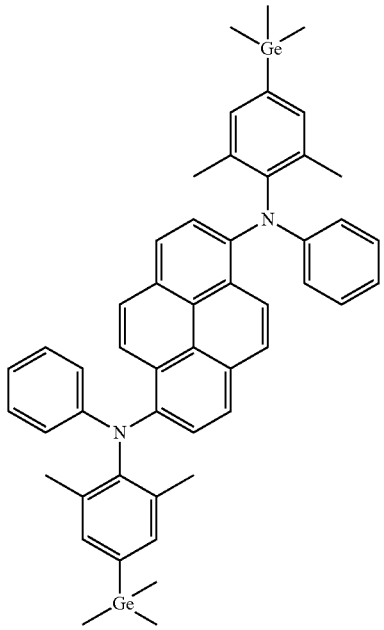
<Chemical Formula 279>
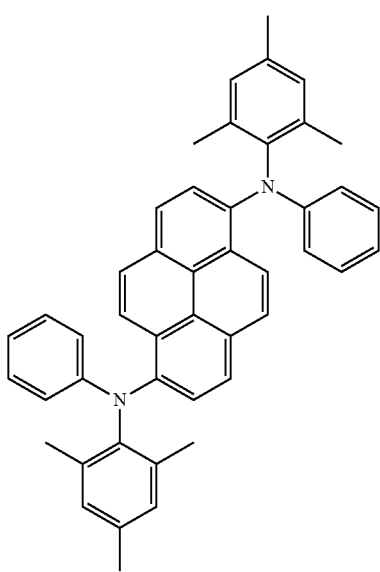

<Chemical Formula 280>
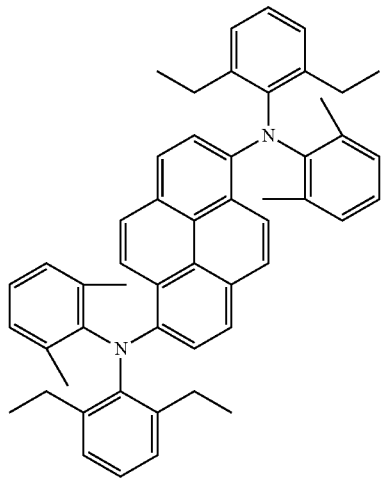
<Chemical Formula 281>
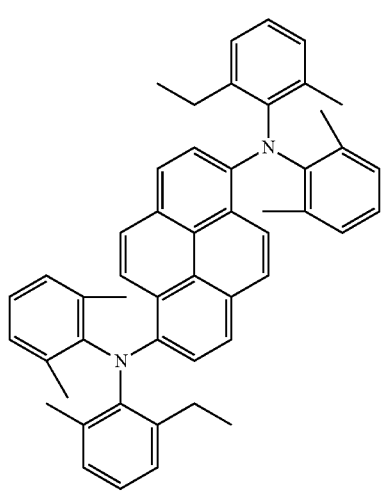
<Chemical Formula 282>
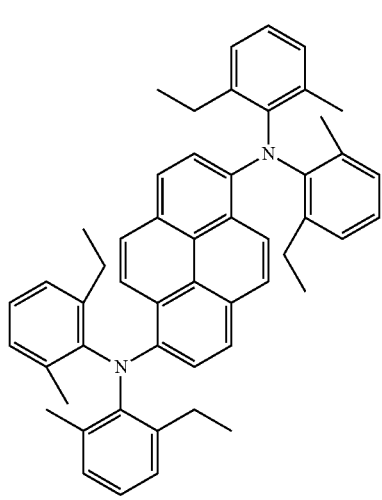
<Chemical Formula 283>
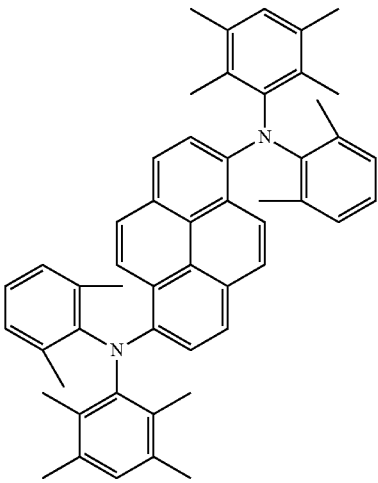
<Chemical Formula 284>
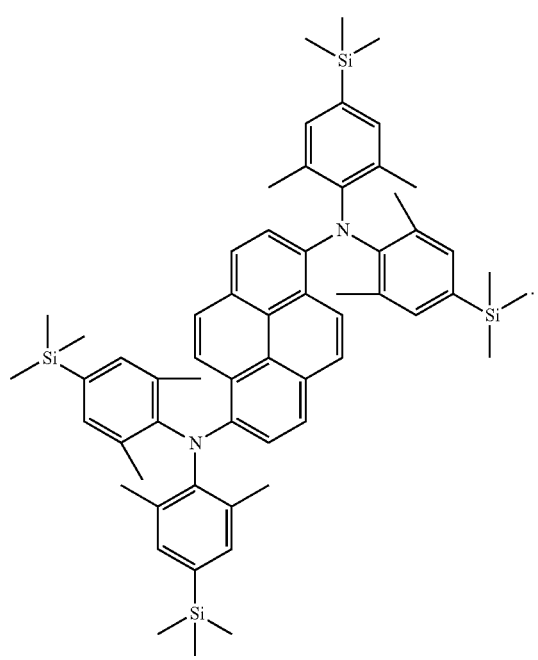
13. The organic light-emitting diode as set forth in claim 1, wherein the anthracene compound represented by Chemical Formula D is any one selected from among the following Compounds 1 to 7, 11 to 15, 18 to 23, 25, 26, and 29:

<Compound 1>
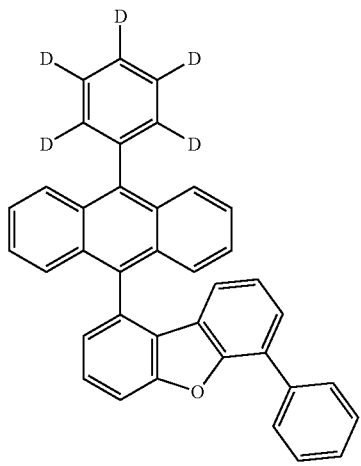
<Compound 2>
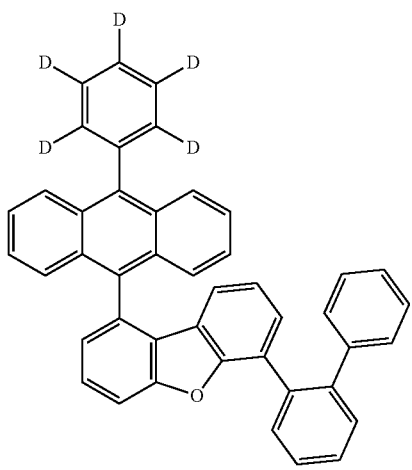
<Compound 3>
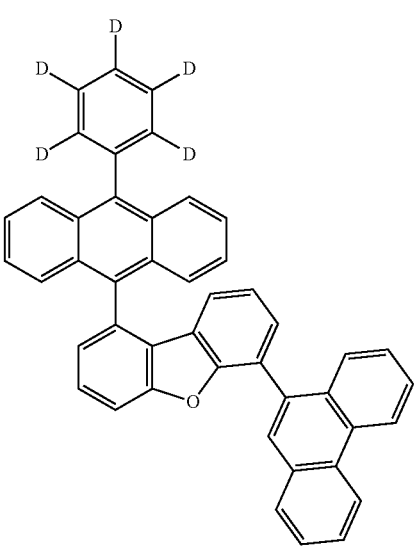
<Compound 4>
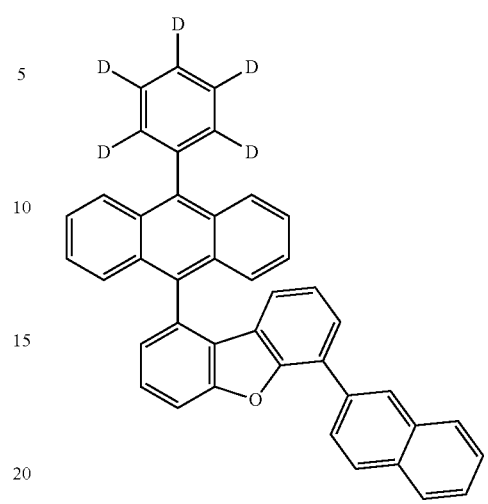
<Compound 5>
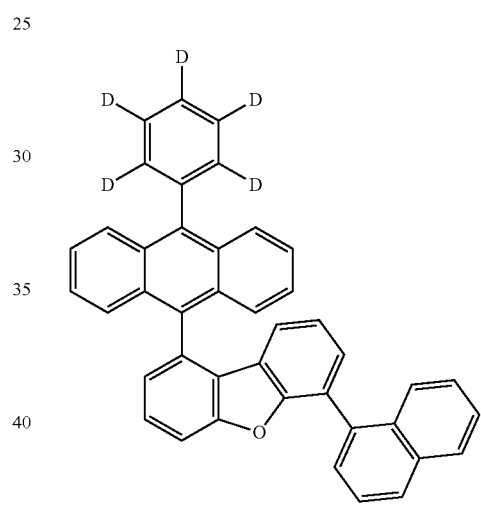
<Compound 6>
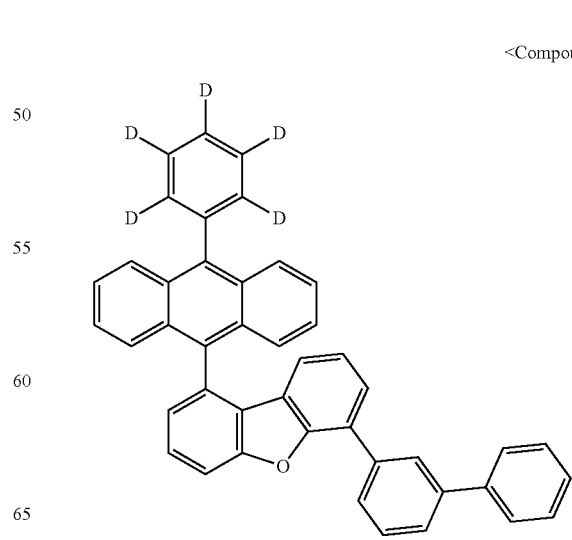

<Compound 7>
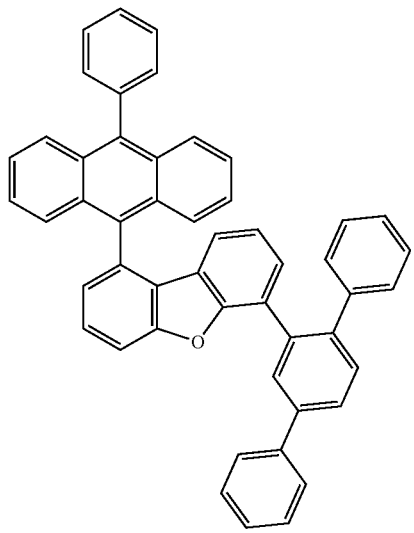
<Compound 11>
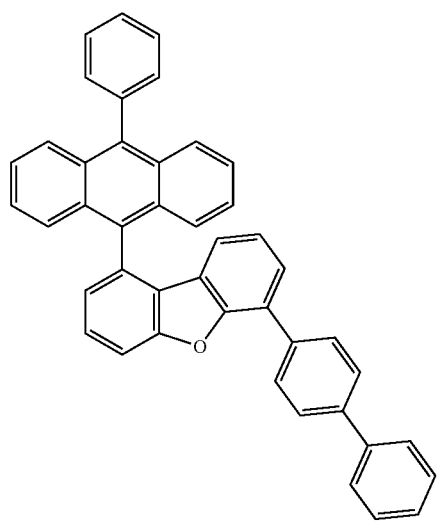
<Compound 12>
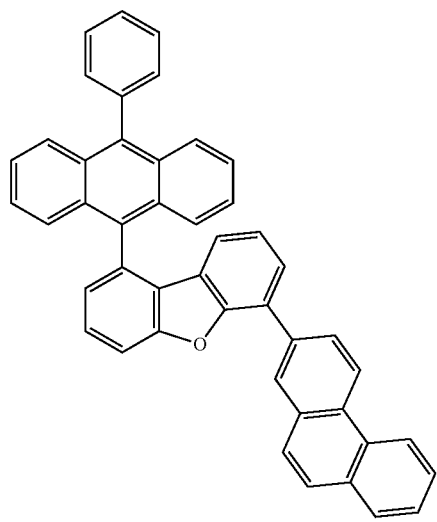
<Compound 13>
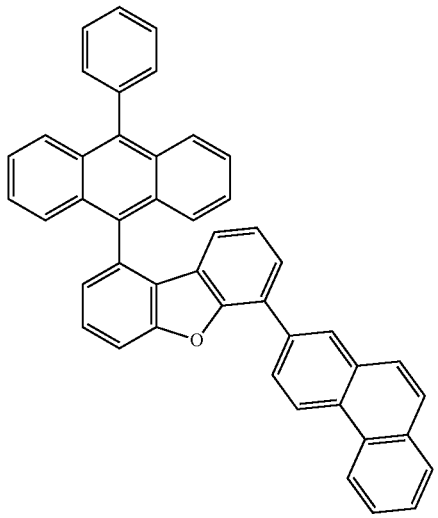
<Compound 14>
<Compound 15>
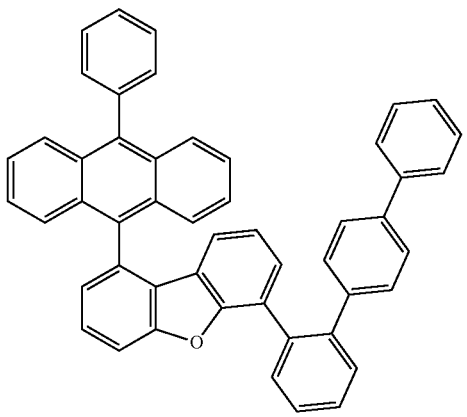

<Compound 18>
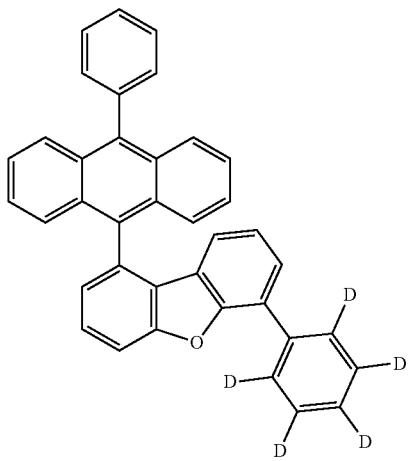
<Compound 19>
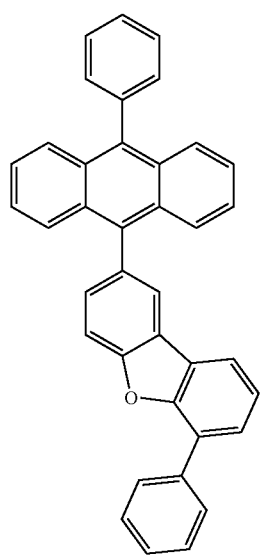
<Compound 20>
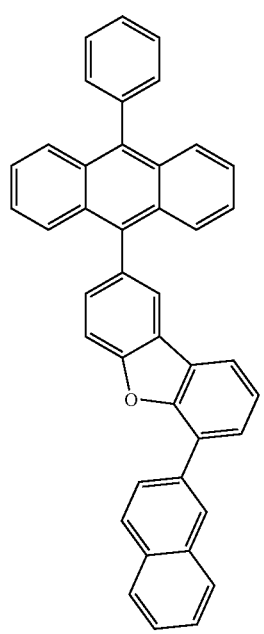
<Compound 21>
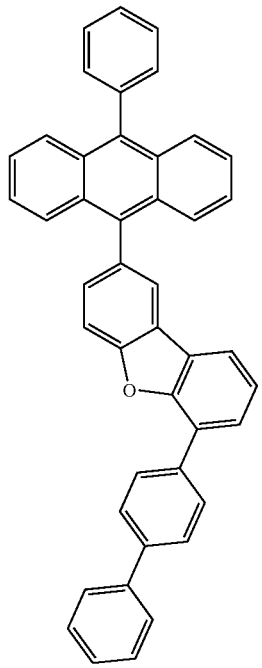
<Compound 22>
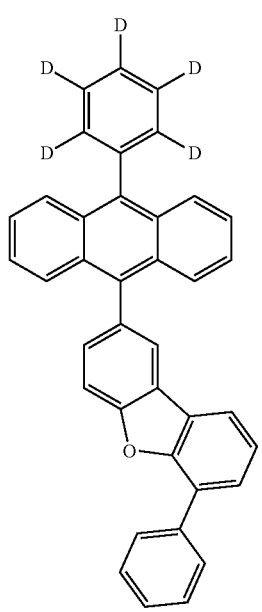

<Compound 23>

<Compound 25>

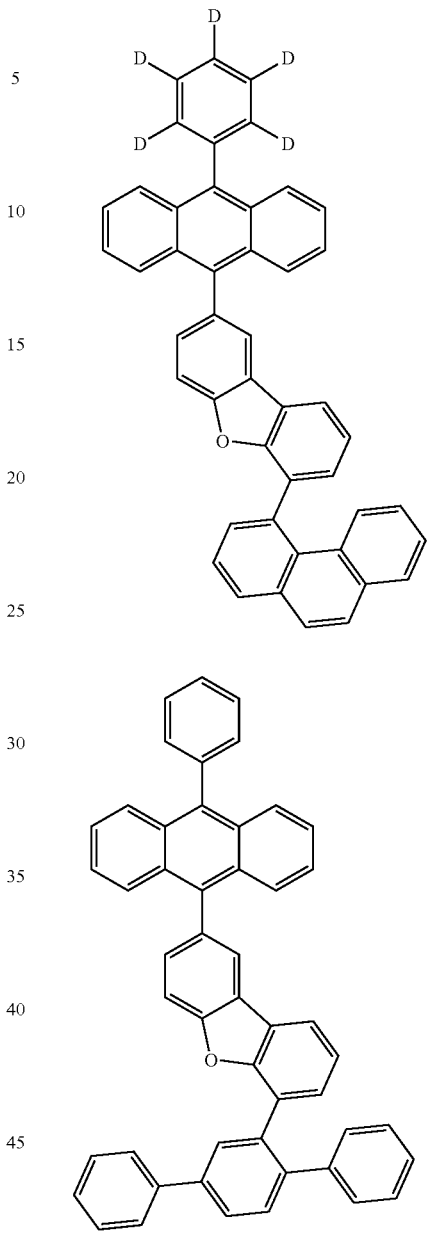

<Compound 26>

<Compound 29>

14. The organic light-emitting diode as set forth in claim 1, further comprising at least one of a hole injection layer, a hole transport layer, a functional layer capable of both hole injection and hole transport, an electron transport layer, and an electron injection layer, in addition to the light-emitting layer.

15. The organic light-emitting diode as set forth in claim 14, wherein at least one of the layers is formed using a deposition process or a solution process.

16. The organic light-emitting diode as set forth in claim 1, wherein the organic light-emitting diode is used for a device selected from among a flat display device, a flexible display device, a monochrome or grayscale flat illumination device, and a monochrome or grayscale flexible illumination device.

* * * * *